(12) United States Patent
Weinschenk et al.

(10) Patent No.: US 11,406,693 B2
(45) Date of Patent: Aug. 9, 2022

(54) PEPTIDES AND COMBINATION OF PEPTIDES FOR USE IN IMMUNOTHERAPY AGAINST HEPATOCELLULAR CARCINOMA (HCC) AND OTHER CANCERS

(71) Applicant: IMMATICS BIOTECHNOLOGIES GMBH, Tuebingen (DE)

(72) Inventors: Toni Weinschenk, Aichwald (DE); Andrea Mahr, Tuebingen (DE); Jens Fritsche, Dusslingen (DE); Phillip Mueller, Tuebingen (DE); Anita Wiebe, Pliezhausen (DE); Sarah Kutscher, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 19 days.

(21) Appl. No.: 15/918,788

(22) Filed: Mar. 12, 2018

(65) Prior Publication Data

US 2018/0207253 A1 Jul. 26, 2018

Related U.S. Application Data

(63) Continuation of application No. 15/357,757, filed on Nov. 21, 2016, now abandoned, which is a continuation of application No. 14/975,952, filed on Dec. 21, 2015, now Pat. No. 10,064,926.

(60) Provisional application No. 62/096,165, filed on Dec. 23, 2014.

(30) Foreign Application Priority Data

Dec. 23, 2014 (GB) .................................. 1423016
Jan. 21, 2015 (GB) .................................. 1501017

(51) Int. Cl.
| | | |
|---|---|---|
| A61K 39/00 | (2006.01) |
| A61K 38/04 | (2006.01) |
| C07K 7/06 | (2006.01) |
| C07K 7/00 | (2006.01) |
| C07K 7/08 | (2006.01) |
| A61K 51/10 | (2006.01) |
| A61K 35/17 | (2015.01) |
| C07K 16/18 | (2006.01) |
| C12N 5/0783 | (2010.01) |
| C12N 15/115 | (2010.01) |
| G01N 33/68 | (2006.01) |
| C07K 14/435 | (2006.01) |
| C07K 14/725 | (2006.01) |
| C07K 14/74 | (2006.01) |
| A61K 35/12 | (2015.01) |

(52) U.S. Cl.
CPC ........ *A61K 39/00111* (2018.08); *A61K 35/17* (2013.01); *A61K 38/04* (2013.01); *A61K 39/0011* (2013.01); *A61K 51/1057* (2013.01); *C07K 7/00* (2013.01); *C07K 7/06* (2013.01); *C07K 7/08* (2013.01); *C07K 14/435* (2013.01); *C07K 14/7051* (2013.01); *C07K 14/70539* (2013.01); *C07K 16/18* (2013.01); *C12N 5/0636* (2013.01); *C12N 15/115* (2013.01); *G01N 33/6803* (2013.01); *A61K 2035/124* (2013.01); *A61K 2039/5154* (2013.01); *A61K 2039/5158* (2013.01); *C07K 2317/70* (2013.01); *C07K 2319/40* (2013.01); *C12N 2310/16* (2013.01); *C12N 2501/998* (2013.01)

(58) Field of Classification Search
CPC ...... A61K 39/011; A61K 35/17; A61K 38/04; A61K 39/00; C07K 7/00; C07K 7/06; C07K 7/08; C07K 14/435; C07K 14/7051; C07K 2310/40

See application file for complete search history.

(56) References Cited

U.S. PATENT DOCUMENTS

| | | | |
|---|---|---|---|
| 6,867,283 B2* | 3/2005 | Barnea ............. | G01N 33/56977 424/278.1 |
| 2003/0096298 A1 | 5/2003 | Barnea et al. | |
| 2004/0033541 A1 | 2/2004 | Zhang et al. | |
| 2004/0096982 A1 | 5/2004 | Barnea | |
| 2005/0053918 A1 | 3/2005 | Barnea et al. | |
| 2009/0075304 A1 | 3/2009 | Weidanz | |
| 2009/0233318 A1 | 9/2009 | Weidanz | |
| 2009/0304679 A1 | 12/2009 | Weidanz | |
| 2010/0215674 A1* | 8/2010 | Thielemans ......... | C12N 5/0639 424/184.1 |

(Continued)

FOREIGN PATENT DOCUMENTS

| | | |
|---|---|---|
| CN | 103739667 A | 4/2014 |
| EP | 1760088 A1 | 3/2007 |

(Continued)

OTHER PUBLICATIONS

Perica et al., (Rambam Maimonides Med J. Jan. 2015:6(1).e0004. ePub Jan. 29, 2015); (Year: 2015).*
Cancer Genetics Web MAGEB2 Datatable ((published at www.cancerindex.org/geneweb/MAGEB2.htm#datatable) (13 pages) (citing papers from 1992-2017) (page last revised Mar. 13, 2017) (last accessed May 12, 2018)) (Year: 2017).*

(Continued)

*Primary Examiner* — Gyan Chandra
(74) *Attorney, Agent, or Firm* — McBee Moore & Vanik IP, LLC

(57) ABSTRACT

A method of eliciting an immune response in a patient who has a cancer includes administering to said patient a composition containing a population of activated T cells that selectively recognize the cancer cells in the patient that aberrantly express a peptide consisting of the amino acid sequence of GVYDGEEHSV (SEQ ID NO: 303), in which the peptide is in a complex with an MHC molecule.

12 Claims, 21 Drawing Sheets
(11 of 21 Drawing Sheet(s) Filed in Color)
Specification includes a Sequence Listing.

(56) References Cited

U.S. PATENT DOCUMENTS

| | | |
|---|---|---|
| 2014/0065708 A1 | 3/2014 | Weidanz |
| 2014/0141455 A1 | 5/2014 | Weidanz |
| 2014/0273275 A1 | 9/2014 | Jacobs et al. |
| 2016/0250307 A1 | 9/2016 | Weinschenk et al. |
| 2018/0171024 A1 | 6/2018 | Peled et al. |
| 2018/0179283 A1 | 6/2018 | Peled et al. |
| 2019/0040378 A1 | 2/2019 | Fotin-Mleczek et al. |
| 2019/0071502 A1 | 3/2019 | Weidanz |
| 2019/0127436 A1 | 5/2019 | Tribble et al. |
| 2019/0135892 A1 | 5/2019 | Tribble et al. |
| 2019/0144521 A1 | 5/2019 | Tribble et al. |
| 2019/0201443 A1 | 7/2019 | Joglekar et al. |
| 2020/0276237 A1 | 9/2020 | Shiku et al. |
| 2020/0291116 A1 | 9/2020 | Weidanz |
| 2020/0291127 A1 | 9/2020 | Weidanz |
| 2020/0291128 A1 | 9/2020 | Weidanz |
| 2020/0325244 A1 | 10/2020 | Weidanz |

FOREIGN PATENT DOCUMENTS

| | | | |
|---|---|---|---|
| JP | 4406607 B2 | 2/2010 | |
| WO | 0144279 A2 | 6/2001 | |
| WO | 02094981 A2 | 11/2002 | |
| WO | 2004061423 A2 | 7/2004 | |
| WO | 2009026547 A1 | 2/2009 | |
| WO | 2010/037514 A2 | 4/2010 | |
| WO | 2011060329 A1 | 5/2011 | |
| WO | 2011095628 A1 | 8/2011 | |
| WO | 2012/065133 A1 | 5/2012 | |
| WO | 2012065135 A2 | 5/2012 | |
| WO | 2012/074725 A2 | 6/2012 | |
| WO | 2013070603 A1 | 5/2013 | |
| WO | WO-2013167897 A1 * | 11/2013 | ............ A61K 39/35 |
| WO | 2014039675 A2 | 3/2014 | |
| WO | 2014118552 A1 | 8/2014 | |
| WO | 2016102272 A1 | 6/2016 | |
| WO | 2016199140 A1 | 12/2016 | |
| WO | 2016199141 A2 | 12/2016 | |
| WO | 2017174822 A1 | 10/2017 | |
| WO | 2017174823 A1 | 10/2017 | |
| WO | 2017174824 A1 | 10/2017 | |
| WO | 201822573 A1 | 2/2018 | |
| WO | 2018140525 A1 | 8/2018 | |
| WO | 2019008001 A1 | 1/2019 | |
| WO | 2019036688 A1 | 2/2019 | |
| WO | 2019133853 A1 | 7/2019 | |
| WO | 2019204683 A1 | 10/2019 | |
| WO | 2019226941 A1 | 11/2019 | |

OTHER PUBLICATIONS

Suzuki et al., (Int J Oncol. Dec. 1999;15(6):1227-32) (Year: 1999).*
Hirohashi,et al., (Cancer Sci. Jan. 2016;107(1): 12-17) (Year: 2016).*
June (J Clin Invest. Jun. 1, 2007;117(6):1466-1476) (Year: 2007).*
Zhang et al., (Mol. Ther. Apr. 2011; 19(4):751 -759) (Year: 2011).*
Bielamowicz et al., (Front Oncol. 2013:3;275, 11 pages. ePub Nov. 11, 2013) (Year: 2013).*
Scarcella et al., (Clin Cancer res. Feb. 1999.;5(2):335-41) (Year: 1999).*
Barbari, C., et al. Immunotherapies and combination strategies for immuno-oncology. International Journal of Molecular Sciences, 2020, 21:5009, p. 1-28.*
Hendrickson, P.G., et al. The promise of adoptive cellular immunotherapies in hepatocellular carcinoma. Oncoimmunology, 2020, 9(1):e1673129, p. 1-8).*
Waldlman, A.D., et al. A guide to cancer immunotherapy: from T cell basic science to clinical practice. Nature Reviews Immunology, May 2020, p. 1-18, published online ahead of print.*
Lee et al. , "Vaccination of Advanced Hepatocellular Carcinoma Patients with Tumor Lysate-Pulsed Dendritic Cells: A Clinical Trial", Clinical Study, J Immunother, vol. 28, No. 5, Sep./Oct. 2005, pp. 496-504.
Shi, M., "Autologous cytokine-induced killer cell therapy in clinical trial phase I is safe in patients with primary hepatocellular carcinoma", World Journal of Gastroenterology, vol. 10(8), Apr. 15, 2004, pp. 1146-1151.
Takayama, "Distribution and therapeutic effect of intraarterially transferred tumor—infiltrating lymphocytes in hepatic malignancies", A Preliminary Report, Cancer, vol. 68 (11), Mar. 19, 1991, pp. 2391-2396.
Enguita-German, et al., "Targeting the insulin-like growth factor pathway in hepatocellular carcinoma", World J Hepatol. vol. 6, Issue 10, Oct. 27, 2014, pp. 716-737.
Chang, et al., "Sorafenib (BAY 43-9006) inhibits tumor growth and vascularization and induces tumor apoptosis and hypoxia in RCC xenograft models", Cancer Chemother.Pharmacol. 59, (2007), pp. 561-574.
Wilhelm et al., "BAY 43-9006 exhibits broad spectrum oral antitumor activity and targets the RAF/MEK/ERK pathway and receptor tyrosine kinases involved in tumor progression and angiogenesis", Cancer Res. vol. 64, Oct. 1, 2004, pp. 7099-7109.
Chapiro, et al., "Combination of intra-arterial therapies and sorafenib: Is there a clinical benefit?," Radiol.Med. 119 (2014), pp. 476-482.
Llovet et al., "Sorafenib in Advanced Hepatocellular Carcinoma", N. Engl. J Med. 359, Dec. 4, 2008, pp. 2497-2499.
Reinisch et al., "Prospective Pilot Study of Recombinant Granulocyte-Macrophage Colony-Stimulating Factor and Interferon-γ in Patients With Inoperable Hepatocellular Carcinoma", J Immunother., vol. 25, (2002), pp. 489-499.
Sangro et al., "Phase I Trial of Intratumoral Injection of an Adenovirus Encoding Interleukin-12 for Advanced Digestive Tumors", Journal of Clinical Oncology, vol. 22, No. 8, Apr. 15, 2004, pp. 1389-1397.
Takayama et al., "Adoptive immunotherapy to lower postsurgical recurrence rates of hepatocellular carcinoma: a randomised trial", The Lancet, vol. 356, Sep. 2, 2000, pp. 802-807.
Butterfield et al., "A Phase I/II Trial Testing Immunization of Hepatocellular Carcinoma Patients with Dendritic Cells Pulsed with Four α-Fetoprotein Peptides", Clinical Cancer Research 12, (2006), pp. 2817-2825.
Palmer et al., "A phase II study of adoptive immunotherapy using dendritic cells pulsed with tumor lysate in patients with hepatocellular carcinoma", Hepatology 49, (2009), pp. 124-132.
Butterfield et al., "Determinant Spreading Associated with Clinical Response in Dendritic Cell-based Immunotherapy for Malignant Melanoma", vol. 9, pp. 998-1008, Mar. 2003, Clinical Cancer Research.
Emanuela Signori et al., "PIVAC-14 The 14th International Conference on Progress in Vaccination against Cancer", Proceedings, Sep. 24-26, 2014; Rome, Italy, pp. 1-60; XP055248053.
Yu Sawada et al., "A glypican-3-derived peptide vaccine against hepatocellular carcinoma", Oncoimmunology, vol. 1, No. 8, Nov. 1, 2012, pp. 1448-1450; XP055248031.
International Search Report of International Application No. PCT/EP2015/080018 dated May 11, 2016.
He et al., "Screening differential expression of serum proteins in AFP-negative HBV-related hepatocellular carcinoma using iTRAQ-MALDIMS/MS." Neoplasma 61(1) 2014.
Search Report dated Sep. 30, 2015, issued by the Intellectual Property Office in GB1423016.3.
Search Report dated Oct. 14, 2015, issued by the Intellectual Property Office in GB1501017.6.
Eilon Barnea et al., "Analysis of endogenous peptides bound by soluble MHC class 1 molecules: a novel approach for identifying tumor-specific antigens." Eur. J. Immunol 2002 32:213-222 (Jan. 2002).
Valenzuela et al, "The roles of IL-12 in providing a third signal for clonal expansion of naive CD8 T cells," J Immunol., (2002), vol. 169(12): 6842-6849.
Peng et al., "Expression of cancer/testis (CT) antigens in Chinese hepatocellular carcinoma and its correlation with clinical parameters," Cancer Lett., (2005), vol. 219(2): 223-232.
Williams et al., "Sequence variants in SLC16A11 are a common risk factor for type 2 diabetes in Mexico," Nature, (2014), vol. 6: 97-101.

(56) References Cited

OTHER PUBLICATIONS

Ye et al., "bKlotho Suppresses Tumor Growth in Hepatocellular Carcinoma by Regulating Akt/GSK-3b/Cyclin D1 Signaling Pathway," PLOS One, (2013), vol. 8, Issue 1: e55615.
Fernandes et al., "The novel putative bile acid transporter SLC10A5 is highly expressed in liver and kidney," Biochemical and Biophysical Research Communications, (2007), vol. 361: 26-32.
Saskia et al., "Benign Recurrent Intrahepatic Cholestasis Type 2 Is Caused by Mutations in ABCB11," Gastroenterology, (2004), vol. 127: 379-384.

\* cited by examiner

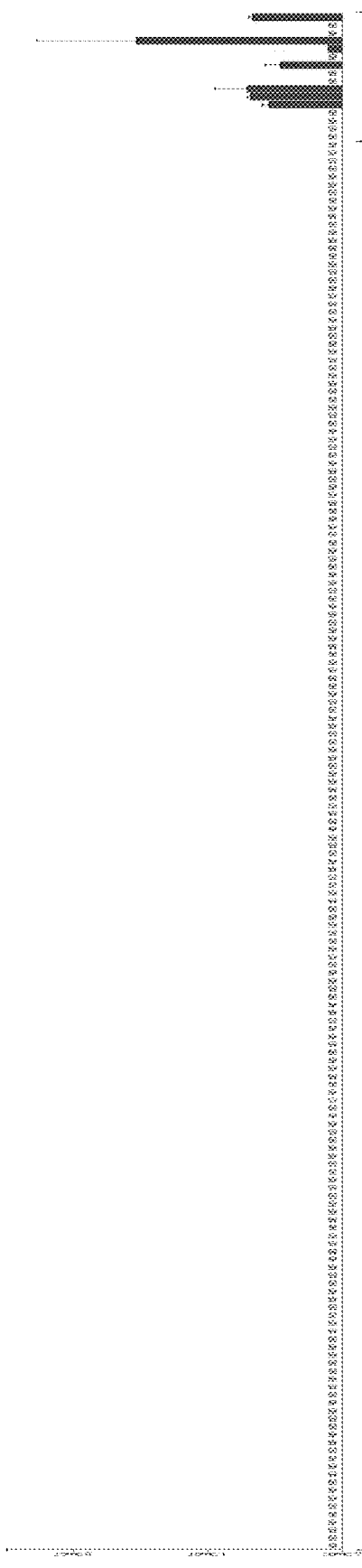

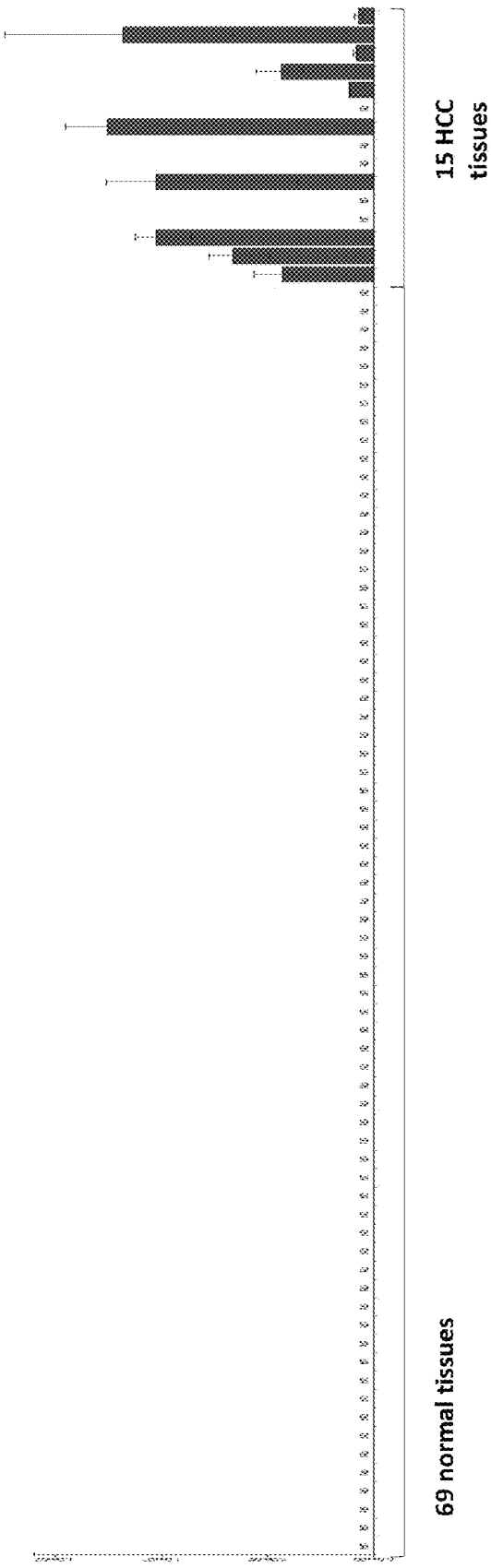

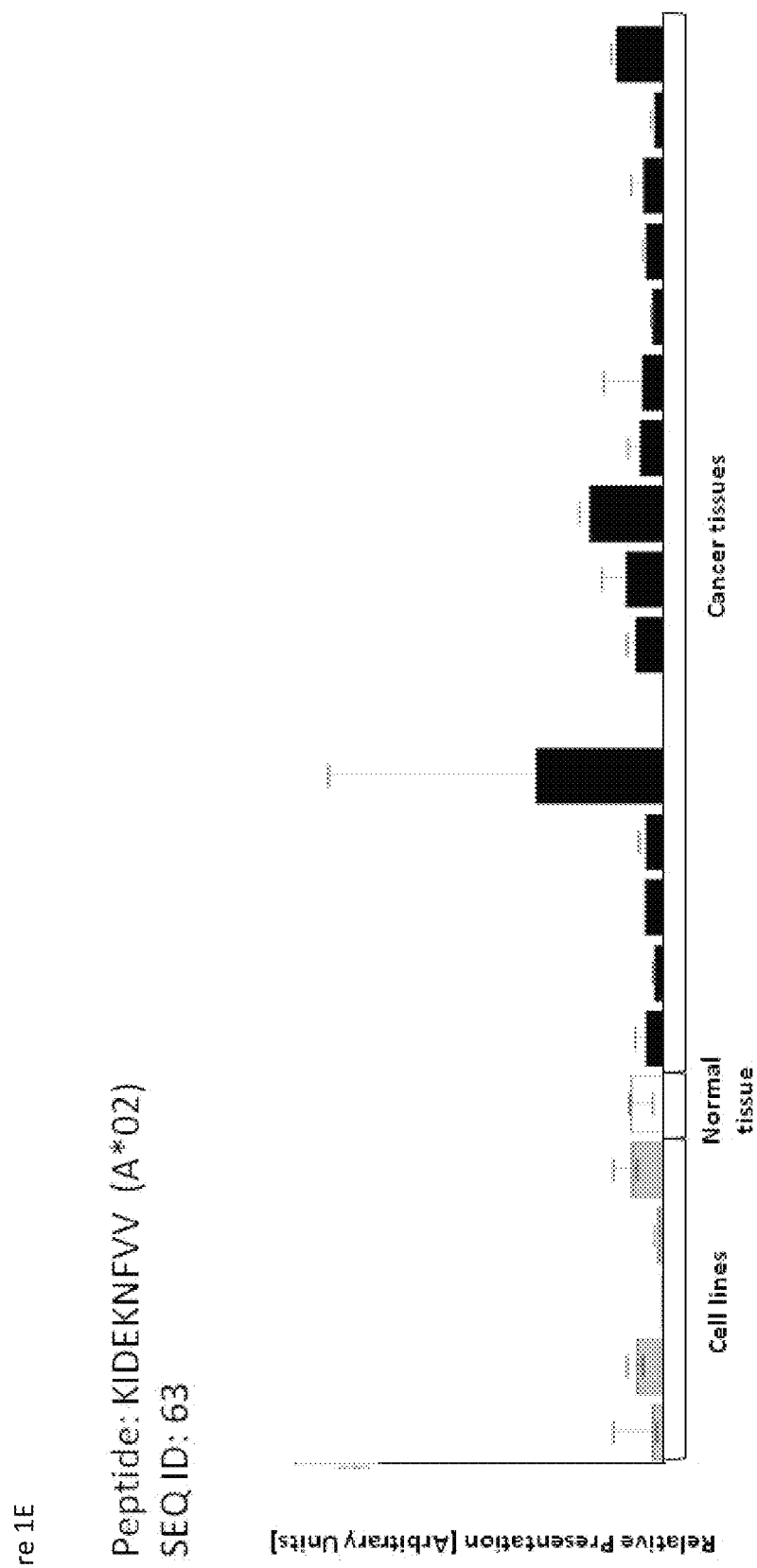

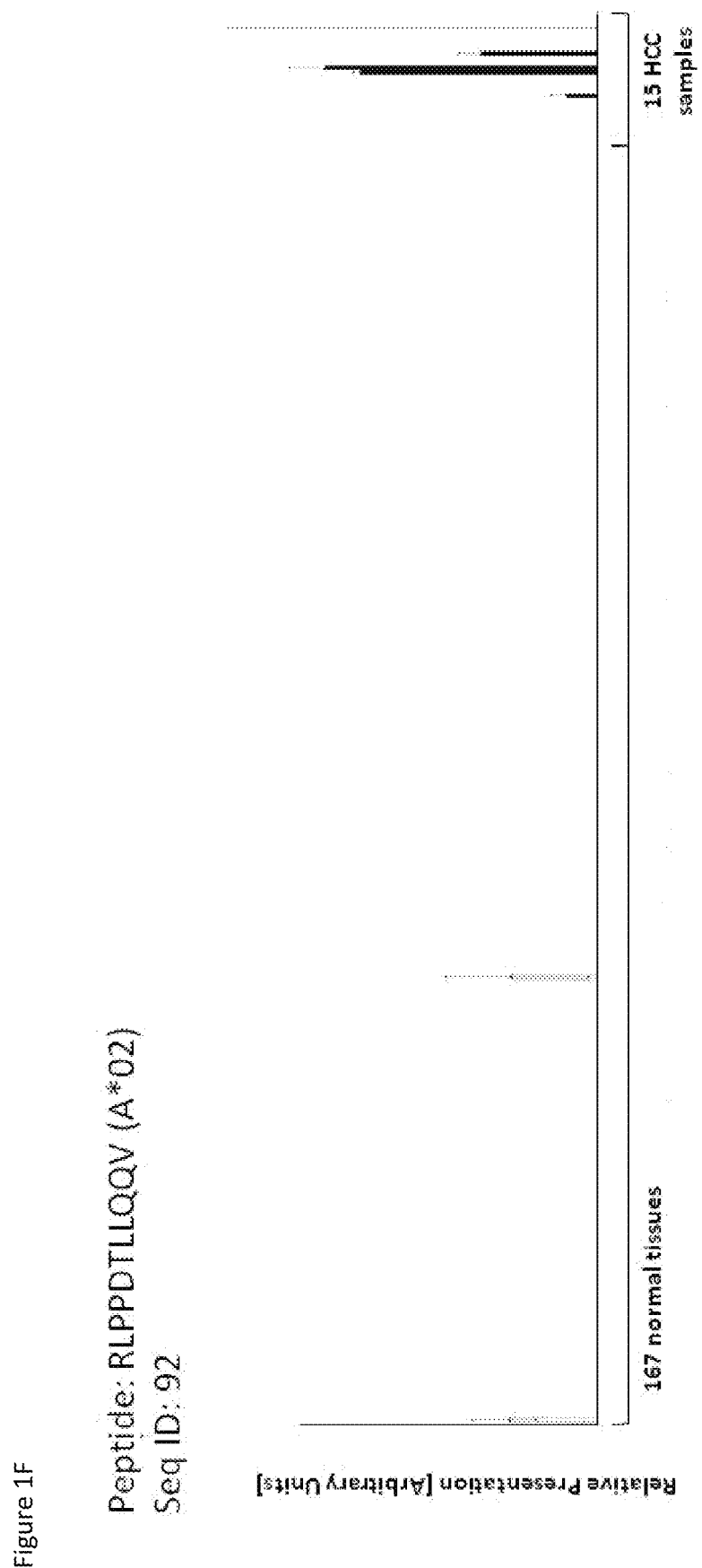

Peptide: RLPPDTLLQQV (A*02)
SEQ ID: 92

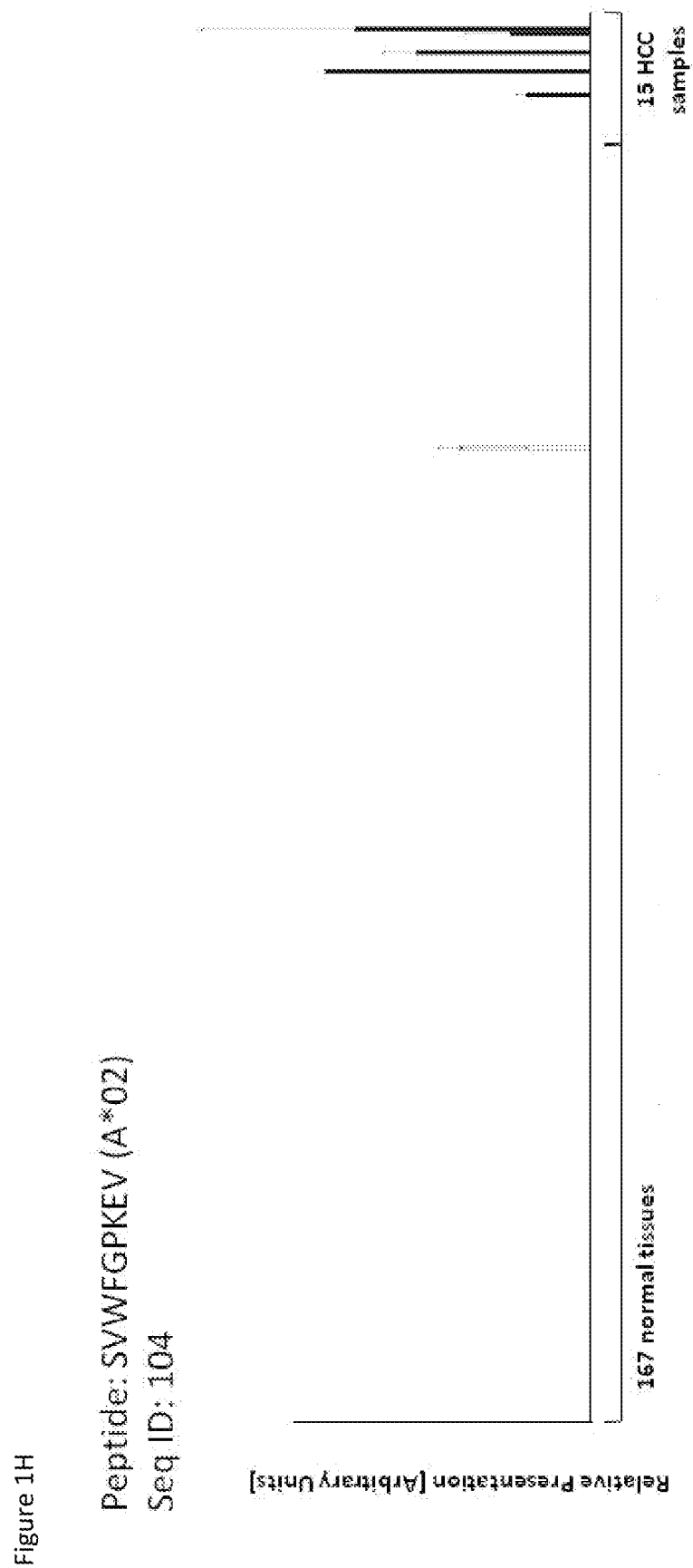

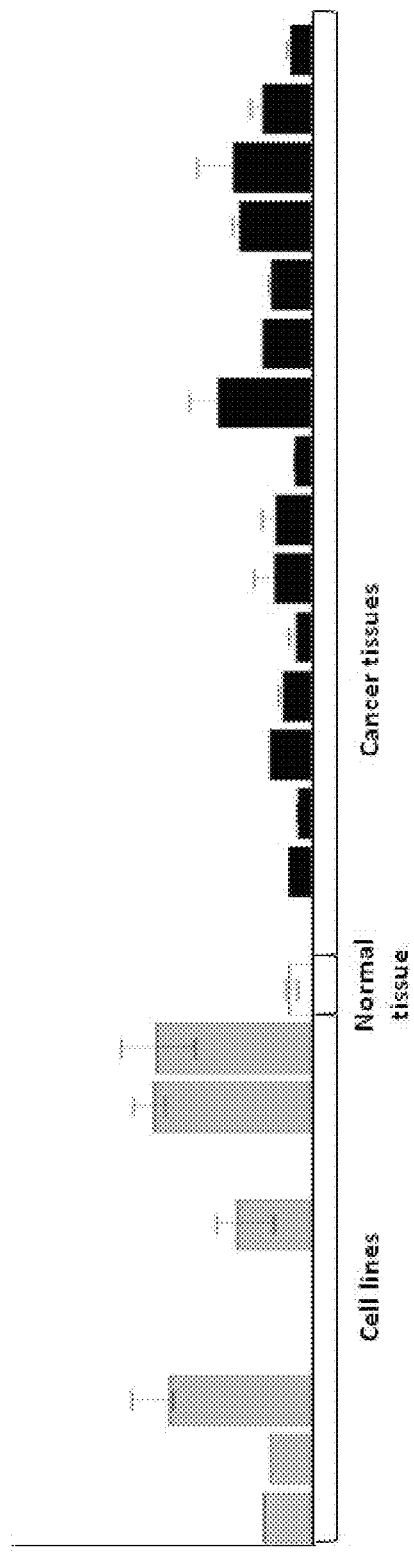

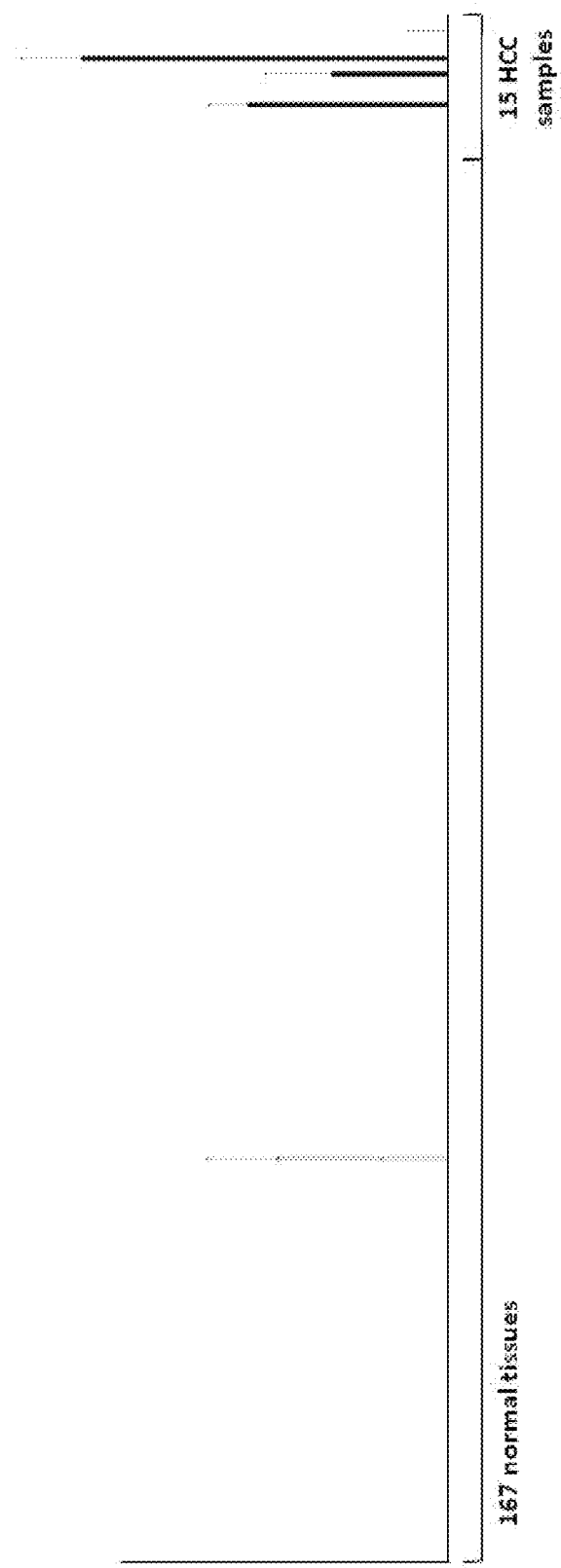

Figure 1K

Peptide: LLFPHPVNQV (A*02)
SEQ ID: 156

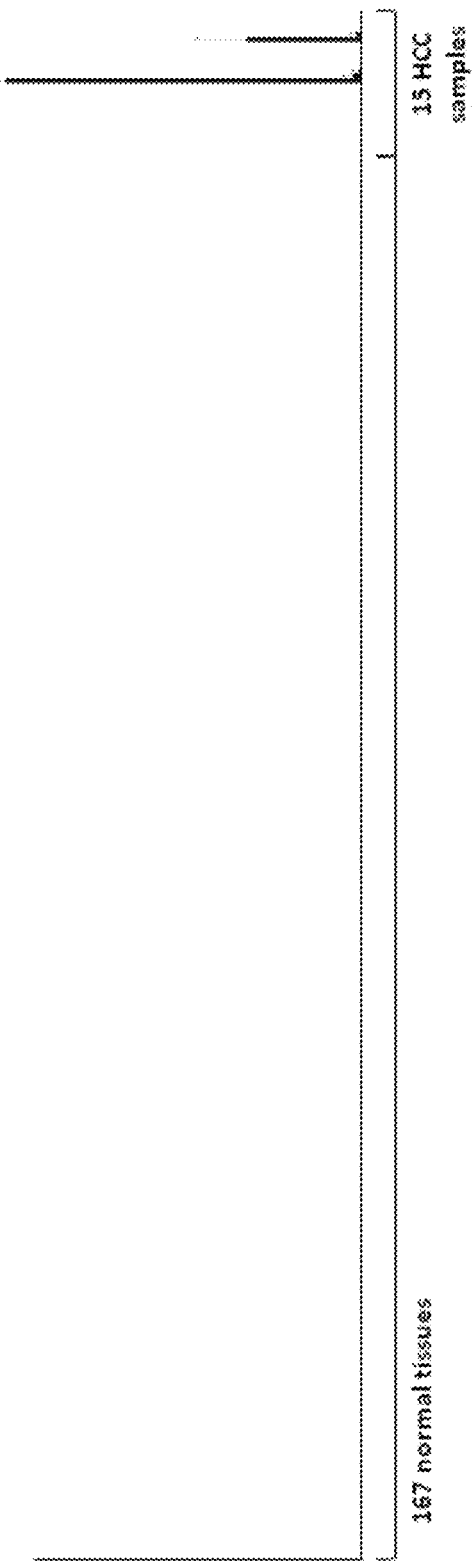

PEPTIDES AND COMBINATION OF PEPTIDES FOR USE IN IMMUNOTHERAPY AGAINST HEPATOCELLULAR CARCINOMA (HCC) AND OTHER CANCERS

CROSS REFERENCE TO RELATED APPLICATIONS

This application is a continuation of U.S. patent application Ser. No. 15/917,098, filed 9 Mar. 2018, which is a continuation of U.S. patent application Ser. No. 15/357,757, filed 21 Nov. 2016, which is a continuation of U.S. patent application Ser. No. 14/975,952 filed 21 Dec. 2015, which claims priority to U.S. Provisional Application No. 62/096,165 filed 23 Dec. 2014, GB 1423016.3 filed 23 Dec. 2014, and GB 1501017.6 filed 21 Jan. 2015, the disclosures of which are incorporated herein by reference in their entireties.

BACKGROUND

Field of the Invention

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules. In particular, the present invention relates to several novel peptide sequences and their variants derived from HLA class I and class II molecules of human tumor cells that can be used in vaccine compositions for eliciting anti-tumor immune responses or as targets for the development of pharmaceutically/immunologically active compounds and cells.

Description of Related Art

Hepatocellular carcinoma (HCC) is one of the most common tumors in the world and accounts for about 6% of all new cancer cases diagnosed worldwide. In 2012 about 782,000 new cases of HCC occurred in the world, making it the fifth most common cancer in men (554,000 cases) and the ninth in women (228,000 cases) (ww w.globocan.iarc.fr). HCC is the most common primary liver malignancy accounting for over 80% of all adult primary liver cancers.

The distribution of HCC varies geographically, and rates of incidence depend on gender. The age-standardized incidence rate (ASR) of HCC in men is highest in Eastern Asia (31.9) and South-Eastern Asia (22.2), intermediate in Southern Europe (9.5) and Northern America (9.3) and lowest in Northern Europe (4.6) and South-Central Asia (3.7). Incident rates of HCC in women are lower than male ASRs. The highest ASR in women occurs in Eastern Asia (10.2) and Western Africa (8.1), the lowest in Northern Europe (1.9) and Micronesia (1.6).

The overall prognosis for patients with HCC is poor. The 5-year relative survival rate (5Y-RSR) from HCC is about 15%, depending on the stage at the time of diagnosis. For localized HCC, where the cancer is still confined to the liver, the 5Y-RSR is about 28%. For regional and distant HCC, were the cancer has grown into nearby or distant organs, 5Y-RSRs are 7% and 2%, respectively.

The incidence of HCC is related to several risk factors, cirrhosis being the most important one. Cirrhosis often occurs alongside alcohol abuse or HBV or HCV infections, but can also be caused by metabolic diseases like type II diabetes. As a result, healthy liver tissue gets replaced by scar tissue, which increases the risk of cancer development.

Disease management depends on the tumor stage at the time of diagnosis and the overall condition of the liver. If possible, parts of the liver (partial hepatectomy) or the whole organ (liver resection) is removed by surgery. Especially patients with small or completely resectable tumors are qualified to receive a liver transplant.

If surgery is not a treatment option, different other therapies are available at hand. For tumor ablation, a probe is injected into the liver and the tumor is destroyed by radio or microwaves or cryotherapy. In embolization procedures, the blood supply of the tumor is blocked by mechanical or chemical means. High energy radio waves can be used to destroy the tumor in radiation therapy.

Chemotherapy against HCC includes combinations of doxorubicin, 5-fluorouracil and cisplatin for systemic therapy and doxorubicin, floxuridine and mitomycin C for hepatic artery infusions. However, most HCC show a high resistance to chemotherapeutics (Enguita-German and Fortes, 2014).

Therapeutic options in advanced non-resectable HCC are limited to Sorafenib, a multi-tyrosine kinase inhibitor (Chang et al., 2007; Wilhelm et al., 2004). Sorafenib is the only systemic drug confirmed to increase survival by about 3 months and currently represents the only experimental treatment option for such patients (Chapiro et al., 2014; Llovet et al., 2008).

Lately, a limited number of immunotherapy trials for HCC have been conducted. Cytokines have been used to activate subsets of immune cells and/or increase the tumor immunogenicity (Reinisch et al., 2002; Sangro et al., 2004). Other trials have focused on the infusion of Tumor-infiltrating lymphocytes or activated peripheral blood lymphocytes (Shi et al., 2004a; Takayama et al., 1991; Takayama et al., 2000).

So far, a small number of therapeutic vaccination trials have been executed. Butterfield et al. conducted two trials using peptides derived from alpha-fetoprotein (AFP) as a vaccine or DCs loaded with AFP peptides ex vivo (Butterfield et al., 2003; Butterfield et al., 2006). In two different studies, autologous dendritic cells (DCs) were pulsed ex vivo with autologous tumor lysate (Lee et al., 2005) or lysate of the hepatoblastoma cell line HepG2 (Palmer et al., 2009). So far, vaccination trials have only shown limited improvements in clinical outcomes.

SUMMARY

In a first aspect of the present invention, the present invention relates to a peptide comprising an amino acid sequence selected from the group consisting of SEQ ID NO: 1 to SEQ ID NO: 300 or a variant sequence thereof which is at least 80%, preferably at least 90%, homologous (preferably at least 80% or at least 90% identical) to SEQ ID NO: 1 to SEQ ID NO: 300, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 300 or a variant thereof, which is at least 80%, preferably at least 88%, homologous (preferably at least 80% or at least 88% identical) to SEQ ID NO: 1 to SEQ ID NO: 300, wherein said peptide or variant thereof has an overall length of between 8 and 100, preferably between 8 and 30, and most preferred of between 8 and 14 amino acids.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1K:
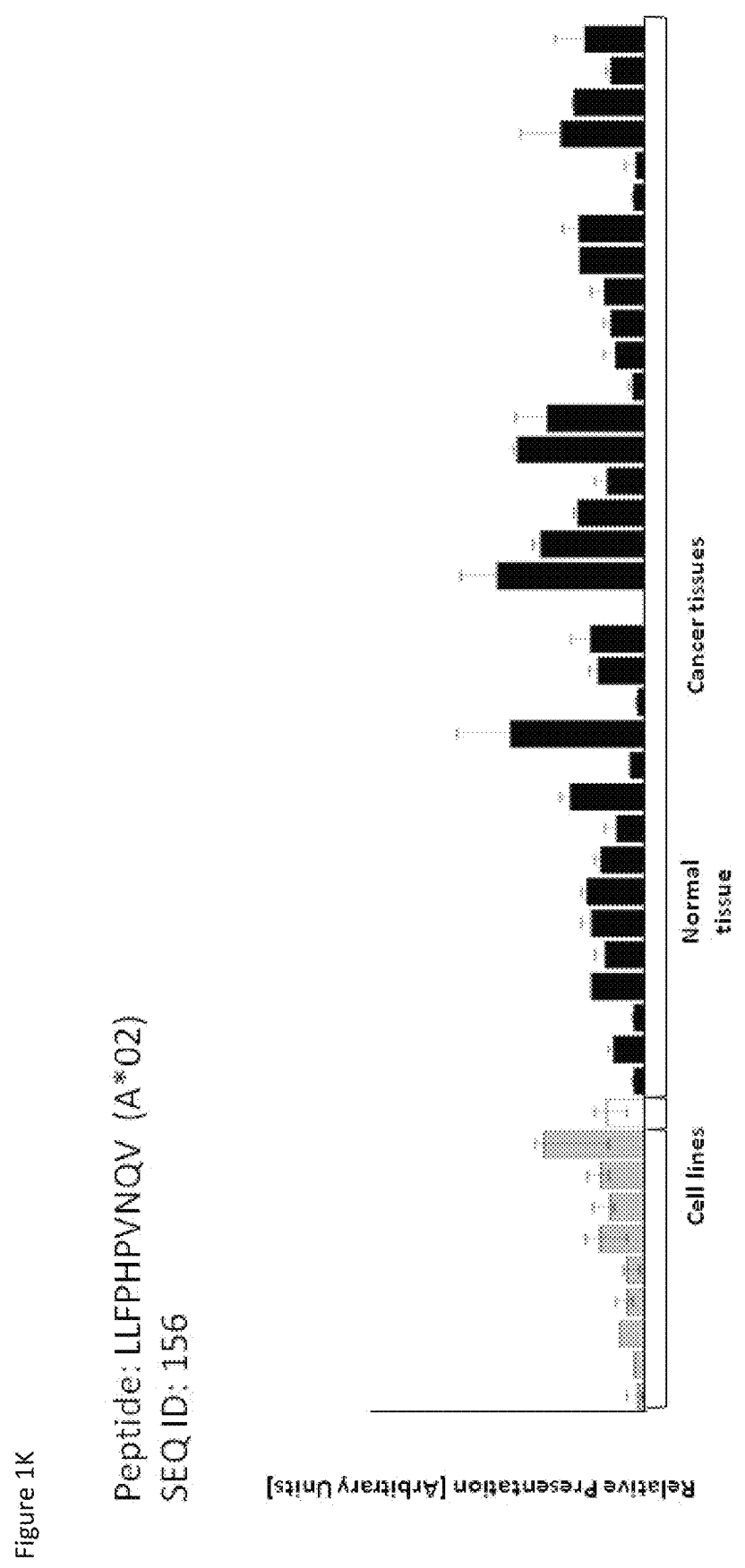

FIGS. 1A-1M show the over-presentation of various peptides in normal tissues (dark gray) and HCC (light gray). FIG. 1A: APOB, Peptide: ALVDTLKFV (A*02) (SEQ ID NO:7). FIG. 1B: ALDH1 L1, Peptide: KLQAGTVFV (A*02) (SEQ. ID NO:2). FIG. 1C: C8B, Peptide: AYLLQPSQF (A*24) (SEQ ID NO:200). FIG. 1D: FIG. 1D) RAD23B Peptide: KIDEKNFVV (SEQ ID NO:63). FIG. 1E: RAD23B Peptide: KIDEKNFVV (SEQ ID NO:63). FIG. 1F: RFNG Peptide: RLPPDTLLQQV (SEQ ID NO:92). FIG. 1G: RFNG Peptide: RLPPDTLLQQV (SEQ ID NO:92). FIG. 1H) FLVCR1 Peptide: SVWFGPKEV (SEQ ID NO:104). FIG. 1I: FLVCR1 Peptide: SVWFGPKEV (SEQ ID NO:104). FIG. 1J: IKBKAP Peptide: LLFPHPVNQV (SEQ ID NO:156). FIG. 1K: IKBKAP Peptide: LLFPHPVNQV (SEQ ID NO: 156). FIG. 1L: NKD1 Peptide: FLDTPIAKV (SEQ ID NO:47). FIG. 1M: NKD1 Peptide: FLDTPIAKV (SEQ ID NO:47).

FIG. 2A: APOB; FIG. 2B: AMACR; FIG. 2C: ALDH1 L1; FIG. 2D: FGG; FIG. 2E: C8B; FIG. 2F: HSD17B6.

DETAILED DESCRIPTION OF A PREFERRED EMBODIMENT

Figure 1B:
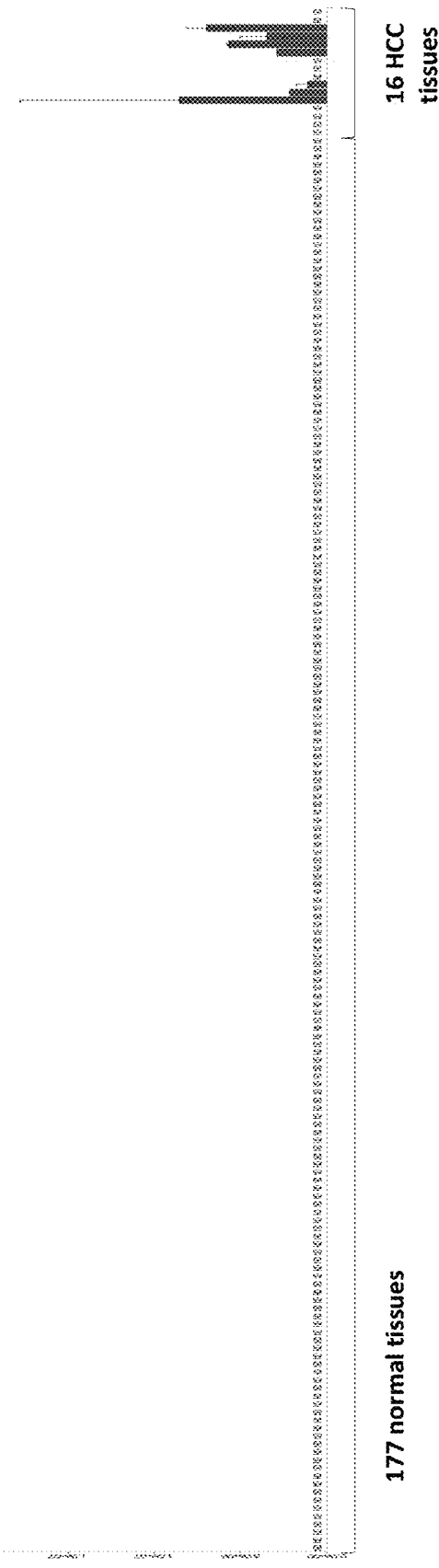

The following tables show the peptides according to the present invention, their respective SEQ ID NOs, and the prospective source (underlying) genes for these peptides. All peptides in Table 1 bind to HLA-A*02, peptides in Table 2 bind to HLA-A*24 alleles. The peptides in Table 3 have been disclosed before in large listings as results of high-throughput screenings with high error rates or calculated using algorithms, but have not been associated with cancer at all before. They bind to HLA-A*02. The peptides in Table 4 are additional peptides that may be useful in combination with the other peptides of the invention. Peptides bind A*02 or, where indicated, A*24. The peptides in Table 5 are furthermore useful in the diagnosis and/or treatment of various malignancies that involve an over-expression or over-presentation of the respective underlying polypeptide.

TABLE 1

HLA-A*02 peptides according to the present invention-

| SEQ ID No. | Sequence | GeneID(s) | Official Gene Symbol(s) |
|---|---|---|---|
| 1 | VMAPFTMTI | 338 | APOB |
| 2 | KLQAGTVFV | 10840 | ALDH1L1 |
| 3 | ILDDNMQKL | 79611 | ACSS3 |
| 4 | KLQDFSDQL | 338 | APOB |
| 5 | ALVEQGFTV | 338 | APOB |
| 6 | KLSPTVVGL | 8313 | AXIN2 |
| 7 | ALVDTLKFV | 338 | APOB |
| 8 | KLLEEATISV | 54808 | DYM |
| 9 | ALANQKLYSV | 23195 | MDN1 |
| 10 | SLLEEFDFHV | 8615 | USO1 |
| 11 | SLSQELVGV | 24149 | ZNF318 |
| 12 | FLAELAYDL | 2719 | GPC3 |
| 13 | GLIDTETAMKAV | 3290 | HSD11B1 |
| 14 | ALADLTGTVV | 23385 | NCSTN |
| 15 | LLYGHTVTV | 347734 | SLC35B2 |
| 16 | SLLGGNIRL | 2181 | ACSL3 |
| 17 | RVAS*PTSGV | 8660 | IRS2 |
| 18 | ALYGKTEVV | 57513 | CASKIN2 |
| 19 | FLEETKATV | 338 | APOB |
| 20 | KLSNVLQQV | 338 | APOB |
| 21 | QLIEVSSPITL | 338 | APOB |
| 22 | RIAGIRGIQGV | 23167 | EFR3A |
| 23 | RLYDPASGTISL | 23456 | ABCB10 |
| 24 | SLAEEKLQASV | 2194 | FASN |
| 25 | SLDGKAALTEL | 338 | APOB |
| 26 | SLLHTIYEV | 85407 | NKD1 |
| 27 | TLPDFRLPEI | 338 | APOB |
| 28 | TLQDHLNSL | 338 | APOB |
| 29 | YIQDEINTI | 338 | APOB |
| 30 | YLGEGPRMV | 5704 | PSMC4 |
| 31 | YQMDIQQEL | 338 | APOB |
| 32 | ALNAVRLLV | 9368 | SLC9A3R1 |
| 33 | LLHGHIVEL | 57678 | GPAM |
| 34 | SLAEGTATV | 540 | ATP7B |
| 35 | SLQESILAQV | 23644 | EDC4 |
| 36 | ILNVDGLIGV | 47 | ACLY |
| 37 | LLLPLLPPLSP | 347252 | IGFBPL1 |

TABLE 1-continued

HLA-A*02 peptides according to the present invention-

| SEQ ID No. | Sequence | GeneID(s) | Official Gene Symbol(s) |
|---|---|---|---|
| 38 | ALADVVHEA | 26873 | OPLAH |
| 39 | ALDPKANFST | 10188 | TNK2 |
| 40 | ALLAEGITWV | 54499 | TMCO1 |
| 41 | ALLELDEPLVL | 2158 | F9 |
| 42 | ALLGGNVRMML | 2182 | ACSL4 |
| 43 | ALLGVWTSV | 444 | ASPH |
| 44 | ALQDAIRQL | 51268 | PIPOX |
| 45 | ALQDQLVLV | 183 | AGT |
| 46 | AMAEMKVVL | 11283, 4051, 57834, 66002, 8529 | CYP4F8, CYP4F3, CYP4F11, CYP4F12, CYP4F2 |
| 47 | FLDTPIAKV | 85407 | NKD1 |
| 48 | FLLEQPEIQV | 5345 | SERPINF2 |
| 49 | FLYPEKDEPT | 338 | APOB |
| 50 | FTIPKLYQL | 338 | APOB |
| 51 | GLAEELVRA | 5091 | PC |
| 52 | GLFNAELLEA | 3929 | LBP |
| 53 | GLIHLEGDTV | 81494 | CFHR5 |
| 54 | GLLDPNVKSIFV | 79033 | ERI3 |
| 55 | GLYGRTIEL | 55908 | C19orf80 |
| 56 | GVLPGLVGV | 162515 | SLC16A11 |
| 57 | HLTEAIQYV | 6097 | RORC |
| 58 | ILADLNLSV | 55705 | IPO9 |
| 59 | ILADTFIGV | 222223 | KIAA1324L |
| 60 | ILSPLSVAL | 5345 | SERPINF2 |
| 61 | KIADFELPTI | 338 | APOB |
| 62 | KIAGTNAEV | 2752 | GLUL |
| 63 | KIDEKNFVV | 5887 | RAD23B |
| 64 | KILEETLYV | 8443 | GNPAT |
| 65 | KLFSGDELLEV | 8777 | MPDZ |
| 66 | KLHEEIDRV | 1571 | CYP2E1 |
| 67 | KLKETIQKL | 338 | APOB |
| 68 | KLLAATVLLL | 336 | APOA2 |
| 69 | KLLDEVTYLEA | 1573 | CYP2J2 |
| 70 | KLLDLETERILL | 2803 | GOLGA4 |
| 71 | KLLDNWDSV | 335 | APOA1 |
| 72 | KLSEAVTSV | 55258 | THNSL2 |
| 73 | KLTLVIISV | 8647 | ABCB11 |
| 74 | KLYDLELIV | 570 | BAAT |
| 75 | KQMEPLHAV | 284111 | SLC13A5 |
| 76 | LLADIGGDPFAA | 3268 | AGFG2 |
| 77 | LLHEENFSV | 6942 | TCF20 |
| 78 | LLIDDEYKV | 23065 | EMC1 |
| 79 | LLLSTGYEA | 23556 | PIGN |
| 80 | LLYEGKLTL | 440107 | PLEKHG7 |
| 81 | NLASFIEQVAV | 5092 | PCBD1 |
| 82 | NVFDGLVRV | 338 | APOB |
| 83 | QLHDFVMSL | 8647 | ABCB11 |
| 84 | QLTPVLVSV | 1244 | ABCC2 |
| 85 | RILPKVLEV | 10840 | ALDH1L1 |
| 86 | RLAAFYSQV | 91289 | LMF2 |
| 87 | RLFEENDVNL | 5053 | PAH |
| 88 | RLIDRIKTV | 60560 | NAA35 |
| 89 | RLIEEIKNV | 347051 | SLC10A5 |
| 90 | RLLDVLAPLV | 80781 | COL18A1 |
| 91 | RLPDIPLRQV | 55656 | INTS8 |
| 92 | RLPPDTLLQQV | 5986 | RFNG |
| 93 | RLYTMDGITV | 1571 | CYP2E1 |
| 94 | RMSDVVKGV | 113251 | LARP4 |
| 95 | SICNGVPMV | 54575, 54576, 54577, 54578, 54579, 54600, 54657, 54658, 54659 | UGT1A10, UGT1A8, UGT1A7, UGT1A6, UGT1A5, UGT1A9, UGT1A4, UGT1A1, UGT1A3 |
| 96 | SLLEEPNVIRV | 4703 | NEB |
| 97 | SLLPQLIEV | 338 | APOB |
| 98 | SLLSPEHLQYL | 7512 | XPNPEP2 |
| 99 | SLSAFLPSL | 54757 | FAM20A |
| 100 | SLVGDIGNVNM | 1401 | CRP |
| 101 | SLWEGGVRGV | 411 | ARSB |
| 102 | SLWSVARGV | 57678 | GPAM |
| 103 | SMGDHLWVA | 2752 | GLUL |
| 104 | SVWFGPKEV | 28982 | FLVCR1 |

TABLE 1-continued

HLA-A*02 peptides according to the present invention-

| SEQ ID No. | Sequence | GeneID(s) | Official Gene Symbol(s) |
|---|---|---|---|
| 105 | SVYDGKLLI | 5445 | PON2 |
| 106 | TLAAIIHGA | 5243 | ABCB1 |
| 107 | TLGQFYQEV | 3700, 375346 | ITIH4, TMEM110 |
| 108 | TLLKKISEA | 84675 | TRIM55 |
| 109 | TLYALSHAV | 338 | APOB |
| 110 | TVGGSEILFEV | 1401 | CRP |
| 111 | TVMDIDTSGTFNV | 26063, 4833 | DECR2, NME4 |
| 112 | VLGEVKVGV | 122622 | ADSSL1 |
| 113 | VLMDKLVEL | 338 | APOB |
| 114 | VLSQVYSKV | 338 | APOB |
| 115 | VVLDDKDYFL | 100292290, 3336 | HSPE1 |
| 116 | WVIPAISAV | 1528 | CYB5A |
| 117 | YAFPKSITV | 6566 | SLC16A1 |
| 118 | YLDDEKNWGL | 5005 | ORM2 |
| 119 | YLDKNLTVSV | 100293534, 720, 721 | C4A, C4B |
| 120 | YLGEEYVKA | 7018 | TF |
| 121 | YLITGNLEKL | 1314 | COPA |
| 122 | YLSQAADGAKVL | 2584 | GALK1 |
| 123 | YLWDLDHGFAGV | 832 | CAPZB |
| 124 | LLIDVVTYL | 338 | APOB |
| 125 | ALYGRLEVV | 23294 | ANKS1A |
| 126 | TLLDSPIKV | 338 | APOB |
| 127 | VLIGSNHSL | 9919 | SEC16A |
| 128 | GLAFSLNGV | 81502 | HM13 |
| 129 | SQADVIPAV | 55034 | MOCOS |
| 130 | ALDAGAVYTL | 10840 | ALDH1L1 |
| 131 | ALDSGAFQSV | 55907 | CMAS |
| 132 | ALHEEVVGV | 1593 | CYP27A1 |
| 133 | ALLEMDARL | 54512 | EXOSC4 |
| 134 | ALLETNPYLL | 1209 | CLPTM1 |
| 135 | ALLGKIEKV | 2590 | GALNT2 |
| 136 | ALLNQHYQV | 2058 | EPRS |
| 137 | ALPTVLVGV | 5351 | PLOD1 |
| 138 | ALSQVTLLL | 392636 | AGMO |
| 139 | ALSSKPAEV | 256987 | SERINC5 |
| 140 | ALTSISAGV | 392636 | AGMO |
| 141 | AMGEKSFSV | 57720 | GPR107 |
| 142 | AVIGGLIYV | 366 | AQP9 |
| 143 | FILPDSLPLDTL | 6632 | SNRPD1 |
| 144 | FIQLITGV | 477, 478 | ATP1A2, ATP1A3 |
| 145 | FLIAEYFEHV | 23743, 635 | BHMT2, BHMT |
| 146 | FLWTEQAHTV | 3953 | LEPR |
| 147 | GLAPGGLAVV | 58525 | WIZ |
| 148 | GLFAPLVFL | 6566 | SLC16A1 |
| 149 | GLLSGLDIMEV | 383 | ARG1 |
| 150 | GLSNLGIKSI | 122553 | TRAPPC6B |
| 151 | HLAKVTAEV | 6184 | RPN1 |
| 152 | KLDNNLDSV | 80232 | WDR26 |
| 153 | KLIEVNEEL | 100507203 | SMLR1 |
| 154 | KLTDHLKYV | 3250 | HPR |
| 155 | LLEPYKPPSAQ | 439 | ASNA1 |
| 156 | LLFPHPVNQV | 8518 | IKBKAP |
| 157 | QLLPNLRAV | 5092 | PCBD1 |
| 158 | RIISGLVKV | 101060372, 2330 | FMO5 |
| 159 | RLFPDGIVTV | 152831 | KLB |
| 160 | RLLAKIICL | 3075 | CFH |
| 161 | RLLDEQFAV | 9026 | HIP1R |
| 162 | RLMSALTQV | 9462 | RASAL2 |
| 163 | RLTESVLYL | 368 | ABCC6 |
| 164 | RMLIKLLEV | 6710, 6711 | SPTB, SPTBN1 |
| 165 | RVIEHVEQV | 3034 | HAL |
| 166 | SILDIVTKV | 130132 | RFTN2 |
| 167 | SLAESSFDV | 54658 | UGT1A1 |
| 168 | SLAVLVPIV | 1361 | CPB2 |
| 169 | SLFEWFHPL | 2519 | FUCA2 |
| 170 | SLHNGVIQL | 1314 | COPA |
| 171 | SLIPAVLTV | 57462 | KIAA1161 |
| 172 | SLLNFLQHL | 2968 | GTF2H4 |
| 173 | SLTSEIHFL | 55755 | CDK5RAP2 |

TABLE 1-continued

HLA-A*02 peptides according to the present invention-

| SEQ ID No. | Sequence | GeneID(s) | Official Gene Symbol(s) |
|---|---|---|---|
| 174 | TLAELGAVQV | 2875 | GPT |
| 175 | TLFEHLPHI | 2888 | GRB14 |
| 176 | TLGQIWDV | 1778 | DYNC1H1 |
| 177 | VLDEPYEKV | 100034743, 5174, 728939 | PDZK1P2, PDZK1, PDZK1P1 |
| 178 | YIFTTPKSV | 22862 | FNDC3A |
| 179 | YIHNILYEV | 160518 | DENND5B |
| 180 | YLGPHIASVTL | 81671 | VMP1 |
| 181 | YLLEKFVAV | 1663, 440081, 642846 | DDX11, DDX12P |
| 182 | YLLHFPMAL | 1109 | AKR1C4 |
| 183 | YLYNNEEQVGL | 1109 | AKR1C4 |
| 184 | VVLDGGQIVTV | 6506 | SLC1A2 |
| 185 | ALFPALRPGGFQA | 8878 | SQSTM1 |
| 186 | VLLAQIIQV | 89797 | NAV2 |

S* = phosphoserine

TABLE 2

HLA-A*24 peptides according to the present invention with SEQ ID numbers-

| SEQ ID No. | Sequence | GeneID(s) | Official Gene Symbol(s) |
|---|---|---|---|
| 187 | SYPTFFPRF | 6596 | HLTF |
| 188 | RYSAGWDAKF | 8630 | HSD17B6 |
| 189 | AFSPDSHYLLF | 3679 | ITGA7 |
| 190 | RYNEKCFKL | 54800 | KLHL24 |
| 191 | KYPDIISRI | 3978 | LIG1 |
| 192 | SYITKPEKW | 79694 | MANEA |
| 193 | IYPGAFVDL | 51360 | MBTPS2 |
| 194 | QYASRFVQL | 10733 | PLK4 |
| 195 | RYAPPPSFSEF | 29066 | ZC3H7A |
| 196 | AYLKWISQI | 60561 | RINT1 |
| 197 | RWPKKSAEF | 100132742, 100526842, 6139, 645296, 645441 | RPL17P7, RPL17-C18orf32, RPL17, RPL17P39, RPL17P6 |
| 198 | LYWSHPRKF | 6235, 648343 | RPS29, RPS29P9 |
| 199 | KFVTVQATF | 718 | C3 |
| 200 | AYLLQPSQF | 732 | C8B |
| 201 | AYVNTFHNI | 1201 | CLN3 |
| 202 | AYGTYRSNF | 9919 | SEC16A |
| 203 | YYGILQEKI | 10237 | SLC35B1 |
| 204 | KYRLTYAYF | 2266 | FGG |
| 205 | VYGLQRNLL | 57159, 84675, 84676 | TRIM54, TRIM55, TRIM63 |
| 206 | KWPETPLLL | 55757 | UGGT2 |
| 207 | IYLERFPIF | 51096 | UTP18 |
| 208 | SYNPAENAVLL | 1314 | COPA |
| 209 | VFHPRQELI | 1314 | COPA |
| 210 | AYPAIRYLL | 7818 | DAP3 |
| 211 | IYIPSYFDF | 27042 | DIEXF |
| 212 | VYGDVISNI | 8893 | EIF2B5 |
| 213 | YNKVSTVF | 8661 | EIF3A |
| 214 | IYVISIEQI | 55879 | GABRQ |
| 215 | IYTGNISSF | 8836 | GGH |
| 216 | IYADVGEEF | 100302182, 11052 | MIR1279, CPSF6 |
| 217 | DYIPYVFKL | 338 | APOB |
| 218 | VYQGAIRQI | 338 | APOB |

S* = phosphoserine

TABLE 3

Additional peptides according to the present invention with no prior known cancer association-

| SEQ ID No. | Sequence | GeneID(s) | Official Gene Symbol(s) |
|---|---|---|---|
| 219 | GVMAGDIYSV | 123 | PLIN2 |
| 220 | SLLEKELESV | 1819 | DRG2 |
| 221 | ALCEENMRGV | 1938 | EEF2 |
| 222 | LTDITKGV | 1938 | EEF2 |
| 223 | FLFNTENKLLL | 3422 | IDI1 |
| 224 | ALASVIKEL | 28981 | IFT81 |
| 225 | KMDPVAYRV | 5859 | QARS |
| 226 | AVLGPLGLQEV | 79178 | THTPA |
| 227 | ALLKVNQEL | 25813 | SAMM50 |

TABLE 3-continued

Additional peptides according to the present invention with no prior known cancer association-

| SEQ ID No. | Sequence | GeneID(s) | Official Gene Symbol(s) |
|---|---|---|---|
| 228 | YLITSVELL | 2182 | ACSL4 |
| 229 | KMFESFIESV | 5576 | PRKAR2A |
| 230 | VLTEFTREV | 55705 | IPO9 |
| 231 | RLFNDPVAMV | 10195 | ALG3 |
| 232 | KLAEIVKQV | 8550 | MAPKAPK5 |
| 233 | ALLGKLDAI | 5876 | RABGGTB |
| 234 | YLEPYLKEV | 727947, 7381 | UQCRB |
| 235 | KLFEEIREI | 255394 | TCP11L2 |
| 236 | ALADKELLPSV | 84883 | AIFM2 |
| 237 | ALRGEIETV | 10128 | LRPPRC |
| 238 | AMPPPPPQGV | 5885 | RAD21 |
| 239 | FLLGFIPAKA | 5976 | UPF1 |
| 240 | FLWERPTLLV | 79922 | MRM1 |
| 241 | FVLPLLGLHEA | 55161 | TMEM33 |
| 242 | GLFAPVHKV | 6249 | CLIP1 |
| 243 | GLLDNPELRV | 26263 | FBXO22 |
| 244 | KIAELLENV | 9100 | USP10 |
| 245 | KLGAVFNQV | 23450 | SF3B3 |
| 246 | KLISSYYNV | 84928 | TMEM209 |
| 247 | KLLDTMVDTFL | 100527963, 11243 | PMF1-BGLAP, PMF1 |
| 248 | KLNDLIQRL | 1314 | COPA |
| 249 | LLLGERVAL | 23475 | QPRT |
| 250 | NLAEVVERV | 26263 | FBXO22 |
| 251 | RLFADILNDV | 64755 | C16orf58 |
| 252 | RTIEYLEEV | 3030 | HADHA |
| 253 | RVPPPPQSV | 6464 | SHC1 |
| 254 | RVQEAIAEV | 57678 | GPAM |
| 255 | SLFGQDVKAV | 26036 | ZNF451 |
| 256 | SLFQGVEFHYV | 3930 | LBR |
| 257 | SLLEKAGPEL | 54625 | PARP14 |
| 258 | SLMGPVVHEV | 5116 | PCNT |
| 259 | TLITDGMRSV | 29894 | CPSF1 |
| 260 | TLMDMRLSQV | 24148 | PRPF6 |
| 261 | VLFQEALWHV | 2194 | FASN |
| 262 | VLPNFLPYNV | 10299 | MARCH6 |
| 263 | VLYPSLKEI | 50717, 5824 | DCAF8, PEX19 |
| 264 | VMQDPEFLQSV | 266971, 5710 | PIPSL, PSMD4 |
| 265 | WLIEDGKVVTV | 10726 | NUDC |
| 266 | SLLESNKDLLL | 6520 | SLC3A2 |
| 267 | ALNENINQV | 80025 | PANK2 |
| 268 | KLYQEVEIASV | 5976 | UPF1 |
| 269 | YLMEGSYNKV | 5714 | PSMD8 |
| 270 | SVLDQKILL | 9875 | URB1 |
| 271 | LLLDKLILL | 85440 | DOCK7 |
| 272 | QQLDSKFLEQV | 6772 | STAT1 |
| 273 | AILETAPKEV | 6238 | RRBP1 |
| 274 | ALAEALKEV | 55164 | SHQ1 |
| 275 | ALIEGAGILL | 10440 | TIMM17A |
| 276 | ALLEADVNIKL | 6729 | SRP54 |
| 277 | ALLEENSTPQL | 83933 | HDAC10 |
| 278 | ALTSVVVTL | 1021 | CDK6 |
| 279 | ALWTGMHTI | 51479 | ANKFY1 |
| 280 | ATLNIIHSV | 51542 | VPS54 |
| 281 | GLLAGDRLVEV | 9368 | SLC9A3R1 |
| 282 | GQFPSYLETV | 54919 | HEATR2 |
| 283 | ILSGIGVSQV | 3703 | STT3A |
| 284 | KLDAFVEGV | 528 | ATP6V1C1 |
| 285 | KLLDLSDSTSV | 6093 | ROCK1 |
| 286 | KVLDKVFRA | 375056 | MIA3 |
| 287 | LIGEFLEKV | 8731 | RNMT |
| 288 | LLDDSLVSI | 25824 | PRDX5 |
| 289 | LLLEEGGLVQV | 7353 | UFD1L |
| 290 | NLIDLDDLYV | 57187 | THOC2 |
| 291 | QLIDYERQL | 11072 | DUSP14 |
| 292 | RIPAYFVTV | 7407 | VARS |
| 293 | FLASESLIKQI | 4736 | RPL10A |
| 294 | RLIDLHTNV | 23256 | SCFD1 |
| 295 | SLFSSPPEI | 252983 | STXBP4 |
| 296 | SLLSGRISTL | 51133, 92799 | KCTD3, SHKBP1 |
| 297 | TLFYSLREV | 80233 | C17orf70 |

TABLE 3-continued

Additional peptides according to the present invention with no prior known cancer association-

| SEQ ID No. | Sequence | GeneID(s) | Official Gene Symbol(s) |
|---|---|---|---|
| 298 | TMAKESSIIGV | 1429 | CRYZ |
| 299 | ALLRVTPFI | 401505 | TOMM5 |
| 300 | TLAQQPTAV | 4802 | NFYC |

S* = phosphoserine

TABLE 4

Peptides useful for e.g. personalized cancer therapies-

| SEQ ID No. | Sequence | GeneID(s) | Official Gene Symbol(s) |
|---|---|---|---|
| 301 | VLADFGARV | 114899, 23600 | C1QTNF3, AMACR |
| 302 | KIQEILTQV | 10643 | IGF2BP3 |
| 303 | GVYDGEEHSV | 4113 | MAGEB2 |
| 304 | SLIDQFFGV | 9097 | USP14 |
| 305 | GVLENIFGV | 399909 | PCNXL3 |
| 306 | KLVEFDFLGA | 10460 | TACC3 |
| 307 | AVVEFLTSV | 29102 | DROSHA |
| 308 | ALLRTVVSV | 2590 | GALNT2 |
| 309 | GLIEIISNA | 23020 | SNRNP200 |
| 310 | SLWGGDVVL | 157680 | VPS13B |
| 311 | FLIPIYHQV | 31 | ACACA |
| 312 | RLGIKPESV | 1466 | CSRP2 |
| 313 | LTAPPEALLMV | 79050 | NOC4L |
| 314 | YLAPFLRNV | 23019 | CNOT1 |
| 315 | KVLDGSPIEV | 29974 | A1CF |
| 316 | LLREKVEFL | 4779 | NFE2L1 |
| 317 | KLPEKWESV | 26156 | RSL1D1 |
| 318 | KLNEINEKI | 1373 | CPS1 |
| 319 | KLFNEFIQL | 10885 | WDR3 |
| 320 | GLADNTVIAKV | 6897 | TARS |
| 321 | GVIAEILRGV | 10528 | NOP56 |
| 322 | ILYDIPDIRL | 10667 | FARS2 |
| 323 | KIIDEDGLLNL | 5981 | RFC1 |
| 324 | RLFETKITQV | 100293534, 720, 721 | C4A, C4B |
| 325 | RLSEAIVTV | 51249 | TMEM69 |
| 326 | ALSDGVHKI | 55179 | FAIM |

TABLE 4-continued

Peptides useful for e.g. personalized cancer therapies-

| SEQ ID No. | Sequence | GeneID(s) | Official Gene Symbol(s) |
|---|---|---|---|
| 327 | GLNEEIARV | 10403 | NDC80 |
| 328 | RLEEDDGDVAM | 10482 | NXF1 |
| 329 | SLIEDLILL | 64754 | SMYD3 |
| 330 | SMSADVPLV | 5111 | PCNA |
| 331 | SLLAQNTSWLL | 7070 | THY1 |
| 332 | AMLAVLHTV | 60673 | C12orf44 |
| 333 | GLAEDIDKGEV | 1938 | EEF2 |
| 334 | SILTIEDGIFEV | 100287551, 3306, 3312 | HSPA8P8, HSPA2, HSPA8 |
| 335 | SLLPVDIRQYL | 6773 | STAT2 |
| 336 | YLPTFFLTV | 54898 | ELOVL2 |
| 337 | TLLAAEFLKQV | 100288772, 10574 | CCT7P2, CCT7 |
| 338 | KLFDSDPITVTV | 1191 | CLU |
| 339 | RLISKFDTV | 1977 | EIF4E |
| 340 | KVFDEVIEV | 8908 | GYG2 |
| 341 | YLAIGIHEL | 3034 | HAL |
| 342 | AMSSKFFLV | 7474 | WNT5A |
| 343 | LLLPDYYLV | 27044 | SND1 |
| 344 | VYISSLALL (A*24) | 10213 | PSMD14 |
| 345 | SYNPLWLRI (A*24) | 259266 | ASPM |
| 346 | LYQILQGIVF (A*24) | 983 | CDK1 |
| 347 | ALNPADITV | 51497 | TH1L |
| 348 | AYKPGALTF | 84883 | AIFM2 |

S* = phosphoserine

The present invention furthermore generally relates to the peptides according to the present invention for use in the treatment of proliferative diseases, such as, for example, pancreatic cancer, colon or rectal cancer, kidney cancer, brain cancer, and/or leukemias.

Particularly preferred are the peptides—alone or in combination—according to the present invention selected from the group consisting of SEQ ID NO: 1 to SEQ ID NO: 300. More preferred are the peptides—alone or in combination—selected from the group consisting of SEQ ID NO: 1 to SEQ ID NO: 124 (see Table 1), preferably for A*02 binding, and from the group consisting of SEQ ID NO: 187 to SEQ ID NO: 218 (see Table 2) preferably for A*24 binding, and their uses in the immunotherapy of HCC, brain cancer, kidney cancer, pancreatic cancer, colon or rectal cancer or leukemia, and preferably HCC.

As shown in the following tables 5A and B, many of the peptides according to the present invention can also be used in the immunotherapy of other indications. The tables show, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

TABLE 5A

Peptides according to the present invention and their specific uses in other proliferative diseases, especially in other cancerous diseases-

| SEQ ID No. | Sequence | Other relevant organs/diseases |
| --- | --- | --- |
| 1 | VMAPFTMTI | Pancreas |
| 6 | KLSPTVVGL | Colon, Rectum |
| 10 | SLLEEFDFHV | Kidney |
| 14 | ALADLTGTVV | Kidney, Brain, Pancreas |
| 15 | LLYGHTVTV | Kidney, Brain, Colon, Rectum, Pancreas |
| 16 | SLLGGNIRL | Brain, Colon, Rectum |
| 17 | RVAS*PTSGV | Brain |
| 22 | RIAGIRGIQGV | Kidney, Colon, Rectum |
| 26 | SLLHTIYEV | Colon, Rectum |
| 30 | YLGEGPRMV | Colon, Rectum, CLL |
| 34 | SLAEGTATV | Colon, Rectum |
| 36 | ILNVDGLIGV | Kidney, Brain, Colon, Rectum |
| 39 | ALDPKANFST | Kidney, Brain |
| 41 | ALLELDEPLVL | Pancreas |
| 43 | ALLGVWTSV | Pancreas |
| 47 | FLDTPIAKV | Brain, Colon, Rectum |
| 51 | GLAEELVRA | Brain |
| 54 | GLLDPNVKSIFV | Kidney, Brain |
| 55 | GLYGRTIEL | Kidney |
| 58 | ILADLNLSV | Pancreas |
| 59 | ILADTFIGV | Colon, Rectum, Pancreas |
| 60 | ILSPLSVAL | Kidney, Pancreas |
| 65 | KLFSGDELLEV | Brain, Colon, Rectum |
| 69 | KLLDEVTYLEA | Colon, Rectum |
| 70 | KLLDLETERILL | Colon, Rectum |

TABLE 5A-continued

Peptides according to the present invention and their specific uses in other proliferative diseases, especially in other cancerous diseases-

| SEQ ID No. | Sequence | Other relevant organs/diseases |
| --- | --- | --- |
| 72 | KLSEAVTSV | Kidney |
| 77 | LLHEENFSV | Kidney, Colon, Rectum |
| 80 | LLYEGKLTL | Colon, Rectum |
| 81 | NLASFIEQVAV | Kidney, Colon, Rectum, Pancreas |
| 88 | RLIDRIKTV | Brain, Colon, Rectum |
| 90 | RLLDVLAPLV | Kidney |
| 96 | SLLEEPNVIRV | Kidney |
| 101 | SLWEGGVRGV | Brain |
| 112 | VLGEVKVGV | Kidney |
| 116 | WVIPAISAV | Kidney |
| 119 | YLDKNLTVSV | Kidney |
| 121 | YLITGNLEKL | Kidney, Colon, Rectum, Pancreas |
| 123 | YLWDLDHGFAGV | Brain, Colon, Rectum |
| 125 | ALYGRLEVV | Brain, Colon, Rectum |
| 127 | VLIGSNHSL | Colon, Rectum |
| 133 | ALLEMDARL | Kidney, Brain, Colon, Rectum |
| 134 | ALLETNPYLL | Brain |
| 135 | ALLGKIEKV | Brain, Pancreas |
| 137 | ALPTVLVGV | Kidney, Brain, Colon, Rectum |
| 138 | ALSQVTLLL | Kidney |
| 139 | ALSSKPAEV | Colon, Rectum, Pancreas |
| 141 | AMGEKSFSV | Brain |
| 144 | FIQLITGV | Pancreas |
| 147 | GLAPGGLAVV | Brain |
| 148 | GLFAPLVFL | Kidney |
| 161 | RLLDEQFAV | Brain |
| 166 | SILDIVTKV | Brain |
| 169 | SLFEWFHPL | Kidney, Brain, Colon, Rectum |
| 170 | SLHNGVIQL | Kidney |
| 172 | SLLNFLQHL | Kidney, Colon, Rectum, CLL |
| 173 | SLTSEIHFL | CLL |
| 176 | TLGQIWDV | Brain, Colon, Rectum, Pancreas |
| 177 | VLDEPYEKV | Kidney |
| 179 | YIHNILYEV | Brain |
| 181 | YLLEKFVAV | Colon, Rectum |
| 184 | VVLDGGQIVTV | Brain |

TABLE 5A-continued

Peptides according to the present invention and their specific uses in other proliferative diseases, especially in other cancerous diseases-

| SEQ ID No. | Sequence | Other relevant organs/diseases |
| --- | --- | --- |
| 186 | VLLAQIIQV | Kidney, Brain, Colon, Rectum |
| 187 | SYPTFFPRF | Kidney, Brain |
| 189 | AFSPDSHYLLF | Kidney, Brain |
| 191 | KYPDIISRI | Brain |
| 192 | SYITKPEKW | Kidney, Brain |
| 193 | IYPGAFVDL | Brain |
| 194 | QYASRFVQL | Brain |
| 195 | RYAPPPSFSEF | Brain |
| 196 | AYLKWISQI | Brain |
| 197 | RWPKKSAEF | Kidney, Brain |
| 198 | LYWSHPRKF | Kidney |
| 199 | KFVTVQATF | Brain |
| 203 | YYGILQEKI | Kidney, Brain |
| 206 | KWPETPLLL | Kidney, Brain |
| 208 | SYNPAENAVLL | Brain |
| 214 | IYVTSIEQI | Brain |
| 219 | GVMAGDIYSV | Kidney |
| 220 | SLLEKELESV | Brain |
| 221 | ALCEENMRGV | Kidney, Brain, Colon, Rectum |
| 223 | FLFNTENKLLL | Colon, Rectum |
| 224 | ALASVIKEL | Brain |
| 229 | KMFESFIESV | Kidney, Brain, Colon, Rectum |
| 230 | VLTEFTREV | Kidney, Brain, Colon, Rectum |
| 231 | RLFNDPVAMV | Brain, Colon, Rectum |
| 232 | KLAEIVKQV | Colon, Rectum |
| 233 | ALLGKLDAI | Kidney, Colon, Rectum |
| 234 | YLEPYLKEV | Kidney, Brain, Colon, Rectum |
| 236 | ALADKELLPSV | Kidney, Colon, Rectum, Pancreas |
| 237 | ALRGEIETV | Colon, Rectum |
| 238 | AMPPPPPQGV | Brain, Colon, Rectum |
| 239 | FLLGFIPAKA | Brain |
| 240 | FLWERPTLLV | CLL |
| 244 | KIAELLENV | Brain, Colon, Rectum |
| 245 | KLGAVFNQV | Brain |
| 247 | KLLDTMVDTFL | Colon, Rectum |
| 248 | KLNDLIQRL | Pancreas |
| 249 | LLLGERVAL | Colon, Rectum |
| 250 | NLAEVVERV | Brain, Colon, Rectum, CLL |
| 251 | RLFADILNDV | Brain, Colon, Rectum |
| 255 | SLFGQDVKAV | Kidney, Brain, Colon, Rectum |
| 258 | SLMGPVVHEV | Brain |
| 259 | TLITDGMRSV | Brain |
| 260 | TLMDMRLSQV | Kidney, Brain, Colon, Rectum |
| 261 | VLFQEALWHV | Colon, Rectum |
| 266 | SLLESNKDLLL | Colon, Rectum |
| 268 | KLYQEVEIASV | Brain |
| 269 | YLMEGSYNKV | Brain, Colon, Rectum |
| 270 | SVLDQKILL | Kidney, Brain |
| 271 | LLLDKLILL | Brain, Colon, Rectum |
| 272 | QQLDSKFLEQV | Kidney, Brain |
| 274 | ALAEALKEV | Colon, Rectum |
| 275 | ALIEGAGILL | Kidney, Colon, Rectum, Pancreas |
| 276 | ALLEADVNIKL | Pancreas |
| 277 | ALLEENSTPQL | Kidney |
| 278 | ALTSVVVTL | Kidney, Brain |
| 279 | ALWTGMHTI | Kidney, Brain |
| 281 | GLLAGDRLVEV | Kidney |
| 282 | GQFPSYLETV | Kidney, Brain, Colon, Rectum |
| 283 | ILSGIGVSQV | Pancreas |
| 285 | KLLDLSDSTSV | Kidney, Colon, Rectum |
| 286 | KVLDKVFRA | Pancreas |
| 287 | LIGEFLEKV | CLL |
| 288 | LLDDSLVSI | Pancreas |
| 289 | LLLEEGGLVQV | Kidney, Colon, Rectum, Pancreas |
| 290 | NLIDLDDLYV | Brain, Colon, Rectum, Pancreas |
| 291 | QLIDYERQL | Kidney, Colon, Rectum, Pancreas |
| 292 | RIPAYFVTV | Kidney |
| 293 | FLASESLIKQI | Brain, Colon, Rectum |
| 295 | SLFSSPPEI | Kidney, Brain |
| 296 | SLLSGRISTL | Kidney |
| 297 | TLFYSLREV | Kidney, Brain, Colon, Rectum |

TABLE 5A-continued

Peptides according to the present invention and their specific uses in other proliferative diseases, especially in other cancerous diseases-

| SEQ ID No. | Sequence | Other relevant organs/diseases |
|---|---|---|
| 299 | ALLRVTPFI | CLL |
| 300 | TLAQQPTAV | Pancreas |
| 301 | VLADFGARV | Kidney, Colon, Rectum |
| 302 | KIQEILTQV | Kidney, Brain, Colon, Rectum, Pancreas, CLL |
| 304 | SLIDQFFGV | Brain, Colon, Rectum, Pancreas |
| 305 | GVLENIFGV | Kidney, Brain |
| 306 | KLVEFDFLGA | Brain, Colon, Rectum |
| 308 | ALLRTVVSV | Kidney, Pancreas |
| 309 | GLIEIISNA | Brain |
| 310 | SLWGGDVVL | Brain, Colon, Rectum |
| 311 | FLIPIYHQV | Kidney, Brain |
| 312 | RLGIKPESV | Brain |
| 313 | LTAPPEALLMV | Kidney, Brain, Colon, Rectum, Pancreas |
| 315 | KVLDGSPIEV | Kidney |
| 316 | LLREKVEFL | Kidney, Brain, Colon, Rectum, Pancreas |
| 317 | KLPEKWESV | Brain, Colon, Rectum, Pancreas |
| 319 | KLFNEFIQL | Kidney, Brain, Colon, Rectum |
| 321 | GVIAEILRGV | Kidney, Brain |
| 324 | RLFETKITQV | Kidney |
| 325 | RLSEAIVTV | Brain, Pancreas |
| 326 | ALSDGVHKI | Pancreas |
| 327 | GLNEEIARV | Brain, Colon, Rectum |
| 328 | RLEEDDGDVAM | Kidney, Brain, Colon, Rectum |
| 329 | SLIEDLILL | Kidney, Brain, Colon, Rectum, Pancreas |
| 330 | SMSADVPLV | Brain, Colon, Rectum |
| 331 | SLLAQNTSWLL | Brain, Colon, Rectum, Pancreas |
| 332 | AMLAVLHTV | Brain, Colon, Rectum |
| 333 | GLAEDIDKGEV | Kidney, Brain |
| 334 | SILTIEDGIFEV | Kidney, Brain, Colon, Rectum, Pancreas, CLL |
| 335 | SLLPVDIRQYL | Kidney, CLL |
| 336 | YLPTFFLTV | Kidney, Brain |
| 337 | TLLAAEFLKQV | Brain |
| 338 | KLFDSDPITVTV | Brain |
| 339 | RLISKFDTV | Brain |
| 340 | KVFDEVIEV | Brain |
| 342 | AMSSKFFLV | Brain, Colon, Rectum, Pancreas |
| 343 | LLLPDYYLV | Brain, Pancreas |
| 344 | VYISSLALL (A*24) | Brain |
| 345 | SYNPLWLRI (A*24) | Brain |
| 346 | LYQILQGIVF (A*24) | Kidney |
| 347 | ALNPADITV | Brain |

S* = phosphoserine

TABLE 5B

Peptides according to the present invention and their specific uses in other proliferative diseases, especially in other cancerous diseases-

| SEQ ID NO. | Sequence | Additional Entities |
|---|---|---|
| 189 | AFSPDSHYLLF | NSCLC, PrC |
| 273 | AILETAPKEV | Esophageal Cancer |
| 236 | ALADKELLPSV | NSCLC, SCLC, GC, Melanoma, OC, Esophageal Cancer, Urinary bladder cancer, Gallbladder Cancer, Bile Duct Cancer, NHL |
| 14 | ALADLTGTVV | NSCLC, SCLC, BRCA, OC, Esophageal Cancer, Urinary bladder cancer, Uterine Cancer, PC |

TABLE 5B-continued

Peptides according to the present invention and their specific uses in other proliferative diseases, especially in other cancerous diseases-

| SEQ ID NO. | Sequence | Additional Entities |
|---|---|---|
| 38 | ALADVVHEA | BRCA, OC |
| 274 | ALAEALKEV | BRCA, MCC, Melanoma, OC, Uterine Cancer, AML |
| 9 | ALANQKLYSV | NSCLC, CRC, MCC, OC, Urinary bladder cancer, Gallbladder Cancer, Bile Duct Cancer, PC |
| 224 | ALASVIKEL | SCLC, PC, Melanoma |
| 221 | ALCEENMRGV | NSCLC, SCLC, MCC, Melanoma |
| 131 | ALDSGAFQSV | CRC, Melanoma, Gallbladder Cancer, Bile Duct Cancer |
| 185 | ALFPALRPGGFQA | Gallbladder Cancer, Bile Duct Cancer |
| 275 | ALIEGAGILL | SCLC, MCC, Melanoma, OC, Esophageal Cancer, Urinary bladder cancer, Uterine Cancer, NHL |
| 276 | ALLEADVNIKL | Gallbladder Cancer, Bile Duct Cancer, OC |
| 277 | ALLEENSTPQL | SCLC, CLL, Melanoma, OC, Esophageal Cancer, Urinary bladder cancer, NHL |
| 133 | ALLEMDARL | NSCLC, SCLC, BRCA, MCC, Melanoma, OC, Esophageal Cancer, Urinary bladder cancer, Uterine Cancer, Gallbladder Cancer, Bile Duct Cancer, AML, NHL |
| 134 | ALLETNPYLL | Urinary bladder cancer, Gallbladder Cancer, Bile Duct Cancer |
| 135 | ALLGKIEKV | NSCLC, SCLC, BRCA, OC, Gallbladder Cancer, Bile Duct Cancer |
| 233 | ALLGKLDAI | CLL, OC, Urinary bladder cancer, Gallbladder Cancer, Bile Duct Cancer, AML, NHL |
| 43 | ALLGVWTSV | SCLC, Brain Cancer, CLL, BRCA, PC |
| 227 | ALLKVNQEL | Melanoma, Uterine Cancer |
| 136 | ALLNQHYQV | BRCA, OC |
| 299 | ALLRVTPFI | NHL, OC |
| 32 | ALNAVRLLV | SCLC |
| 267 | ALNENINQV | SCLC, Brain Cancer, MCC, Melanoma, Esophageal Cancer, Urinary bladder cancer, Gallbladder Cancer, Bile Duct Cancer |
| 137 | ALPTVLVGV | NSCLC, GC, BRCA, Melanoma, Esophageal Cancer, Urinary bladder cancer, Uterine Cancer, Gallbladder Cancer, Bile Duct Cancer, PC |
| 45 | ALQDQLVLV | SCLC, Brain Cancer |
| 237 | ALRGEIETV | SCLC, BRCA, OC, Esophageal Cancer, Urinary bladder cancer, NHL |
| 139 | ALSSKPAEV | PrC, OC, Uterine Cancer |
| 278 | ALTSVVVTL | NSCLC, SCLC, GC, Esophageal Cancer, Urinary bladder cancer, Gallbladder Cancer, Bile Duct Cancer, AML, NHL |
| 279 | ALWTGMHTI | Esophageal Cancer, Urinary bladder cancer, PC |
| 125 | ALYGRLEVV | BRCA, MCC, Melanoma, OC, Urinary bladder cancer, Uterine Cancer |

TABLE 5B-continued

Peptides according to the present
invention and their specific uses in
other proliferative diseases, especially
in other cancerous diseases-

| SEQ ID NO. | Sequence | Additional Entities |
|---|---|---|
| 141 | AMGEKSFSV | Melanoma |
| 238 | AMPPPPPQGV | NSCLC, SCLC, BRCA, MCC, Melanoma, OC, Esophageal Cancer, Urinary bladder cancer, Gallbladder Cancer, Bile Duct Cancer, NHL |
| 342 | AMSSKFFLV | NSCLC, GC, PrC, BRCA, Melanoma, OC, Esophageal Cancer, Urinary bladder cancer, Uterine Cancer, Gallbladder Cancer, Bile Duct Cancer, PC |
| 280 | ATLNIIHSV | Urinary bladder cancer |
| 226 | AVLGPLGLQEV | PrC, Melanoma, OC |
| 202 | AYGTYRSNF | NSCLC |
| 196 | AYLKWISQI | NSCLC |
| 210 | AYPAIRYLL | NSCLC, GC |
| 144 | FIQLITGV | NSCLC, Brain Cancer, Urinary bladder cancer |
| 293 | FLASESLIKQI | NSCLC, PrC, MCC, Melanoma, OC, Esophageal Cancer, Urinary bladder cancer, Uterine Cancer, Gallbladder Cancer, Bile Duct Cancer, NHL, PC |
| 47 | FLDTPIAKV | NSCLC, GC, Esophageal Cancer |
| 223 | FLFNTENKLLL | Melanoma, Urinary bladder cancer, NHL |
| 145 | FLIAEYFEHV | SCLC |
| 239 | FLLGFIPAKA | Urinary bladder cancer, AML, NHL |
| 128 | GLAFSLNGV | Melanoma, Uterine Cancer, Gallbladder Cancer, Bile Duct Cancer |
| 147 | GLAPGGLAVV | NSCLC, SCLC, PrC, BRCA, Melanoma, OC, Esophageal Cancer, Urinary bladder cancer, Uterine Cancer |
| 148 | GLFAPLVFL | Esophageal Cancer, Gallbladder Cancer, Bile Duct Cancer, NHL |
| 242 | GLFAPVHKV | Urinary bladder cancer |
| 52 | GLFNAELLEA | SCLC |
| 281 | GLLAGDRLVEV | NSCLC, SCLC, OC, Urinary bladder cancer, Uterine Cancer, Gallbladder Cancer, Bile Duct Cancer, NHL |
| 243 | GLLDNPELRV | Urinary bladder cancer |
| 54 | GLLDPNVKSIFV | NSCLC, SCLC, OC, Urinary bladder cancer |
| 149 | GLLSGLDIMEV | SCLC |
| 150 | GLSNLGIKSI | Urinary bladder cancer, NHL |
| 55 | GLYGRTIEL | SCLC |
| 282 | GQFPSYLETV | NSCLC, CLL, Melanoma, OC, Esophageal Cancer, Urinary bladder cancer, NHL |
| 219 | GVMAGDIYSV | SCLC, Gallbladder Cancer, Bile Duct Cancer, PC |
| 151 | HLAKVTAEV | SCLC, OC, Urinary bladder cancer |
| 57 | HLTEAIQYV | NHL |

TABLE 5B-continued

Peptides according to the present invention and their specific uses in other proliferative diseases, especially in other cancerous diseases-

| SEQ ID NO. | Sequence | Additional Entities |
|---|---|---|
| 58 | ILADLNLSV | BRCA |
| 59 | ILADTFIGV | NSCLC, SCLC, GC, OC, Urinary bladder cancer, Gallbladder Cancer, Bile Duct Cancer, NHL |
| 36 | ILNVDGLIGV | NSCLC, SCLC, PrC, Melanoma, OC, Urinary bladder cancer, Uterine Cancer, Gallbladder Cancer, Bile Duct Cancer, NHL, PC |
| 283 | ILSGIGVSQV | NSCLC, PrC, BRCA, Melanoma, OC, Esophageal Cancer, Urinary bladder cancer, Uterine Cancer, Gallbladder Cancer, Bile Duct Cancer, NHL, PC |
| 216 | IYADVGEEF | NSCLC, GC, PrC |
| 211 | IYIPSYFDF | NSCLC, Brain Cancer, GC |
| 207 | IYLERFPIF | NSCLC, GC |
| 193 | IYPGAFVDL | NSCLC |
| 214 | IYVTSIEQI | NSCLC, RCC |
| 244 | KIAELLENV | NSCLC, SCLC, PrC, CLL, BRCA, Melanoma, OC, Uterine Cancer, AML, NHL |
| 62 | KIAGTNAEV | BRCA |
| 63 | KIDEKNFVV | SCLC, Brain Cancer, Urinary bladder cancer, Uterine Cancer |
| 64 | KILEETLYV | Esophageal Cancer, Urinary bladder cancer, Uterine Cancer |
| 302 | KIQEILTQV | NSCLC, SCLC, GC, Melanoma, OC, Esophageal Cancer, Urinary bladder cancer, Uterine Cancer, Gallbladder Cancer, Bile Duct Cancer, AML, NHL, PC |
| 232 | KLAEIVKQV | NSCLC, SCLC, BRCA, Melanoma, OC, Urinary bladder cancer |
| 284 | KLDAFVEGV | BRCA, OC |
| 152 | KLDNNLDSV | BRCA, Melanoma |
| 235 | KLFEEIREI | NSCLC, CRC, Melanoma, Urinary bladder cancer |
| 245 | KLGAVFNQV | NSCLC, SCLC, RCC, PrC, BRCA, Melanoma, Esophageal Cancer, Urinary bladder cancer, Uterine Cancer |
| 246 | KLISSYYNV | OC |
| 69 | KLLDEVTYLEA | Urinary bladder cancer |
| 70 | KLLDLETERILL | OC, Uterine Cancer |
| 285 | KLLDLSDSTSV | SCLC, Uterine Cancer |
| 247 | KLLDTMVDTFL | NSCLC, SCLC, RCC, Brain Cancer, CLL, BRCA, OC, Esophageal Cancer, Urinary bladder cancer, Uterine Cancer, AML, NHL |
| 8 | KLLEEATISV | SCLC, MCC, Melanoma, Urinary bladder cancer, Uterine Cancer |
| 248 | KLNDLIQRL | GC, Uterine Cancer |
| 20 | KLSNVLQQV | SCLC |

TABLE 5B-continued

Peptides according to the present invention and their specific uses in other proliferative diseases, especially in other cancerous diseases-

| SEQ ID NO. | Sequence | Additional Entities |
|---|---|---|
| 6 | KLSPTVVGL | CLL, OC |
| 154 | KLTDHLKYV | SCLC |
| 268 | KLYQEVEIASV | CRC, MCC, Melanoma, Urinary bladder cancer |
| 225 | KMDPVAYRV | CRC, PrC, BRCA, Urinary bladder cancer, Uterine Cancer |
| 229 | KMFESFIESV | NSCLC, SCLC, PrC, OC, Urinary bladder cancer |
| 286 | KVLDKVFRA | CRC, Gallbladder Cancer, Bile Duct Cancer |
| 206 | KWPETPLLL | GC |
| 191 | KYPDIISRI | NSCLC, GC |
| 287 | LIGEFLEKV | SCLC, RCC, Melanoma, OC, Esophageal Cancer, Urinary bladder cancer, NHL |
| 288 | LLDDSLVSI | Melanoma, Urinary bladder cancer, AML |
| 156 | LLFPHPVNQV | NSCLC, SCLC, OC, Esophageal Cancer, Urinary bladder cancer |
| 77 | LLHEENFSV | NSCLC, SCLC, OC, Esophageal Cancer, Urinary bladder cancer, Uterine Cancer, Gallbladder Cancer, Bile Duct Cancer, NHL |
| 78 | LLIDDEYKV | Esophageal Cancer, Urinary bladder cancer, PC |
| 271 | LLLDKLILL | CLL, Melanoma, OC, Urinary bladder cancer, Uterine Cancer |
| 289 | LLLEEGGLVQV | NSCLC, SCLC, PrC, Melanoma, OC, Urinary bladder cancer, NHL |
| 249 | LLLGERVAL | OC |
| 37 | LLLPLLPPLSP | SCLC, PC, MCC, Uterine Cancer, Gallbladder Cancer, Bile Duct Cancer |
| 80 | LLYEGKLTL | OC |
| 15 | LLYGHTVTV | NSCLC, SCLC, BRCA, Melanoma, OC, Esophageal Cancer, Urinary bladder cancer, NHL, PC |
| 222 | LTDITKGV | BRCA, NHL |
| 346 | LYQILQGIVF | NSCLC, Brain Cancer, GC |
| 198 | LYWSHPRKF | NSCLC |
| 250 | NLAEVVERV | NSCLC, SCLC, PrC, BRCA, MCC, OC, Gallbladder Cancer, Bile Duct Cancer |
| 81 | NLASFIEQVAV | SCLC, PrC, OC, Uterine Cancer, NHL |
| 290 | NLIDLDDLYV | SCLC, PrC, MCC, OC, Urinary bladder cancer, Uterine Cancer |
| 291 | QLIDYERQL | NSCLC, SCLC, Brain Cancer, BRCA, Melanoma, Esophageal Cancer, Urinary bladder cancer, NHL, PC |
| 157 | QLLPNLRAV | RCC |
| 272 | QQLDSKFLEQV | MCC, OC, NHL |
| 194 | QYASRFVQL | NSCLC, GC |
| 22 | RIAGIRGIQGV | NSCLC, PrC, BRCA, OC, NHL |

TABLE 5B-continued

Peptides according to the present invention and their specific uses in other proliferative diseases, especially in other cancerous diseases-

| SEQ ID NO. | Sequence | Additional Entities |
|---|---|---|
| 292 | RIPAYFVTV | GC, BRCA, Melanoma, NHL |
| 86 | RLAAFYSQV | AML |
| 251 | RLFADILNDV | NSCLC, SCLC, PrC, Melanoma, Urinary bladder cancer, Uterine Cancer |
| 231 | RLFNDPVAMV | NSCLC, SCLC, MCC, Melanoma, OC, Urinary bladder cancer, Gallbladder Cancer, Bile Duct Cancer |
| 294 | RLIDLHTNV | Esophageal Cancer |
| 88 | RLIDRIKTV | NSCLC, SCLC, OC, AML, NHL |
| 89 | RLIEEIKNV | SCLC |
| 161 | RLLDEQFAV | SCLC, BRCA |
| 90 | RLLDVLAPLV | BRCA |
| 91 | RLPDIPLRQV | NSCLC, CLL, Urinary bladder cancer, NHL |
| 92 | RLPPDTLLQQV | Urinary bladder cancer |
| 23 | RLYDPASGTISL | CLL, Melanoma, NHL |
| 164 | RMLIKLLEV | SCLC, CRC |
| 94 | RMSDVVKGV | BRCA, OC |
| 252 | RTIEYLEEV | Melanoma |
| 17 | RVAJPTSGV | AML |
| 197 | RWPKKSAEF | NSCLC |
| 195 | RYAPPPSFSEF | NSCLC |
| 190 | RYNEKCFKL | NSCLC |
| 95 | SICNGVPMV | Urinary bladder cancer |
| 166 | SILDIVTKV | SCLC, CLL, MCC, Melanoma, Urinary bladder cancer, AML |
| 24 | SLAEEKLQASV | PrC, BRCA, Urinary bladder cancer |
| 169 | SLFEWFHPL | NSCLC, Gallbladder Cancer, Bile Duct Cancer |
| 255 | SLFGQDVKAV | NSCLC, SCLC, CLL, BRCA, MCC, Melanoma, OC, Esophageal Cancer, Urinary bladder cancer, Uterine Cancer, Gallbladder Cancer, Bile Duct Cancer, NHL, PC |
| 256 | SLFQGVEFHYV | CRC, CLL, MCC, NHL |
| 295 | SLFSSPPEI | NSCLC, SCLC, CRC, PrC, BRCA, Melanoma, OC, Urinary bladder cancer, Uterine Cancer |
| 170 | SLHNGVIQL | NSCLC, Urinary bladder cancer, Uterine Cancer, NHL |
| 331 | SLLAQNTSWLL | NSCLC, RCC, GC, BRCA, Melanoma, Esophageal Cancer, Urinary bladder cancer |
| 10 | SLLEEFDFHV | NSCLC, BRCA, OC, Esophageal Cancer, Uterine Cancer |
| 96 | SLLEEPNVIRV | Melanoma, Gallbladder Cancer, Bile Duct Cancer |

TABLE 5B-continued

Peptides according to the present invention and their specific uses in other proliferative diseases, especially in other cancerous diseases-

| SEQ ID NO. | Sequence | Additional Entities |
|---|---|---|
| 257 | SLLEKAGPEL | CLL, Melanoma, OC |
| 220 | SLLEKELESV | NSCLC, SCLC, PrC, CLL, BRCA, OC, Esophageal Cancer, Urinary bladder cancer, NHL |
| 266 | SLLESNKDLLL | SCLC, MCC, Uterine Cancer |
| 16 | SLLGGNIRL | GC, PrC, Esophageal Cancer, Urinary bladder cancer, Uterine Cancer, PC |
| 26 | SLLHTIYEV | PrC, BRCA, Esophageal Cancer, NHL |
| 172 | SLLNFLQHL | AML |
| 97 | SLLPQLIEV | SCLC |
| 296 | SLLSGRISTL | BRCA, Urinary bladder cancer |
| 258 | SLMGPVVHEV | SCLC, MCC, Melanoma, OC, Urinary bladder cancer, NHL |
| 35 | SLQESILAQV | NSCLC, SCLC, PrC, MCC, Melanoma, Urinary bladder cancer, AML |
| 99 | SLSAFLPSL | OC, Esophageal Cancer, Gallbladder Cancer, Bile Duct Cancer, NHL |
| 11 | SLSQELVGV | Brain Cancer, Melanoma, Uterine Cancer, NHL |
| 173 | SLTSEIHFL | Uterine Cancer, NHL |
| 101 | SLWEGGVRGV | Melanoma |
| 103 | SMGDHLWVA | BRCA, Urinary bladder cancer, NHL |
| 330 | SMSADVPLV | NSCLC, SCLC, BRCA, MCC, Melanoma, Esophageal Cancer, Urinary bladder cancer, Uterine Cancer, Gallbladder Cancer, Bile Duct Cancer, AML, NHL |
| 129 | SQADVIPAV | Urinary bladder cancer |
| 270 | SVLDQKILL | Melanoma, Urinary bladder cancer, Uterine Cancer, Gallbladder Cancer, Bile Duct Cancer, NHL |
| 104 | SVWFGPKEV | SCLC, Melanoma, Urinary bladder cancer, PC |
| 192 | SYITKPEKW | NSCLC |
| 208 | SYNPAENAVLL | NSCLC |
| 345 | SYNPLWLRI | NSCLC, RCC, GC |
| 187 | SYPTFFPRF | NSCLC, PrC |
| 300 | TLAQQPTAV | Urinary bladder cancer, Uterine Cancer, Gallbladder Cancer, Bile Duct Cancer, NHL |
| 297 | TLFYSLREV | BRCA, Uterine Cancer, AML |
| 176 | TLGQIWDV | NSCLC, GC, Melanoma, Urinary bladder cancer, PC |
| 259 | TLITDGMRSV | RCC, CRC, OC, Esophageal Cancer, Urinary bladder cancer, Gallbladder Cancer, Bile Duct Cancer, PC |
| 260 | TLMDMRLSQV | SCLC, PrC, CLL, OC, Uterine Cancer, Gallbladder Cancer, Bile Duct Cancer |
| 298 | TMAKESSIIGV | SCLC, Gallbladder Cancer, Bile Duct Cancer |

TABLE 5B-continued

Peptides according to the present invention and their specific uses in other proliferative diseases, especially in other cancerous diseases-

| SEQ ID NO. | Sequence | Additional Entities |
|---|---|---|
| 110 | TVGGSEILFEV | SCLC, Gallbladder Cancer, Bile Duct Cancer |
| 111 | TVMDIDTSGTFNV | SCLC, CRC, CLL, Melanoma, OC, Urinary bladder cancer, Gallbladder Cancer, Bile Duct Cancer, NHL |
| 209 | VFHPRQELI | NSCLC |
| 261 | VLFQEALWHV | Urinary bladder cancer |
| 127 | VLIGSNHSL | PC, BRCA, Esophageal Cancer, Urinary bladder cancer, Uterine Cancer, AML |
| 186 | VLLAQIIQV | Melanoma, OC, Uterine Cancer, Gallbladder Cancer, Bile Duct Cancer |
| 262 | VLPNFLPYNV | NSCLC, SCLC, Brain Cancer, GC, BRCA, MCC, Melanoma, Esophageal Cancer, Urinary bladder cancer, Uterine Cancer, Gallbladder Cancer, Bile Duct Cancer, NHL, PC |
| 114 | VLSQVYSKV | SCLC |
| 230 | VLTEFTREV | NSCLC, SCLC, CLL, BRCA, Melanoma, OC, Esophageal Cancer, Urinary bladder cancer, Uterine Cancer, Gallbladder Cancer, Bile Duct Cancer, NHL |
| 263 | VLYPSLKEI | RCC, BRCA, Uterine Cancer |
| 1 | VMAPFTMTI | SCLC, Melanoma, NHL |
| 264 | VMQDPEFLQSV | SCLC, CRC, PC, CLL, Melanoma, OC, Esophageal Cancer, Urinary bladder cancer, Gallbladder Cancer, Bile Duct Cancer, NHL |
| 115 | VVLDDKDYFL | CLL |
| 344 | VYISSLALL | NSCLC, GC, CRC |
| 265 | WLIEDGKVVTV | Melanoma |
| 117 | YAFPKSITV | PC |
| 178 | YIFTTPKSV | AML |
| 179 | YIHNILYEV | CLL, NHL |
| 341 | YLAIGIHEL | SCLC |
| 234 | YLEPYLKEV | NSCLC, SCLC, BRCA, Melanoma, OC, Esophageal Cancer, Urinary bladder cancer, Uterine Cancer, Gallbladder Cancer, Bile Duct Cancer, AML, NHL, PC |
| 30 | YLGEGPRMV | NSCLC, Melanoma, Urinary bladder cancer, Uterine Cancer, Gallbladder Cancer, Bile Duct Cancer |
| 180 | YLGPHIASVTL | Melanoma |
| 121 | YLITGNLEKL | NSCLC, CLL, BRCA, Melanoma, OC, Esophageal Cancer, Urinary bladder cancer, Uterine Cancer, Gallbladder Cancer, Bile Duct Cancer, NHL, PC |
| 228 | YLITSVELL | OC, NHL |
| 181 | YLLEKFVAV | NSCLC, SCLC, CLL, OC, Urinary bladder cancer, AML, NHL |

TABLE 5B-continued

Peptides according to the present
invention and their specific uses in
other proliferative diseases, especially
in other cancerous diseases-

| SEQ ID NO. | Sequence | Additional Entities |
|---|---|---|
| 269 | YLMEGSYNKV | NSCLC, SCLC, PrC, BRCA, MCC, Melanoma, OC, Esophageal Cancer, Urinary bladder cancer, Gallbladder Cancer, Bile Duct Cancer |
| 123 | YLWDLDHGFAGV | NSCLC, SCLC, PrC, BRCA, Melanoma, OC, Esophageal Cancer, AML, NHL |
| 31 | YQMDIQQEL | SCLC |
| 203 | YYGILQEKI | NSCLC |
| 213 | YYNKVSTVF | NSCLC |

S* = phosphoserine

NSCLC=non-small cell lung cancer, SCLC=small cell lung cancer, RCC=kidney cancer, CRC=colon or rectum cancer, GC=stomach cancer, HCC=liver cancer, PC=pancreatic cancer, PrC=prostate cancer, leukemia, BRCA=breast cancer, MCC=Merkel cell carcinoma, OC=ovarian cancer, NHL=non-Hodgkin lymphoma, AML=acute myeloid leukemia, CLL=chronic lymphocytic leukemia.

Thus, another aspect of the present invention relates to the use of at least one peptide according to the present invention according to any one of SEQ ID No. 1, 14, 15, 41, 43, 58, 59, 60, 81, 121, 135, 139, 144, 176, 236, 248, 275, 276, 283, 286, 288, 289, 290, 291, 300, 302, 304, 308, 313, 316, 317, 325, 326, 329, 331, 334, 342, and 343 for the—in one preferred embodiment combined—treatment of pancreatic cancer.

Thus, another aspect of the present invention relates to the use of at least one peptide according to the present invention according to SEQ ID No. 6, 15, 16, 22, 26, 30, 34, 36, 47, 59, 65, 69, 70, 77, 80, 81, 88, 121, 123, 125, 127, 133, 137, 139, 169, 172, 176, 181, 186, 221, 223, 229, 230, 231, 232, 233, 234, 236, 237, 238, 244, 247, 249, 250, 251, 255, 260, 261, 266, 269, 271, 274, 275, 282, 285, 289, 290, 291, 293, 297, 301, 302, 304, 306, 310, 313, 316, 317, 319, 327, 328, 329, 330, 331, 332, 334, and 342 for the—in one preferred embodiment combined—treatment of colon cancer or renal cancer.

Thus, another aspect of the present invention relates to the use of at least one peptide according to the present invention according to SEQ ID No. 10, 14, 15, 22, 36, 39, 54, 55, 60, 72, 77, 81, 90, 96, 112, 116, 119, 121, 133, 137, 138, 148, 169, 170, 172, 177, 186, 187, 189, 192, 197, 198, 203, 206, 219, 221, 229, 230, 233, 234, 236, 255, 260, 270, 272, 275, 277, 278, 279, 281, 282, 285, 289, 291, 292, 295, 296, 297, 301, 302, 305, 308, 311, 313, 315, 316, 319, 321, 324, 328, 329, 333, 334, 335, 336, and 346 for the—in one preferred embodiment combined—treatment of kidney cancer.

Thus, another aspect of the present invention relates to the use of at least one peptide according to the present invention according to SEQ ID No. 14, 15, 16, 17, 36, 39, 47, 51, 54, 65, 88, 101, 123, 125, 133, 134, 135, 137, 141, 147, 161, 166, 169, 176, 179, 184, 186, 187, 189, 191, 192, 193, 194, 195, 196, 197, 199, 203, 206, 208, 214, 220, 221, 224, 229, 230, 231, 234, 238, 239, 244, 245, 250, 251, 255, 258, 259, 260, 268, 269, 270, 271, 272, 278, 279, 282, 295, 297, 302, 304, 305, 306, 309, 310, 311, 312, 313, 316, 317, 319, 321, 325, 327, 328, 329, 330, 331, 332, 333, 334, 336, 337, 338, 339, 340, 342, 343, 344, 345, and 347 for the—in one preferred embodiment combined—treatment of brain cancer.

Thus, another aspect of the present invention relates to the use of at least one peptide according to the present invention according to SEQ ID No. 172, 173, 240, 250, 287, 299, 302, 334, and 335 for the—in one preferred embodiment combined—treatment of CLL.

Similarly, the peptides as listed in Table 5B as above can form the basis for the—in one preferred embodiment combined—treatment of the diseases as indicated.

Thus, another aspect of the present invention relates to the use of the peptides according to the present invention for the—preferably combined—treatment of a proliferative disease selected from the group of HCC, brain cancer, kidney cancer, pancreatic cancer, colon or rectal cancer, and leukemia.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 300.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of diseases including cancer and autoimmune/inflammatory/immune pathological diseases.

The present invention further relates to antibodies against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 300, preferably containing SEQ ID No. 1 to SEQ ID No. 124, and SEQ ID No. 187 to SEQ ID No.: 218 or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, the medicament is active against cancer.

Preferably, said medicament is for a cellular therapy, a vaccine or a protein based on a soluble TCR or antibody.

The present invention further relates to a use according to the present invention, wherein said cancer cells are HCC, brain cancer, kidney cancer, pancreatic cancer, colon or rectal cancer or leukemia, and preferably HCC cells.

The present invention further relates to particular marker proteins and biomarkers based on the peptides according to the present invention, herein called "targets" that can be used in the diagnosis and/or prognosis of HCC. The present invention also relates to the use of these novel targets in the context of cancer treatment.

There are two classes of MHC-molecules, MHC class I and MHC class II. MHC molecules are composed of an alpha heavy chain and beta-2-microglobulin (MHC class I receptors) or an alpha and a beta chain (MHC class II receptors), respectively. Their three-dimensional conformation results in a binding groove, which is used for non-covalent interaction with peptides. MHC class I molecules can be found on most nucleated cells. They present peptides that result from proteolytic cleavage of predominantly endogenous proteins, defective ribosomal products (DRiPs) and larger peptides. MHC class II molecules can be found predominantly on professional antigen presenting cells (APCs), and primarily present peptides of exogenous or transmembrane proteins that are taken up by APCs during endocytosis, and are subsequently processed. Complexes of peptide and MHC class I are recognized by CD8-positive T cells bearing the appropriate TCR (T-cell receptor), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic S, et al. Survey of naturally occurring CD4+ T cell responses against NY-ESO-1 in cancer patients: correlation with antibody responses. Proc Natl Acad Sci USA. 2003 Jul. 22; 100(15):8862-7). At the tumor site, T helper cells, support a cytotoxic T cell-(CTL-) friendly cytokine milieu Mortara L, et al. CIITA-induced MHC class II expression in mammary adenocarcinoma leads to a Th1 polarization of the tumor microenvironment, tumor rejection, and specific anti-tumor memory. Clin Cancer Res. 2006 Jun. 1; 12(11 Pt 1):3435-43) and attract effector cells, e.g. CTLs, NK cells, macrophages, granulocytes (Hwang M L, et al. Cognate memory CD4+ T cells generated with dendritic cell priming influence the expansion, trafficking, and differentiation of secondary CD8+ T cells and enhance tumor control. J Immunol. 2007 Nov. 1; 179(9):5829-38).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel J, et al. Unexpected abundance of HLA class II presented peptides in primary renal cell carcinomas. Clin Cancer Res. 2006 Jul. 15; 12(14 Pt 1):4163-70).

Elongated (longer) peptides of the invention can act as MHC class II active epitopes. T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ).

There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was not considered possible. However, Dengjel et al. were successful in identifying a number of MHC Class II epitopes directly from tumors (WO 2007/028574, EP 1 760 088 B1).

The antigens that are recognized by the tumor specific cytotoxic T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

The current classification of tumor associated antigens comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

b) Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

d) Tumor specific antigens: These unique TAAs arise from mutations of normal genes (such as ß-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be upregulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are based on the use of T-cells that can be isolated from patients or healthy subjects, or they are based on the generation of differential transcription profiles or differential peptide expression patterns between tumors and normal tissues.

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of TCRs and antibodies according to the invention the immunogenicity of the underlying peptides is secondary. For TCRs and antibodies according to the invention the presentation is the determining factor.

Both therapeutic and diagnostic uses against additional cancerous diseases are disclosed in the following more detailed description of the underlying proteins (polypeptides) of the peptides according to the invention.

Differential expression of COL18A1 was reported for bladder cancer, rhabdoid tumors and ovarian carcinoma and specific polymorphisms within the gene were shown to increase the risk for sporadic breast cancer (Fang et al., 2013; Gadd et al., 2010; Peters et al., 2005; Lourenco et al., 2006).

Changes in COPA gene expression and RNA editing were shown to be associated with hepatocellular carcinoma and an experimental study revealed anti-apoptotic effects of COPA in mesothelioma cells (Sudo et al., 2010; Qi et al., 2014; Wong et al., 2003).

The activity of CPB2 was shown to be significantly reduced in acute promyelocytic leukemia (Meijers et al., 2000).

CRP, an acute phase protein synthesized in the liver, was shown to be a prognostic marker in a variety of cancer types, amongst others renal cell carcinoma and multiple myeloma (Ljungberg, 2007; Fassas and Tricot, 2004).

CRYZ is a target gene of the tumor-suppressor p53 (Bansal et al., 2011). Its encoded protein zeta-crystallin was shown to directly interact with the mRNA of the anti-apoptotic molecule bcl-2 and to stabilize the over-expression of bcl-2 in T-cell acute lymphocytic leukemia (Lapucci et al., 2010).

Over-expression of CSRP2 is associated with de-differentiation of hepatocellular carcinoma (Midorikawa et al., 2002).

CYB5A encodes an enzyme which detoxifies carcinogenic molecules and is a prognostic factor for pancreatic cancer (Blanke et al., 2014; Giovannetti et al., 2014).

Increased expression levels of CYP27A1 are associated with endometrial carcinoma, breast cancer and colorectal cancer (Bergada et al., 2014; Nelson et al., 2013; Matusiak and Benya, 2007).

Over-expression of CYP2E1 was reported in colorectal cancer, specific polymorphisms are associated with bladder and lung cancer and in breast cancer cells (Ye et al., 2014; Patel et al., 2014; Deng et al., 2014; Leung et al., 2013).

CYP2J2 is an enzyme, which was shown to be over-expressed in a variety of human cancers, including esophageal, lung, breast, stomach, liver and colon cancer (Jiang et al., 2005; Narjoz et al., 2014).

CYP4F8 was shown to be highly expressed in prostate cancer (Vainio et al., 2011). CYP4F2 and CYP4F3 were both shown to be over-expressed in pancreatic ductal adenocarcinoma and CYP4F2 alone in ovarian cancer (Gandhi et al., 2013; Alexanian et al., 2012).

Expression of CYP4F11 was shown to be regulated by NF-κB and p53 (Kalsotra et al., 2004; Bell and Strobel, 2012; Goldstein et al., 2013).

Genetic variants of CYPAF12 are significantly associated with gemcitabine response in pancreatic cancer patients (Goldstein et al., 2013; Harris et al., 2014).

High levels of DAP3 correlate on the one hand with better responses to chemotherapy in gastric cancer and better clinical outcome in breast cancer, but on the other hand over-expression of DAP3 was reported in thyroid oncocytic tumors and invasive glioblastoma (Jia et al., 2014; Wazir et al., 2012; Jacques et al., 2009; Mariani et al., 2001).

PEX19 is essential for peroxisomal biogenesis, but was also shown to directly interact with p19ARF, ultimately leading to a retention of this factor in the cytoplasm and to an inactivation of p53 tumor-suppressive function (Sugihara et al., 2001).

DDX11, belonging to the DEAH family of DNA helicases, is highly expressed in advanced melanoma (Bhattacharya et al., 2012).

NME4 is a nucleoside diphosphate kinase, over-expressed in colon and gastric cancer, as well as in myelodysplastic syndrome, in the latter disease being associated with poor prognosis (Kracmarova et al., 2008; Seifert et al., 2005).

DENND5B acts as GDP-GTP exchange factor to activate Rab-GTPases (Yoshimura et al., 2010).

DIEXF was shown to mediate the non-proteasomal degradation of the tumor-suppressor p53 (Tao et al., 2013).

DOCK7 is a guanine nucleotide exchange factor, which was shown to be over-expressed in glioblastoma and to increase glioblastoma cell invasion in response to HGF by activating Rac-1 (Murray et al., 2014).

In hepatocellular carcinoma cell lines, DRG2 was shown to be down-regulated during chemotherapeutic drug induced apoptosis, and over-expression of DRG2 inhibits doxorubicin induced apoptosis in these cells (Chen et al., 2012a).

DROSHA, one of the two critical enzymes in microRNA biosynthesis, is over-expressed in a number of cancers including gastrointestinal tumors, breast cancer and cervical cancer and appears to enhance proliferation, colony formation and migration of tumor cells (Avery-Kiejda et al., 2014; Havens et al., 2014; Zhou et al., 2013b).

SNPs in the DUSP14 gene are associated with altered melanoma risk (Yang et al., 2014a; Liu et al., 2013b).

A whole exome sequencing study uncovered somatic mutations within the DYNC1H1 gene in patients with intra-ductal papillary mucinous neoplasm of the pancreas (Furukawa et al., 2011).

EEF2 protein was shown to be over-expressed in lung, esophageal, pancreatic, breast and prostate cancer, in glioblastoma multiforme and in non-Hodgkin's lymphoma and to play an oncogenic role in cancer cell growth (Oji et al., 2014; Zhu et al., 2014a).

Mutations within the gene of EFR3A were identified in colorectal adenoma samples (Bojjireddy et al., 2014; Zhou et al., 2013a).

EIF2B5 encodes one subunit of the translation initiation factor B. Single nucleotide polymorphisms in this gene were described to be associated with survival time in ovarian cancer (Goode et al., 2010).

EIF3A, the eukaryotic translation initiation factor 3, subunit A is over-expressed in cancers of breast, lung, cervix, esophagus, stomach and colon and was shown to be involved in cell cycle regulation (Dong and Zhang, 2006).

EIF4E is a potent oncogene elevated in up to 30% of human malignancies, including carcinomas of the breast, prostate, lung, head, and neck as well as in many leukemias and lymphomas (Carroll and Borden, 2013).

ELOVL2 was shown to be over-expressed in hepatocellular carcinoma (Jakobsson et al., 2006; Zekri et al., 2012).

EPRS encodes a multifunctional aminoacyl-tRNA synthetase, which was reported to be a tumor-associated antigen in colon cancer (Line et al., 2002).

EXOSC4 promotor activity is increased in hepatocellular carcinoma, due to DNA hypomethylation. EXOSC4 effectively and specifically inhibits cancer cell growth and cell invasive capacities (Drazkowska et al., 2013; Stefanska et al., 2014).

The hydrolytic enzyme FUCA2 was found to be essential for H. pylori adhesion to human gastric cancer cells (Liu et al., 2009a).

GABRQ encodes the GABAA receptor theta subunit. GABA was shown to stimulate human hepatocellular carcinoma growth through the over-expressed GABAA receptor theta subunit (Li et al., 2012).

In squamous cell carcinoma over-expression of GALNT2 was reported to enhance the invasive potential of tumor cells by modifying O-glycosylation and EGFR activity (Lin et al., 2014; Hua et al., 2012a; Wu et al., 2011).

High levels of GGH have been associated with cellular resistance to anti-folates, in particular methotrexate and with poor prognosis in invasive breast cancer and pulmonary endocrine tumors (Schneider and Ryan, 2006; Shubbar et al., 2013; He et al., 2004).

GLUL is over-expressed in human breast carcinoma cells and astrocytomas (Zhuang et al., 2011; Collins et al., 1997; Christa et al., 1994; Cadoret et al., 2002).

GNPAT was reported to be implicated in growth inhibition and apoptosis induction in metastatic melanoma (Ofman et al., 2001; Qin et al., 2013).

Deletions in the chromosomal region of GOLGA4 have been reported in cervical carcinoma and in-frame mRNA fusion of GOLGA4 with PDGFRB in myeloproliferative neoplasms (Senchenko et al., 2003; Hidalgo-Curtis et al., 2010).

GPAM is expressed in human breast cancer, which is associated with changes in the cellular metabolism and better overall survival (Brockmoller et al., 2012).

High serum levels of GPT were reported to increase the risk of gastrointestinal cancer and are associated with carcinogenesis and recurrence in hepatitis C virus-induced hepatocellular carcinoma (Kunutsor et al., 2014; Tarao et al., 1997; Tarao et al., 1999).

GRB14 has been shown to be up-regulated in breast cancer, where high expression was significantly associated with better disease-free and overall survival (Huang et al., 2013; Balogh et al., 2012).

Single nucleotide polymorphisms in the GTF2H4 gene were reported to increase the risk to develop smoking-related lung cancer and papilloma virus-induced cervical cancer (Mydlikova et al., 2010; Buch et al., 2012; Wang et al., 2010).

Different studies suggest an important role of HSPA2 in disease progression of cervical cancer, renal cell carcinoma and bladder cancer. Polymorphisms within the gene are associated with the development of gastric cancer (Singh and Suri, 2014; Ferrer-Ferrer et al., 2013; Garg et al., 2010a; Garg et al., 2010b).

HSPA8 was shown to be over-expressed in esophageal squamous cell carcinoma. Furthermore, HSPA8 is over-expressed in multiple myeloma and colonic carcinoma and BCR-ABL1-induced expression of HSPA8 promotes cell survival in chronic myeloid leukemia (Dadkhah et al., 2013; Wang et al., 2013a; Chatterjee et al., 2013; Kubota et al., 2010; Jose-Eneriz et al., 2008).

MDN1 was described to be a candidate tumor suppressor gene, mutated in breast cancers of the luminal B type (Cornen et al., 2014).

MIA3, also known as transport and Golgi organization protein 1 (TANGO), was reported to be down-regulated in colon and hepatocellular carcinomas and to play a tumor-suppressive role in these entities (Arndt and Bosserhoff, 2007). In contrast, a study in oral squamous cell carcinoma indicates an association of MIA3 expression with tumor progression, metastasis formation and clinical stage, pointing towards an oncogenic action of MIA3 (Sasahira et al., 2014).

CPSF6 was identified as one gene within a "poised gene cassette" associated with significant differences in metastatic and invasive potential of several tumor types, like breast, colon, liver, lung, esophageal and thyroid cancer (Yu et al., 2008).

Low levels of MPDZ expression were reported to be associated with poor prognosis in breast cancer patients (Martin et al., 2004).

NAA35, also known as MAK10, encodes the N(alpha)-acetyltransferase 35, NatC auxiliary subunit. In patients with esophageal squamous cell carcinoma a highly cancer enriched chimeric GOLM1-MAK10 RNA was detected, which encodes a secreted fusion protein, potentially useful as molecular marker (Zhang et al., 2013b).

NAV2 was shown to be specifically expressed in a group of colon cancers and treatment of colon-cancer cells with antisense oligonucleotides for NAV2 induced apoptosis (Ishiguro et al., 2002).

NCSTN over-expression is indicative of worse overall survival in estrogen-receptor-negative breast cancer patients and high levels of Nicastrin and Notch4 were detected in endocrine therapy resistant breast cancer cells, where their activation ultimately drives invasive behavior (Sarajlic et al., 2014; Lombardo et al., 2014).

NKD1 protein is reduced, but NKD1 mRNA is elevated in non-small cell lung cancer, the former correlating with increased invasive potential and poor prognosis (Zhang et al., 2011). NKD1 mRNA was also found to be elevated in cells from human colon tumors (Yan et al., 2001; Zhang et al., 2011).

In esophageal cancer, NUDC was reported to be associated with nodal metastasis, whereas over-expression of NUDC in prostate cancer cells leads to a block in cell division (Hatakeyama et al., 2006; Lin et al., 2004).

A study investigating the role of the Notch signaling pathway in ovarian cancer reported a higher frequency of RFNG expression in adenoma compared to carcinoma (Gu et al., 2012; Hopfer et al., 2005).

RINT1 is described as an oncogene in glioblastoma multiforme and as a moderately penetrant cancer susceptibility gene seen in breast cancer as well as in Lynch syndrome-related cancers (Ngeow and Eng, 2014; Quayle et al., 2012).

High expression of RORC was found to be associated with longer metastasis-free survival in breast cancer. Attenuated RORC expression in somatotroph adenomas is associated with increased tumor size and a blunted clinical response to somatostatin treatment (Cadenas et al., 2014; Lekva et al., 2013).

RPL17 was reported to promote multidrug resistance by suppressing drug-induced apoptosis (Shi et al., 2004b).

Increased expression of RPS29 was reported in gastric and colorectal cancer (Takemasa et al., 2012; Sun et al., 2005).

SAMM50 encodes a component of the Sorting and Assembly Machinery (SAM) of the mitochondrial outer membrane, which functions in the assembly of beta-barrel proteins into the outer mitochondrial membrane. A growth promoting chimeric mRNA (SAMM50-PARVB) was detected in breast and ovarian cancer cells and in a number of samples from breast, stomach, colon, kidney and uterus cancer (Plebani et al., 2012).

SERPINF2 encodes the major inhibitor of plasmin, which degrades fibrin and various other proteins. The plasma level of the plasmin-alpha 2-plasmin inhibitor complex was shown to be a predictor of survival in non-small cell lung carcinoma and low activity of alpha 2-antiplasmin has been observed in the blood of the patients with prostatic carcinoma (Zietek et al., 1996; Taguchi et al., 1996).

Over-expression of SF3B3 is significantly correlated with overall survival and endocrine resistance in estrogen receptor-positive breast cancer (Gokmen-Polar et al., 2014).

Protein levels of SHC1 are elevated in prostate, metastatic breast, ovarian and thyroid cancer and different isoforms and are thought to function as a primary adaptor protein for mediating the mitogenic signals of steroids at the non-genomic level (Alam et al., 2009; Rajendran et al., 2010).

AMACR is used as a biomarker in prostate cancer, since it is highly over-expressed in this entity (Wu et al., 2014). Furthermore, it is used as an immunohistochemical marker for the diagnosis of renal cell carcinoma (Ross et al., 2012).

Experimental data suggest that C1QTNF3 expression may play a role in osteosarcoma tumor growth, associated with activation of the ERK1/2 signaling pathway and that it is a novel anti-apoptotic adipokine that protects mesenchymal stem cells from hypoxia/serum deprivation-induced apoptosis through the PI3K/Akt signaling pathway (Hou et al., 2014; Akiyama et al., 2009).

GPC3 is expressed by most hepatocellular carcinomas. Two therapeutic approaches for HCC that target GPC3 are currently being tested in phase II clinical trials: a humanized GPC3 monoclonal antibody and a vaccine that consists of two GPC3-derived peptides. The peptides used in the latter study are distinct from the peptide presented in this document. GPC3 expression has also been identified in all yolk sac tumors, some squamous cell carcinomas of the lung and clear cell carcinomas of the ovary (Filmus and Capurro, 2013; Kandil and Cooper, 2009).

MAGEB2 is classified as cancer testis antigen, since it is expressed in testis and placenta, and in a significant fraction of tumors of various histological types, amongst others multiple myeloma and head and neck squamous cell carcinoma (Pattani et al., 2012; van et al., 2011).

MAPKAPK5 encodes a tumor suppressor and member of the serine/threonine kinase family. MAPKAPK5 was shown to be under-expressed in colorectal cancer, leading to an increased activity of the myc oncoprotein and to decrease cancer formation by suppressing oncogenic ras activity in a murine model of hematopoietic cancer (Yoshizuka et al., 2012; Kress et al., 2011).

Over-expression of USP14 is associated with increased tumor cell proliferation and poor prognosis in epithelial ovarian, non-small cell lung and colorectal cancer (Wang et al., 2015; Wu et al., 2013a; Shinji et al., 2006).

C4A has been described as a biomarker for polycystic ovary syndrome and endometrial cancer and experimental data suggest that C4 can mediate cancer growth (Galazis et al., 2013; Rutkowski et al., 2010).

CAPZB was reported to be over-expressed in human papillomaviruses 18-positive oral squamous cell carcinomas and was identified as prostate cancer susceptibility locus (Lo et al., 2007; Nwosu et al., 2001).

Single nucleotide polymorphisms within the gene for CFHR5 are associated with event-free survival in follicular lymphoma (Charbonneau et al., 2012).

CLIP1 encodes the CAP-GLY domain containing linker protein 1, which links endocytic vesicles to microtubules. This gene is highly expressed in Reed-Sternberg cells of Hodgkin disease and breast cancer and appears to be implicated in the migration and invasion of breast cancer and pancreatic cancer cells (Sun et al., 2013; Suzuki and Takahashi, 2008; Li et al., 2014a; Sun et al., 2012).

CLU may inhibit tumor progression, whereas in advanced neoplasia, it may offer a significant survival advantage in the tumor by suppressing many therapeutic stressors and enhancing metastasis. CLU has been shown to play a critical role in prostate cancer pathogenesis, to regulate the aggressive behavior of human clear renal cell carcinoma cells through modulating ERK1/2 signaling and MMP-9 expression and to confer resistance to treatment in advanced stages of lung cancer (Trougakos, 2013; Panico et al., 2009; Takeuchi et al., 2014; Wang et al., 2014).

The fusion gene SEC16A-NOTCH1 was reported as first recurrent fusion gene in breast cancer (Edwards and Howarth, 2012).

Recurrent deletion of the SHQ1 gene has been observed in prostate and cervical cancer, implicating a tumor-suppressive role of SHQ1 (Krohn et al., 2013; Lando et al., 2013).

In clear cell renal cell carcinomas and bladder cancer high SLC16A1 expression is associated with poor prognostic factors and predicts tumor progression. In colorectal cancer single nucleotide polymorphisms in the SLC16A1 gene may affect clinical outcomes and can be used to predict the response to adjuvant chemotherapy (Kim et al., 2015; Fei et al., 2014a; Fei et al., 2014a).

Glioblastoma have been shown to release glutamate at high levels, which may stimulate tumor cell proliferation and facilitates tumor invasion, and to down-regulate SLC1A2, which correlated with higher tumor grade, implicating its potential role in glial tumor progression. Furthermore, in gastric cancer a fusion gene of SLC1A2 with CD44 has been detected and may represent a class of gene fusions that establish a pro-oncogenic metabolic milieu favoring tumor growth and survival (Tao et al., 2011; de Groot et al., 2005).

High expression of SLC3A2 is associated with tumor growth, biological aggressiveness, and survival of patients with biliary tract cancer and significantly contributes to poor prognosis of non-small cell lung cancer patients through promoting cell proliferation via the PI3K/Akt pathway.

Furthermore, over-expression of SLC3A2 together with integrin ß1, integrin ß3 and Fak is associated with the progression and liver metastases of colorectal cancer (Kaira et al., 2014; Fei et al., 2014b; Sun et al., 2014).

Evidences of SLC9A3R1 involvement in cancer development are present in hepatocellular carcinoma, schwannoma, glioblastoma, colorectal cancer and particularly in breast cancer (Saponaro et al., 2014).

NFYC has been reported to promote the expression of oncogenes in gastric cancer and prostate cancer cells (Zhang et al., 2014a; Gong et al., 2013).

THY1 is a candidate tumor suppressor gene in nasopharyngeal carcinoma bearing anti-invasive activity (Lung et al., 2010).

TIMM17A is over-expressed in 21T breast cancer cells and mRNA expression in breast cancer tissues was correlated with tumor progression (Xu et al., 2010).

TMEM209 is widely expressed in lung cancer (Fujitomo et al., 2012).

TNK2 also known as ACK1 tyrosine kinase is activated, amplified or mutated in a wide variety of human cancers. The de-regulated kinase is oncogenic and its activation correlates with progression to metastatic stage. ACK1 inhibitors have shown promise in pre-clinical studies (Mahajan and Mahajan, 2013).

TRIM55 encodes a RING zinc finger protein which associates transiently with microtubules, myosin and titin during muscle sarcomere assembly and is also involved in signaling from the sarcomere to the nucleus (Pizon et al., 2002).

RNA interference of Ufd1 protein can sensitize a hydroxycamptothecin-resistant colon cancer cell line SW1116/HCPT to hydroxyl-camptothecin (Chen et al., 2011a; Chen et al., 2011c).

In colorectal cancer the UGT1A1 gene is silenced through methylation and thus is regarded as the target point of research for irinotecan (CPT-11) drug resistance and control mechanisms for the reversal of drug resistance (Xie et al., 2014).

UGT1A10 is expressed in gastric and biliary tissue (Strassburg et al., 1997) and its over-expression significantly increased the cytotoxicity of the antitumor agent 5-dimethylaminopropylamino-8-hydroxytriazoloacridinone C-1305 (Pawlowska et al., 2013). Furthermore UGT1A10 catalyzes the glucuronidation of xenobiotics, mutagens, and reactive metabolites and thus acts as indirect antioxidant. Xenobiotic (XRE) and antioxidant (ARE) response elements were detected in the promoters of UGT1A8, UGT1A9, and UGT1A10 (Kalthoff et al., 2010).

UGT1A8 is primarily expressed in the gastrointestinal tract (Gregory et al., 2003) and mRNA expression is up-regulated upon treatment with chemo-preventive agent sulforaphane (SFN) (Wang et al., 2012).

UGT1A7 haplotype is associated with an increased risk of hepatocellular carcinoma in hepatitis B carriers (Kong et al., 2008).

UGT1A6 is over-expressed in breast cancer cells resistant to methotrexate (de Almagro et al., 2011) and induced by ß-Naphthoflavone a putative chemo-preventive agent (Hanioka et al., 2012).

UGT1A9 is mainly expressed in liver and kidneys (Gregory et al., 2003). UGT1A9 germline polymorphisms are potential predictors for prostate cancer recurrence after prostatectomy (Laverdiere et al., 2014).

UGT1A4 promoter and coding region polymorphisms lead to a variability in the glucuronidation of anastrozole, an aromatase inhibitor for breast cancer patients (Edavana et al., 2013).

UPF1 is part of the nonsense-mediated mRNA decay (NMD) machinery and may have a functional role in prostate cancer progression and metastasis (Yang et al., 2013). Further the UPF1 RNA surveillance gene is commonly mutated in pancreatic adenosquamous carcinoma (Liu et al., 2014).

UQCRB is a subunit of mitochondrial complex III. Inhibition of UQCRB in tumor cells suppresses hypoxia-induced tumor angiogenesis (Jung et al., 2013). Two SNPs in the 3' untranslated region of UQCRB are candidates as prognostic markers for colorectal cancer (Lascorz et al., 2012).

Copy number alterations of USO1 correlated with differential gene expression in superficial spreading melanoma compared to nodular melanoma (Rose et al., 2011).

Significant reductions in both USP10 and SIRT6 protein expression was detected in human colon cancers (Lin et al., 2013).

UTP18 also alters translation to promote stress resistance and growth, and is frequently gained and over-expressed in cancer (Yang et al., 2014b).

VARS rs2074511 polymorphism was associated with survival in patients with triple negative type breast cancer and thus may be considered as a prognostic factor for survival in patients with early breast cancer (Chae et al., 2011).

VMP1, a stress-induced autophagy-associated protein, is also induced by the oncogene KRAS (Lo Re et al., 2012). VMP1 is over-expressed in poorly differentiated human pancreatic cancer as a response to chemotherapeutic drugs (Gilabert et al., 2013). A significant down-regulation of VMP1 was found in human HCC tissues and closely correlated with multiple tumor nodes, absence of capsular formation, vein invasion and poor prognosis of HCC (Guo et al., 2012).

WDR26 protects myocardial cells against oxidative stress (Feng et al., 2012).

ZC3H7A is part of the CCCH zinc finger protein family known as regulators of macrophage activation (Liang et al., 2008). ZC3H7A was found to have higher allele frequencies of functional mutations in the metastatic tumor of pancreatic ductal adenocarcinoma (Zhou et al., 2012).

FASN is a fatty acid synthase and involved in the enhanced lipid synthesis in different types of cancer, including breast, pancreatic, prostate, liver, ovarian, colon and endometrial cancer (Wu et al., 2014; Zhao et al., 2013).

FGG is up-regulated in hepatocellular carcinoma as well as in prostate, lung and breast cancers (Vejda et al., 2002; Zhu et al., 2009).

FMO5 is a monooxygenase that is the dominant liver-specific FMO, and it is up-regulated in estrogen receptor alpha-positive breast tumors (Bieche et al., 2004; Zhang and Cashman, 2006).

HADHA mRNA is reduced with the progression of de-differentiation in HCC (Tanaka et al., 2013) and in estrogen receptor alpha-negative breast tumors (Mamtani and Kulkarni, 2012).

Genetic variation in the HAL gene might play a role in the development of skin cancer (Welsh et al., 2008).

HLTF is a member of the SWI/SNF family of transcriptional regulators with helicase and E3 ubiquitin ligase activity and was found to be inactivated by hypermethylation in colon, gastric, uterine, bladder and lung tumors (Debauve et al., 2008; Castro et al., 2010; Garcia-Baquero et al., 2014).

HDAC10 is a histone deacetylase and transcriptional regulator. Expression of HDAC10 was significantly decreased in gastric cancer tissues as compared with adjacent tissues (Jin et al., 2014). HDAC10 is inversely related to lymph node metastasis in human patients with cervical squamous cell carcinoma (Song et al., 2013). HDAC10 is hypermethylated in malignant adrenocortical tumors (Fonseca et al., 2012). HDAC10 levels are increased in chronic lymphocytic leukemia (Wang et al., 2011). HDAC10-589C>T promoter polymorphism was significantly associated with HCC occurrence among chronic HBV patients as well as HCC acceleration among chronic HBV patients (Park et al., 2007). Reduced expression of class II histone deacetylase genes is associated with poor prognosis in lung cancer patients (Osada et al., 2004).

Low HIP1R expression is strongly associated with poor outcome in diffuse large B-cell lymphoma patients (Wong et al., 2014).

HM13 is a signal peptide peptidase and affected cell viability in colorectal adenoma (Sillars-Hardebol et al., 2012).

Serum HPR levels in patients with malignant lymphoma were significantly higher than in non-diseased control groups and HPR expression increased with disease progress (Epelbaum et al., 1998). HPR expression parallels increased malignant potential in breast cancers and HPR-positive breast cancers are more likely to recur after primary resection and are associated with shorter disease-free intervals (Shurbaji et al., 1991).

A variant (rs932335) in the HSD11B1 gene is associated with colorectal cancer and breast cancer (Feigelson et al., 2008; Wang et al., 2013b).

HSD17B6 expression in tissues from prostate cancer patients undergoing androgen deprivation therapy (ADT) was significantly higher than that in tissues of untreated individuals (Ishizaki et al., 2013).

HSPE1 is a mitochondrial chaperonin with functions in protein folding and cell signaling (NF-kappaB and WNT signaling). Increased Hsp10 levels have been found in tumor cells in large bowel cancer, exocervical cancer, prostate cancer, mantle cell lymphoma, and serous ovarian cancer. In bronchial carcinogenesis, decreased levels of Hsp10 have been reported (David et al., 2013).

Ovarian carcinoma xenografts transplanted into the flanks of nude mice and treated with paclitaxel showed a diminished IDH expression compared to untreated xenograft (Bani et al., 2004).

IGFBPL1 is a regulator of insulin-growth factors and is down-regulated in breast cancer cell lines by aberrant hypermethylation. Methylation in IGFBPL1 was clearly associated with worse overall survival and disease-free survival (Smith et al., 2007).

The androgen-sensitive microsome-associated protein IKBKAP modulated the expression of prostate epithelial and neuronal markers, attenuated proliferation through an androgen receptor-dependent mechanism, and co-regulated androgen receptor-mediated transcription in LNCaP prostate adenocarcinoma cells (Martinez et al., 2011).

INTS8 is part of a marker panel that discriminates gastric carcinomas from adjacent noncancerous tissues (Cheng et al., 2013).

A IRS2-derived peptide pIRS-21097-1105 was presented on HLA-A2(+) melanomas and breast, ovarian, and colorectal carcinomas (Zarling et al., 2014). IRS-2 1057 DD genotype and D allele were significantly associated with HCC risk (Rashad et al., 2014).

ITGA7 is the alpha chain of the laminin-1 receptor dimer integrin alpha-7/beta-1. ITGA7 is a tumor-suppressor gene that is critical for suppressing the growth of malignant tumors. Mutational analysis revealed ITGA7 mutations in prostate cancer, hepatocellular carcinoma, soft tissue leiomyosarcoma, and glioblastoma multiforme. ITGA7 was down-regulated in non-metastatic prostate cancer and leiomyosarcoma (Tan et al., 2013).

ITIH4 was down-regulated in several tumor tissues including colon, stomach, ovary, lung, kidney, rectum and prostate (Hamm et al., 2008). Low serum ITIH4 levels are associated with shorter survival in HBV-associated HCC patients (Noh et al., 2014). Significantly increased ITIH4 serum concentrations were observed in breast cancer and ITIH4 serum levels were significantly decreased after surgery (van, I et al., 2010).

A missense mutation was identified in SHKBP1, which acts downstream of FLT3, a receptor tyrosine kinase mutated in about 30% of AML cases (Greif et al., 2011). SHKBP1 is one of several potential protein biomarker candidates for classifying well-differentiated small intestine neuroendocrine tumors (WD-SI-NETs) at different stage of disease (Darmanis et al., 2013).

KLB expression is elevated in HCC tissues compared to matched non-tumor tissue (Poh et al., 2012).

The LBP polymorphism rs2232596 is associated with a significantly increased risk of colorectal carcinoma in Han Chinese (Chen et al., 2011b). LBP is a candidate serum biomarker in ovarian carcinoma (Boylan et al., 2010). LBP was reduced significantly after treatment with chemotherapy in small-cell lung carcinoma patients (Staal-van den Brekel A J et al., 1997).

LBR mRNA expression was directly associated with tumor grade and Nottingham Prognostic Index in breast cancer (Wazir et al., 2013). LBR is heavily expressed in papillary thyroid carcinoma cells, but an abnormal folding of the protein might explain its lack of immunohistochemical reactivity and be associated with an anomalous folding of the nuclear membrane (Recupero et al., 2010).

LEPR dysregulation has been reported in a variety of malignant cells including colon cancer, hepatocellular carcinoma, endometrial cancer, thyroid cancer, breast cancer and lung cancer (Ntikoudi et al., 2014; Surmacz, 2013; Uddin et al., 2011).

LIG1 single-nucleotide polymorphisms are associated with the risk of lung cancer, endometrial cancer and glioma (Doherty et al., 2011; Lee et al., 2008; Liu et al., 2009b).

LRPPRC expression in gastric cancer tissues is significantly higher than that in paired control tissue (Li et al., 2014b). LRPPRC levels serve as a prognosis marker of patients with prostate adenocarcinomas (PCA), and patients with high LRPPRC levels survive a shorter period after surgery than those with low levels of LRPPRC (Jiang et al., 2014). LRPPRC is abundantly expressed in various types of tumors, such as lung adenocarcinoma, esophageal squamous cell carcinoma, stomach, colon, mammary and endometrial adenocarcinoma, and lymphoma (Tian et al., 2012).

MANEA expression is regulated by androgens in prostate cancer cells (Romanuik et al., 2009).

OPLAH is expressed in lung, breast, kidney, colon and ovary normal and tumor tissues and OPLAH levels are significantly higher in normal specimens than tumors for individual patients (Srivenugopal and Ali-Osman, 1997).

ORM2 glycoforms provide valuable information for differentiation between primary and secondary liver cancer (Mackiewicz and Mackiewicz, 1995). ORM2 levels in plasma were confirmed to be significantly elevated in patients suffering from colorectal carcinoma compared with the controls (Zhang et al., 2012). Fucosylated glycoform ORM2 levels were significantly higher in adenocarcinoma lung cancer cases compared to controls (Ahn et al., 2014). ORM2 is a putative biomarkers for early diagnosis of cholangiocarcinoma (Rucksaken et al., 2012).

Increased tetrahydrobiopterin levels result in an enhancement of PAH activity and PAH protein in human hepatoma cells (McGuire, 1991).

PARP14 is highly expressed in myeloma plasma cells and associated with disease progression and poor survival. PARP14 is critically involved in JNK2-dependent survival. PARP14 was found to promote the survival of myeloma cells by binding and inhibiting JNK1 (Barbarulo et al., 2013).

PC levels are elevated in liver tumors and lung cancer (Chang and Morris, 1973; Fan et al., 2009).

Increased PCNT levels and centrosomal abnormalities have been described in a variety of hematologic malignancies and solid tumors, including AML, CML, mantle cell lymphoma, breast cancer and prostate cancer (Delaval and Doxsey, 2010).

PIGN is a cancer chromosomal instability (CIN)-suppressor gene that is subject to frequent copy number loss in CIN(+) colorectal cancer (Burrell et al., 2013).

PIPOX expression varied according to subtype of breast cancer, with HER-2 type tumors showing elevated expression and triple negative breast cancer subtype showing decreased expression. Tumoral PIPOX negativity was associated with shorter disease-free survival (Yoon et al., 2014). PIPOX was reduced in prostate tumors and reduced the oncogenic potential of prostate cells by metabolizing sarcosine (Khan et al., 2013).

Increased PSMD4 levels were detected in colon cancer, myeloma and hepatocellular carcinoma (Arlt et al., 2009; Midorikawa et al., 2002; Shaughnessy, Jr. et al., 2011).

PLIN2 is significantly increased in patients with clear cell and papillary renal cell carcinoma compared with controls. The preoperative urinary concentrations of PLIN2 reflects the tumor size and stage (Morrissey et al., 2014). PLIN2 expression is significantly higher in lung adenocarcinoma specimens than in normal tissues and lung squamous cell carcinomas (Zhang et al., 2014b).

PLK4 frequently undergoes rearrangement or loss in human cancers, at a particularly high rate in hepatocellular carcinomas, but also in colorectal cancer, head and neck cancer (Swallow et al., 2005). PLK4 is over-expressed in breast cancer (Marina and Saavedra, 2014).

QARS is a member of the aminoacyl-tRNA synthetases (ARS) and charges tRNAs with glutamine. ARS expression and polymorphisms are associated with breast cancer and glioblastoma (He et al., 2014b; Kim et al., 2012).

The methylated PMF1 gene is a diagnostic and prognostic biomarker for patients with bladder cancer (Kandimalla et al., 2013).

Several human tumors and hematologic malignancies up-regulated PON2, including thyroid gland, prostate, pancreas, testis, endometrium/uterus, liver and kidney cancer, lymphoid tissues, urinary bladder tumors, ALL and CML, and such over-expression provided resistance to different chemotherapeutics (imatinib, doxorubicine, staurosporine, or actinomycin) (Witte et al., 2011).

PRKAR2A is a regulatory subunit of protein kinase A. PRKAR2A markedly increased survival of prostate cancer cells lines treated with Taxol and Taxotere (Zynda et al., 2014). PRKAR2A is over-expressed in lung adenocarcinoma (Bidkhori et al., 2013).

PRPF6 is a member of the tri-snRNP (small ribonucleoprotein) spliceosome complex that drives colon cancer proliferation by preferential splicing of genes associated with growth regulation (Adler et al., 2014). PRPF6 is over-expressed in lung adenocarcinoma (Bidkhori et al., 2013).

PSMC4 is significantly and coherently up-regulated in prostate carcinoma cells compared with the corresponding adjacent normal prostate tissue (Hellwinkel et al., 2011).

QPRT expression increases with malignancy in glioma and, in recurrent glioblastomas after radiochemotherapy, QPRT expression is associated with a poor prognosis (Sahm et al., 2013). QPRT is a potential marker for the immunohistochemical screening of follicular thyroid nodules (Hinsch et al., 2009).

RABGGTB is over-expressed in chemotherapy-refractory diffuse large B-cell lymphoma (Linderoth et al., 2008).

RAD21 is over-expressed in gastrointestinal tumors, colorectal carcinoma, advanced endometrial cancer, prostate cancer and breast cancer (Atienza et al., 2005; Deb et al., 2014; Porkka et al., 2004; Supernat et al., 2012; Xu et al., 2014).

RAD23B has a potential role in breast cancer progression (Linge et al., 2014). The single nucleotide polymorphism RAD23B rs1805329 was significantly associated with development and recurrence of HCC in Japanese patients with HCV (Tomoda et al., 2012).

RASAL2 is a RAS-GTPase-activating protein with tumor suppressor functions in estrogen receptor-positive breast cancer, ovarian cancer and lung cancer (Li and Li, 2014; Huang et al., 2014). In contrast, RASAL2 is oncogenic in triple-negative breast cancer and drives mesenchymal invasion and metastasis (Feng et al., 2014a).

Depletion of RNMT effectively and specifically inhibits cancer cell growth and cell invasive capacities in different types of cancer, including liver cancer (Stefanska et al., 2014).

Over-expression of ROCK1 or mutations in the ROCK1 gene that lead to an elevated kinase activity have been reported for several cancers, including lung cancer, gastric carcinoma, CML and AML (Rath and Olson, 2012).

RPL10A is a c-Myc targeted gene and may contribute to hepatocyte transformation (Hunecke et al., 2012).

Inv(3) and t(3;3) breakpoints, which are associated with a particularly poor prognosis in myeloid leukemia or myelodysplasia, cluster in a region that is located centromeric and downstream of the RPN1 gene (Wieser, 2002).

RRBP1 is over-expressed in lung cancer and breast cancer (Telikicherla et al., 2012; Tsai et al., 2013).

SCFD1 expression is increased in erosive gastritis, which is linked to gastric carcinoma (Galamb et al., 2008).

ABCB1 encodes P-glycoprotein (P-gp) which is expressed in normal cells of various organs such as intestine, liver, kidney, brain, and placenta. P-gp overexpression and genetic polymorphisms have been detected in colorectal carcinoma, tumors derived from the adrenal gland, lung cancer and ALL (Zhang et al., 2013a; Fojo et al., 1987; Gervasini et al., 2006; Jamroziak et al., 2004).

ABCB10 encodes for an ABC transporter of the subfamily B (MDR/TAP). ABCB10 was shown to be involved in the cisplatin resistance of KCP-4 human epidermoid carcinoma cells (Oiso et al., 2014).

The expression of ABCB11 was shown to be up-regulated in the pancreatic ductal adenocarcinoma, one of the most drug-resistant cancers. Thus it may contribute to the generally poor treatment response of this cancer (Mohelnikova-Duchonova et al., 2013).

The up-regulated expression of ABCC2 in primary fallopian tube carcinomas is associated with poor prognosis (Halon et al., 2013).

ABCC6 was down-regulated in colorectal cancer of non-responders to palliative chemotherapy (Hlavata et al., 2012). In contrast, it was up-regulated in the gemcitabine-resistant human NSCLC A549 cells (Ikeda et al., 2011).

The expression of ACACA was shown to be up-regulated in numerous human cancers, such as breast, prostate and liver carcinoma and correlated with enhanced lipogenesis of cancer cells. The various ACACA inhibitors showed a therapeutical effect in treatment of cancer cell lines by suppression of cell proliferation and inducing of cell death through apoptosis (Zu et al., 2013).

ACLY is aberrantly expressed in various tumors, such as breast, liver, colon, lung and prostate cancers, and is correlated reversely with tumor stage and differentiation (Zu et al., 2012).

ACSL3 is over-expressed in lung cancer and based on preclinical investigation is a promising new therapeutic target in lung cancer (Pei et al., 2013). The up-regulated expression of ACSL3 can serve as a potential biomarker of estrogen receptor-specific breast cancer risk (Wang et al., 2013c).

ACSL4 is over-expressed in estrogen receptor-negative breast tumors and androgen receptor-negative breast and prostate tumors. The loss of steroid hormone sensitivity was associated with induction of ACSL4 expression (Monaco et al., 2010). The onset up-regulation of ACSL4 was shown to occur during the transformation from adenoma to adenocarcinoma (Cao et al., 2001).

The methylation of ACSS3 was found to be associated with at least one of the classical risk factors, namely age, stage or MYCN status in neuroblastoma (Decock et al., 2012).

The deletion of ADSSL1 was frequently observed in carcinogen-induced mouse primary lung adenocarcinomas, mouse and human lung adenocarcinomas cell lines and associated with a more extensive chromosome instability phenotype in the primary mouse lung tumors (Miller et al., 2009).

AGFG2 was identified to be one of 14 prognostic gene candidates in identifying cases of hormone receptor-negative or triple-negative breast cancers likely to remain free of metastatic relapse (Yau et al., 2010).

AGT is a very potent anti-angiogenic factor, which was shown to exert anti-tumoral effects in vitro and in vivo (Bouquet et al., 2006). In transgenic mice, the over-expression of human AGT was shown to decrease angiogenesis and thus delaying tumor progression of hepatocarcinoma (Vincent et al., 2009).

AKR1C4 encodes for a human aldo-keto reductase family 1 member C4 and catalyzes the reduction of retinaldehyde to retinol (Ruiz et al., 2011). Thus, the depletion of retinaldehyde down-regulates the biosynthesis of retinoic acid and is followed by blockage of retinoid signaling, which favors tumor progression (Tang and Gudas, 2011; Ruiz et al., 2012)

The expression of ALDH1 L1 was shown to be down-regulated in HCC and gliomas. The down-regulation of ALDH1 L1 in those cancers was associated with poorer prognosis and more aggressive phenotype (Rodriguez et al., 2008; Chen et al., 2012b)

The expression of ALG3 was shown to be enhanced in esophageal squamous cell carcinoma and cervical cancer (Shi et al., 2014; Choi et al., 2007). In esophageal squamous cell carcinoma the increased expression of ALG3 correlated with lymph node metastasis (Shi et al., 2014).

ANKS1A was identified as a novel target of Src family kinases which are known to be implicated in the development of some colorectal cancers (Emaduddin et al., 2008).

APOA1 encodes for apolipoprotein A-I, the major protein component of high density lipoprotein (HDL) in plasma. In multiple animal tumor models, APOA1 showed a potent immune-modulatory role in the tumorigenesis and was shown to suppress tumor growth and metastasis by supporting innate and adaptive immune processes (Zamanian-Daryoush et al., 2013).

APOA2 was shown to be significantly decreased in pancreatic cancer patients (Honda et al., 2012). In contrast, the increased expression of APOA2 was associated with HCC (Liu et al., 2007).

In alpha-fetoprotein-negative HBV-related HCC, APOB was found to be one of the 14 differentially expressed proteins which could be associated with HCC progression (He et al., 2014a). In advanced breast cancer, APOB was found to be the one of six differentially expressed proteins which could predict the responsiveness to neoadjuvant chemotherapy and relapse-free survival of patients (Hyung et al., 2011).

By stage III colorectal cancer patients and in human melanoma cells, AQP9 was associated with increased chemoresistance (Dou et al., 2013; Gao et al., 2012).

ARG1 was shown to be a sensitive and specific marker in distinguishing of HCC from other metastatic tumors in liver (Sang et al., 2013). ARG1 may contribute to local immune suppression in NSCLC (Rotondo et al., 2009).

The phosphorylated and thus more active form of ARSB protein was found to be increased in peripheral leukocytes from patients with chronic myelogenous leukemia compared to healthy donors (Uehara et al., 1983).

In ovarian cancer cells, the down-regulation of ASNA1 was shown to increase the sensitivity to the chemotherapy drugs cisplatin, carboplatin, oxaliplatin and arsenite (Hemmingsson et al., 2009).

ASPH was shown to be over-expressed in various cancers and cancer cell lines (Yang et al., 2010). Immunization with ASPH-loaded dendritic cells generated cytotoxicity against cholangiocarcinoma cells in vitro and significantly suppressed intrahepatic tumor growth and metastasis (Noda et al., 2012).

ATP1A2 was found among 31 proteins which were significantly up-regulated in glioblastoma (Com et al., 2012). In contrast, ATP1A2 was shown to be down-regulated in bone marrow-infiltrating metastatic neuroblastomas (Morandi et al., 2012).

ATP1A3 was found among 31 proteins, which were significantly up-regulated in glioblastoma (Com et al., 2012).

ATP6V1C1 may promote breast cancer growth and bone metastasis through regulation of lysosomal V-ATPase activity. ATP6V1C1 knockdown significantly inhibited mouse 4T1 mammary tumor cell xenograft tumor growth, metastasis, and osteolytic lesions in vivo (Feng et al., 2013). ATP6V1C1 was shown to be over-expressed in oral squamous cell carcinoma and was associated with tumor cell mobility (Otero-Rey et al., 2008).

ATP7B is associated with cancer resistance to cisplatin, the widely used anti-cancer drug (Dmitriev, 2011).

AXIN2 encodes for Axin-(axis inhibition) related protein 2, which presumably plays an important role in the regulation of the stability of beta-catenin in the Wnt signaling pathway (Salahshor and Woodgett, 2005). Furthermore, AXIN2 was shown to repress the expression of the oncogene c-MYC (Rennoll et al., 2014).

In HCC, the low expression of BAAT was associated with poorer survival compared to the patients with higher expression of BAAT (Furutani et al., 1996).

A strong decrease of transcripts of BHMT and BHMT2 was shown in HepG2 cells and in HCC samples compared to normal liver tissue (Pellanda et al., 2012).

C12orf44 was shown to be essential for autophagy and interact with ULK1 in an Atg13-dependent manner (Mercer et al., 2009). Autophagy has dual roles in cancer, acting as both a tumor suppressor by preventing the accumulation of damaged proteins and organelles and as a mechanism of cell survival that can promote the growth of established tumors (Yang et al., 2011b).

C17orf70 is a component of the Fanconi anemia core complex and is essential for the complex stability. The Fanconi anemia core complex plays a central role in the DNA damage response network. The Fanconi anemia core complex-mediated DNA damage response involves breast cancer susceptibility gene products, BRCA1 and BRCA2 (Ling et al., 2007).

C19orf80 encodes for hepatocellular carcinoma-associated gene TD26 and was shown to be one of 5 loci with highest methylation levels in HCC and lowest in control tissue (Ammerpohl et al., 2012).

CCT7 was found to be a part of a protein sub-network, which is significantly discriminative of late stage human colorectal cancer (Nibbe et al., 2009).

CDK6 has been shown to regulate the activity of tumor suppressor protein Rb. CDK6 can exert its tumor-promoting function by enhancing proliferation and stimulating angiogenesis (Kollmann et al., 2013). The pharmacological inhibition of CDK6 was shown to inhibit the growth differentiation of abnormal leukemic cells (Placke et al., 2014).

CFH may play a role in cutaneous squamous cell carcinoma progression (Riihila et al., 2014). CFH may play a key role in the resistance of complement-mediated lysis in various cancer cells and was shown to be over-expressed in NSCLC, which was associated with poorer prognosis (Cui et al., 2011).

An inactivating mutation of CLPTM1 was found in prostate cancer cells (Rossi et al., 2005).

CMAS encodes for cytidine monophosphate N-acetylneuraminic acid synthetase, which catalyzes the activation of sialic acid and its transformation to a cytidine monophosphate diester. The activated sialic acid is used for N-glycosylation, a common post-translational modification during cellular differentiation. The increased expression of sialic acid sugars on the surface of cancer cells is one of well-known tumor characteristics (Bull et al., 2014).

TF (Transferrin) is one of the most widely used tumor-targeted ligands, because TF receptors (TFRs) are over-expressed on malignant cells and play a key role in cellular iron uptake through the interaction with TF (Biswas et al., 2013). The expression level of TFRs has been suggested to correlate with tumor stage or cancer progression (Tortorella and Karagiannis, 2014).

TH1 L might play an important role in regulation of proliferation and invasion in human breast cancer, and could be a potential target for human breast cancer treatment (Zou et al., 2010).

THTPA hydrolysis might be responsible for the antiproliferative effects of Ndrg-1. Ndrg-1 has been shown to reduce the invasion and metastasis of breast, colon, prostate and pancreatic cancer (Kovacevic et al., 2008).

SMYD3 promotes cancer invasion by epigenetic up-regulation of the metalloproteinase MMP-9 (Medjkane et al., 2012). Expression of SMYD3 is undetectable or very weak in many types of normal human tissue, whereas over-expression of SMYD3 has been linked with the development and progression of gastric, colorectal, hepatocellular, prostate and breast cancers (Hamamoto et al., 2006; Liu et al., 2014; Liu et al., 2013a).

A link between STAT2 and tumorigenesis was observed in transgenic mice lacking STAT2 (Yue et al., 2015) or expressing constitutively IFN-α in the brain (Wang et al., 2003).

TACC3 is over-expressed in many human cancers, including ovarian cancer, breast cancer, squamous cell carcinoma and lymphoma (Ma et al., 2003; Jacquemier et al., 2005; Lauffart et al., 2005).

SPBP is also shown to repress the transcriptional activity of estrogen receptor a (ERa). Over-expression of SPBP inhibited the proliferation of an ERa-dependent breast cancer cell line (Gburcik et al., 2005). In the cell nucleus, SPBP displays relatively low mobility and is enriched in chromatin dense regions, clearly indicating that it is a chromatin binding protein (Darvekar et al., 2012). TCF20 is important for enhanced induction of proteins involved in the cellular defensive program against oxidative stress (Darvekar et al., 2014).

C3 is a prominent element of the inflammatory tumor microenvironment (Rutkowski et al., 2010) and activation can give a tumor growth advantage (Markiewski et al., 2008). Enzymatic cleavage of C3 leads to the production of the anaphylatoxin C3a, an inflammatory mediator and chemoattractant, and C3b (Sahu et al., 1998).

CLN3 is an anti-apoptotic gene in NT2 neuronal precursor cells and a few types of cancers (Zhu et al., 2014b). It is involved in intracellular trafficking and regulation in neuronal and non-neuronal cells (Rakheja et al., 2008; Getty and Pearce, 2011) and it is implicated in several important signaling pathways (Persaud-Sawin et al., 2002). CLN3 mRNA and protein are over-expressed in a number of cancer cell lines including breast, colon, malignant melanoma, prostate, ovarian, neuroblastoma, and glioblastoma multiforme, but not lung or pancreatic cancer cell lines (Rylova et al., 2002).

SLC13A5 is one of 7 CIMP-marker genes. CIMP (CpG island methylator phenotype) of clear cell renal cell carcinomas (ccRCCs) is characterized by accumulation of DNA methylation at CpG islands and poorer patient outcome (Tian et al., 2014; Arai et al., 2012).

SLC35B2 is involved in in coordinated transcriptional regulation during induction of sialyl sulfo-Lex glycan biosynthesis during acute inflammation (Huopaniemi et al., 2004) and in the sulfation of the 6-sulfolactosamine epitope in a human colorectal carcinoma cell line (Kamiyama et al., 2006). Colorectal carcinoma cell lines as well as human colorectal tissues express SLC35B2 (Kamiyama et al., 2011).

PLOD1 expression is associated with human breast cancer progression (Gilkes et al., 2013).

PRDX5 is up-regulated in many malignant tumors (Urig and Becker, 2006) and inhibition of PRDX5 could prevent the tumor initiation and progression, suggesting PRDX5 to be a promising target for cancer therapy. Its highly nucleophilic and accessible selenocysteine active site might be the prime target for drug design (Liu et al., 2012).

Increased expression of PSMD8 in the peripheral lung may be potentially informative as to what critical cell populations are involved in the development of invasive cancers (Zhou et al., 1996).

SNRPD1 is a core spliceosomal protein, which is up-regulated in malignant tumors.

Reduced expression of the SPTBN1 is associated with worsened prognosis in pancreatic cancer (Jiang et al., 2010).

SQSTM1 functions as a signaling hub for various signal transduction pathways, such as NF-κB signaling, apoptosis, and Nrf2 activation, whose dysregulation is associated with Paget disease of bone and tumorigenesis (Komatsu et al., 2012).

PCNA expression predicts survival in anorectal malignant melanoma (Ben-lzhak et al., 2002). A cancer-associated isoform of PCNA (caPCNA) was identified that contained an unusual pattern of methyl ester groups on numerous glutamic and aspartic acid residues within PCNA (Hoelz et al., 2006).

Depleting SRP54 in several tumor cell lines did not produce overt cellular phenotypes, such as growth arrest or death, even in cells selected for stable reduction of SRP components (Ren et al., 2004).

At the molecular level, STAT1 inhibits the proliferation of both mouse and human tumor cells treated with IFN-γ via its ability to increase the expression of cyclin-dependent kinase inhibitor p21Cip1, or to decrease c-myc expression (Ramana et al., 2000). The anti-tumor activity of STAT1 is further supported by its ability to inhibit angiogenesis and tumor metastasis in mouse models (Huang et al., 2002). Increased STAT1 mRNA levels were shown to be part of a molecular signature associated with better prediction of the metastatic outcome for patients with hormone receptor negative and triple-negative breast cancers (Yau et al., 2010).

Fine-needle aspirate samples from follicular neoplasms demonstrated that malignant nodules over-express STT3A as compared with benign disease (Patel et al., 2011).

A meta-analysis showed that the STXBP4/COX11 rs6504950 polymorphism is significantly correlated with breast cancer risk (Tang et al., 2012).

A peptide consisting or consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The present invention further relates to a peptide according to the present invention, wherein said peptide is modified and/or includes non-peptide bonds as described herein below.

The present invention further relates to a peptide according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells, i.e. binds to dendritic cells.

The present invention further relates to a nucleic acid, encoding for a peptide according to the present invention. The present invention further relates to the nucleic acid according to the present invention that is DNA, cDNA, PNA, RNA or combinations thereof.

The present invention further relates to an expression vector capable of expressing, expressing, and/or presenting a nucleic acid according to the present invention.

The present invention further relates to a peptide according to the present invention, a nucleic acid according to the present invention or an expression vector according to the present invention for use in medicine.

The present invention further relates to antibodies as described further below, and methods of making them. Preferred are antibodies that are specific for the peptides of the present invention, and/or for the peptides of the present invention when bound to their MHC. Preferred antibodies can be monoclonal.

The present invention further relates to T-cell receptors (TCR), in particular soluble TCR (sTCRs) targeting the peptides according to the invention and/or the peptide-MHC complexes thereof, and methods of making them.

The present invention further relates to antibodies or other binding molecules targeting the peptides according to the invention and/or the peptide-MHC complexes thereof, and methods of making them.

The present invention further relates to a host cell comprising a nucleic acid according to the present invention or an expression vector as described before. The present invention further relates to the host cell according to the present invention that is an antigen presenting cell. The present invention further relates to the host cell according to the present invention, wherein the antigen presenting cell is a dendritic cell.

The present invention further relates to aptamers. Aptamers (see for example WO 2014/191359 and the literature cited therein) are short single-stranded nucleic acid or peptide molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumour cell lines have been identified.

DNA aptamers can be selected to reveal broad-spectrum recognition properties for various cancer cells, and particularly those derived from solid tumours, while non-tumourgenic and primary healthy cells are not recognized. If the identified aptamers recognise not only a specific tumour sub-type but rather interact with a series of tumours, this renders the aptamers applicable as so-called broad-spectrum diagnostics and therapeutics.

Further, investigation of cell-binding behaviour with flow cytometry showed that aptamers revealed very good apparent affinities in the nanomolar range.

Aptamers are useful for diagnostic and therapeutic purposes. Further, it could be shown that some of the aptamers are taken up by tumour cells and thus can function as molecular vehicles for the targeted delivery of anti-cancer agents such as siRNA into tumour cells.

Aptamers can be selected against complex targets such as cells and tissues and complexes of the peptides comprising, preferably consisting of, a sequence according to any of SEQ ID NO 1 to SEQ ID NO 300, according to the present invention with the MHC molecule, using the cell-SELEX (Systematic Evolution of Ligands by Exponential enrichment) technique.

As used herein, the term "scaffold" refers to a molecule that specifically binds to an (eg antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and Single domain antigen binding (SDAB) molecules, apatmers, (soluble) TCRs and (modified) cells such as allogenic or autologous T cells.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualisation of the bound aptamer by fluorescence or laser scanning microscopy or flow cytometry.

Each scaffold can be conjugated with a second active molecule such as for example IL-21, anti-CD3, anti-CD28. Polypeptide scaffolds are described, for example, in the background section of WO 2014/071978A1, and the references as cited therein.

The present invention further relates to a method of producing a peptide according to the present invention, said method comprising culturing the host cell according to the present invention, and isolating the peptide from the host cell and/or its culture medium.

The present invention further relates to an in vitro method for producing activated T-cells, the method comprising contacting in vitro T cells with antigen loaded human class I or II MHC molecules expressed on the surface of a suitable antigen-presenting cell for a period of time sufficient to activate said T cells in an antigen specific manner, wherein said antigen is at least one peptide according to the present invention. The present invention further relates to a method, wherein the antigen is loaded onto class I or II MHC molecules expressed on the surface of a suitable antigen-presenting cell by contacting a sufficient amount of the antigen with an antigen-presenting cell.

The present invention further relates to the method according to the present invention, wherein the antigen-presenting cell comprises an expression vector capable of expressing said peptide containing SEQ ID NO: 1 to SEQ ID NO: 300, or a variant amino acid sequence thereof.

The present invention further relates to activated T cells, produced by the method according to the present invention, which selectively recognize a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated T-cell according to the present invention as a medicament or in the manufacture of a medicament.

The present invention further relates to a use according to the present invention, wherein said medicament is a vaccine, a cell, a cell population, such as, for example, a cell line, sTCRs and monoclonal antibodies.

The present invention further relates to a use according to the present invention, wherein the medicament is active against cancer.

The present invention further relates to a use according to the present invention, wherein said cancer cells are cells of HCC.

The present invention further relates to particular marker proteins and biomarkers based on the peptides according to the present invention that can be used in the diagnosis and/or prognosis of HCC.

Furthermore, the present invention relates to the use of these novel targets for cancer treatment.

Further, the present invention relates to a method for producing a personalized anti-cancer vaccine for an individual patient using a database (herein designated also as "warehouse") of pre-screened tumor associated peptides.

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize Class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, or 13 and in case of MHC class II peptides (elongated variants of the peptides of the invention) they can be as long as 14, 15, 16, 17, 18, 19 or 20 amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "the peptides of the present invention" shall also include the peptides consisting of or comprising a peptide as defined above according to SEQ ID NO: 1 to SEQ ID NO: 300.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

Table 6: Expression frequencies F of HLA-A*02 and HLA-A*24 and the most frequent HLA-DR serotypes. Frequencies are deduced from haplotype frequencies Gf within the American population adapted from Mori et al. (Mori M, et al. HLA gene and haplotype frequencies in the North American population: the National Marrow Donor Program Donor Registry. Transplantation. 1997 Oct. 15; 64(7):1017-27) employing the Hardy-Weinberg formula $F=1-(1-Gf)^2$. Combinations of A*02 or A*24 with certain HLA-DR alleles might be enriched or less frequent than expected from their single frequencies due to linkage disequilibrium. For details refer to Chanock et al. (S. J. Chanock, et al (2004) HLA-A, -B, -Cw, -DQA1 and DRB1 in an African American population from Bethesda, USA Human Immunology, 65: 1223-1235).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02 or A*24. A vaccine may also include pan-binding MHC class II peptides. Therefore, the vaccine of the invention can be used to treat cancer in patients that are either A*02 positive, A*24 positive or positive for A*02 and A*24, whereas no selection for MHC class II allotypes is necessary due to the pan-binding nature of these peptides.

Combining for example A*02 and A*24 peptides in one vaccine has the advantage that a higher percentage of any patient population can be treated compared with addressing either MHC class I allele alone. While in most populations less than 50% of patients could be addressed by either allele alone, the vaccine of the invention can treat at least 60% of patients in any relevant population. Specifically, the following percentages of patients will be positive for at least one of these alleles in various regions: USA 61%, Western Europe 62%, China 75%, South Korea 77%, Japan 86% (calculated from ww w.allelef requencies. net).

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding (or encoding) for a peptide" refers to a nucleotide sequence coding for the peptide including artificial (man-made) start and stop codons compatible for the biological system the sequence is to be expressed by, for example, a dendritic cell or another cell system useful for the production of TCRs.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent homology", "percent identity" or "percent identical", when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

$$\text{Percent Identity} = 100[1-(C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the Percent Identity as calculated above is about equal to or greater than a specified minimum Percent Identity then the Compared Sequence has the specified minimum Percent Identity to the Reference Sequence even though alignments may exist in which the herein above calculated Percent Identity is less than the specified Percent Identity.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The peptides of the invention can be elongated by up to four amino acids, that is 1, 2, 3 or 4 amino acids can be added to either end in any combination between 4:0 and 0:4.

Combinations of the elongations according to the invention can be depicted from Table 7:

| C-terminus | N-terminus |
| --- | --- |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |
| N-terminus | C-terminus |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 µM. It is also preferred that the substituted peptide be recognized by T cells from more than one individual, at least two, and more preferably three individuals.

Thus, the epitopes of the present invention may be identical to naturally occurring tumor-associated or tumor-specific epitopes or may include epitopes that differ by no more than four residues from the reference peptide, as long as they have substantially identical antigenic activity.

MHC class I molecules can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature.

Since both types of response, CD8 and CD4 dependent, contribute jointly and synergistically to the anti-tumor effect, the identification and characterization of tumor-associated antigens recognized by either CD8-positive T cells (MHC class I molecule) or by CD4-positive T cells (MHC class II molecule) is important in the development of tumor vaccines. It is therefore an object of the present invention, to provide compositions of peptides that contain peptides binding to MHC complexes of either class.

Considering the severe side-effects and expense associated with treating cancer better prognosis and diagnostic methods are desperately needed. Therefore, there is a need to identify other factors representing biomarkers for cancer in general and HCC in particular. Furthermore, there is a need to identify factors that can be used in the treatment of cancer in general and HCC in particular.

The present invention provides peptides that are useful in treating cancers/tumors, preferably HCC that over- or exclusively present the peptides of the invention. These peptides were shown by mass spectrometry to be naturally presented by HLA molecules on primary human HCC samples.

The source gene/protein (also designated "full-length protein" or "underlying protein") from which the peptides are derived were shown to be highly overexpressed in cancer compared with normal tissues—"normal tissues" in relation to this invention shall mean either healthy liver cells or other normal tissue cells, demonstrating a high degree of tumor association of the source genes (see example 2). Moreover, the peptides themselves are strongly over-presented on tumor tissue—"tumor tissue" in relation to this invention shall mean a sample from a patient suffering from HCC, but not on normal tissues (see Example 1).

HLA-bound peptides can be recognized by the immune system, specifically T lymphocytes. T cells can destroy the cells presenting the recognized HLA/peptide complex, e.g. HCC cells presenting the derived peptides.

The peptides of the present invention have been shown to be capable of stimulating T cell responses and/or are over-presented and thus can be used for the production of antibodies and/or TCRs, in particular sTCRs, according to the present invention (see Example 3). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

A "pharmaceutical composition" preferably is preferably a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Especially preferred is a composition and/or the use of said composition, e.g. in the form of a vaccine, comprising the peptides having a sequence according to the SEQ ID NOs 1, 2, 7, 225, 228, 301, 303, and 312 or a scaffold reactive against the peptides having a sequence according to the SEQ ID NOs 1, 2, 7, 225, 228, 301, 303, and 312 and their complexes to MHC molecules.

In addition to being useful for treating cancer, the peptides of the present invention are also useful as diagnostics. Since the peptides were generated from HCC cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for HCC. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Yet another aspect of the present invention then relates to a method of producing said antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen. Respective methods for producing such antibodies and single chain class I major histocompatibility complexes, as well as other tools for the production of these antibodies are disclosed in WO 03/068201, WO 2004/084798, WO 01/72768, WO 03/070752, and Cohen C J, et al. Recombinant antibodies with MHC-restricted, peptide-specific, T-cell receptor-like specificity: new tools to study antigen presentation and TCR-peptide-MHC interactions. J Mol Recognit. 2003 September-October; 16(5):324-32; Denkberg G, et al. Selective targeting of melanoma and APCs using a recombinant antibody with TCR-like specificity directed toward a melanoma differentiation antigen. J Immunol. 2003 Sep. 1; 171(5):2197-207; and Cohen C J, et al. Direct phenotypic analysis of human MHC class I antigen presentation: visualization, quantitation, and in situ detection of human viral epitopes using peptide-specific, MHC-restricted human recombinant antibodies. J Immunol. 2003 Apr. 15; 170(8): 4349-61, which for the purposes of the present invention are all explicitly incorporated by reference in their entireties.

Preferably, the antibody is binding with a binding affinity of below 20 nanomolar, preferably of below 10 nanomolar, to the complex, which is regarded as "specific" in the context of the present invention.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, Liddy N, et al. Monoclonal TCR-redirected tumor cell killing. Nat Med 2012 June; 18(6):980-987). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (see Boulter J M, et al. Stable, soluble T-cell receptor molecules for crystallization and therapeutics. Protein Eng 2003 September; 16(9):707-711; Card K F, et al. A soluble single-chain T-cell receptor IL-2 fusion protein retains MHC-restricted peptide specificity and IL-2 bioactivity. Cancer Immunol Immunother 2004 April; 53(4): 345-357; and Willcox B E, et al. Production of soluble alphabeta T-cell receptor heterodimers suitable for biophysical analysis of ligand binding. Protein Sci 1999 November; 8 (11):2418-2423). The T-cell receptor can be linked to toxins, drugs, cytokines (see, for example, US 2013/ 0115191), domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/ 057586A1.

In addition, the peptides and/or the TCRs or antibodies or other binding molecules of the present invention can be used to verify a pathologist's diagnosis of a cancer based on a biopsied sample.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (J. Pinheiro, et al. The nlme Package: Linear and Nonlinear Mixed Effects Models. 2007) adjusting for multiple testing by False Discovery Rate (Y. Benjamini and Y. Hochberg. Controlling the False Discovery Rate: A Practical and Powerful Approach to Multiple Testing. Journal of the Royal Statistical Society. Series B (Methodological), Vol. 57 (No. 1):289-300, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from HCC samples (N=16 A*02-positive samples including thirteen A*02:01-positive samples, N=15 A*24-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 31 HCC patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from HCC tissue samples were purified and HLA-associated peptides were isolated and analyzed by LC-MS (see examples). All TUMAPs contained in the present application were identified with this approach on primary HCC samples confirming their presentation on primary HCC.

TUMAPs identified on multiple HCC tumor and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention relates to a peptide comprising a sequence that is selected from the group consisting of SEQ ID NO: 1 to SEQ ID NO: 300, or a variant thereof which is at least 90% homologous (preferably identical) to SEQ ID NO: 1 to SEQ ID NO: 300 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 300 or a variant thereof which is at least 90% homologous (preferably identical) to SEQ ID NO: 1 to SEQ ID NO: 300, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 300.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of HCC.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 300 or said variant amino acid sequence.

The present invention further relates to the use of any peptide described, a nucleic acid ac-cording to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are HCC cells or other solid or haematological tumor cells such as pancreatic cancer, brain cancer, kidney cancer, colon or rectal cancer, or leukemia.

The present invention further relates to particular marker proteins and biomarkers based on the peptides according to the present invention, herein called "targets" that can be used in the diagnosis and/or prognosis of HCC. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a HCC marker polypeptide, delivery of a toxin to a HCC cell expressing a cancer marker gene at an increased level, and/or inhibiting the activity of a HCC marker polypeptide) according to the invention.

Whenever possible, the antibodies of the invention may be purchased from commercial sources. The antibodies of the invention may also be generated using well-known methods. The skilled artisan will understand that either full length HCC marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 300 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the HCC marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Harlow and Lane, Antibodies: A Laboratory Manual, Cold Spring Harbor Laboratory Press, Cold Spring Harbor, N.Y., 1988, new 2nd edition 2013). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating HCC, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

Because the peptides as mentioned in the Tables above of the invention and thus their underlying polypeptides are highly expressed in HCC, and are expressed at rather to extremely low levels in normal cells, the inhibition of a protein selected from the group consisting of protein products of the following genes: Preferred for the inhibition and for antibodies and/or TCRs against are GLUL, GPAM, PLIN2, SLC16A1, SLC9A3R1, PCBD1, SEC16A, AKR1C4, ABCB11, HAL, CYP2E1, C4A, C4B, ALDH1L1, CRP, ACSL4, EEF2, HLTF, FBXO22, GALK1, TMCO1, TMEM33, ZNF318, IPO9, AMACR, C1QTNF3, CYP4F8, CYP4F3, CYP4F11, CYP4F12, CYP4F2, MOCOS, A1CF, COL18A1, HPR, LBP, C19orf80, CFHR5, ITIH4, TMEM110, LARP4, LMF2, SLC10A5, and SLC16A11; still preferred for the inhibition and for antibodies and/or TCRs against are ANKFY1, Cl 2orf44, Cl 6orf58, CPSF1, DCAF8, PEX19, DDX11, DDX12P, DECR2, NME4, DENND5B, DYM, EDC4, ERI3, FAM20A, FNDC3A, GPR107, GYG2, HEATR2, IFT81, KCTD3, SHKBP1, KIAA1324L, KLHL24, MARCH6, MBTPS2, MIR1279, CPSF6, NOC4L, NXF1, PANK2, PCNXL3, PIPSL, PSMD4, PSMD14, SLC35B1, TCP11L2, THNSL2, THOC2, TOMM5, TRAPPC6B, TRIM54, TRIM55, TRIM63, UGGT2, URB1, VPS54, WIZ, ZNF451, RFTN2, SCFD1, SERINC5, CCT7P2, CMAS, ANKS1A, C17orf70, CCT7, CDK5RAP2, CLPTM1, and most preferred for the inhibition and for antibodies and/or TCRs against are APOB, FASN, and/or COPA; and expression or of the activity of these markers may be preferably integrated into a therapeutic strategy, e.g. for treating or preventing HCC.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids can be delivered by a variety of approaches. For example, antisense oligonucleotides or antisense RNA can be directly administered (e.g., by intravenous injection) to a subject in a form that allows uptake into tumor cells. Alternatively, viral or plasmid vectors that encode antisense RNA (or RNA fragments) can be introduced into cells in vivo. Antisense effects can also be induced by sense sequences; however, the extent of phenotypic changes is highly variable. Phenotypic changes induced by effective antisense therapy are assessed according to changes in, e.g., target mRNA levels, target protein levels, and/or target protein activity levels.

In a specific example, inhibition of HCC target/marker function by antisense gene therapy may be accomplished by direct administration of antisense tumor marker RNA to a subject. The antisense tumor marker RNA may be produced and isolated by any standard technique, but is most readily produced by in vitro transcription using an antisense tumor marker cDNA under the control of a high efficiency promoter (e.g., the T7 promoter). Administration of anti-sense tumor marker RNA to cells can be carried out by any of the methods for direct nucleic acid administration described below.

An alternative strategy for inhibiting the function of a protein selected from the group consisting of the abovementioned proteins, and most preferred of APOB, FASN, and/or COPA, involves use of a nucleic acid (e.g. siRNA, or a nucleic acid coding for an anti-protein antibody or a portion thereof, which can be transferred into cancer cells or other cells, leading to intracellular antibody expression and secretion), a protein or small molecule, or any other compound targeting the expression, translation, and/or biological function of this protein.

In the methods described above, which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for inhibition of HCC marker protein expression. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as Lipofectin, Lipofectamine (GIBCO-25 BRL, Inc., Gaithersburg, Md.), Superfect (Qiagen, Inc. Hilden, Germany) and Transfectam (Promega Biotec, Inc., Madison, Wis., US), as well as other liposomes developed according to procedures standard in the art. In addition, the nucleic acid or vector of this invention can be delivered in vivo by electroporation, the technology for which is available from Genetronics, Inc. (San Diego, US) as well as by means of a Sonoporation machine (ImaRx Pharmaceutical Corp., Tucson, Ariz., US).

As one example, vector delivery can be via a viral system, such as a retroviral vector system that can package a recombinant retroviral genome. The recombinant retrovirus can then be used to infect and thereby deliver to the infected cells antisense nucleic acid that inhibits expression of a protein selected from the group consisting of the abovementioned proteins. The exact method of introducing the altered nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

As mentioned above, the present invention thus provides a peptide comprising a sequence that is selected from the group of consisting of SEQ ID NO: 1 to SEQ ID NO: 300 or a variant thereof which is 90% homologous to SEQ ID NO: 1 to SEQ ID NO: 300, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see Percent Identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other analysis tools are provided by public databases.

A person skilled in the art will be able to assess, whether T cells induced by a variant of a specific peptide will be able to cross-react with the peptide itself (Fong L, et al. Altered peptide ligand vaccination with Flt3 ligand expanded dendritic cells for tumor immunotherapy. Proc Natl Acad Sci USA. 2001 Jul. 17; 98(15):8809-14; Zaremba S, et al. Identification of an enhancer agonist cytotoxic T lymphocyte peptide from human carcinoembryonic antigen. Cancer Res. 1997 Oct. 15; 57(20):4570-7; Colombetti S, et al. Impact of orthologous melan-A peptide immunizations on the anti-self melan-A/HLA-A2 T cell cross-reactivity. J Immunol. 2006 Jun. 1; 176(11):6560-7; Appay V, et al. Decreased specific CD8+ T cell cross-reactivity of antigen recognition following vaccination with Melan-A peptide. Eur J Immunol. 2006 July; 36(7):1805-14).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 300. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature (Godkin A, et al. Use of eluted peptide sequence data to identify the binding characteristics of peptides to the insulin-dependent diabetes susceptibility allele HLA-DQ8 (DQ 3.2). Int Immunol. 1997 June; 9(6): 905-11) and databases (Rammensee H. et al. SYFPEITHI: database for MHC ligands and peptide motifs. Immunogenetics. 1999 November; 50(3-4):213-9), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 300, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The amino acid residues that do not substantially contribute to interactions with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

Those amino acid residues that do not substantially contribute to interactions with the TCR can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 8

Variants and motif of the peptides according to SEQ ID NO: 1, 117, and 246

| | Position | | | | | | | | |
|---|---|---|---|---|---|---|---|---|---|
| | 1 | 2 | 3 | 4 | 5 | 6 | 7 | 8 | 9 |
| SEQ ID NO. 1 Variants | V | M | A | P | F | T | M | T | I |
| | | | | | | | | | V |
| | | | | | | | | | L |
| | | | | | | | | | A |
| | | L | | | | | | | V |
| | | L | | | | | | | L |
| | | L | | | | | | | |
| | | L | | | | | | | A |
| | | A | | | | | | | V |

TABLE 8-continued

Variants and motif of the peptides according to SEQ ID NO: 1, 117, and 246

| | Position | | | | | | | | |
|---|---|---|---|---|---|---|---|---|---|
| | 1 | 2 | 3 | 4 | 5 | 6 | 7 | 8 | 9 |
| | | A | | | | | | | L |
| | | A | | | | | | | |
| | | A | | | | | | | A |
| | | V | | | | | | | V |
| | | V | | | | | | | L |
| | | V | | | | | | | |
| | | V | | | | | | | A |
| | | T | | | | | | | V |
| | | T | | | | | | | L |
| | | T | | | | | | | |
| | | T | | | | | | | A |
| | | Q | | | | | | | V |
| | | Q | | | | | | | L |
| | | Q | | | | | | | |
| | | Q | | | | | | | A |
| SEQ ID NO 246 Variants | K | L | I | S | S | Y | Y | N | V |
| | | I | | | | | | | L |
| | | I | | | | | | | I |
| | | I | | | | | | | |
| | | I | | | | | | | A |
| | | M | | | | | | | L |
| | | M | | | | | | | I |
| | | M | | | | | | | |
| | | M | | | | | | | A |
| | | A | | | | | | | L |
| | | A | | | | | | | I |
| | | A | | | | | | | |
| | | A | | | | | | | A |
| | | V | | | | | | | L |
| | | V | | | | | | | I |
| | | V | | | | | | | |
| | | V | | | | | | | A |
| | | T | | | | | | | L |
| | | T | | | | | | | I |
| | | T | | | | | | | |
| | | T | | | | | | | A |
| | | Q | | | | | | | L |
| | | Q | | | | | | | I |
| | | Q | | | | | | | |
| | | Q | | | | | | | A |
| SEQ ID NO. 117 Variants | Y | A | F | P | K | S | I | T | V |
| | | | | | | | | | L |
| | | | | | | | | | I |
| | | | | | | | | | A |
| | | M | | | | | | | L |
| | | M | | | | | | | I |
| | | M | | | | | | | |
| | | M | | | | | | | A |
| | | L | | | | | | | L |
| | | L | | | | | | | I |
| | | L | | | | | | | |
| | | L | | | | | | | A |
| | | V | | | | | | | L |
| | | V | | | | | | | I |
| | | V | | | | | | | |
| | | V | | | | | | | A |
| | | T | | | | | | | L |
| | | T | | | | | | | I |
| | | T | | | | | | | |
| | | T | | | | | | | A |
| | | Q | | | | | | | L |
| | | Q | | | | | | | I |
| | | Q | | | | | | | |
| | | Q | | | | | | | A |

Longer peptides may also be suitable. It is also possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

In a particularly preferred embodiment of the invention the peptide consists or consists essentially of an amino acid sequence according to SEQ ID NO: 1 to SEQ ID NO: 300.

"Consisting essentially of" shall mean that a peptide according to the present invention, in addition to the sequence according to any of SEQ ID NO: 1 to SEQ ID NO 300 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH═CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Solid-phase peptide synthesis under continuous-flow conditions. Proc Natl Acad Sci USA. May 1981; 78(5): 2791-2795), and references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethandithiol, phenol, anisole and water, the exact choice depending on the constituent amino acids of the peptide being synthesized. Also a combination of solid phase and solution phase methodologies for the synthesis of peptides is possible (see, for example, Bruckdorfer et al., 2004, and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA.

The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Diagnosis of sickle cell anemia and beta-thalassemia with enzymatically amplified DNA and nonradioactive allele-specific oligonucleotide probes. N Engl J Med. 1988 Sep. 1; 319(9):537-41). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275,104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Small E J, et al. Placebo-controlled phase III trial of immunologic therapy with sipuleucel-T (APC8015) in patients with metastatic, asymptomatic hormone refractory prostate cancer. J Clin Oncol. 2006 Jul. 1; 24(19):3089-94. Rini et al. Combination immunotherapy with prostatic acid phosphatase pulsed antigen-presenting cells (provenge) plus bevacizumab in patients with serologic progression of prostate cancer after definitive local therapy. Cancer. 2006 Jul. 1; 107(1):67-74).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al Nature Medicine 18, 1254-1261 (2012)).

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Karre et al. (Ljunggren, H.-G., and K. Karre. 1985. J. Exp. Med. 162:1745).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 300, or a variant amino acid sequence thereof.

A number of other methods may be used for generating T cells in vitro. For example, autologous tumor-infiltrating lymphocytes can be used in the generation of CTL. Plebanski et al. (Induction of peptide-specific primary cytotoxic T lymphocyte responses from human peripheral blood. Eur J Immunol. 1995 June; 25(6):1783-7) make use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. 2003 (Cutting edge: predetermined avidity of human CD8 T cells expanded on calibrated MHC/anti-CD28-coated microspheres. J Immunol. 2003 Nov. 15; 171(10):4974-8) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to *drosophila* cells and T2 cells, other cells may be used to present antigens such as CHO cells, baculovirus-infected insect cells, bacteria, yeast, vaccinia-infected target cells. In addition plant viruses may be used (see, for example, Porta et al. (1994) Development of cowpea mosaic virus as a high-yielding system for the presentation of foreign peptides. Virology. 1994 Aug. 1; 202(2):949-55) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 300.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattinoni L, et al. Adoptive immunotherapy for cancer: building on success. Nat Rev Immunol. 2006 May; 6(5):383-93. Review. and Morgan R A, et al. Cancer regression in patients after transfer of genetically engineered lymphocytes. Science. 2006 Oct. 6; 314(5796):126-9).

Any molecule of the invention, i.e. the peptide, nucleic acid, antibody, expression vector, cell, activated T cell, T-cell receptor or the nucleic acid encoding it is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Preferably, the medicament of the present invention is a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see for example WO 95/18145). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 300, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

In another aspect, the vaccine comprises at least one peptide having the amino acid sequence set forth in SEQ ID NO: 1 to SEQ ID NO: 300, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

The polynucleotide may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. (Pascolo et al., Human peripheral blood mononuclear cells transfected with messenger RNA stimulate antigen-specific cytotoxic T-lymphocytes in vitro. Cell Mol Life Sci. 2005 August; 62(15):1755-62). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLRS ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-

MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995 The Yin and Yang of T cell costimulation. Science. 1995 Nov. 10; 270(5238):932-3). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich, 1996 Production of vascular endothelial growth factor by human tumors inhibits the functional maturation of dendritic cells Nat Med. 1996 October; 2(10):1096-103).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonal®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3rd Ed., 2000, American Pharmaceutical Association and pharmaceutical press. The composition can be used for a prevention, prophylaxis and/or therapy of adenomateous or cancerous diseases. Exemplary formulations can be found in, for example, EP2112253.

The present invention provides a medicament that useful in treating cancer, in particular HCC and other malignancies.

The present invention is further directed at a kit comprising:

(a) a container containing a pharmaceutical composition as described above, in solution or in lyophilized form;

(b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g.

dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from HCC, the medicament of the invention is preferably used to treat HCC.

The present invention further includes a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of HCC patients with various HLA-A HLA-B and HLA-C alleles. It may contain MHC class I and MHC class II peptides or elongated MHC class I peptides. In addition to the tumor associated peptides collected from several HCC tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And third, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, HCC samples from patients and blood from healthy donors were analyzed in a stepwise approach:

1. HLA ligands from the malignant material were identified by mass spectrometry

2. Genome-wide messenger ribonucleic acid (mRNA) expression analysis was used to identify genes over-expressed in the malignant tissue (HCC) compared with a range of normal organs and tissues 3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.

4. Literature research was performed in order to identify additional evidence supporting the relevance of the identified peptides as TUMAPs 5. The relevance of over-expression at the mRNA level was confirmed by redetection of selected TUMAPs from step 3 on tumor tissue and lack of (or infrequent) detection on healthy tissues.

6. In order to assess, whether an induction of in vivo T-cell responses by the selected peptides may be feasible, in vitro immunogenicity assays were performed using human T cells from healthy donors as well as from HCC patients.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition was specifically designed in such a way that each HLA-A*02 and/or HLA-A*24-positive tumor is expected to express several of the antigens and cover several independent pathways necessary for tumor growth and maintenance. For each of the peptide subsets specific for the two HLA class I alleles (A*02 and A*24) this is independently ensured based on the underlying experimental analyses. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 μm sterile filter. The final bulk solution is obtained.

Final bulk solution is filled into vials and stored at −20° C. until use. One vial contains 700 μL solution, containing 0.578 mg of each peptide. Of this, 500 μL (approx. 400 μg per peptide) will be applied for intradermal injection.

The present invention will now be described in the following examples which describe preferred embodiments thereof, nevertheless, without being limited thereto. For the purposes of the present invention, all references as cited herein are incorporated by reference in their entireties.

Figure 1D:
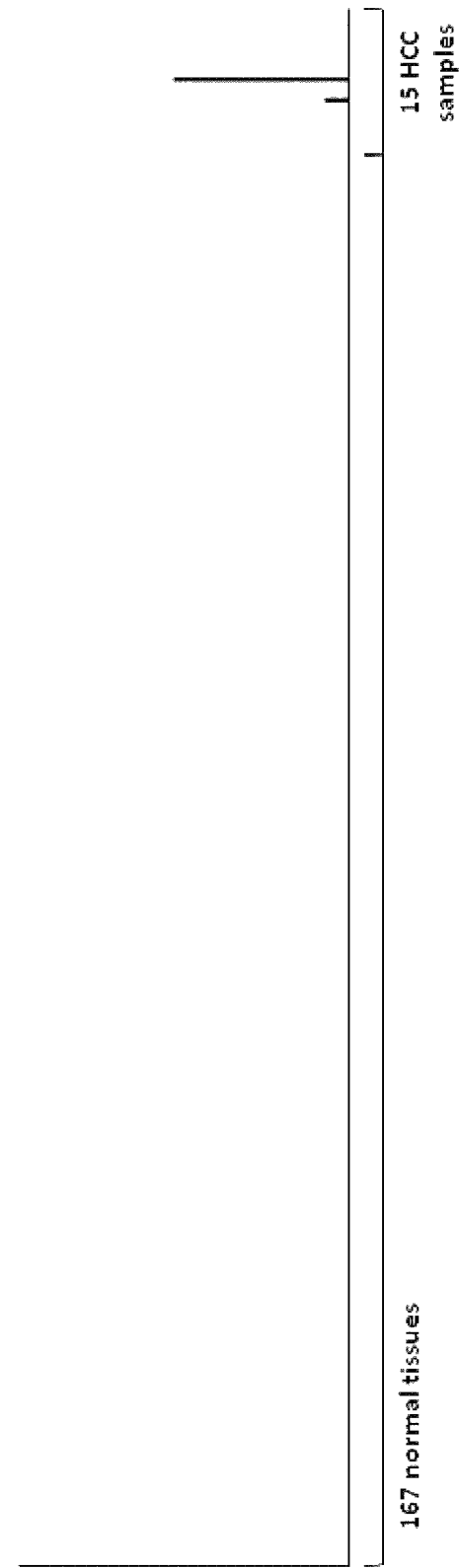
Figure 1G:
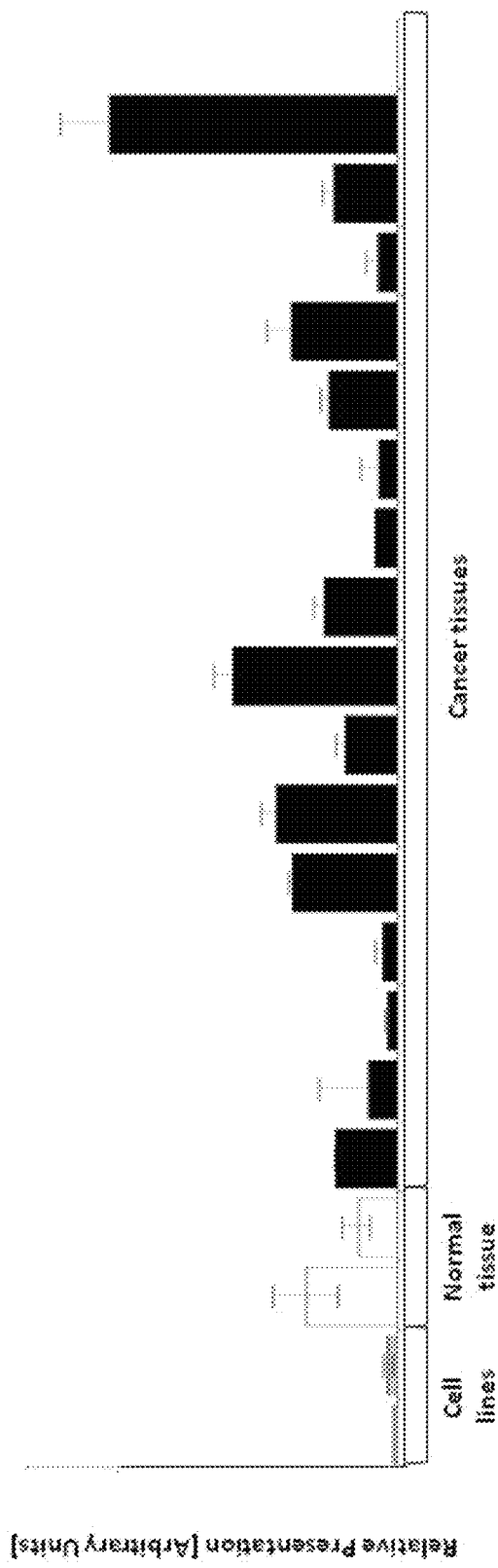
Figure 1M:
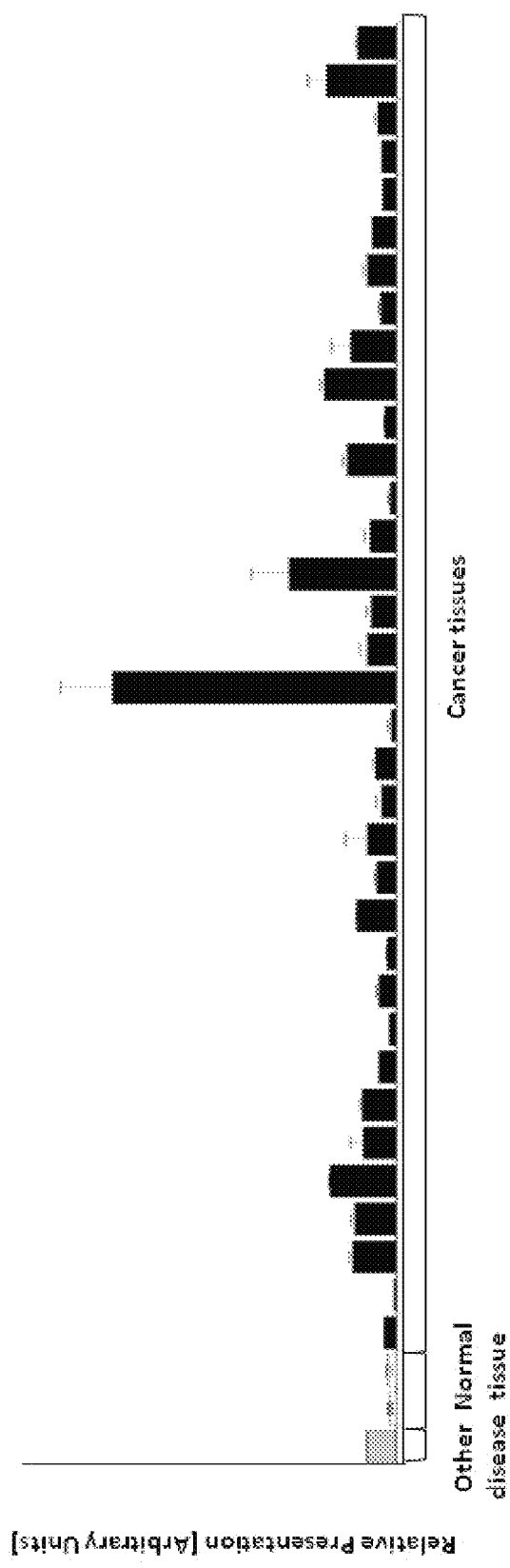

In the Figures,

FIGS. 1A-1M show the over-presentation of various peptides in normal tissues (dark gray) and HCC (light gray). FIG. 1A) APOB, Peptide: ALVDTLKFV (A*02) (SEQ ID NO: 7), tissues from left to right; 1 adipose tissues, 3 adrenal glands, 2 arteries, 2 bone marrows, 7 brains, 3 breasts, 13 colons, 4 esophagi, 2 gallbladders, 3 GI tracts, 3 hearts, 16 kidneys, 4 leukocyte samples, 45 lungs, 1 lymph node, 1 ovary, 7 pancreas, 1 peripheral nerve, 1 pituitary gland, 3 pleuras, 1 prostate, 6 recti, 3 sceletal muscles, 1 serous membrane, 3 skins, 4 spleens, 7 stomachs, 1 testis, 2 thymi, 3 thyroid glands, 2 uteri, 2 veins, and 20 livers; FIG. 1B) ALDH1 L1, Peptide: KLQAGTVFV (A*02) (SEQ ID NO: 2), tissues from left to right: 1 adipose tissues, 3 adrenal glands, 2 arteries, 2 bone marrows, 7 brains, 3 breasts, 13 colons, 4 esophagi, 2 gallbladders, 3 GI tracts, 3 hearts, 16 kidneys, 4 leukocyte samples, 45 lungs, 1 lymph node, 1 ovary, 7 pancreas, 1 peripheral nerve, 1 pituitary gland, 3 pleuras, 1 prostate, 6 recti, 3 sceletal muscles, 1 serous membrane, 3 skins, 4 spleens, 7 stomachs, 1 testis, 2 thymi, 3 thyroid glands, 2 uteri, 2 veins, and 20 livers; FIG. 1C) C8B, Peptide: AYLLQPSQF (A*24) (SEQ ID NO: 200), tissues from left to right: including 2 adrenal glands, 1 artery, 4 brains, 1 breast, 5 colons, 1 hearts, 13 kidneys, 9 lungs, 3 pancreas, 2 recti, 3 skins, 1 spleen, 12 stomachs, 1 thymus, 2 uteri, and 9 livers; FIG. 1D) RAD23B Peptide: KIDEKNFVV (SEQ ID NO: 63) 1 serous membrane, 1 adipose tissue, 3 adrenal glands, 2 arteries, 2 bone marrows, 7 brains, 3 breasts, 13 colons, 2 gallbladders, 3 GI tracts, 3 hearts, 12 kidneys, 4 leukocytes, 19 livers, 43 lungs, 1 lymph node, 1 ovary, 6 pancreases, 1 peripheral nerve, 1 pituitary gland, 3 pleuras, 1 prostate, 6 rectums, 3 skeletal muscles, 3 skins, 4 spleens, 5 stomachs, 1 testis, 2 thymi, 3 thyroid glands, 2 uteri, 2 veins, 4 esophagi; FIG. 1E) RAD23B Peptide: KIDEKNFVV (SEQ ID NO: 63), shown are only samples on which the peptide was presented: 5 cell-lines, 1 normal tissue (1 adrenal gland), 16 cancer tissues (2 brain cancers, 4 liver cancers, 5 lung cancers, 1 rectum cancer, 1 urinary bladder cancer, 3 uterus cancers) (from left to right); FIG. 1F) RFNG RLPPDTLLQQV (SEQ ID NO: 92), shown are only samples on which the peptide was presented: 1 serous membrane, 1 adipose tissue, 3 adrenal glands, 2 arteries, 2 bone marrows, 7 brains, 3 breasts, 13 colons, 2 gallbladders, 3 GI tracts, 3 hearts, 12 kidneys, 4 leukocytes, 19 livers, 43 lungs, 1 lymph node, 1 ovary, 6 pancreases, 1 peripheral nerve, 1 pituitary gland, 3 pleuras, 1 prostate, 6 rectums, 3 skeletal muscles, 3 skins, 4 spleens, 5 stomachs, 1 testis, 2 thymi, 3 thyroid glands, 2 uteri, 2 veins, 4 esophagi; FIG. 1G) RFNG Peptide: RLPPDTLLQQV (SEQ ID NO: 92), shown are only samples on which the peptide was presented: 2 cell-lines, 2 normal tissues (2 adrenal glands), 17 cancer tissues (1 brain cancer, 1 breast cancer, 1 esophageal cancer, 5 liver cancers, 4 lung cancers, 1 ovarian cancer, 1 prostate cancer, 2 urinary bladder cancers, 1 uterus cancer) (from left to right); FIG. 1H) FLVCR1 Peptide: SVWFGPKEV (SEQ ID NO: 104) 1 serous membrane, 1 adipose tissue, 3 adrenal glands, 2 arteries, 2 bone marrows, 7 brains, 3 breasts, 13 colons, 2 gallbladders, 3 GI tracts, 3 hearts, 12 kidneys, 4 leukocytes, 19 livers, 43 lungs, 1 lymph node, 1 ovary, 6 pancreases, 1 peripheral nerve, 1 pituitary gland, 3 pleuras, 1 prostate, 6 rectums, 3 skeletal muscles, 3 skins, 4 spleens, 5 stomachs, 1 testis, 2 thymi, 3 thyroid glands, 2 uteri, 2 veins, 4 esophagi; FIG. 1I) FLVCR1 Peptide: SVWFGPKEV (SEQ ID NO: 104), shown are only samples on which the peptide was presented: 9 cell lines, 1 normal tissue (1 small intestine), 16 cancer tissues (1 brain cancer, 1 breast cancer, 5 liver cancers, 5 lung cancers, 1 skin cancer, 1 stomach cancer, 1 urinary bladder cancer, 1 uterus cancer) (from left to right); FIG. 1J) IKBKAP Peptide: LLFPHPVNQV (SEQ ID NO: 156) 1 serous membrane, 1 adipose tissue, 3 adrenal glands, 2 arteries, 2 bone marrows, 7 brains, 3 breasts, 13 colons, 2 gallbladders, 3 GI tracts, 3 hearts, 12 kidneys, 4 leukocytes, 19 livers, 43 lungs, 1 lymph node, 1 ovary, 6 pancreases, 1 peripheral nerve, 1 pituitary gland, 3 pleuras, 1 prostate, 6 rectums, 3 skeletal muscles, 3 skins, 4 spleens, 5 stomachs, 1 testis, 2 thymi, 3 thyroid glands, 2 uteri, 2 veins, 4 esophagi; FIG. 1K) IKBKAP Peptide: LLFPHPVNQV (SEQ ID NO: 156), shown are only samples on which the peptide was presented: 7 cell-lines, 2 primary cultures, 1 normal tissue (1 colon), 34 cancer tissues (1 bone marrow cancer, 1 breast cancer, 1 colon cancer, 2 esophageal cancers, 2 leukocytic leukemia cancers, 4 liver cancers, 11 lung cancers, 3 lymph node cancers, 5 ovarian cancers, 4 urinary bladder cancers) (from left to right); FIG. 1L) NKD1 Peptide: FLDTPIAKV (SEQ ID NO: 47), 1 serous membrane, 1 adipose tissue, 3 adrenal glands, 2 arteries, 2 bone marrows, 7 brains, 3 breasts, 13 colons, 2 gallbladders, 3 GI tracts, 3 hearts, 12 kidneys, 4 leukocytes, 19 livers, 43 lungs, 1 lymph node, 1 ovary, 6 pancreases, 1 peripheral nerve, 1 pituitary gland, 3 pleuras, 1 prostate, 6 rectums, 3 skeletal muscles, 3 skins, 4 spleens, 5 stomachs, 1 testis, 2 thymi, 3 thyroid glands, 2 uteri, 2 veins, 4 esophagi; FIG. 1M) NKD1 Peptide: FLDTPIAKV (SEQ ID NO: 47), shown are only samples on which the peptide was presented: 1 other disease (encephalocele), 2 normal tissues (1 lung, 1 spleen), 35 cancer tissues (5 brain cancers, 6 colon cancers, 1 esophageal cancer, 6 liver cancers, 9 lung cancers, 1 ovarian cancer, 1 prostate cancer, 4 rectum cancers, 2 stomach cancers) (from left to right).

Figure 2A:
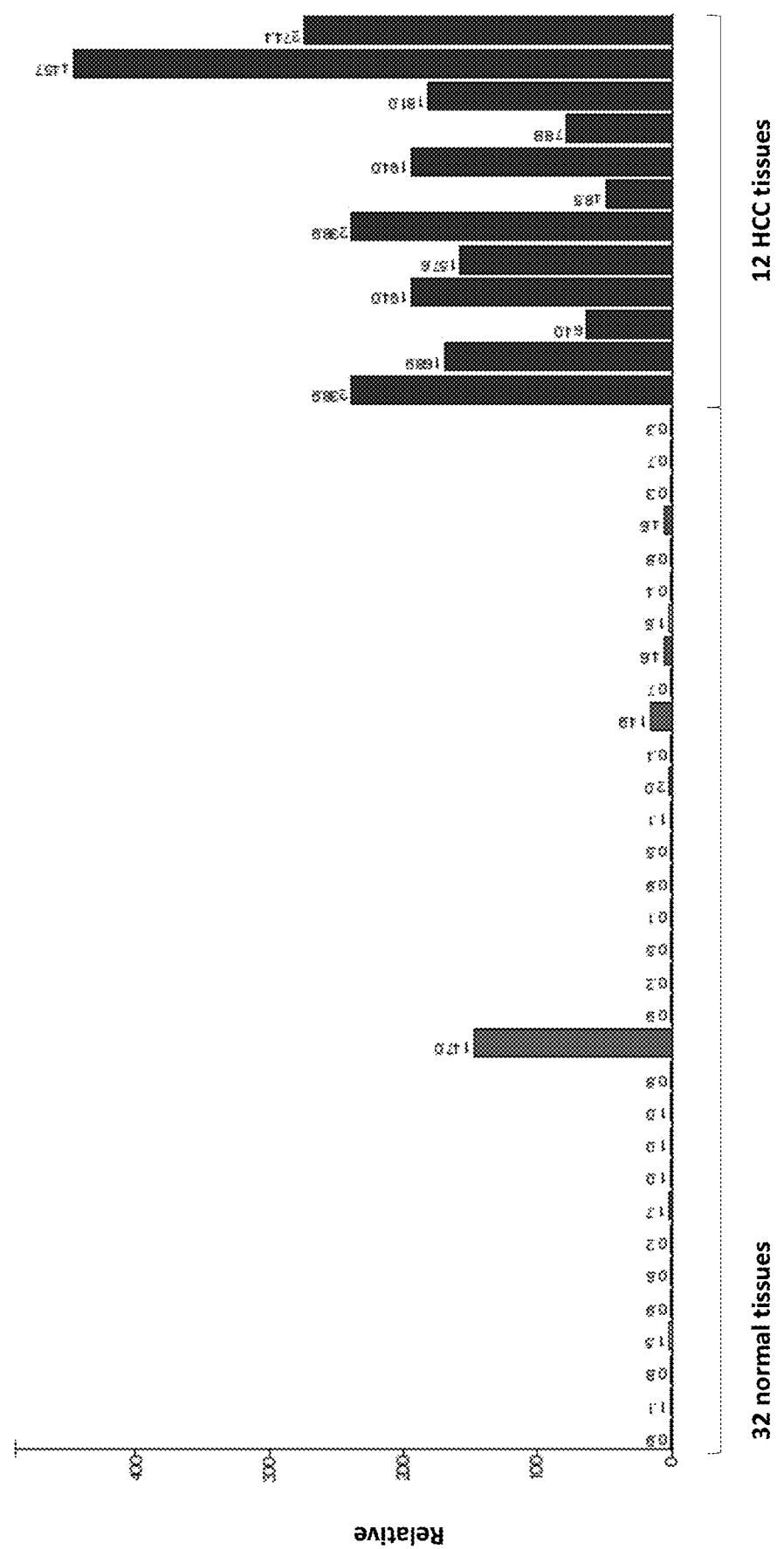
FIGS. 2A-2F show exemplary expression profiles (relative expression compared to normal kidney) of source genes of the present invention that are highly over-expressed or exclusively expressed in HCC in a panel of normal tissues (dark gray) and 12 HCC samples (gray).
Figure 2B:
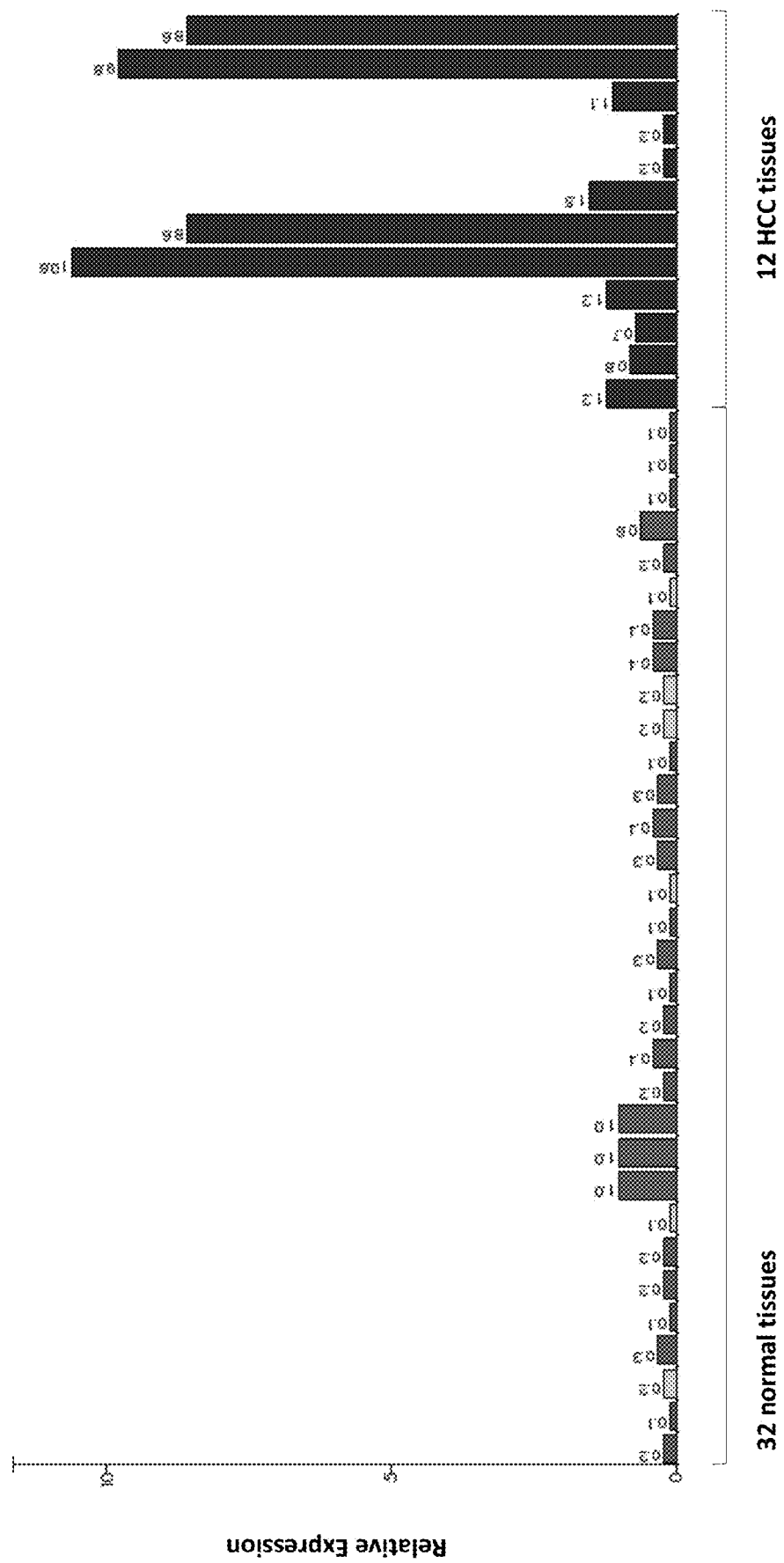
Figure 2C:
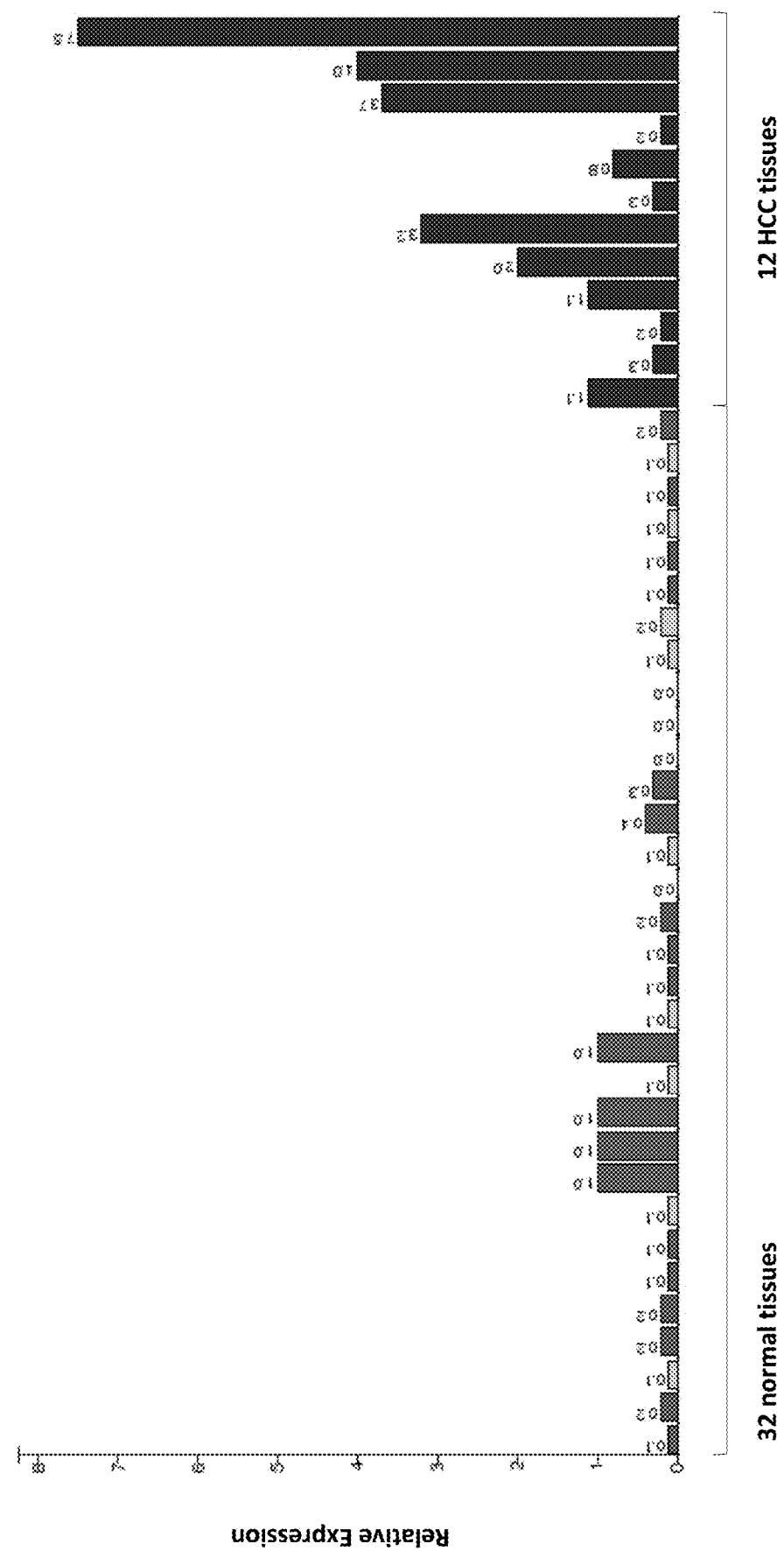
Figure 2D:
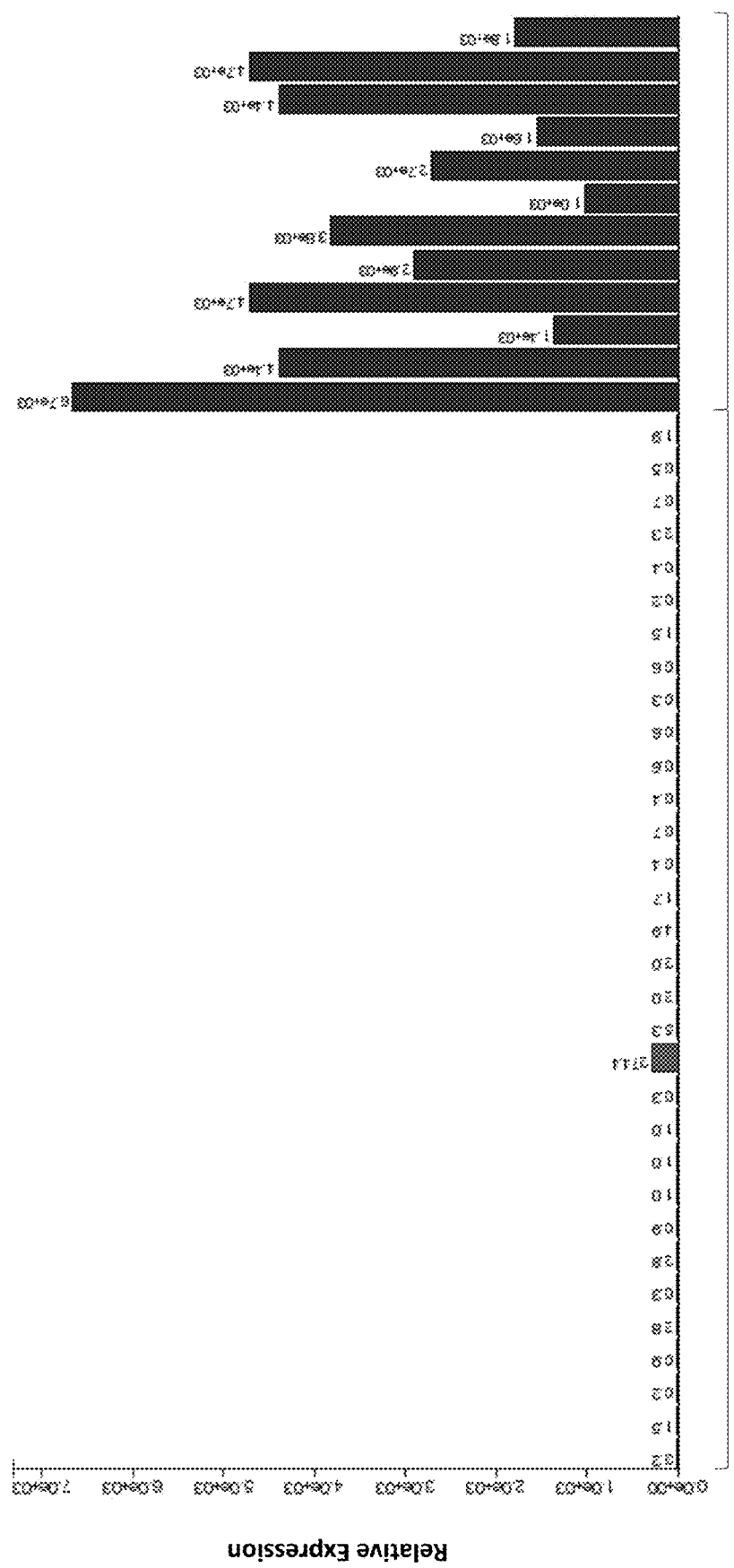
Figure 2E:
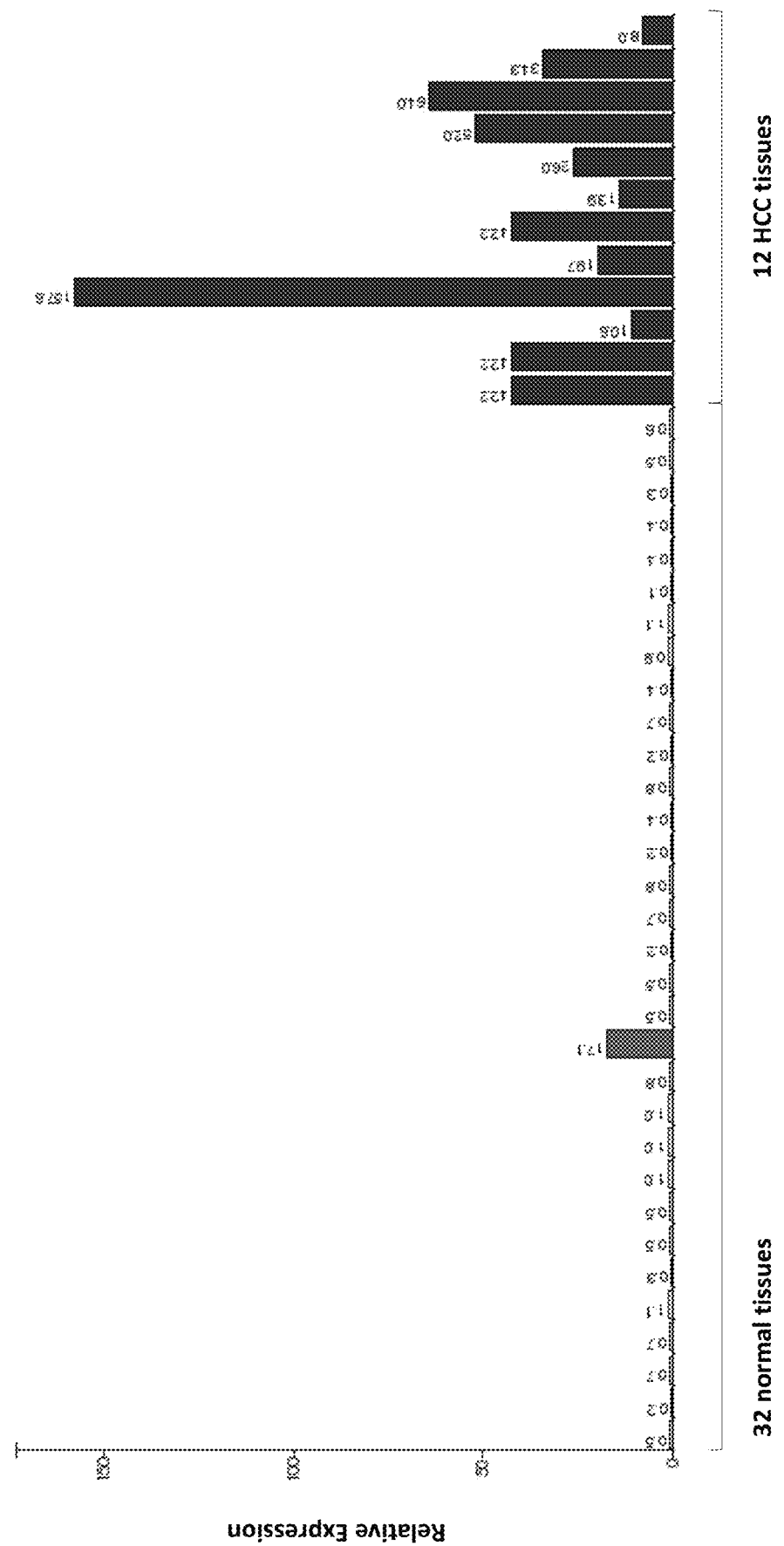
Figure 2F:
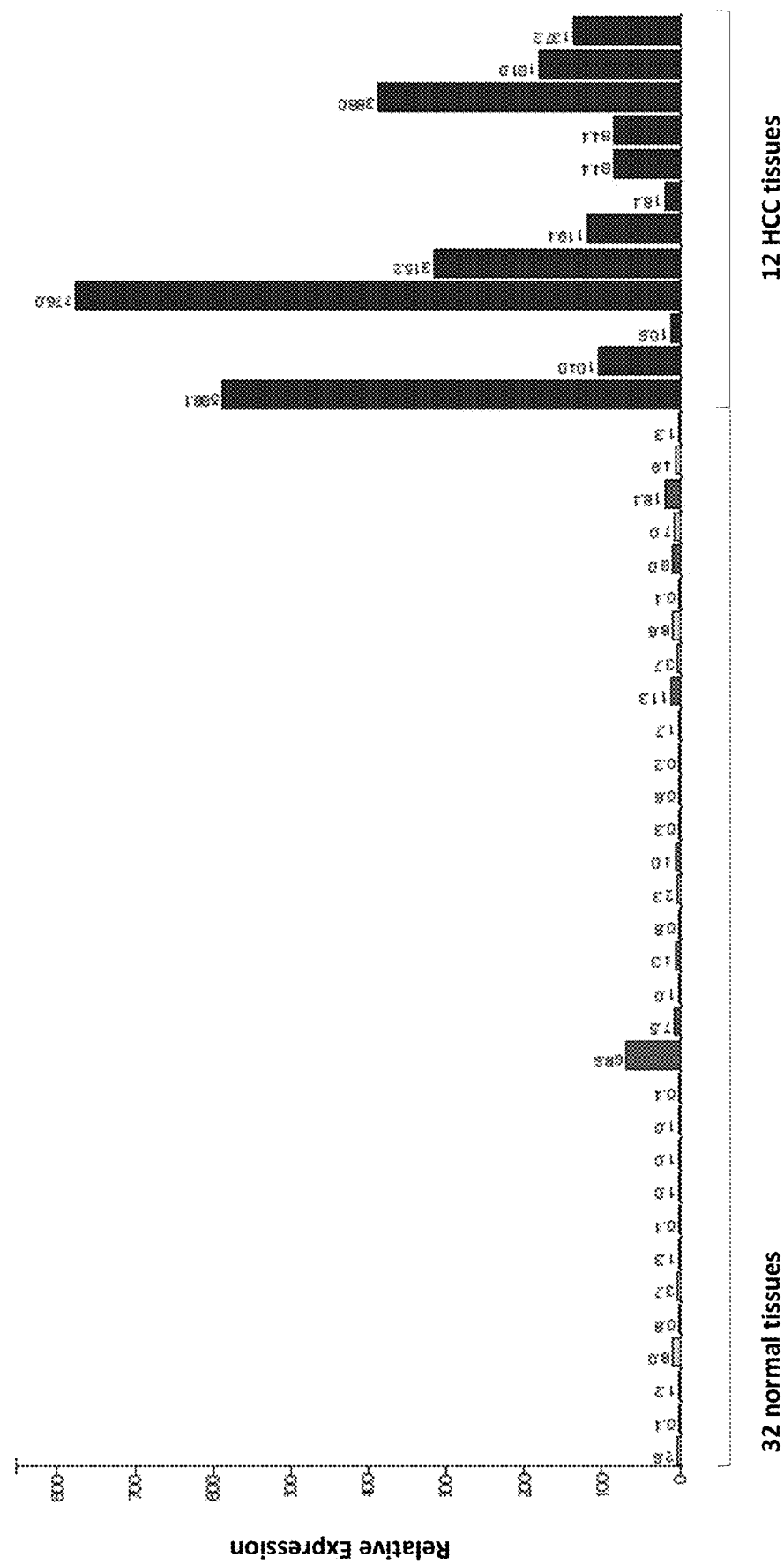

FIGS. 2A-2F show exemplary expression profiles (relative expression compared to normal kidney) of source genes of the present invention that are highly over-expressed or exclusively expressed in HCC in a panel of normal tissues (dark gray) and 12 HCC samples (gray). FIG. 2A) APOB, tissues from left to right: 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1 lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, 1 vein; FIG. 2B) AMACR, tissues from left to right: 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1 lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, 1 vein; FIG. 2C) ALDH1 L1, tissues from left to right: 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, 1 vein; FIG. 2D) FGG, tissues from left to right: 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1 lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, 1 vein; FIG. 2E) C8B, tissues from left to right: 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1 lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, 1 vein; and FIG. 2F) HSD17B6, tissues from left to right: including 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1 lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, and 1 vein.

Figure 3:
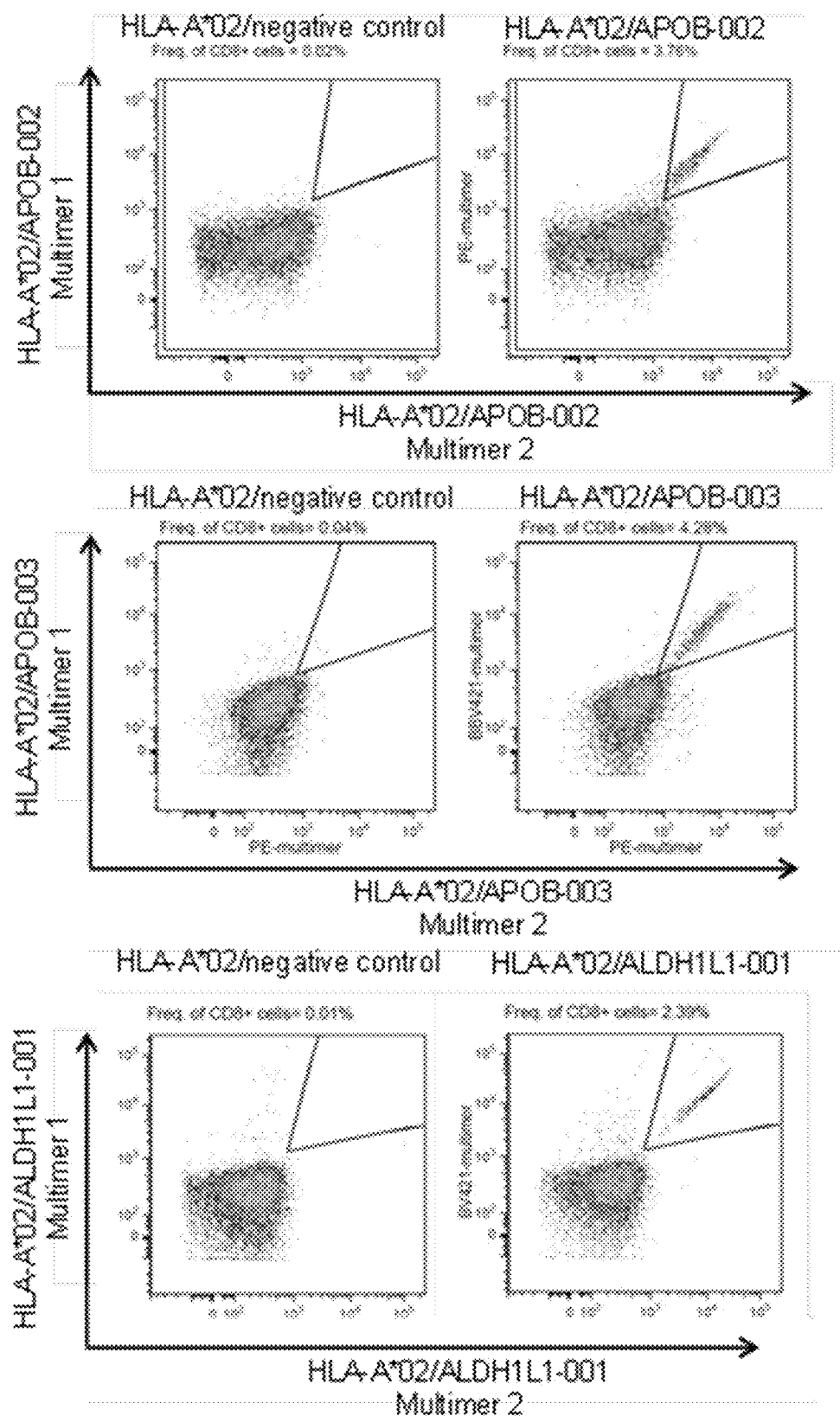
FIG. 3 shows exemplary flow cytometry results after peptide-specific multimer staining.

FIG. 3 shows exemplary flow cytometry results after peptide-specific multimer staining. Further explanations see example 4.

Figure 4A:
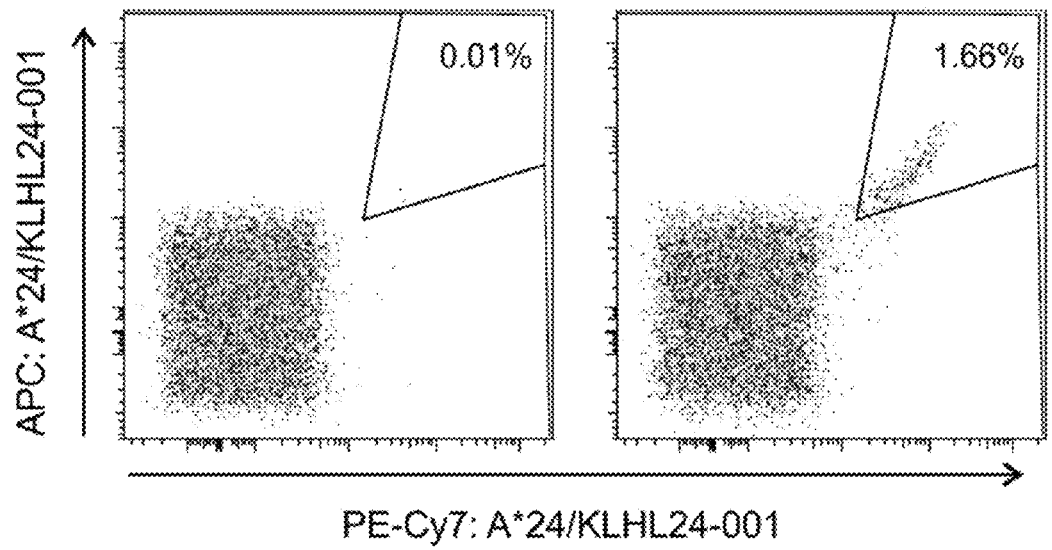
FIGS. 4A and 4B show exemplary flow cytometry results after peptide-specific multimer staining.
Figure 4B:
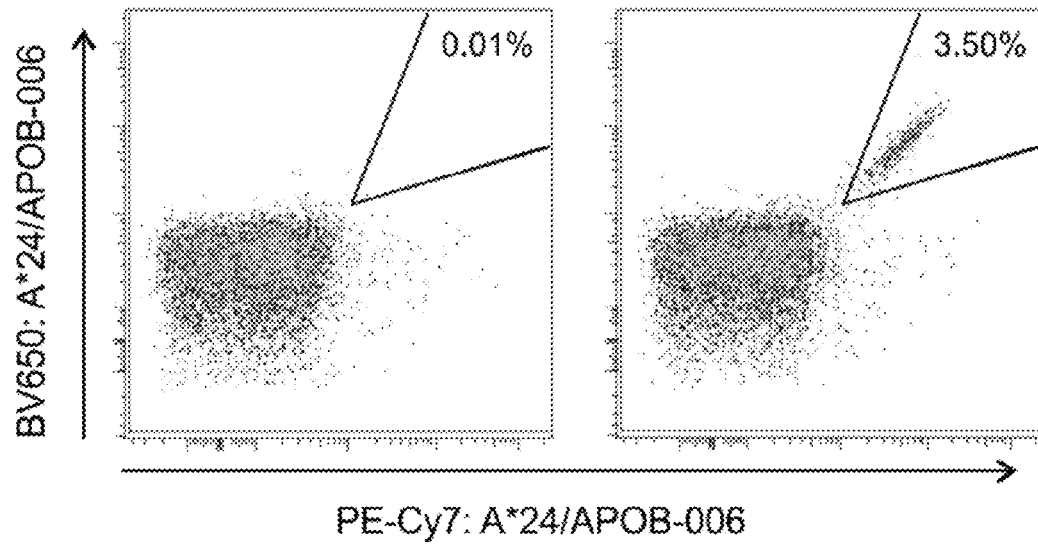

FIGS. 4A and 4B show exemplary flow cytometry results after peptide-specific multimer staining. Further explanations see example 4.

EXAMPLES

Example 1

Identification and Quantitation of Tumor Associated Peptides Presented on the Cell Surface Tissue Samples Patients' tumor tissues were obtained from Universitätsklinik für Allgemeine, Viszeral-und Transplantationschirurgie, Tübingen, Germany; Istituto Nazionale Tumori "Pascale". Molecular Biology and Viral Oncology Unit, Via Mariano, Naples, Italy; Bio-Options Inc., Brea, Calif., USA; ProteoGenex Inc., Culver City, Calif., USA; Asterand Europe, Royston Herts, United Kingdom. Written informed consents of all patients had been given before surgery. Tissues were shock-frozen immediately after surgery and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk, K., 1991; Seeger, F. H. T., 1999) using the HLA-A*02-specific antibody BB7.2, the HLA-A, -B, -C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 µm i.d.× 250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESl source. The LTQ-Orbitrap mass spectrometers were operated in the data-dependent mode using a TOPS strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al. 2007a). The method assumes that the peptide's LC-MS signal area correlates with its abundance in the sample. Extracted features were further processed by charge state deconvolution and retention time alignment (Mueller et al. 2007b; Sturm et al. 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose HCC samples to a baseline of normal tissue samples.

Presentation profiles of exemplary over-presented peptides are shown in FIGS. 1A-1M. Presentation scores for exemplary peptides are shown in Table 8.

TABLE 8

Presentation scores. The table lists peptides that are very highly over-presented on tumors compared to a panel of normal tissues (+++), highly over-presented on tumors compared to a panel of normal tissues (++) or over-presented on tumor compared to a panel of normal tissues (+).

| SEQ ID No. | Sequence | Peptide Presentation |
|---|---|---|
| 1 | VMAPFTMTI | +++ |
| 2 | KLQAGTVFV | +++ |
| 4 | KLQDFSDQL | +++ |
| 5 | ALVEQGFTV | +++ |
| 6 | KLSPTVVGL | +++ |
| 7 | ALVDTLKFV | +++ |
| 8 | KLLEEATISV | + |
| 9 | ALANQKLYSV | + |
| 10 | SLLEEFDFHV | +++ |
| 11 | SLSQELVGV | + |
| 12 | FLAELAYDL | +++ |
| 14 | ALADLTGTVV | +++ |
| 15 | LLYGHTVTV | + |
| 16 | SLLGGNIRL | ++ |
| 17 | RVAS*PTSGV | + |
| 19 | FLEETKATV | +++ |
| 20 | KLSNVLQQV | +++ |
| 21 | QLIEVSSPITL | +++ |
| 22 | RIAGIRGIQGV | +++ |
| 23 | RLYDPASGTISL | + |
| 24 | SLAEEKLQASV | +++ |
| 25 | SLDGKAALTEL | +++ |
| 26 | SLLHTIYEV | +++ |
| 27 | TLPDFRLPEI | +++ |
| 28 | TLQDHLNSL | +++ |
| 29 | YIQDEINTI | +++ |
| 30 | YLGEGPRMV | ++ |
| 31 | YQMDIQQEL | ++ |
| 32 | ALNAVRLLV | +++ |
| 33 | LLHGHIVEL | + |
| 34 | SLAEGTATV | +++ |
| 38 | ALADVVHEA | + |
| 39 | ALDPKANFST | +++ |
| 40 | ALLAEGITWV | + |
| 42 | ALLGGNVRMML | +++ |
| 44 | ALQDAIRQL | + |
| 47 | FLDTPIAKV | + |
| 49 | FLYPEKDEPT | +++ |
| 51 | GLAEELVRA | + |
| 52 | GLFNAELLEA | + |
| 53 | GLIHLEGDTV | +++ |
| 54 | GLLDPNVKSIFV | +++ |
| 55 | GLYGRTIEL | + |
| 56 | GVLPGLVGV | + |
| 57 | HLTEAIQYV | ++ |
| 58 | ILADLNLSV | + |
| 59 | ILADTFIGV | ++ |
| 60 | ILSPLSVAL | + |
| 61 | KIADFELPTI | +++ |
| 62 | KIAGTNAEV | ++ |
| 66 | KLHEEIDRV | ++ |
| 67 | KLKETIQKL | +++ |
| 70 | KLLDLETERILL | ++ |
| 71 | KLLDNWDSV | +++ |
| 72 | KLSEAVTSV | + |
| 75 | KQMEPLHAV | + |
| 76 | LLADIGGDPFAA | +++ |
| 77 | LLHEENFSV | + |
| 79 | LLLSTGYEA | +++ |
| 81 | NLASFIEQVAV | ++ |
| 82 | NVFDGLVRV | + |
| 83 | QLHDFVMSL | +++ |
| 84 | QLTPVLVSV | ++ |
| 85 | RILPKVLEV | + |
| 86 | RLAAFYSQV | +++ |
| 88 | RLIDRIKTV | +++ |
| 89 | RLIEEIKNV | +++ |
| 91 | RLPDIPLRQV | + |
| 93 | RLYTMDGITV | +++ |
| 94 | RMSDVVKGV | +++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumor compared to a panel of normal tissues (+).

| SEQ ID No. | Sequence | Peptide Presentation |
|---|---|---|
| 96 | SLLEEPNVIRV | ++ |
| 97 | SLLPQLIEV | ++ |
| 98 | SLLSPEHLQYL | ++ |
| 99 | SLSAFLPSL | +++ |
| 101 | SLWEGGVRGV | +++ |
| 103 | SMGDHLWVA | +++ |
| 107 | TLGQFYQEV | +++ |
| 108 | TLLKKISEA | +++ |
| 109 | TLYALSHAV | + |
| 111 | TVMDIDTSGTFNV | + |
| 113 | VLMDKLVEL | ++ |
| 114 | VLSQVYSKV | +++ |
| 116 | WVIPAISAV | +++ |
| 117 | YAFPKSITV | +++ |
| 119 | YLDKNLTVSV | + |
| 120 | YLGEEYVKA | +++ |
| 121 | YLITGNLEKL | + |
| 122 | YLSQAADGAKVL | +++ |
| 123 | YLWDLDHGFAGV | ++ |
| 124 | LLIDVVTYL | +++ |
| 126 | TLLDSPIKV | ++ |
| 127 | VLIGSNHSL | + |
| 128 | GLAFSLNGV | + |
| 129 | SQADVIPAV | + |
| 130 | ALDAGAVYTL | ++ |
| 131 | ALDSGAFQSV | ++ |
| 132 | ALHEEVVGV | + |
| 133 | ALLEMDARL | + |
| 134 | ALLETNPYLL | ++ |
| 135 | ALLGKIEKV | + |
| 137 | ALPTVLVGV | ++ |
| 139 | ALSSKPAEV | + |
| 142 | AVIGGLIYV | ++ |
| 144 | FIQLITGV | + |
| 146 | FLWTEQAHTV | + |

TABLE 8-continued

Presentation scores. The table lists peptides that are very highly over-presented on tumors compared to a panel of normal tissues (+++), highly over-presented on tumors compared to a panel of normal tissues (++) or over-presented on tumor compared to a panel of normal tissues (+).

| SEQ ID No. | Sequence | Peptide Presentation |
|---|---|---|
| 147 | GLAPGGLAVV | + |
| 148 | GLFAPLVFL | +++ |
| 151 | HLAKVTAEV | + |
| 154 | KLTDHLKYV | + |
| 161 | RLLDEQFAV | + |
| 162 | RLMSALTQV | ++ |
| 163 | RLTESVLYL | ++ |
| 164 | RMLIKLLEV | + |
| 167 | SLAESSFDV | ++ |
| 168 | SLAVLVPIV | + |
| 169 | SLFEWFHPL | + |
| 170 | SLHNGVIQL | + |
| 171 | SLIPAVLTV | + |
| 172 | SLLNFLQHL | + |
| 173 | SLTSEIHFL | + |
| 174 | TLAELGAVQV | + |
| 176 | TLGQIWDV | + |
| 177 | VLDEPYEKV | + |
| 179 | YIHNILYEV | ++ |
| 180 | YLGPHIASVTL | ++ |
| 181 | YLLEKFVAV | + |
| 184 | VVLDGGQIVTV | + |
| 185 | ALFPALRPGGFQA | ++ |
| 186 | VLLAQIIQV | + |
| 187 | SYPTFFPRF | + |
| 188 | RYSAGWDAKF | + |
| 189 | AFSPDSHYLLF | +++ |
| 190 | RYNEKCFKL | +++ |
| 191 | KYPDIISRI | ++ |
| 192 | SYITKPEKW | + |
| 193 | IYPGAFVDL | +++ |
| 194 | QYASRFVQL | +++ |
| 195 | RYAPPPSFSEF | +++ |
| 196 | AYLKWISQI | +++ |
| 197 | RWPKKSAEF | + |

TABLE 8-continued

Presentation scores. The table lists peptides that are very highly over-presented on tumors compared to a panel of normal tissues (+++), highly over-presented on tumors compared to a panel of normal tissues (++) or over-presented on tumor compared to a panel of normal tissues (+).

| SEQ ID No. | Sequence | Peptide Presentation |
|---|---|---|
| 198 | LYWSHPRKF | + |
| 200 | AYLLQPSQF | +++ |
| 201 | AYVNTFHNI | +++ |
| 202 | AYGTYRSNF | +++ |
| 203 | YYGILQEKI | +++ |
| 204 | KYRLTYAYF | ++ |
| 205 | VYGLQRNLL | + |
| 206 | KWPETPLLL | +++ |
| 208 | SYNPAENAVLL | ++ |
| 210 | AYPAIRYLL | ++ |
| 211 | IYIPSYFDF | ++ |
| 212 | VYGDVISNI | +++ |
| 213 | YYNKVSTVF | + |
| 214 | IYVISIEQ1 | +++ |
| 217 | DYIPYVFKL | +++ |
| 218 | VYQGAIRQI | + |
| 219 | GVMAGDIYSV | + |
| 220 | SLLEKELESV | ++ |
| 221 | ALCEENMRGV | + |
| 224 | ALASVIKEL | + |
| 225 | KMDPVAYRV | + |
| 226 | AVLGPLGLQEV | + |
| 227 | ALLKVNQEL | + |
| 228 | YLITSVELL | ++ |
| 229 | KMFESFIESV | ++ |
| 230 | VLTEFTREV | + |
| 231 | RLFNDPVAMV | ++ |
| 233 | ALLGKLDAI | + |
| 234 | YLEPYLKEV | + |
| 236 | ALADKELLPSV | ++ |
| 237 | ALRGEIETV | +++ |
| 238 | AMPPPPPQGV | ++ |
| 239 | FLLGFIPAKA | + |
| 240 | FLWERPTLLV | +++ |
| 241 | FVLPLLGLHEA | ++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumor compared to a panel of normal tissues (+).

| SEQ ID No. | Sequence | Peptide Presentation |
|---|---|---|
| 242 | GLFAPVHKV | + |
| 243 | GLLDNPELRV | +++ |
| 244 | KIAELLENV | + |
| 245 | KLGAVFNQV | + |
| 248 | KLNDLIQRL | + |
| 249 | LLLGERVAL | +++ |
| 250 | NLAEVVERV | ++ |
| 251 | RLFADILNDV | ++ |
| 252 | RTIEYLEEV | + |
| 253 | RVPPPPQSV | + |
| 255 | SLFGQDVKAV | +++ |
| 256 | SLFQGVEFHYV | + |
| 257 | SLLEKAGPEL | +++ |
| 258 | SLMGPVVHEV | + |
| 260 | TLMDMRLSQV | ++ |
| 261 | VLFQEALWHV | ++ |
| 263 | VLYPSLKEI | + |
| 264 | VMQDPEFLQSV | ++ |
| 265 | WLIEDGKVVTV | ++ |
| 266 | SLLESNKDLLL | + |
| 267 | ALNENINQV | + |
| 268 | KLYQEVEIASV | + |
| 269 | YLMEGSYNKV | + |
| 270 | SVLDQKILL | ++ |
| 271 | LLLDKLILL | + |
| 272 | QQLDSKFLEQV | + |
| 273 | AILETAPKEV | ++ |
| 274 | ALAEALKEV | + |
| 275 | ALIEGAGILL | ++ |
| 276 | ALLEADVNIKL | + |
| 277 | ALLEENSTPQL | + |
| 278 | ALTSVVVTL | + |
| 279 | ALWTGMHTI | + |
| 281 | GLLAGDRLVEV | + |
| 282 | GQFPSYLETV | ++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumor compared to a panel of normal tissues (+).

| SEQ ID No. | Sequence | Peptide Presentation |
|---|---|---|
| 283 | ILSGIGVSQV | + |
| 284 | KLDAFVEGV | + |
| 286 | KVLDKVFRA | + |
| 288 | LLDDSLVSI | + |
| 289 | LLLEEGGLVQV | ++ |
| 290 | NLIDLDDLYV | ++ |
| 292 | RIPAYFVTV | + |
| 293 | FLASESLIKQI | ++ |
| 295 | SLFSSPPEI | ++ |
| 297 | TLFYSLREV | + |
| 298 | TMAKESSIIGV | ++ |
| 299 | ALLRVTPFI | + |
| 301 | VLADFGARV | +++ |
| 302 | KIQEILTQV | +++ |
| 303 | GVYDGEEHSV | + |
| 304 | SLIDQFFGV | +++ |
| 305 | GVLENIFGV | + |
| 308 | ALLRTVVSV | + |
| 309 | GLIEIISNA | + |
| 310 | SLWGGDVVL | + |
| 311 | FLIPIYHQV | + |
| 312 | RLGIKPESV | +++ |
| 313 | LTAPPEALLMV | + |
| 314 | YLAPFLRNV | + |
| 315 | KVLDGSPIEV | + |
| 316 | LLREKVEFL | + |
| 317 | KLPEKWESV | ++ |
| 318 | KLNEINEKI | + |
| 319 | KLFNEFIQL | + |
| 320 | GLADNTVIAKV | + |
| 322 | ILYDIPDIRL | + |
| 324 | RLFETKITQV | ++ |
| 326 | ALSDGVHKI | ++ |
| 327 | GLNEEIARV | ++ |
| 328 | RLEEDDGDVAM | + |

TABLE 8-continued

Presentation scores. The table lists peptides that are very highly over-presented on tumors compared to a panel of normal tissues (+++), highly over-presented on tumors compared to a panel of normal tissues (++) or over-presented on tumor compared to a panel of normal tissues (+).

| SEQ ID No. | Sequence | Peptide Presentation |
|---|---|---|
| 329 | SLIEDLILL | +++ |
| 330 | SMSADVPLV | ++ |
| 332 | AMLAVLHTV | + |
| 334 | SILTIEDGIFEV | + |
| 335 | SLLPVDIRQYL | ++ |
| 336 | YLPTFFLTV | + |
| 337 | TLLAAEFLKQV | + |
| 338 | KLFDSDPITVTV | +++ |
| 340 | KVFDEVIEV | + |
| 342 | AMSSKFFLV | + |
| 343 | LLLPDYYLV | + |
| 345 | SYNPLWLRI (A*24) | +++ |
| 346 | LYQILQGIVF (A*24) | +++ |
| 347 | ALNPADITV | + |

S* = phosphoserine

Example 2

Expression Profiling of Genes Encoding the Peptides of the Invention Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; Bio-Chain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 μg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0. Exemplary expression profiles of source genes of the present invention that are highly over-expressed or exclusively expressed in HCC are shown in FIGS. 2A-2F. Expression scores for further exemplary genes are shown in Table 9.

TABLE 9

Expression scores. The table lists peptides from genes that are very highly overexpressed in tumors compared to a panel of normal tissues (+++), highly overexpressed in tumors compared to a panel of normal tissues (++) or overexpressed in tumors compared to a panel of normal tissues (+).

| SEQ ID No | Sequence | Gene Expression |
|---|---|---|
| 1 | VMAPFTMTI | +++ |
| 2 | KLQAGTVFV | ++ |
| 3 | ILDDNMQKL | + |
| 4 | KLQDFSDQL | +++ |
| 5 | ALVEQGFTV | +++ |
| 7 | ALVDTLKFV | +++ |
| 10 | SLLEEFDFHV | + |
| 13 | GLIDTETAMKAV | +++ |
| 19 | FLEETKATV | +++ |
| 20 | KLSNVLQQV | +++ |
| 21 | QLIEVSSPITL | +++ |
| 25 | SLDGKAALTEL | +++ |
| 27 | TLPDFRLPEI | +++ |
| 28 | TLQDHLNSL | +++ |
| 29 | YIQDEINTI | +++ |
| 31 | YQMDIQQEL | +++ |
| 38 | ALADVVHEA | + |
| 39 | ALDPKANFST | + |
| 41 | ALLELDEPLVL | +++ |
| 42 | ALLGGNVRMML | + |
| 44 | ALQDAIRQL | + |
| 45 | ALQDQLVLV | ++ |
| 46 | AMAEMKVVL | ++ |
| 48 | FLLEQPEIQV | + |
| 49 | FLYPEKDEPT | +++ |
| 50 | FTIPKLYQL | +++ |
| 52 | GLFNAELLEA | +++ |
| 53 | GLIHLEGDTV | +++ |
| 55 | GLYGRTIEL | +++ |
| 60 | ILSPLSVAL | + |
| 61 | KIADFELPTI | +++ |
| 62 | KIAGTNAEV | + |
| 66 | KLHEEIDRV | +++ |
| 67 | KLKETIQKL | +++ |
| 68 | KLLAATVLLL | +++ |
| 73 | KLTLVIISV | +++ |
| 74 | KLYDLELIV | +++ |
| 76 | LLADIGGDPFAA | + |
| 81 | NLASFIEQVAV | + |
| 82 | NVFDGLVRV | +++ |
| 83 | QLHDFVMSL | +++ |
| 84 | QLTPVLVSV | ++ |
| 85 | RILPKVLEV | ++ |
| 87 | RLFEENDVNL | +++ |
| 90 | RLLDVLAPLV | + |
| 93 | RLYTMDGITV | +++ |
| 94 | RMSDVVKGV | + |
| 95 | SICNGVPMV | ++ |
| 97 | SLLPQLIEV | +++ |

TABLE 9-continued

Expression scores. The table lists peptides from genes that are very highly overexpressed in tumors compared to a panel of normal tissues (+++), highly overexpressed in tumors compared to a panel of normal tissues (++) or overexpressed in tumors compared to a panel of normal tissues (+).

| SEQ ID No | Sequence | Gene Expression |
|---|---|---|
| 100 | SLVGDIGNVNM | +++ |
| 103 | SMGDHLWVA | + |
| 105 | SVYDGKLLI | + |
| 106 | TLAAIIHGA | ++ |
| 107 | TLGQFYQEV | +++ |
| 109 | TLYALSHAV | +++ |
| 110 | TVGGSEILFEV | +++ |
| 113 | VLMDKLVEL | +++ |
| 114 | VLSQVYSKV | +++ |
| 116 | WVIPAISAV | ++ |
| 117 | YAFPKSITV | + |
| 119 | YLDKNLTVSV | ++ |
| 120 | YLGEEYVKA | +++ |
| 124 | LLIDVVTYL | +++ |
| 126 | TLLDSPIKV | +++ |
| 129 | SQADVIPAV | ++ |
| 130 | ALDAGAVYTL | ++ |
| 132 | ALHEEVVGV | ++ |
| 141 | AMGEKSFSV | + |
| 142 | AVIGGLIYV | +++ |
| 145 | FLIAEYFEHV | ++ |
| 146 | FLWTEQAHTV | ++ |
| 148 | GLFAPLVFL | + |
| 149 | GLLSGLDIMEV | +++ |
| 154 | KLTDHLKYV | +++ |
| 157 | QLLPNLRAV | + |
| 158 | RIISGLVKV | ++ |
| 160 | RLLAKIICL | +++ |
| 163 | RLTESVLYL | ++ |
| 165 | RVIEHVEQV | ++ |
| 168 | SLAVLVPIV | +++ |
| 172 | SLLNFLQHL | + |
| 173 | SLTSEIHFL | + |
| 175 | TLFEHLPHI | ++ |
| 177 | VLDEPYEKV | ++ |

TABLE 9-continued

Expression scores. The table lists peptides from genes that are very highly overexpressed in tumors compared to a panel of normal tissues (+++), highly overexpressed in tumors compared to a panel of normal tissues (++) or overexpressed in tumors compared to a panel of normal tissues (+).

| SEQ ID No | Sequence | Gene Expression |
|---|---|---|
| 182 | YLLHFPMAL | +++ |
| 183 | YLYNNEEQVGL | +++ |
| 187 | SYPTFFPRF | + |
| 188 | RYSAGWDAKF | +++ |
| 192 | SYITKPEKW | + |
| 193 | IYPGAFVDL | + |
| 200 | AYLLQPSQF | +++ |
| 204 | KYRLTYAYF | +++ |
| 206 | KWPETPLLL | + |
| 215 | IYTGNISSF | +++ |
| 217 | DYIPYVFKL | +++ |
| 218 | VYQGAIRQI | +++ |
| 228 | YLITSVELL | + |
| 233 | ALLGKLDAI | + |
| 249 | LLLGERVAL | + |
| 255 | SLFGQDVKAV | + |
| 259 | TLITDGMRSV | + |
| 263 | VLYPSLKEI | + |
| 273 | AILETAPKEV | + |
| 275 | ALIEGAGILL | + |
| 286 | KVLDKVFRA | + |
| 296 | SLLSGRISTL | + |
| 298 | TMAKESSIIGV | + |
| 301 | VLADFGARV | ++ |
| 302 | KIQEILTQV | + |
| 315 | KVLDGSPIEV | ++ |
| 318 | KLNEINEKI | +++ |
| 320 | GLADNTVIAKV | + |
| 324 | RLFETKITQV | ++ |
| 327 | GLNEEIARV | + |
| 336 | YLPTFFLTV | + |
| 341 | YLAIGIHEL | ++ |
| 345 | SYNPLWLRI (A*24) | ++ |

Example 3

UV-Ligand Exchange/Peptide Binding to HLA-A*02 and HLA-A*24

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (ß2m) of stabilized MHC complexes. The assay was performed as generally described in Rodenko et al. (Rodenko B, Toebes M, Hadrup S R, van Esch W J, Molenaar A M, Schumacher T N, Ovaa H. Generation of peptide-MHC class I complexes through UV-mediated ligand exchange. Nat Protoc. 2006; 1(3):1120-32).

96 well MAXISorp plates (NUNC) were coated over night with 2 ug/ml streptavidin in PBS at room temperature, washed 4× and blocked for 1h at 37° C. in 2% BSA containing blocking buffer. Refolded HLA-A*0201/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-ß2m for 1h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 10A

MHC class I binding scores
<20% = +; 20%-49% = ++; 50%-75% = +++; >=75% = ++++

| Seq ID | Peptide code | Peptide exchange |
|---|---|---|
| 12 | GPC3-001 | ++++ |
| 5 | APOB-001 | ++++ |
| 7 | APOB-002 | ++++ |
| 1 | APOB-003 | ++++ |
| 13 | HSD11B1-001 | ++++ |
| 227 | SAMM-001 | ++++ |
| 4 | APOB-004 | ++++ |
| 232 | MAPKAPK5-001 | ++++ |
| 10 | USO-001 | ++++ |
| 304 | USP14-001 | ++++ |
| 219 | ADF-012 | ++++ |
| 223 | IDI1-001 | ++++ |
| 224 | IFT81-001 | ++++ |
| 14 | NCST-001 | ++++ |
| 228 | ACSL4-001 | ++++ |
| 230 | IPO9-001 | ++++ |
| 15 | SLC35B2-001 | ++++ |
| 16 | ACSL3-001 | ++++ |
| 303 | MAGEB2-001 | +++ |
| 226 | THT-001 | +++ |
| 8 | DYM-001 | +++ |
| 6 | AXIN2-001 | +++ |
| 225 | QAR-001 | +++ |
| 2 | ALDH1L1-001 | +++ |
| 221 | EEF2-001 | +++ |
| 220 | DRG2-001 | +++ |
| 301 | C1QTNF3-001 | +++ |
| 11 | ZNF318-001 | +++ |

TABLE 10B

MHC class I binding scores
Binding of HLA-class I restricted peptides to HLA-A*02 or HLA-A*24 depending from peptide sequence was classified by peptide exchange yield: ≥10% = +; ≥20% = ++; ≥50 = +++; ≥75% = ++++.

| SEQ ID No | Sequence | Peptide exchange |
|---|---|---|
| 1 | VMAPFTMTI | "++++" |
| 2 | KLQAGTVFV | "+++" |
| 3 | ILDDNMQKL | "+++" |
| 4 | KLQDFSDQL | "++++" |
| 5 | ALVEQGFTV | "++++" |
| 6 | KLSPTVVGL | "+++" |
| 7 | ALVDTLKFV | "++++" |
| 8 | KLLEEATISV | "+++" |
| 9 | ALANQKLYSV | "+++" |
| 10 | SLLEEFDFHV | "++++" |
| 11 | SLSQELVGV | "+++" |
| 12 | FLAELAYDL | "++++" |
| 13 | GLIDTETAMKAV | "++++" |
| 14 | ALADLTGTVV | "++++" |
| 15 | LLYGHTVTV | "++++" |
| 16 | SLLGGNIRL | "++++" |
| 17 | RVAS*PTSGV | "+++" |
| 18 | ALYGKTEVV | "+++" |
| 19 | FLEETKATV | "+++" |
| 20 | KLSNVLQQV | "++++" |
| 21 | QLIEVSSPITL | "++++" |
| 22 | RIAGIRGIQGV | "++++" |
| 23 | RLYDPASGTISL | "+++" |
| 24 | SLAEEKLQASV | "+++" |
| 25 | SLDGKAALTEL | "+++" |
| 26 | SLLHTIYEV | "+++" |
| 27 | TLPDFRLPEI | "++++" |

TABLE 10B-continued

MHC class I binding scores
Binding of HLA-class I restricted peptides
to HLA-A*02 or HLA-A*24 depending from
peptide sequence was classified by peptide
exchange yield: ≥10% = +; ≥20% = ++; ≥50 = +++;
≥75% = ++++.

| SEQ ID No | Sequence | Peptide exchange |
|---|---|---|
| 28 | TLQDHLNSL | "+++" |
| 29 | YIQDEINTI | "+++" |
| 30 | YLGEGPRMV | "+++" |
| 31 | YQMDIQQEL | "+++" |
| 32 | ALNAVRLLV | "++++" |
| 33 | LLHGHIVEL | "+++" |
| 34 | SLAEGTATV | "+++" |
| 35 | SLQESILAQV | "+++" |
| 36 | ILNVDGLIGV | "+++" |
| 37 | LLLPLLPPLSP | "+++" |
| 38 | ALADVVHEA | "+++" |
| 39 | ALDPKANFST | "+++" |
| 40 | ALLAEGITWV | "+++" |
| 41 | ALLELDEPLVL | "++++" |
| 42 | ALLGGNVRMML | "+++" |
| 43 | ALLGVWTSV | "++" |
| 44 | ALQDAIRQL | "++++" |
| 45 | ALQDQLVLV | "++++" |
| 46 | AMAEMKVVL | "+++" |
| 47 | FLDTPIAKV | "++" |
| 48 | FLLEQPEIQV | "+++" |
| 49 | FLYPEKDEPT | "++" |
| 50 | FTIPKLYQL | "++" |
| 51 | GLAEELVRA | "++" |
| 52 | GLFNAELLEA | "+++" |
| 53 | GLIHLEGDTV | "+++" |
| 54 | GLLDPNVKSIFV | "+++" |
| 55 | GLYGRTIEL | "+++" |
| 56 | GVLPGLVGV | "+++" |
| 57 | HLTEAIQYV | "+++" |
| 58 | ILADLNLSV | "++++" |
| 59 | ILADTFIGV | "+++" |
| 60 | ILSPLSVAL | "++++" |
| 61 | KIADFELPTI | "++++" |
| 62 | KIAGTNAEV | "++" |
| 63 | KIDEKNFVV | "+++" |
| 64 | KILEETLYV | "+++" |
| 65 | KLFSGDELLEV | "+++" |
| 66 | KLHEEIDRV | "+++" |
| 67 | KLKETIQKL | "+++" |
| 68 | KLLAATVLLL | "++" |
| 69 | KLLDEVTYLEA | "++++" |
| 70 | KLLDLETERILL | "++++" |
| 71 | KLLDNWDSV | "++++" |
| 72 | KLSEAVTSV | "+++" |
| 74 | KLYDLELIV | "+++" |
| 75 | KQMEPLHAV | "++" |
| 76 | LLADIGGDPFAA | "+++" |
| 77 | LLHEENFSV | "+++" |
| 78 | LLIDDEYKV | "+++" |
| 80 | LLYEGKLTL | "++++" |
| 81 | NLASFIEQVAV | "+++" |
| 82 | NVFDGLVRV | "+++" |
| 83 | QLHDFVMSL | "++++" |
| 84 | QLTPVLVSV | "+++" |
| 85 | RILPKVLEV | "+++" |
| 86 | RLAAFYSQV | "+++" |
| 87 | RLFEENDVNL | "+++" |
| 88 | RLIDRIKTV | "++" |
| 89 | RLIEEIKNV | "++" |
| 90 | RLLDVLAPLV | "+++" |
| 91 | RLPDIPLRQV | "+++" |
| 92 | RLPPDTLLQQV | "+++" |
| 93 | RLYTMDGITV | "++" |
| 94 | RMSDVVKGV | "+++" |
| 95 | SICNGVPMV | "+++" |
| 96 | SLLEEPNVIRV | "++++" |
| 97 | SLLPQLIEV | "++++" |
| 98 | SLLSPEHLQYL | "+++" |
| 99 | SLSAFLPSL | "++++" |

TABLE 10B-continued

MHC class I binding scores
Binding of HLA-class I restricted peptides
to HLA-A*02 or HLA-A*24 depending from
peptide sequence was classified by peptide
exchange yield: ≥10% = +; ≥20% = ++; ≥50 = +++;
≥75% = ++++.

| SEQ ID No | Sequence | Peptide exchange |
|---|---|---|
| 100 | SLVGDIGNVNM | "++" |
| 101 | SLWEGGVRGV | "+++" |
| 102 | SLWSVARGV | "+++" |
| 103 | SMGDHLWVA | "+++" |
| 104 | SVWFGPKEV | "+++" |
| 105 | SVYDGKLLI | "++++" |
| 106 | TLAAIIHGA | "+++" |
| 107 | TLGQFYQEV | "++++" |
| 108 | TLLKKISEA | "+++" |
| 109 | TLYALSHAV | "+++" |
| 110 | TVGGSEILFEV | "++++" |
| 111 | TVMDIDTSGTFNV | "+++" |
| 112 | VLGEVKVGV | "++++" |
| 113 | VLMDKLVEL | "++++" |
| 114 | VLSQVYSKV | "+++" |
| 115 | VVLDDKDYFL | "+++" |
| 116 | WVIPAISAV | "++++" |
| 117 | YAFPKSITV | "+++" |
| 118 | YLDDEKNWGL | "+++" |
| 119 | YLDKNLTVSV | "+++" |
| 120 | YLGEEYVKA | "++" |
| 121 | YLITGNLEKL | "+++" |
| 122 | YLSQAADGAKVL | "++" |
| 123 | YLWDLDHGFAGV | "+++" |
| 124 | LLIDVVTYL | "++++" |
| 125 | ALYGRLEVV | "++++" |
| 126 | TLLDSPIKV | "+++" |
| 127 | VLIGSNHSL | "++++" |
| 128 | GLAFSLNGV | "++++" |
| 129 | SQADVIPAV | "+++" |
| 130 | ALDAGAVYTL | "++++" |
| 131 | ALDSGAFQSV | "+++" |
| 132 | ALHEEVVGV | "+++" |
| 133 | ALLEMDARL | "+++" |
| 134 | ALLETNPYLL | "++++" |
| 135 | ALLGKIEKV | "+++" |
| 136 | ALLNQHYQV | "+++" |
| 137 | ALPTVLVGV | "++++" |
| 138 | ALSQVTLLL | "++++" |
| 139 | ALSSKPAEV | "+++" |
| 140 | ALTSISAGV | "++++" |
| 141 | AMGEKSFSV | "++++" |
| 142 | AVIGGLIYV | "++++" |
| 145 | FLIAEYFEHV | "++" |
| 146 | FLWTEQAHTV | "++" |
| 147 | GLAPGGLAVV | "+++" |
| 148 | GLFAPLVFL | "++++" |
| 149 | GLLSGLDIMEV | "++++" |
| 150 | GLSNLGIKSI | "++++" |
| 151 | HLAKVTAEV | "+++" |
| 152 | KLDNNLDSV | "+++" |
| 154 | KLTDHLKYV | "+++" |
| 156 | LLFPHPVNQV | "++++" |
| 157 | QLLPNLRAV | "+++" |
| 158 | RIISGLVKV | "++" |
| 159 | RLFPDGIVTV | "+++" |
| 160 | RLLAKIICL | "++" |
| 161 | RLLDEQFAV | "+++" |
| 162 | RLMSALTQV- | "++" |
| 163 | RLTESVLYL | "+++" |
| 164 | RMLIKLLEV | "+++" |
| 165 | RVIEHVEQV | "++++" |
| 166 | SILDIVTKV | "+++" |
| 167 | SLAESSFDV | "+++" |
| 168 | SLAVLVPIV | "+++" |
| 169 | SLFEWFHPL | "+++" |
| 170 | SLHNGVIQL | "+++" |
| 171 | SLIPAVLTV | "+++" |
| 172 | SLLNFLQHL | "+++" |
| 173 | SLTSEIHFL | "+++" |

TABLE 10B-continued

MHC class I binding scores
Binding of HLA-class I restricted peptides to HLA-A*02 or HLA-A*24 depending from peptide sequence was classified by peptide exchange yield: ≥10% = +; ≥20% = ++; ≥50 = +++; ≥75% = ++++.

| SEQ ID No | Sequence | Peptide exchange |
|---|---|---|
| 174 | TLAELGAVQV | "+++" |
| 175 | TLFEHLPHI | "+++" |
| 176 | TLGQIWDV | "++++" |
| 177 | VLDEPYEKV | "+++" |
| 178 | YIFTTPKSV | "+++" |
| 179 | YIHNILYEV | "++++" |
| 180 | YLGPHIASVTL | "+++" |
| 181 | YLLEKFVAV | "+++" |
| 182 | YLLHFPMAL | "+++" |
| 183 | YLYNNEEQVGL | "++" |
| 184 | VVLDGGQIVTV | "+++" |
| 185 | ALFPALRPGGFQA | "+++" |
| 186 | VLLAQIIQV | "+++" |
| 187 | SYPTFFPRF | "++++" |
| 188 | RYSAGWDAKF | "++++" |
| 189 | AFSPDSHYLLF | "+++" |
| 190 | RYNEKCFKL | "++++" |
| 191 | KYPDIISRI | "++++" |
| 192 | SYITKPEKW | "++++" |
| 193 | IYPGAFVDL | "++++" |
| 195 | RYAPPPSFSEF | "++++" |
| 196 | AYLKWISQ1 | "++++" |
| 197 | RWPKKSAEF | "++++" |
| 198 | LYWSHPRKF | "++++" |
| 199 | KFVTVQATF | "++++" |
| 200 | AYLLQPSQF | "++++" |
| 201 | AYVNTFHNI | "++++" |
| 202 | AYGTYRSNF | "++++" |
| 203 | YYGILQEKI | "++++" |
| 205 | VYGLQRNLL | "++++" |
| 206 | KWPETPLLL | "++++" |
| 207 | IYLERFPIF | "++++" |
| 208 | SYNPAENAVLL | "++++" |
| 209 | VFHPRQELI | "+++" |
| 210 | AYPAIRYLL | "++++" |
| 211 | IYIPSYFDF | "++++" |
| 212 | VYGDVISNI | "++++" |
| 213 | YYNKVSTVF | "++++" |
| 214 | IYVTSIEQI | "++++" |
| 215 | IYTGNISSF | "++++" |
| 216 | IYADVGEEF | "++++" |
| 217 | DYIPYVFKL | "++++" |
| 218 | VYQGAIRQI | "++++" |
| 219 | GVMAGDIYSV | "++++" |
| 220 | SLLEKELESV | "+++" |
| 221 | ALCEENMRGV | "+++" |
| 222 | LTDITKGV | "++" |
| 223 | FLFNTENKLLL | "++++" |
| 224 | ALASVIKEL | "+++" |
| 225 | KMDPVAYRV | "+++" |
| 226 | AVLGPLGLQEV | "+++" |
| 227 | ALLKVNQEL | "++++" |
| 228 | YLITSVELL | "++++" |
| 229 | KMFESFIESV | "+++" |
| 230 | VLTEFTREV | "++++" |
| 231 | RLFNDPVAMV | "++++" |
| 232 | KLAEIVKQV | "++++" |
| 233 | ALLGKLDAI | "++++" |
| 234 | YLEPYLKEV | "++++" |
| 235 | KLFEEIREI | "++++" |
| 236 | ALADKELLPSV | "+++" |
| 237 | ALRGEIETV | "+++" |
| 238 | AMPPPPPQGV | "++" |
| 239 | FLLGFIPAKA | "+++" |
| 240 | FLWERPTLLV | "+++" |
| 241 | FVLPLLGLHEA | "++" |
| 242 | GLFAPVHKV | "+++" |
| 243 | GLLDNPELRV | "+++" |
| 244 | KIAELLENV | "++++" |
| 245 | KLGAVFNQV | "++++" |

TABLE 10B-continued

MHC class I binding scores
Binding of HLA-class I restricted peptides
to HLA-A*02 or HLA-A*24 depending from
peptide sequence was classified by peptide
exchange yield: ≥10% = +; ≥20% = ++; ≥50 = +++;
≥75% = ++++.

| SEQ ID No | Sequence | Peptide exchange |
|---|---|---|
| 246 | KLISSYYNV | "+++" |
| 247 | KLLDTMVDTFL | "++++" |
| 248 | KLNDLIQRL | "+++" |
| 249 | LLLGERVAL | "++++" |
| 250 | NLAEVVERV | "++++" |
| 251 | RLFADILNDV | "++++" |
| 252 | RTIEYLEEV | "+++" |
| 253 | RVPPPPQSV | "++" |
| 254 | RVQEAIAEV | "+++" |
| 255 | SLFGQDVKAV | "+++" |
| 256 | SLFQGVEFHYV | "+++" |
| 257 | SLLEKAGPEL | "+++" |
| 258 | SLMGPVVHEV | "+++" |
| 259 | TLITDGMRSV- | "++" |
| 260 | TLMDMRLSQV | "+++" |
| 261 | VLFQEALWHV | "+++" |
| 262 | VLPNFLPYNV | "+++" |
| 263 | VLYPSLKEI | "+++" |
| 264 | VMQDPEFLQSV | "++++" |
| 265 | WLIEDGKVVTV | "++++" |
| 266 | SLLESNKDLLL | "+++" |
| 267 | ALNENINQV | "+++" |
| 268 | KLYQEVEIASV | "++++" |
| 269 | YLMEGSYNKV | "+++" |
| 270 | SVLDQKILL | "+++" |
| 271 | LLLDKLILL | "++++" |
| 272 | QQLDSKFLEQV | "+++" |
| 273 | AILETAPKEV | "+++" |
| 274 | ALAEALKEV | "++++" |
| 275 | ALIEGAGILL | "+++" |
| 276 | ALLEADVNIKL | "++++" |
| 277 | ALLEENSTPQL | "+++" |
| 278 | ALTSVVVTL | "++++" |
| 279 | ALWTGMHTI | "+++" |
| 280 | ATLNIIHSV | "+++" |
| 281 | GLLAGDRLVEV | "+++" |
| 282 | GQFPSYLETV | "+++" |
| 283 | ILSGIGVSQV | "+++" |
| 284 | KLDAFVEGV | "+++" |
| 285 | KLLDLSDSTSV | "+++" |
| 286 | KVLDKVFRA | "++++" |
| 287 | LIGEFLEKV | "++++" |
| 288 | LLDDSLVSI | "+++" |
| 290 | NLIDLDDLYV | "++++" |
| 291 | QLIDYERQL | "+++" |
| 292 | RIPAYFVTV | "++" |
| 293 | FLASESLIKQI | "++" |
| 294 | RLIDLHTNV | "++++" |
| 295 | SLFSSPPEI | "+++" |
| 296 | SLLSGRISTL | "+++" |
| 297 | TLFYSLREV | "+++" |
| 298 | TMAKESSIIGV | "++" |
| 299 | ALLRVTPFI | "+++" |
| 300 | TLAQQPTAV | "++" |
| 302 | KIQEILTQV | "++++" |

S* = phosphoserine.

Example 4

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for 22 HLA-A*0201 restricted TUMAPs of the invention so far, demonstrating that these peptides are T-cell epitopes against which CD8+ precursor T cells exist in humans (Table 11).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Ill., USA).

pMHC used for positive and negative control stimulations were A*0201/MLA-001 (peptide ELAGIGILTV from modified Melan-A/MART-1) and A*0201/DDX5-001 (YLL-PAIVHI from DDX5), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10⁶ CD8+ T cells with 2×10⁵ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oreg., USA). In vitro priming of specific multimer+ CD8+ lymphocytes was detected by by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for HCC Peptides

For tested HLA class I peptides, in vitro immunogenicity could be demonstrated by generation of peptide specific T-cell lines. Exemplary flow cytometry results after TUMAP-specific multimer staining for three peptides of the invention are shown in FIG. 3 and FIGS. 4A and 4B together with corresponding negative controls. Results for 22 peptides from the invention are summarized in Table 11A.

TABLE 11A in vitro immunogenicity of HLA class I peptides of the invention Exemplary results of in vitro immunogenicity experiments conducted by the applicant for the peptides of the invention. <20% = +; 20%-49% = ++; 50%-69% = +++; >=70% = ++++

| Seq ID | Peptide ID | wells | donors |
|---|---|---|---|
| 225 | QAR-001 | +++ | ++++ |
| 1 | APOB-003 | ++ | ++++ |
| 2 | ALDH1L1-001 | ++ | ++++ |
| 301 | C1QTNF3-001 | ++ | ++++ |
| 15 | SLC35B2-001 | ++ | ++++ |
| 16 | ACSL3-001 | ++ | ++++ |
| 12 | GPC3-001 | + | ++++ |
| 7 | APOB-002 | + | ++++ |
| 303 | MAGEB2-001 | + | ++ |
| 227 | SAMM-001 | + | +++ |
| 4 | APOB-004 | + | ++++ |
| 226 | THT-001 | + | ++++ |
| 6 | AXIN2-001 | + | ++ |
| 232 | MAPKAPK5-001 | + | +++ |
| 10 | USO-001 | + | ++ |
| 304 | USP14-001 | + | ++++ |
| 219 | ADF-012 | + | ++++ |
| 224 | IFT81-001 | + | +++ |
| 11 | ZNF318-001 | + | ++ |
| 14 | NCST-001 | + | ++ |
| 228 | ACSL4-001 | + | ++ |
| 230 | IPO9-001 | + | ++++ |

TABLE 11B in vitro immunogenicity of additional HLA class I peptides of the invention Exemplary results of in vitro immunogenicity experiments conducted by the applicant for HLA-A*24 restricted peptides of the invention. Results of in vitro immunogenicity experiments are indicated. Percentage of positive wells and donors (among evaluable) are summarized as indicated 1-20% = +; 20%-49% = ++; 50%-69% = +++; ≥70% = ++++

| SEQ ID No | Sequence | Wells positive [%] | Donors positive [%] |
|---|---|---|---|
| 187 | SYPTFFPRF | "+" | "++++" |
| 189 | AFSPDSHYLLF | "+" | "++" |
| 190 | RYNEKCFKL | "+" | "++" |
| 191 | KYPDIISRI | "+" | "++++" |
| 192 | SYITKPEKW | "+" | "+++" |
| 193 | IYPGAFVDL | "+" | "+++" |
| 194 | QYASRFVQL | "+" | "+++" |
| 196 | AYLKWISQI | "+" | "+++" |
| 197 | RWPKKSAEF | "+" | "++" |
| 198 | LYWSHPRKF | "+" | "++" |
| 199 | KFVTVQATF | "+" | "++" |
| 201 | AYVNTFHNI | "++" | "++++" |
| 202 | AYGTYRSNF | "+" | "++++" |
| 203 | YYGILQEKI | "+" | "+++" |
| 205 | VYGLQRNLL | "+" | "+++" |

TABLE 11B-continued in vitro immunogenicity of additional
HLA class I peptides of the invention
Exemplary results of in vitro immunogenicity
experiments conducted by the applicant for
HLA-A*24 restricted peptides of the invention.
Results of in vitro immunogenicity
experiments are indicated. Percentage of positive
wells and donors (among evaluable) are summarized
as indicated 1-20% = +; 20%-49% = ++;
50%-69% = +++; ≥70% = ++++

| SEQ ID No | Sequence | Wells positive [%] | Donors positive [%] |
|---|---|---|---|
| 207 | IYLERFPIF | "++" | "++++" |
| 208 | SYNPAENAVLL | "+" | "+++" |
| 209 | VFHPRQELI | "++" | "++++" |
| 210 | AYPAIRYLL | "+" | "++++" |
| 211 | IYIPSYFDF | "++" | "++++" |
| 212 | VYGDVISNI | "+" | "++++" |
| 215 | IYTGNISSF | "+" | "++" |
| 216 | IYADVGEEF | "+" | "++" |
| 217 | DYIPYVFKL | "+++" | "++++" |
| 218 | VYQGAIRQI | "+" | "+++" |

Exemplary Results of Peptide-Specific In Vitro CD8+ T Cell Responses of a Healthy HLA-A*02+ Donor (FIG. 3)

CD8+ T cells were primed using artificial APCs coated with anti-CD28 mAb and HLA-A*02 in complex with IMA-APOB-002 (Seq ID No 7) peptide (A, right panel) or IMA-APOB-003 (B, right panel, Seq ID No 1), or IMA-ALDH1L1-001 (C, right panel, Seq ID No 2), respectively. After three cycles of stimulation, the detection of peptide-reactive cells was performed by 2D multimer staining with A*02/APOB-002 (A) or A*02/APOB-003 (B), or A*02/ALDH1L1-001. Left panels (A, B, C) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Exemplary Results of Peptide-Specific In Vitro CD8+ T Cell Responses of a Healthy HLA-A*24+ Donor (FIGS. 4A and 4B)

CD8+ T cells were primed using artificial APCs coated with anti-CD28 mAb and HLA-A*24 in complex with IMA-KLHL24-001 (Seq ID No 190) peptide (FIG. 4A, right panel) or IMA-APOB-006 (FIG. 4B, right panel, Seq ID No 218), respectively. After three cycles of stimulation, the detection of peptide-reactive cells was performed by 2D multimer staining with A*24/KLHL24-001 (FIG. 4A) or A*24/APOB-006 (FIG. 4B). Left panels (FIGS. 4A and 4B) show control staining of cells stimulated with irrelevant A*24/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Example 5

Syntheses of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

REFERENCE LIST

Adler, A. S. et al., Genes Dev. 28 (2014)
Ahn, Y. H. et al., J Proteomics. 106 (2014)
Akiyama, H. et al., Oncol Rep. 21 (2009)
Alam, S. M. et al., Endocr. Relat Cancer 16 (2009)
Aleman, G. et al., Am J Physiol Endocrinol. Metab 289 (2005)
Alexanian, A. et al., Cancer Genomics Proteomics. 9 (2012)
Altenhofer, S. et al., J Biol. Chem. 285 (2010)
Alvarez, C. et al., J Biol. Chem. 276 (2001)
Ammerpohl, O. et al., Int. J Cancer 130 (2012)
Andersen, R. S. et al., Nat. Protoc. 7 (2012)
Arai, E. et al., Carcinogenesis 33 (2012)
Araki, T. et al., J Biol. Chem. 286 (2011)
Arlt, A. et al., Oncogene 28 (2009)
Arndt, S. et al., Oncol Rep. 18 (2007)
Arner, E. S. et al., Eur. J Biochem. 267 (2000)
Atienza, J. M. et al., Mol Cancer Ther 4 (2005)
Avery-Kiejda, K. A. et al., BMC. Cancer 14 (2014)
Bachmann, S. B. et al., Mol Cancer 13 (2014)
Balogh, K. et al., Oncogene 31 (2012)
Bani, M. R. et al., Mol Cancer Ther 3 (2004)
Bansal, N. et al., PLoS. One. 6 (2011)
Barbarulo, A. et al., Oncogene 32 (2013)
Bell, J. C. et al., Drug Metab Dispos. 40 (2012)
Ben-Izhak, O. et al., Histopathology 41 (2002)
Bergada, L. et al., Lab Invest 94 (2014)
Bergeron, M. J. et al., Mol Aspects Med. 34 (2013)
Bhattacharya, C. et al., Mol Cancer 11 (2012)
Bhogaraju, S. et al., Science 341 (2013)
Bidkhori, G. et al., PLoS. One. 8 (2013)
Bieche, I. et al., Breast Cancer Res 6 (2004)
Biswas, S. et al., Biochim. Biophys. Acta 1832 (2013)
Blanke, K. L. et al., Cancer Causes Control 25 (2014)
Bodine, S. C. et al., Science 294 (2001)
Boehringer, J. et al., Biochem. J 448 (2012)
Bojjireddy, N. et al., J Cell Sci. (2014)
Booth, D. G. et al., EMBO J 30 (2011)
Bouquet, C. et al., Mol Ther 14 (2006)
Boylan, K. L. et al., Proteome. Sci. 8 (2010)
Braumuller, H. et al., Nature (2013)
Brockmoller, S. F. et al., J Proteome. Res 11 (2012)
Buch, S. C. et al., Mol Carcinog. 51 Suppl 1 (2012)
Bull, C. et al., Cancer Res 74 (2014)
Burrell, R. A. et al., Nature 494 (2013)
Butterfield, L. H. et al., Clin Cancer Res 12 (2006)
Butterfield, L. H. et al., Clin. Cancer Res. 9 (2003)
Byrne, A. et al., Exp. Cell Res 316 (2010)
Cadenas, C. et al., Cell Cycle 13 (2014)
Cadoret, A. et al., Oncogene 21 (2002)
Cao, H. et al., Biochemistry 41 (2002)
Cao, Y. et al., Cancer Research 61 (2001)

Cao-Ehlker, X. et al., J Biol. Chem. 288 (2013)
Carroll, M. et al., J Interferon Cytokine Res 33 (2013)
Carrouel, F. et al., J Dent. Res 87 (2008)
Castro, M. et al., J Transl. Med. 8 (2010)
Chae, Y. S. et al., Med. Oncol 28 (2011)
Chang, L. O. et al., Cancer Res 33 (1973)
Chang, Y. S. et al., Cancer Chemother. Pharmacol. 59 (2007)
Chapiro, J. et al., Radiol. Med. 119 (2014)
Charbonneau, B. et al., Am J Hematol. 87 (2012)
Chatterjee, M. et al., Haematologica 98 (2013)
Chen, J. et al., Biochem. Biophys. Res Commun. 420 (2012a)
Chen, M. et al., Proc. Natl. Acad. Sci. U.S.A 108 (2011a)
Chen, R. et al., World J Gastroenterol. 17 (2011b)
Chen, X. et al., J Dig. Dis. 12 (2011c)
Chen, X. Q. et al., Med. Oncol 29 (2012b)
Cheng, L. et al., Genomics 102 (2013)
Choi, Y. W. et al., Int. J Gynecol. Cancer 17 (2007)
Christa, L. et al., Gastroenterology 106 (1994)
Clark, A. G. et al., Cytoskeleton (Hoboken) 69 (2012)
Claro da, Silva T. et al., Mol. Aspects Med. 34 (2013)
Cohen, L. et al., Nature 395 (1998)
Collins, C. L. et al., Surgery 122 (1997)
Com, E. et al., J Proteomics. 75 (2012)
Copps, K. D. et al., Diabetologia 55 (2012)
Cornen, S. et al., PLoS. ONE. 9 (2014)
Cornez, I. et al., Biochem. Pharmacol. 75 (2008)
Cowling, V. H., Oncogene 29 (2010)
Cui, T. et al., Int. J Oncol 39 (2011)
da Silva, M. G. et al., Exp. Clin Cardiol. 17 (2012)
Dadkhah, E. et al., Arch. Iran Med. 16 (2013)
Darmanis, S. et al., PLoS. One. 8 (2013)
Darvekar, S. et al., Biochem. J 442 (2012)
Darvekar, S. R. et al., PLoS. One. 9 (2014)
Datta, K. et al., J Biol. Chem. 284 (2009)
David, S. et al., Front Biosci. (Elite. Ed) 5 (2013)
de Almagro, M. C. et al., Biochem. Pharmacol. 81 (2011)
de Groot, J. F. et al., Cancer Res 65 (2005)
Deb, S. et al., Br. J Cancer 110 (2014)
Debauve, G. et al., Cell Mol Life Sci. 65 (2008)
Decker, T. et al., J Clin Invest 109 (2002)
Decock, A. et al., Genome Biol. 13 (2012)
Del Campo, E. M. et al., Mol Phylogenet. Evol. 66 (2013)
Delaval, B. et al., J Cell Biol. 188 (2010)
Deng, X. D. et al., Asian Pac. J Cancer Prev. 15 (2014)
Di, Gregorio E. et al., J Med. Genet. 50 (2013)
Diggle, C. P. et al., PLoS. Genet. 10 (2014)
Dimitrov, A. et al., Hum. Mol Genet. 18 (2009)
Dmitriev, O. Y., Biochem. Cell Biol. 89 (2011)
Doherty, J. A. et al., Cancer Epidemiol. Biomarkers Prev. 20 (2011)
Dong, Z. et al., Crit Rev. Oncol Hematol. 59 (2006)
Dou, R. et al., Cancer Lett. 336 (2013)
Drazkowska, K. et al., Nucleic Acids Res 41 (2013)
Edavana, V. K. et al., Drug Metab Dispos. 41 (2013)
Edwards, P. A. et al., Breast Cancer Res 14 (2012)
Elvenes, J. et al., PLoS. One. 6 (2011)
Emaduddin, M. et al., Cell Commun. Signal. 6 (2008)
Enguita-German, M. et al., World J Hepatol. 6 (2014)
Epelbaum, R. et al., Pathol. Oncol Res 4 (1998)
Fan, T. W. et al., Mol Cancer 8 (2009)
Fang, Z. Q. et al., Genet. Mol Res 12 (2013)
Fassas, A. B. et al., Leuk. Lymphoma 45 (2004)
Feferman, L. et al., Prostate Cancer Prostatic. Dis. 16 (2013)
Fei, F. et al., J Cancer Res Clin Oncol (2014a)
Fei, F. et al., Ann Surg. Oncol 21 (2014b)
Feigelson, H. S. et al., Breast Cancer Res 10 (2008)
Feng, L. et al., Cell Biochem. Funct. 29 (2011)
Feng, M. et al., J Clin Invest 124 (2014a)
Feng, S. et al., Int. J Biol. Sci. 9 (2013)
Feng, Y. et al., J Biol. Chem. 289 (2014b)
Feng, Y. et al., Free Radic. Res 46 (2012)
Fernandes, C. F. et al., Biochem. Biophys. Res Commun. 361 (2007)
Ferre, S. et al., J Am Soc Nephrol. 25 (2014)
Ferrer-Ferrer, M. et al., Arch. Med. Res 44 (2013)
Filmus, J. et al., FEBS J 280 (2013)
Fiorito, V. et al., Biochim. Biophys. Acta 1839 (2014)
Fojo, A. T. et al., Proc. Natl. Acad. Sci. U.S.A 84 (1987)
Fonseca, A. L. et al., Genes Chromosomes. Cancer 51 (2012)
Fossdal, G. et al., ScientificWorldJournal. 2012 (2012)
Fournier, T. et al., Biochim. Biophys. Acta 1482 (2000)
Fu, W. et al., J Cell Sci. 123 (2010)
Fujitomo, T. et al., Cancer Res 72 (2012)
Furukawa, T. et al., Sci. Rep. 1 (2011)
Furutani, M. et al., Hepatology 24 (1996)
Gadd, S. et al., Lab Invest 90 (2010)
Gailani, D., Trends Cardiovasc. Med. 10 (2000)
Galamb, O. et al., Helicobacter. 13 (2008)
Galazis, N. et al., Gynecol. Endocrinol. 29 (2013)
Gandhi, A. V. et al., Ann Surg. Oncol 20 Suppl 3 (2013)
Gao, L. et al., Mol Oncol 6 (2012)
Garcia-Baquero, R. et al., Tumour. Biol. 35 (2014)
Gardner-Stephen, D. A. et al., Drug Metab Dispos. 35 (2007)
Garg, M. et al., Cancer 116 (2010a)
Garg, M. et al., Eur. J Cancer 46 (2010b)
Gburcik, V. et al., Mol Cell Biol. 25 (2005)
Gergely, F. et al., Proc. Natl. Acad. Sci. U.S.A 97 (2000)
Gervasini, G. et al., Cancer 107 (2006)
Getty, A. L. et al., Cell Mol Life Sci. 68 (2011)
Gilabert, M. et al., J Cell Physiol 228 (2013)
Gilkes, D. M. et al., Mol Cancer Res 11 (2013)
Giovannetti, E. et al., J Natl. Cancer Inst. 106 (2014)
Gokmen-Polar, Y. et al., Mod. Pathol. (2014)
Goldstein, I. et al., Carcinogenesis 34 (2013)
Gong, Y. et al., Genet. Mol Res 12 (2013)
Goode, E. L. et al., Clin Cancer Res 16 (2010)
Gordon, E. M. et al., Am. J Pediat. Hematol. Oncol 15 (1993)
Gotzmann, J. et al., Crit Rev. Eukaryot. Gene Expr. 9 (1999)
Gray, L. R. et al., Cell Mol Life Sci. 71 (2014)
Gregory, P. A. et al., J Biol. Chem. 278 (2003)
Greif, P. A. et al., Leukemia 25 (2011)
Gu, W. et al., PLoS. One. 7 (2012)
Guo, L. et al., Cancer Sci. 103 (2012)
Halon, A. et al., Arch. Gynecol. Obstet. 287 (2013)
Hamamoto, R. et al., Cancer Sci. 97 (2006)
Hamilton, S. R. et al., Glycobiology 15 (2005)
Hamm, A. et al., BMC. Cancer 8 (2008)
Hanioka, N. et al., Basic Clin Pharmacol. Toxicol. 110 (2012)
Harris, M. et al., Pharmacogenet. Genomics 24 (2014)
Hatakeyama, H. et al., Proteomics. 6 (2006)
Havens, M. A. et al., PLoS. Genet. 10 (2014)
He, P. et al., Hum. Pathol. 35 (2004)
He, X. et al., Neoplasma 61 (2014a)
He, Y. et al., Mol Carcinog. (2014b)
Hellwinkel, O. J. et al., Prostate Cancer Prostatic. Dis. 14 (2011)

Hemmingsson, O. et al., Oncol Rep. 22 (2009)
Hidalgo-Curtis, C. et al., Br. J Haematol. 148 (2010)
Hider, J. L. et al., BMC. Evol. Biol. 13 (2013)
Hinsch, N. et al., BMC. Cancer 9 (2009)
Hirota, Y. et al., Nucleic Acids Res 28 (2000)
Hlavata, I. et al., Mutagenesis 27 (2012)
Hoelz, D. J. et al., Proteomics. 6 (2006)
Holden, H. M. et al., Cell Mol Life Sci. 61 (2004)
Honda, K. et al., PLoS. One. 7 (2012)
Hong, Y. et al., J Biol. Chem. 274 (1999)
Hood, F. E. et al., Bioarchitecture. 1 (2011)
Hood, F. E. et al., J Cell Biol. 202 (2013)
Hopfer, O. et al., Br. J Cancer 93 (2005)
Horani, A. et al., Am J Hum. Genet. 91 (2012)
Hou, M. et al., Int. J Mol Med. 33 (2014)
Hu, D. G. et al., Drug Metab Rev. 46 (2014)
Hua, D. et al., Int. J Mol Med. 30 (2012a)
Hua, T. et al., J Biol. Chem. 287 (2012b)
Huang, O. et al., Jpn. J Clin Oncol 43 (2013)
Huang, S. et al., Oncogene 21 (2002)
Huang, Y. et al., Oncotarget. 5 (2014)
Hughes, H. et al., J Cell Sci. 123 (2010)
Hunecke, D. et al., J Pathol. 228 (2012)
Huopaniemi, L. et al., Glycobiology 14 (2004)
Hyung, S. W. et al., Mol Cell Proteomics. 10 (2011)
Iannitti, T. et al., Mar. Drugs 8 (2010)
Ichida, K. et al., Biochem. Biophys. Res Commun. 282 (2001)
Ignatova, I. D. et al., Am J Physiol Endocrinol. Metab 296 (2009)
Ikeda, R. et al., Int. J Oncol 38 (2011)
Inuzuka, M. et al., J Biol. Chem. 280 (2005)
Ishiguro, H. et al., Oncogene 21 (2002)
Ishizaki, F. et al., Sci. Rep. 3 (2013)
Ivashchenko, A. T. et al., Biomed. Res Int. 2013 (2013)
Jacquemier, J. et al., Cancer Res 65 (2005)
Jacques, C. et al., Br. J Cancer 101 (2009)
Jaffe, E. K. et al., Arch. Biochem. Biophys. 530 (2013)
Jakobsson, A. et al., Prog. Lipid Res 45 (2006)
Jamroziak, K. et al., Eur. J Haematol. 72 (2004)
Jeung, H. C. et al., Oncologist. 12 (2007)
Jia, Y. et al., Br. J Cancer 110 (2014)
Jiang, J. G. et al., Cancer Res 65 (2005)
Jiang, X. et al., Histol. Histopathol. 25 (2010)
Jiang, X. et al., Mol Carcinog. (2014)
Jin, Z. et al., Int. J Clin Exp. Pathol. 7 (2014)
Jockusch, H. et al., Proteomics. 14 (2014)
Johnson, M. A. et al., Ann N. Y. Acad. Sci. 1012 (2004)
Jose-Eneriz, E. S. et al., Br. J Haematol. 142 (2008)
Jung, G. et al., Proc Natl Acad Sci USA 84 (1987)
Jung, H. J. et al., J Mol Med. (Berl) 91 (2013)
Kaira, K. et al., Hepatobiliary. Pancreat. Dis. Int. 13 (2014)
Kalsotra, A. et al., Toxicol. Appl. Pharmacol. 199 (2004)
Kalthoff, S. et al., J Biol. Chem. 285 (2010)
Kamiyama, S. et al., Glycobiology 21 (2011)
Kamiyama, S. et al., J Biol. Chem. 281 (2006)
Kandil, D. H. et al., Adv. Anat. Pathol. 16 (2009)
Kandimalla, R. et al., Nat Rev. Urol. 10 (2013)
Karvonen, U. et al., J Mol Biol. 382 (2008)
Kelleher, D. J. et al., Glycobiology 16 (2006)
Khan, A. P. et al., Neoplasia. 15 (2013)
Kim, Y. et al., Hum. Pathol. 46 (2015)
Kim, Y. W. et al., PLoS. One. 7 (2012)
Klein, C. J. et al., Neurology 82 (2014)
Kobayashi, T. et al., Biochem. J 400 (2006)
Kollmann, K. et al., Cancer Cell 24 (2013)
Komatsu, M. et al., Pharmacol. Res 66 (2012)
Kong, S. Y. et al., Cancer Sci. 99 (2008)
Kovacevic, Z. et al., Biochim. Biophys. Acta 1783 (2008)
Kracmarova, A. et al., Leuk. Lymphoma 49 (2008)
Kraemer, N. et al., Cell Mol Life Sci. 68 (2011)
Kress, T. R. et al., Mol Cell 41 (2011)
Krohn, A. et al., J Pathol. 231 (2013)
Krupenko, S. A. et al., Cell Growth Differ. 13 (2002)
Kubota, H. et al., Cell Stress. Chaperones. 15 (2010)
Kummel, D. et al., EMBO Rep. 6 (2005)
Kunutsor, S. K. et al., Int. J Cancer (2014)
Kuriyama, H. et al., Gene 253 (2000)
Laezza, F. et al., Mol Cell Neurosci. 34 (2007)
Lahiri, S. et al., PLoS. Biol. 12 (2014)
Lando, M. et al., J Pathol. 230 (2013)
Lapucci, A. et al., FASEB J 24 (2010)
Lascorz, J. et al., BMC. Med. Genet. 13 (2012)
Lauffart, B. et al., BMC. Womens Health 5 (2005)
Laverdiere, I. et al., Endocr. Relat Cancer (2014)
Leasure, C. D. et al., Plant Physiol 150 (2009)
Lee, C. H. et al., Hum. Reprod. 24 (2009)
Lee, K. W. et al., J Biol. Chem. 288 (2013)
Lee, S. J. et al., Toxicol. Lett. (2014)
Lee, W. C. et al., J Immunother. 28 (2005)
Lee, Y. C. et al., Int. J Cancer 122 (2008)
Lekva, T. et al., PLoS. One. 8 (2013)
LeRoy, P. J. et al., Cancer Res 67 (2007)
Leung, T. et al., Breast Cancer Res 15 (2013)
Levenson, V. V. et al., Somat. Cell Mol Genet. 25 (1999)
Levi, S. et al., Front Pharmacol. 5 (2014)
Li, D. et al., Protein Cell 5 (2014a)
Li, N. et al., Biochem. Biophys. Res Commun. 455 (2014)
Li, X. et al., Med. Oncol 31 (2014b)
Li, Y. et al., Mol Cell Biol. 29 (2009)
Li, Y. H. et al., World J Gastroenterol. 18 (2012)
Liang, J. et al., PLoS. One. 3 (2008)
Lillig, C. H. et al., Antioxid. Redox. Signal. 9 (2007)
Lin, C. H. et al., J Cell Biol. 189 (2010)
Lin, M. C. et al., Oral Oncol 50 (2014)
Lin, S. H. et al., Oncogene 23 (2004)
Lin, Z. et al., Cell Rep. 5 (2013)
Linderoth, J. et al., Br. J Haematol. 141 (2008)
Line, A. et al., Cancer Immunol Immunother. 51 (2002)
Ling, C. et al., EMBO J 26 (2007)
Linge, A. et al., J Proteome. Res 13 (2014)
Lioutas, A. et al., EMBO Rep. 14 (2013)
Liu, C. et al., Nat Med. 20 (2014)
Liu, C. et al., J Natl. Cancer Inst. 105 (2013a)
Liu, H. et al., Carcinogenesis 34 (2013b)
Liu, T. W. et al., Proc. Natl. Acad. Sci. U.S.A 106 (2009a)
Liu, W. et al., J Biol. Chem. 279 (2004)
Liu, Y. et al., Curr. Drug Targets. 13 (2012)
Liu, Y. et al., Cancer Epidemiol. Biomarkers Prev. 18 (2009b)
Liu, Y. et al., Oncol Rep. 18 (2007)
Ljungberg, B., Curr. Opin. Urol. 17 (2007)
Llovet, J. M. et al., N. Engl. J Med. 359 (2008)
Lo Re, A. E. et al., J Biol. Chem. 287 (2012)
Lo, W. Y. et al., J Proteome. Res 6 (2007)
Lombardo, Y. et al., Breast Cancer Res 16 (2014)
Lourenco, G. J. et al., Breast Cancer Res Treat. 100 (2006)
Lovelace, L. L. et al., J Biol. Chem. 286 (2011)
Lung, H. L. et al., Int J Cancer 127 (2010)
Lutcke, H., Eur. J Biochem. 228 (1995)
Ma, X. J. et al., Proc. Natl. Acad. Sci. U.S.A 100 (2003)
Mackiewicz, A. et al., Glycoconj. J 12 (1995)
Mahajan, K. et al., Cancer Lett. 338 (2013)

Mamtani, M. et al., BMC. Res Notes 5 (2012)
Mariani, L. et al., Clin Cancer Res 7 (2001)
Marina, M. et al., Front Biosci. (Landmark. Ed) 19 (2014)
Markiewski, M. M. et al., Nat Immunol 9 (2008)
Martin, T. A. et al., Eur. J Cancer 40 (2004)
Martinez, H. D. et al., Genes Cancer 2 (2011)
Mathison, J. et al., Pathobiology 59 (1991)
Matsubara, J. et al., Cancer Epidemiol. Biomarkers Prev. 20 (2011)
Matusiak, D. et al., J Histochem. Cytochem. 55 (2007)
McGuire, T. A., Md Med. J 40 (1991)
Medjkane, S. et al., Cell Cycle 11 (2012)
Meijers, J. C. et al., Br. J Haematol. 108 (2000)
Mercer, C. A. et al., Autophagy. 5 (2009)
Mercurio, F. A. et al., Biochemistry 51 (2012)
Midorikawa, Y. et al., Jpn. J Cancer Res. 93 (2002)
Miled, C. et al., Cancer Res 65 (2005)
Milkereit, P. et al., J Biol. Chem. 278 (2003)
Miller, J. C. et al., Mol Carcinog. 48 (2009)
Mohelnikova-Duchonova, B. et al., Pancreas 42 (2013)
Monaco, M. E. et al., Transl. Oncol 3 (2010)
Morandi, F. et al., PLoS. One. 7 (2012)
Morrissey, J. J. et al., Urology 83 (2014)
Mu, J. et al., J Biol. Chem. 272 (1997)
Murray, D. W. et al., Br. J Cancer 110 (2014)
Murray, J. I. et al., Mol Biol. Cell 15 (2004)
Murrin, L. C. et al., J Neuroimmune. Pharmacol. 2 (2007)
Murthy, K. G. et al., Genes Dev. 9 (1995)
Mydlikova, Z. et al., Neoplasma 57 (2010)
Narita, T. et al., Mol Cell Biol. 23 (2003)
Narjoz, C. et al., PLoS. One. 9 (2014)
Nelson, E. R. et al., Science 342 (2013)
Ngeow, J. et al., Cancer Discov. 4 (2014)
Nibbe, R. K. et al., Mol. Cell Proteomics. 8 (2009)
Nielsen, M. J. et al., Blood 108 (2006)
Noda, T. et al., Hepatology 55 (2012)
Noh, C. K. et al., Clin Biochem. 47 (2014)
Ntikoudi, E. et al., Cancer Treat. Rev. 40 (2014)
Nwosu, V. et al., Hum. Mol Genet. 10 (2001)
Obholz, K. L. et al., Dev. Biol. 298 (2006)
Oeffner, F. et al., Am J Hum. Genet. 84 (2009)
Ofman, R. et al., Biochem. Biophys. Res Commun. 281 (2001)
Ohshima, K. et al., Mol Biol. Evol. 27 (2010)
Oiso, S. et al., Oncol Rep. 31 (2014)
Oji, Y. et al., Int. J Oncol 44 (2014)
Osada, H. et al., Int. J Cancer 112 (2004)
Otero-Rey, E. M. et al., Oral Oncol 44 (2008)
Palmer, D. H. et al., Hepatology 49 (2009)
Panico, F. et al., Adv. Cancer Res 105 (2009)
Park, B. L. et al., Biochem. Biophys. Res Commun. 363 (2007)
Patel, M. R. et al., Laryngoscope 121 (2011)
Patel, S. A. et al., Br. J Cancer (2014)
Pattani, K. M. et al., PLoS. ONE. 7 (2012)
Pavelec, D. M. et al., Genetics 183 (2009)
Pawlowska, M. et al., Drug Metab Dispos. 41 (2013)
Pehlivan, D. et al., Eur. J Hum. Genet. 22 (2014)
Pei, Z. et al., PLoS. One. 8 (2013)
Pellanda, H. et al., Int. J Biochem. Cell Biol. 44 (2012)
Peng, R. et al., J Cell Biol. 157 (2002)
Perera, S. et al., J Muscle Res Cell Motil. 33 (2012)
Persaud-Sawin, D. A. et al., Hum. Mol Genet. 11 (2002)
Peters, D. G. et al., Cancer Epidemiol. Biomarkers Prev. 14 (2005)
Pizon, V. et al., J Cell Sci. 115 (2002)
Placke, T. et al., Blood 124 (2014)
Plebani, R. et al., Neoplasia. 14 (2012)
Poh, W. et al., Mol Cancer 11 (2012)
Porkka, K. P. et al., Genes Chromosomes. Cancer 39 (2004)
Pylypenko, O. et al., Mol Cell 11 (2003)
Qi, L. et al., Cancer Res 74 (2014)
Qin, Y. et al., Pigment Cell Melanoma Res 26 (2013)
Quayle, S. N. et al., Neuro Oncol 14 (2012)
Quek, H. H. et al., DNA Cell Biol. 16 (1997)
Quidville, V. et al., Cancer Res 73 (2013)
Rajadhyaksha, A. M. et al., Am. J Hum. Genet. 87 (2010)
Rajasekaran, A. K. et al., Nucleic Acids Res 23 (1995)
Rajendran, M. et al., Cancer Metastasis Rev. 29 (2010)
Rakheja, D. et al., Mol Genet. Metab 93 (2008)
Ramana, C. V. et al., EMBO J 19 (2000)
Rashad, N. M. et al., Cytokine 68 (2014)
Rath, N. et al., EMBO Rep. 13 (2012)
Recupero, D. et al., Rom. J Morphol. Embryol. 51 (2010)
Reinisch, W. et al., J Immunother. 25 (2002)
Rekdal, C. et al., J Biol. Chem. 275 (2000)
Ren, Y. G. et al., Mol Biol. Cell 15 (2004)
Rennoll, S. A. et al., Biochem. Biophys. Res Commun. 443 (2014)
Rifas, L. et al., Arthritis Rheum. 60 (2009)
Riihila, P. M. et al., J Invest Dermatol. 134 (2014)
Rodriguez, F. J. et al., J Neuropathol. Exp. Neurol. 67 (2008)
Rogov, V. et al., Mol Cell 53 (2014)
Romanuik, T. L. et al., BMC. Genomics 10 (2009)
Roodman, G. D., Ann N.Y. Acad. Sci. 1192 (2010)
Rosado, I. V. et al., RNA. 10 (2004)
Rose, A. E. et al., Cancer Res 71 (2011)
Ross, H. et al., Arch. Pathol. Lab Med. 136 (2012)
Rossi, M. R. et al., Cancer Genet. Cytogenet. 161 (2005)
Rotondo, R. et al., Int. J Cancer 125 (2009)
Rucksaken, R. et al., Cancer Biomark. 12 (2012)
Ruiz, F. X. et al., Biochem. J 440 (2011)
Ruiz, F. X. et al., Front Pharmacol. 3 (2012)
Rutkowski, M. J. et al., Mol Cancer Res 8 (2010)
Rylova, S. N. et al., Cancer Res 62 (2002)
Sahm, F. et al., Cancer Res 73 (2013)
Sahu, A. et al., Immunol Res 17 (1998)
Saito, T. et al., J Biol. Chem. 278 (2003)
Salahshor, S. et al., J Clin Pathol. 58 (2005)
Sang, W. et al., Zhonghua Bing. Li Xue. Za Zhi. 42 (2013)
Sangro, B. et al., J Clin Oncol 22 (2004)
Sanz, L. et al., Mol Cell Biol. 15 (1995)
Saponaro, C. et al., Cancer Biomark. 14 (2014)
Sarajlic, A. et al., Breast Cancer Res Treat. 143 (2014)
Sasahira, T. et al., Eur. J Cancer 50 (2014)
Schneider, E. et al., Clin Chim. Acta 374 (2006)
Schofield, A. V. et al., Crit Rev. Biochem. Mol Biol. 48 (2013)
Schulz, E. G. et al., Immunity. 30 (2009)
Seifert, M. et al., J Pathol. 205 (2005)
Senchenko, V. et al., Oncogene 22 (2003)
Shaughnessy, J. D., Jr. et al., Blood 118 (2011)
Shen, F. et al., J Cell Biochem. 112 (2011)
Shi, M. et al., World J Gastroenterol. 10 (2004a)
Shi, Y. et al., Exp. Cell Res 296 (2004b)
Shi, Z. Z. et al., Clin Transl. Oncol 16 (2014)
Shinji, S. et al., Oncol Rep. 15 (2006)
Shodeinde, A. et al., J Mol Biochem. 2 (2013)
Shubbar, E. et al., BMC. Cancer 13 (2013)
Shurbaji, M. S. et al., Am J Clin Pathol. 96 (1991)
Sillars-Hardebol, A. H. et al., Gut 61 (2012)
Singh, S. et al., Tumour. Biol. (2014)

Smith, P. et al., Clin Cancer Res 13 (2007)
Song, C. et al., J Biol. Chem. 288 (2013)
Srivenugopal, K. S. et al., Cancer Lett. 117 (1997)
Staal-van den Brekel A J et al., Br. J Cancer 76 (1997)
Steen, H. C. et al., J Interferon Cytokine Res. 32 (2012)
Stefanska, B. et al., Clin Cancer Res 20 (2014)
Strassburg, C. P. et al., J Biol. Chem. 273 (1998)
Strassburg, C. P. et al., Mol Pharmacol. 52 (1997)
Sudo, H. et al., Genomics 95 (2010)
Sugihara, T. et al., J Biol. Chem. 276 (2001)
Sun, C. et al., Pathol. Res Pract. 210 (2014)
Sun, X. et al., J Pathol. 226 (2012)
Sun, X. et al., Protein Cell 4 (2013)
Sun, X. J. et al., Zhonghua Yi. Xue. Yi. Chuan Xue. Za Zhi. 22 (2005)
Supernat, A. et al., Oncol Lett. 4 (2012)
Surmacz, E., J Mammary. Gland. Biol. Neoplasia. 18 (2013)
Suzuki, K. et al., Biochem. Biophys. Res Commun. 368 (2008)
Swallow, C. J. et al., Oncogene 24 (2005)
Tabuchi, K. et al., J Neurosci. 22 (2002)
Taguchi, O. et al., Clin Chim. Acta 244 (1996)
Takayama, T. et al., Cancer 68 (1991)
Takayama, T. et al., Lancet 356 (2000)
Takeda, Y. et al., Glycobiology 24 (2014)
Takemasa, I. et al., Int. J Oncol 40 (2012)
Takeuchi, A. et al., Mol Cell Endocrinol. 384 (2014)
Tan, L. Z. et al., Am J Pathol. 183 (2013)
Tan, M. K. et al., Mol Cell Biol. 31 (2011)
Tanahashi, N. et al., Biochem. Biophys. Res Commun. 243 (1998)
Tanaka, M. et al., Mol Med. Rep. 7 (2013)
Tang, L. et al., Arch. Med. Res 43 (2012)
Tang, X. H. et al., Annu. Rev. Pathol. 6 (2011)
Tao, J. et al., Sci. Transl. Med. 3 (2011)
Tao, R. H. et al., Biochem. Biophys. Res Commun. 341 (2006)
Tao, T. et al., Cell Res 23 (2013)
Tarao, K. et al., Cancer 86 (1999)
Tarao, K. et al., Cancer 79 (1997)
Tasker, P. N. et al., Osteoporos. Int. 17 (2006)
Telikicherla, D. et al., Clin Proteomics. 9 (2012)
Tian, T. et al., Eur. J Cancer 48 (2012)
Tian, Y. et al., BMC. Cancer 14 (2014)
Tomiyama, K. et al., Proc. Natl. Acad. Sci. U.S.A 107 (2010)
Tomoda, T. et al., J Gastroenterol. Hepatol. 27 (2012)
Tong, J. et al., PLoS. One. 8 (2013)
Tortorella, S. et al., J Membr. Biol. 247 (2014)
Tran, E. et al., Science 344 (2014)
Trougakos, I. P., Gerontology 59 (2013)
Tsai, H. Y. et al., Oncogene 32 (2013)
Uddin, S. et al., Int. J Clin Exp. Pathol. 4 (2011)
Uehara, Y. et al., Cancer Res 43 (1983)
Urig, S. et al., Semin. Cancer Biol. 16 (2006)
Vainio, P. et al., Am. J Pathol. 178 (2011)
van der Spek, P. J. et al., Genomics 31 (1996)
van Zuylen, W. J. et al., PLoS. Pathog. 8 (2012)
van, den Broek, I et al., Proteomics. Clin Appl. 4 (2010)
van, Duin M. et al., Haematologica 96 (2011)
Vejda, S. et al., Mol Cell Proteomics. 1 (2002)
Vincent, F. et al., Cancer Res 69 (2009)
Wang, B. S. et al., Cell Stress. Chaperones. 18 (2013a)
Wang, D. et al., J Biol. Chem. 277 (2002)
Wang, J. et al., Eur. J Cancer Prev. 22 (2013b)
Wang, J. et al., J Clin Invest 112 (2003)
Wang, J. et al., Cancer Prev. Res (Phila) 6 (2013c)
Wang, J. C. et al., Oncology 81 (2011)
Wang, M. et al., Chin J Physiol 55 (2012)
Wang, S. K. et al., PLoS. Genet. 9 (2013d)
Wang, S. S. et al., PLoS. One. 5 (2010)
Wang, X. et al., Urol. Int. 92 (2014)
Wang, Y. et al., J Biol. Chem. 274 (1999)
Wang, Y. et al., Med. Oncol 32 (2015)
Wazir, U. et al., Cell Mol Biol. Lett. 18 (2013)
Wazir, U. et al., Anticancer Res 32 (2012)
Weiss, J. et al., Int. J Antimicrob. Agents 41 (2013)
Welsh, M. M. et al., Carcinogenesis 29 (2008)
Wieser, R., Leuk. Lymphoma 43 (2002)
Wilhelm, S. M. et al., Cancer Res. 64 (2004)
Williams, A. L. et al., Nature 506 (2014)
Witte, I. et al., Cell Death. Dis. 2 (2011)
Wong, K. K. et al., Leukemia 28 (2014)
Wong, N. et al., J Hepatol. 38 (2003)
Wu, L. et al., Ann Hematol. 91 (2012)
Wu, N. et al., Int. J Mol Sci. 14 (2013a)
Wu, W. et al., Sci. China Life Sci. 56 (2013b)
Wu, X. et al., Am. J Clin Exp. Urol. 2 (2014)
Wu, Y. M. et al., Cancer Res 71 (2011)
Xiao, J. et al., J Biol. Chem. 276 (2001)
Xie, F. W. et al., Neoplasma 61 (2014)
Xu, H. et al., Cell Rep. 9 (2014)
Xu, X. et al., Proteomics. 10 (2010)
Yan, D. et al., Proc. Natl. Acad. Sci. U.S.A 98 (2001)
Yang, C. et al., Virchows Arch. 463 (2013)
Yang, C. Y. et al., J Immunol 192 (2014a)
Yang, H. et al., Oncol Rep. 24 (2010)
Yang, H. W. et al., Oncogene 0 (2014b)
Yang, R. et al., Mol Cell Biol. 31 (2011a)
Yang, Z. J. et al., Mol Cancer Ther 10 (2011b)
Yau, C. et al., Breast Cancer Res 12 (2010)
Ye, X. H. et al., Mol Genet. Genomics (2014)
Yoon, J. K. et al., J Transl. Med. 12 (2014)
Yoshimura, S. et al., J Cell Biol. 191 (2010)
Yoshizuka, N. et al., Mol Cancer Res 10 (2012)
Yosten, G. L. et al., Am J Physiol Regul. Integr. Comp Physiol 303 (2012)
Yu, J. H. et al., RNA. 11 (2005)
Yu, K. et al., PLoS. Genet. 4 (2008)
Yue, C. et al., Int. J Cancer 136 (2015)
Zamanian-Daryoush, M. et al., J Biol. Chem. 288 (2013)
Zarling, A. L. et al., Cancer Res 74 (2014)
Zekri, A. R. et al., Asian Pac. J Cancer Prev. 13 (2012)
Zelcer, N. et al., Mol Cell Biol. 34 (2014)
Zhang, D. et al., Pak. J Med. Sci. 29 (2013a)
Zhang, H. et al., Oncotarget. 4 (2013b)
Zhang, H. T. et al., Biochim. Biophys. Acta 1839 (2014a)
Zhang, J. et al., Drug Metab Dispos. 34 (2006)
Zhang, S. et al., BMC. Cancer 11 (2011)
Zhang, X. et al., PLoS. One. 7 (2012)
Zhang, X. D. et al., Int. J Clin Exp. Med. 7 (2014b)
Zhao, Y. et al., Cell Death. Dis. 4 (2013)
Zhou, B. et al., Cancer Biol. Ther 13 (2012)
Zhou, D. et al., PLoS. One. 8 (2013a)
Zhou, J. et al., Oncol Rep. 30 (2013b)
Zhou, J. et al., Lung Cancer 14 (1996)
Zhu, H. et al., Cell Stress. Chaperones. (2014a)
Zhu, W. L. et al., Anticancer Res 29 (2009)
Zhu, X. et al., Biomed. Pharmacother. 68 (2014b)
Zhuang, Z. et al., J Neurosurg. 115 (2011)
Zietek, Z. et al., Pol. Tyg. Lek. 51 (1996)
Zou, W. et al., Cancer Sci. 101 (2010)
Zu, X. et al., Molecules. 18 (2013)
Zu, X. Y. et al., Recent Pat Anticancer Drug Discov. 7 (2012)
Zynda, E. R. et al., Cell Cycle 13 (2014)

The invention claimed is:

1. A method of eliciting a CD8+ cytotoxic T cell response in an HLA-A*02+ patient who has hepatocellular carcinoma (HCC), comprising
identifying the patient who has HCC cells that overpresent on the cell surface a peptide consisting of the amino acid sequence of GVYDGEEHSV (SEQ ID NO: 303) as compared to a panel of normal tissues, wherein the peptide is in a complex with HLA-A*02, and
administering to said identified patient a composition comprising a population of activated antigen-specific CD8+ cytotoxic T cells to kill the HCC cells in the identified patient,
wherein the population of activated antigen-specific CD8+ cytotoxic T cells recognize the HCC cells by interacting through their TCR with a peptide consisting of the amino acid sequence of GVYDGEEHSV (SEQ ID NO: 303) in a complex with HLA-A*02 presented at the surface of the HCC cells.

2. The method of claim 1, wherein the activated antigen-specific CD8+ cytotoxic T cells are autologous to the patient.

3. The method of claim 1, wherein the activated antigen-specific CD8+ cytotoxic T cells are obtained from a healthy donor.

4. The method of claim 1, wherein the activated antigen-specific CD8+ cytotoxic T cells are obtained from tumor infiltrating lymphocytes or peripheral blood mononuclear cells.

5. The method of claim 1, wherein the composition further comprises an adjuvant.

6. The method of claim 5, wherein the adjuvant is selected from the group consisting of anti-CD40 antibody, imiquimod, resiquimod, GM-CSF, cyclophosphamide, Sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

7. A method of eliciting a CD8+ cytotoxic T cell response in an HLA-A*02+ patient who has hepatocellular carcinoma (HCC), wherein the HCC cells overexpress a MAGEB2 polypeptide comprising the amino acid sequence of GVYDGEEHSV (SEQ ID NO: 303) as compared to a panel of normal tissues, wherein the HCC cells present at the cell surface a peptide consisting of the amino acid sequence of GVYDGEEHSV (SEQ ID NO: 303) in a complex with HLA-A*02, comprising
isolating CD8+ cytotoxic T cells,
contacting the CD8+ cytotoxic T cells with an antigen presenting cell that present at the cell surface a peptide consisting of SEQ ID NO. 303 in a complex with HLA-A*02 in vitro, thereby activating the CD8+ cytotoxic T cells, and
administering to said patient who has HCC a composition comprising a population of the activated antigen-specific CD8+ cytotoxic T cells to kill the HCC cells in the patient,
wherein the population of the activated antigen-specific CD8+ cytotoxic T cells recognize the HCC cells by interacting through their TCR with a peptide consisting of the amino acid sequence of GVYDGEEHSV (SEQ ID NO: 303) in a complex with HLA-A*02 presented at the surface of the HCC cells.

8. The method of claim 7, further comprising expanding the activated T cells in vitro.

9. The method of claim 7, wherein the composition further comprises an adjuvant.

10. The method of claim 9, wherein the adjuvant is selected from the group consisting of anti-CD40 antibody, imiquimod, resiquimod, OM-CSF, cyclophosphamide, Sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

11. The method of claim 7, wherein the antigen presenting cell in a dendritic cell or a macrophage.

12. The method of claim 8, wherein the expanding is in the presence of an anti-CD28 antibody and IL-12.

* * * * *

SEQUENCE LISTING

<160> NUMBER OF SEQ ID NOS: 348

<210> SEQ ID NO 1
<211> LENGTH: 9
<212> TYPE: PRT
<213> ORGANISM: Homo sapiens

<400> SEQUENCE: 1

Val Met Ala Pro Phe Thr Met Thr Ile
1               5

<210> SEQ ID NO 2
<211> LENGTH: 9
<212> TYPE: PRT
<213> ORGANISM: Homo sapiens

<400> SEQUENCE: 2

Lys Leu Gln Ala Gly Thr Val Phe Val
1               5

<210> SEQ ID NO 3
<211> LENGTH: 9
<212> TYPE: PRT
<213> ORGANISM: Homo sapiens

<400> SEQUENCE: 3

Ile Leu Asp Asp Asn Met Gln Lys Leu
1               5

<210> SEQ ID NO 4
<211> LENGTH: 9
<212> TYPE: PRT
<213> ORGANISM: Homo sapiens

<400> SEQUENCE: 4

Lys Leu Gln Asp Phe Ser Asp Gln Leu
1               5

<210> SEQ ID NO 5
<211> LENGTH: 9
<212> TYPE: PRT
<213> ORGANISM: Homo sapiens

<400> SEQUENCE: 5

Ala Leu Val Glu Gln Gly Phe Thr Val
1               5

<210> SEQ ID NO 6
<211> LENGTH: 9
<212> TYPE: PRT
<213> ORGANISM: Homo sapiens

<400> SEQUENCE: 6

Lys Leu Ser Pro Thr Val Val Gly Leu
1               5

<210> SEQ ID NO 7
<211> LENGTH: 9
<212> TYPE: PRT
<213> ORGANISM: Homo sapiens

<400> SEQUENCE: 7

Ala Leu Val Asp Thr Leu Lys Phe Val
1               5

```
<210> SEQ ID NO 8
<211> LENGTH: 10
<212> TYPE: PRT
<213> ORGANISM: Homo sapiens

<400> SEQUENCE: 8

Lys Leu Leu Glu Glu Ala Thr Ile Ser Val
1               5                   10

<210> SEQ ID NO 9
<211> LENGTH: 10
<212> TYPE: PRT
<213> ORGANISM: Homo sapiens

<400> SEQUENCE: 9

Ala Leu Ala Asn Gln Lys Leu Tyr Ser Val
1               5                   10

<210> SEQ ID NO 10
<211> LENGTH: 10
<212> TYPE: PRT
<213> ORGANISM: Homo sapiens

<400> SEQUENCE: 10

Ser Leu Leu Glu Glu Phe Asp Phe His Val
1               5                   10

<210> SEQ ID NO 11
<211> LENGTH: 9
<212> TYPE: PRT
<213> ORGANISM: Homo sapiens

<400> SEQUENCE: 11

Ser Leu Ser Gln Glu Leu Val Gly Val
1               5

<210> SEQ ID NO 12
<211> LENGTH: 9
<212> TYPE: PRT
<213> ORGANISM: Homo sapiens

<400> SEQUENCE: 12

Phe Leu Ala Glu Leu Ala Tyr Asp Leu
1               5

<210> SEQ ID NO 13
<211> LENGTH: 12
<212> TYPE: PRT
<213> ORGANISM: Homo sapiens

<400> SEQUENCE: 13

Gly Leu Ile Asp Thr Glu Thr Ala Met Lys Ala Val
1               5                   10

<210> SEQ ID NO 14
<211> LENGTH: 10
<212> TYPE: PRT
<213> ORGANISM: Homo sapiens

<400> SEQUENCE: 14

Ala Leu Ala Asp Leu Thr Gly Thr Val Val
1               5                   10

<210> SEQ ID NO 15
```

```
<211> LENGTH: 9
<212> TYPE: PRT
<213> ORGANISM: Homo sapiens

<400> SEQUENCE: 15

Leu Leu Tyr Gly His Thr Val Thr Val
1               5

<210> SEQ ID NO 16
<211> LENGTH: 9
<212> TYPE: PRT
<213> ORGANISM: Homo sapiens

<400> SEQUENCE: 16

Ser Leu Leu Gly Gly Asn Ile Arg Leu
1               5

<210> SEQ ID NO 17
<211> LENGTH: 9
<212> TYPE: PRT
<213> ORGANISM: Homo sapiens

<400> SEQUENCE: 17

Arg Val Ala Ser Pro Thr Ser Gly Val
1               5

<210> SEQ ID NO 18
<211> LENGTH: 9
<212> TYPE: PRT
<213> ORGANISM: Homo sapiens

<400> SEQUENCE: 18

Ala Leu Tyr Gly Lys Thr Glu Val Val
1               5

<210> SEQ ID NO 19
<211> LENGTH: 9
<212> TYPE: PRT
<213> ORGANISM: Homo sapiens

<400> SEQUENCE: 19

Phe Leu Glu Glu Thr Lys Ala Thr Val
1               5

<210> SEQ ID NO 20
<211> LENGTH: 9
<212> TYPE: PRT
<213> ORGANISM: Homo sapiens

<400> SEQUENCE: 20

Lys Leu Ser Asn Val Leu Gln Gln Val
1               5

<210> SEQ ID NO 21
<211> LENGTH: 11
<212> TYPE: PRT
<213> ORGANISM: Homo sapiens

<400> SEQUENCE: 21

Gln Leu Ile Glu Val Ser Ser Pro Ile Thr Leu
1               5                   10

<210> SEQ ID NO 22
<211> LENGTH: 11
<212> TYPE: PRT
```

```
<213> ORGANISM: Homo sapiens

<400> SEQUENCE: 22

Arg Ile Ala Gly Ile Arg Gly Ile Gln Gly Val
1               5                   10

<210> SEQ ID NO 23
<211> LENGTH: 12
<212> TYPE: PRT
<213> ORGANISM: Homo sapiens

<400> SEQUENCE: 23

Arg Leu Tyr Asp Pro Ala Ser Gly Thr Ile Ser Leu
1               5                   10

<210> SEQ ID NO 24
<211> LENGTH: 11
<212> TYPE: PRT
<213> ORGANISM: Homo sapiens

<400> SEQUENCE: 24

Ser Leu Ala Glu Glu Lys Leu Gln Ala Ser Val
1               5                   10

<210> SEQ ID NO 25
<211> LENGTH: 11
<212> TYPE: PRT
<213> ORGANISM: Homo sapiens

<400> SEQUENCE: 25

Ser Leu Asp Gly Lys Ala Ala Leu Thr Glu Leu
1               5                   10

<210> SEQ ID NO 26
<211> LENGTH: 9
<212> TYPE: PRT
<213> ORGANISM: Homo sapiens

<400> SEQUENCE: 26

Ser Leu Leu His Thr Ile Tyr Glu Val
1               5

<210> SEQ ID NO 27
<211> LENGTH: 10
<212> TYPE: PRT
<213> ORGANISM: Homo sapiens

<400> SEQUENCE: 27

Thr Leu Pro Asp Phe Arg Leu Pro Glu Ile
1               5                   10

<210> SEQ ID NO 28
<211> LENGTH: 9
<212> TYPE: PRT
<213> ORGANISM: Homo sapiens

<400> SEQUENCE: 28

Thr Leu Gln Asp His Leu Asn Ser Leu
1               5

<210> SEQ ID NO 29
<211> LENGTH: 9
<212> TYPE: PRT
<213> ORGANISM: Homo sapiens
```

```
<400> SEQUENCE: 29

Tyr Ile Gln Asp Glu Ile Asn Thr Ile
1               5

<210> SEQ ID NO 30
<211> LENGTH: 9
<212> TYPE: PRT
<213> ORGANISM: Homo sapiens

<400> SEQUENCE: 30

Tyr Leu Gly Glu Gly Pro Arg Met Val
1               5

<210> SEQ ID NO 31
<211> LENGTH: 9
<212> TYPE: PRT
<213> ORGANISM: Homo sapiens

<400> SEQUENCE: 31

Tyr Gln Met Asp Ile Gln Gln Glu Leu
1               5

<210> SEQ ID NO 32
<211> LENGTH: 9
<212> TYPE: PRT
<213> ORGANISM: Homo sapiens

<400> SEQUENCE: 32

Ala Leu Asn Ala Val Arg Leu Leu Val
1               5

<210> SEQ ID NO 33
<211> LENGTH: 9
<212> TYPE: PRT
<213> ORGANISM: Homo sapiens

<400> SEQUENCE: 33

Leu Leu His Gly His Ile Val Glu Leu
1               5

<210> SEQ ID NO 34
<211> LENGTH: 9
<212> TYPE: PRT
<213> ORGANISM: Homo sapiens

<400> SEQUENCE: 34

Ser Leu Ala Glu Gly Thr Ala Thr Val
1               5

<210> SEQ ID NO 35
<211> LENGTH: 10
<212> TYPE: PRT
<213> ORGANISM: Homo sapiens

<400> SEQUENCE: 35

Ser Leu Gln Glu Ser Ile Leu Ala Gln Val
1               5                   10

<210> SEQ ID NO 36
<211> LENGTH: 10
<212> TYPE: PRT
<213> ORGANISM: Homo sapiens

<400> SEQUENCE: 36
```

```
Ile Leu Asn Val Asp Gly Leu Ile Gly Val
1               5                   10

<210> SEQ ID NO 37
<211> LENGTH: 11
<212> TYPE: PRT
<213> ORGANISM: Homo sapiens

<400> SEQUENCE: 37

Leu Leu Leu Pro Leu Leu Pro Pro Leu Ser Pro
1               5                   10

<210> SEQ ID NO 38
<211> LENGTH: 9
<212> TYPE: PRT
<213> ORGANISM: Homo sapiens

<400> SEQUENCE: 38

Ala Leu Ala Asp Val Val His Glu Ala
1               5

<210> SEQ ID NO 39
<211> LENGTH: 10
<212> TYPE: PRT
<213> ORGANISM: Homo sapiens

<400> SEQUENCE: 39

Ala Leu Asp Pro Lys Ala Asn Phe Ser Thr
1               5                   10

<210> SEQ ID NO 40
<211> LENGTH: 10
<212> TYPE: PRT
<213> ORGANISM: Homo sapiens

<400> SEQUENCE: 40

Ala Leu Leu Ala Glu Gly Ile Thr Trp Val
1               5                   10

<210> SEQ ID NO 41
<211> LENGTH: 11
<212> TYPE: PRT
<213> ORGANISM: Homo sapiens

<400> SEQUENCE: 41

Ala Leu Leu Glu Leu Asp Glu Pro Leu Val Leu
1               5                   10

<210> SEQ ID NO 42
<211> LENGTH: 11
<212> TYPE: PRT
<213> ORGANISM: Homo sapiens

<400> SEQUENCE: 42

Ala Leu Leu Gly Gly Asn Val Arg Met Met Leu
1               5                   10

<210> SEQ ID NO 43
<211> LENGTH: 9
<212> TYPE: PRT
<213> ORGANISM: Homo sapiens

<400> SEQUENCE: 43

Ala Leu Leu Gly Val Trp Thr Ser Val
1               5
```

```
<210> SEQ ID NO 44
<211> LENGTH: 9
<212> TYPE: PRT
<213> ORGANISM: Homo sapiens

<400> SEQUENCE: 44

Ala Leu Gln Asp Ala Ile Arg Gln Leu
1               5

<210> SEQ ID NO 45
<211> LENGTH: 9
<212> TYPE: PRT
<213> ORGANISM: Homo sapiens

<400> SEQUENCE: 45

Ala Leu Gln Asp Gln Leu Val Leu Val
1               5

<210> SEQ ID NO 46
<211> LENGTH: 9
<212> TYPE: PRT
<213> ORGANISM: Homo sapiens

<400> SEQUENCE: 46

Ala Met Ala Glu Met Lys Val Val Leu
1               5

<210> SEQ ID NO 47
<211> LENGTH: 9
<212> TYPE: PRT
<213> ORGANISM: Homo sapiens

<400> SEQUENCE: 47

Phe Leu Asp Thr Pro Ile Ala Lys Val
1               5

<210> SEQ ID NO 48
<211> LENGTH: 10
<212> TYPE: PRT
<213> ORGANISM: Homo sapiens

<400> SEQUENCE: 48

Phe Leu Leu Glu Gln Pro Glu Ile Gln Val
1               5                   10

<210> SEQ ID NO 49
<211> LENGTH: 10
<212> TYPE: PRT
<213> ORGANISM: Homo sapiens

<400> SEQUENCE: 49

Phe Leu Tyr Pro Glu Lys Asp Glu Pro Thr
1               5                   10

<210> SEQ ID NO 50
<211> LENGTH: 9
<212> TYPE: PRT
<213> ORGANISM: Homo sapiens

<400> SEQUENCE: 50

Phe Thr Ile Pro Lys Leu Tyr Gln Leu
1               5
```

```
<210> SEQ ID NO 51
<211> LENGTH: 9
<212> TYPE: PRT
<213> ORGANISM: Homo sapiens

<400> SEQUENCE: 51

Gly Leu Ala Glu Glu Leu Val Arg Ala
1               5

<210> SEQ ID NO 52
<211> LENGTH: 10
<212> TYPE: PRT
<213> ORGANISM: Homo sapiens

<400> SEQUENCE: 52

Gly Leu Phe Asn Ala Glu Leu Leu Glu Ala
1               5                   10

<210> SEQ ID NO 53
<211> LENGTH: 10
<212> TYPE: PRT
<213> ORGANISM: Homo sapiens

<400> SEQUENCE: 53

Gly Leu Ile His Leu Glu Gly Asp Thr Val
1               5                   10

<210> SEQ ID NO 54
<211> LENGTH: 12
<212> TYPE: PRT
<213> ORGANISM: Homo sapiens

<400> SEQUENCE: 54

Gly Leu Leu Asp Pro Asn Val Lys Ser Ile Phe Val
1               5                   10

<210> SEQ ID NO 55
<211> LENGTH: 9
<212> TYPE: PRT
<213> ORGANISM: Homo sapiens

<400> SEQUENCE: 55

Gly Leu Tyr Gly Arg Thr Ile Glu Leu
1               5

<210> SEQ ID NO 56
<211> LENGTH: 9
<212> TYPE: PRT
<213> ORGANISM: Homo sapiens

<400> SEQUENCE: 56

Gly Val Leu Pro Gly Leu Val Gly Val
1               5

<210> SEQ ID NO 57
<211> LENGTH: 9
<212> TYPE: PRT
<213> ORGANISM: Homo sapiens

<400> SEQUENCE: 57

His Leu Thr Glu Ala Ile Gln Tyr Val
1               5

<210> SEQ ID NO 58
<211> LENGTH: 9
```

```
<212> TYPE: PRT
<213> ORGANISM: Homo sapiens

<400> SEQUENCE: 58

Ile Leu Ala Asp Leu Asn Leu Ser Val
1               5

<210> SEQ ID NO 59
<211> LENGTH: 9
<212> TYPE: PRT
<213> ORGANISM: Homo sapiens

<400> SEQUENCE: 59

Ile Leu Ala Asp Thr Phe Ile Gly Val
1               5

<210> SEQ ID NO 60
<211> LENGTH: 9
<212> TYPE: PRT
<213> ORGANISM: Homo sapiens

<400> SEQUENCE: 60

Ile Leu Ser Pro Leu Ser Val Ala Leu
1               5

<210> SEQ ID NO 61
<211> LENGTH: 10
<212> TYPE: PRT
<213> ORGANISM: Homo sapiens

<400> SEQUENCE: 61

Lys Ile Ala Asp Phe Glu Leu Pro Thr Ile
1               5                   10

<210> SEQ ID NO 62
<211> LENGTH: 9
<212> TYPE: PRT
<213> ORGANISM: Homo sapiens

<400> SEQUENCE: 62

Lys Ile Ala Gly Thr Asn Ala Glu Val
1               5

<210> SEQ ID NO 63
<211> LENGTH: 9
<212> TYPE: PRT
<213> ORGANISM: Homo sapiens

<400> SEQUENCE: 63

Lys Ile Asp Glu Lys Asn Phe Val Val
1               5

<210> SEQ ID NO 64
<211> LENGTH: 9
<212> TYPE: PRT
<213> ORGANISM: Homo sapiens

<400> SEQUENCE: 64

Lys Ile Leu Glu Glu Thr Leu Tyr Val
1               5

<210> SEQ ID NO 65
<211> LENGTH: 11
<212> TYPE: PRT
<213> ORGANISM: Homo sapiens
```

```
<400> SEQUENCE: 65

Lys Leu Phe Ser Gly Asp Glu Leu Leu Glu Val
1               5                   10

<210> SEQ ID NO 66
<211> LENGTH: 9
<212> TYPE: PRT
<213> ORGANISM: Homo sapiens

<400> SEQUENCE: 66

Lys Leu His Glu Glu Ile Asp Arg Val
1               5

<210> SEQ ID NO 67
<211> LENGTH: 9
<212> TYPE: PRT
<213> ORGANISM: Homo sapiens

<400> SEQUENCE: 67

Lys Leu Lys Glu Thr Ile Gln Lys Leu
1               5

<210> SEQ ID NO 68
<211> LENGTH: 10
<212> TYPE: PRT
<213> ORGANISM: Homo sapiens

<400> SEQUENCE: 68

Lys Leu Leu Ala Ala Thr Val Leu Leu Leu
1               5                   10

<210> SEQ ID NO 69
<211> LENGTH: 11
<212> TYPE: PRT
<213> ORGANISM: Homo sapiens

<400> SEQUENCE: 69

Lys Leu Leu Asp Glu Val Thr Tyr Leu Glu Ala
1               5                   10

<210> SEQ ID NO 70
<211> LENGTH: 12
<212> TYPE: PRT
<213> ORGANISM: Homo sapiens

<400> SEQUENCE: 70

Lys Leu Leu Asp Leu Glu Thr Glu Arg Ile Leu Leu
1               5                   10

<210> SEQ ID NO 71
<211> LENGTH: 9
<212> TYPE: PRT
<213> ORGANISM: Homo sapiens

<400> SEQUENCE: 71

Lys Leu Leu Asp Asn Trp Asp Ser Val
1               5

<210> SEQ ID NO 72
<211> LENGTH: 9
<212> TYPE: PRT
<213> ORGANISM: Homo sapiens

<400> SEQUENCE: 72
```

Lys Leu Ser Glu Ala Val Thr Ser Val
1               5

<210> SEQ ID NO 73
<211> LENGTH: 9
<212> TYPE: PRT
<213> ORGANISM: Homo sapiens

<400> SEQUENCE: 73

Lys Leu Thr Leu Val Ile Ile Ser Val
1               5

<210> SEQ ID NO 74
<211> LENGTH: 9
<212> TYPE: PRT
<213> ORGANISM: Homo sapiens

<400> SEQUENCE: 74

Lys Leu Tyr Asp Leu Glu Leu Ile Val
1               5

<210> SEQ ID NO 75
<211> LENGTH: 9
<212> TYPE: PRT
<213> ORGANISM: Homo sapiens

<400> SEQUENCE: 75

Lys Gln Met Glu Pro Leu His Ala Val
1               5

<210> SEQ ID NO 76
<211> LENGTH: 12
<212> TYPE: PRT
<213> ORGANISM: Homo sapiens

<400> SEQUENCE: 76

Leu Leu Ala Asp Ile Gly Gly Asp Pro Phe Ala Ala
1               5                   10

<210> SEQ ID NO 77
<211> LENGTH: 9
<212> TYPE: PRT
<213> ORGANISM: Homo sapiens

<400> SEQUENCE: 77

Leu Leu His Glu Glu Asn Phe Ser Val
1               5

<210> SEQ ID NO 78
<211> LENGTH: 9
<212> TYPE: PRT
<213> ORGANISM: Homo sapiens

<400> SEQUENCE: 78

Leu Leu Ile Asp Asp Glu Tyr Lys Val
1               5

<210> SEQ ID NO 79
<211> LENGTH: 9
<212> TYPE: PRT
<213> ORGANISM: Homo sapiens

<400> SEQUENCE: 79

Leu Leu Leu Ser Thr Gly Tyr Glu Ala

```
1               5
```

<210> SEQ ID NO 80
<211> LENGTH: 9
<212> TYPE: PRT
<213> ORGANISM: Homo sapiens

<400> SEQUENCE: 80

```
Leu Leu Tyr Glu Gly Lys Leu Thr Leu
1               5
```

<210> SEQ ID NO 81
<211> LENGTH: 11
<212> TYPE: PRT
<213> ORGANISM: Homo sapiens

<400> SEQUENCE: 81

```
Asn Leu Ala Ser Phe Ile Glu Gln Val Ala Val
1               5                   10
```

<210> SEQ ID NO 82
<211> LENGTH: 9
<212> TYPE: PRT
<213> ORGANISM: Homo sapiens

<400> SEQUENCE: 82

```
Asn Val Phe Asp Gly Leu Val Arg Val
1               5
```

<210> SEQ ID NO 83
<211> LENGTH: 9
<212> TYPE: PRT
<213> ORGANISM: Homo sapiens

<400> SEQUENCE: 83

```
Gln Leu His Asp Phe Val Met Ser Leu
1               5
```

<210> SEQ ID NO 84
<211> LENGTH: 9
<212> TYPE: PRT
<213> ORGANISM: Homo sapiens

<400> SEQUENCE: 84

```
Gln Leu Thr Pro Val Leu Val Ser Val
1               5
```

<210> SEQ ID NO 85
<211> LENGTH: 9
<212> TYPE: PRT
<213> ORGANISM: Homo sapiens

<400> SEQUENCE: 85

```
Arg Ile Leu Pro Lys Val Leu Glu Val
1               5
```

<210> SEQ ID NO 86
<211> LENGTH: 9
<212> TYPE: PRT
<213> ORGANISM: Homo sapiens

<400> SEQUENCE: 86

```
Arg Leu Ala Ala Phe Tyr Ser Gln Val
1               5
```

```
<210> SEQ ID NO 87
<211> LENGTH: 10
<212> TYPE: PRT
<213> ORGANISM: Homo sapiens

<400> SEQUENCE: 87

Arg Leu Phe Glu Glu Asn Asp Val Asn Leu
1               5                   10

<210> SEQ ID NO 88
<211> LENGTH: 9
<212> TYPE: PRT
<213> ORGANISM: Homo sapiens

<400> SEQUENCE: 88

Arg Leu Ile Asp Arg Ile Lys Thr Val
1               5

<210> SEQ ID NO 89
<211> LENGTH: 9
<212> TYPE: PRT
<213> ORGANISM: Homo sapiens

<400> SEQUENCE: 89

Arg Leu Ile Glu Glu Ile Lys Asn Val
1               5

<210> SEQ ID NO 90
<211> LENGTH: 10
<212> TYPE: PRT
<213> ORGANISM: Homo sapiens

<400> SEQUENCE: 90

Arg Leu Leu Asp Val Leu Ala Pro Leu Val
1               5                   10

<210> SEQ ID NO 91
<211> LENGTH: 10
<212> TYPE: PRT
<213> ORGANISM: Homo sapiens

<400> SEQUENCE: 91

Arg Leu Pro Asp Ile Pro Leu Arg Gln Val
1               5                   10

<210> SEQ ID NO 92
<211> LENGTH: 11
<212> TYPE: PRT
<213> ORGANISM: Homo sapiens

<400> SEQUENCE: 92

Arg Leu Pro Pro Asp Thr Leu Leu Gln Gln Val
1               5                   10

<210> SEQ ID NO 93
<211> LENGTH: 10
<212> TYPE: PRT
<213> ORGANISM: Homo sapiens

<400> SEQUENCE: 93

Arg Leu Tyr Thr Met Asp Gly Ile Thr Val
1               5                   10

<210> SEQ ID NO 94
```

```
<211> LENGTH: 9
<212> TYPE: PRT
<213> ORGANISM: Homo sapiens

<400> SEQUENCE: 94

Arg Met Ser Asp Val Val Lys Gly Val
1               5

<210> SEQ ID NO 95
<211> LENGTH: 9
<212> TYPE: PRT
<213> ORGANISM: Homo sapiens

<400> SEQUENCE: 95

Ser Ile Cys Asn Gly Val Pro Met Val
1               5

<210> SEQ ID NO 96
<211> LENGTH: 11
<212> TYPE: PRT
<213> ORGANISM: Homo sapiens

<400> SEQUENCE: 96

Ser Leu Leu Glu Glu Pro Asn Val Ile Arg Val
1               5                   10

<210> SEQ ID NO 97
<211> LENGTH: 9
<212> TYPE: PRT
<213> ORGANISM: Homo sapiens

<400> SEQUENCE: 97

Ser Leu Leu Pro Gln Leu Ile Glu Val
1               5

<210> SEQ ID NO 98
<211> LENGTH: 11
<212> TYPE: PRT
<213> ORGANISM: Homo sapiens

<400> SEQUENCE: 98

Ser Leu Leu Ser Pro Glu His Leu Gln Tyr Leu
1               5                   10

<210> SEQ ID NO 99
<211> LENGTH: 9
<212> TYPE: PRT
<213> ORGANISM: Homo sapiens

<400> SEQUENCE: 99

Ser Leu Ser Ala Phe Leu Pro Ser Leu
1               5

<210> SEQ ID NO 100
<211> LENGTH: 11
<212> TYPE: PRT
<213> ORGANISM: Homo sapiens

<400> SEQUENCE: 100

Ser Leu Val Gly Asp Ile Gly Asn Val Asn Met
1               5                   10

<210> SEQ ID NO 101
<211> LENGTH: 10
<212> TYPE: PRT
```

-continued

```
<213> ORGANISM: Homo sapiens

<400> SEQUENCE: 101

Ser Leu Trp Glu Gly Gly Val Arg Gly Val
1               5                   10

<210> SEQ ID NO 102
<211> LENGTH: 9
<212> TYPE: PRT
<213> ORGANISM: Homo sapiens

<400> SEQUENCE: 102

Ser Leu Trp Ser Val Ala Arg Gly Val
1               5

<210> SEQ ID NO 103
<211> LENGTH: 9
<212> TYPE: PRT
<213> ORGANISM: Homo sapiens

<400> SEQUENCE: 103

Ser Met Gly Asp His Leu Trp Val Ala
1               5

<210> SEQ ID NO 104
<211> LENGTH: 9
<212> TYPE: PRT
<213> ORGANISM: Homo sapiens

<400> SEQUENCE: 104

Ser Val Trp Phe Gly Pro Lys Glu Val
1               5

<210> SEQ ID NO 105
<211> LENGTH: 9
<212> TYPE: PRT
<213> ORGANISM: Homo sapiens

<400> SEQUENCE: 105

Ser Val Tyr Asp Gly Lys Leu Leu Ile
1               5

<210> SEQ ID NO 106
<211> LENGTH: 9
<212> TYPE: PRT
<213> ORGANISM: Homo sapiens

<400> SEQUENCE: 106

Thr Leu Ala Ala Ile Ile His Gly Ala
1               5

<210> SEQ ID NO 107
<211> LENGTH: 9
<212> TYPE: PRT
<213> ORGANISM: Homo sapiens

<400> SEQUENCE: 107

Thr Leu Gly Gln Phe Tyr Gln Glu Val
1               5

<210> SEQ ID NO 108
<211> LENGTH: 9
<212> TYPE: PRT
<213> ORGANISM: Homo sapiens
```

```
<400> SEQUENCE: 108

Thr Leu Leu Lys Lys Ile Ser Glu Ala
1               5

<210> SEQ ID NO 109
<211> LENGTH: 9
<212> TYPE: PRT
<213> ORGANISM: Homo sapiens

<400> SEQUENCE: 109

Thr Leu Tyr Ala Leu Ser His Ala Val
1               5

<210> SEQ ID NO 110
<211> LENGTH: 11
<212> TYPE: PRT
<213> ORGANISM: Homo sapiens

<400> SEQUENCE: 110

Thr Val Gly Gly Ser Glu Ile Leu Phe Glu Val
1               5                   10

<210> SEQ ID NO 111
<211> LENGTH: 13
<212> TYPE: PRT
<213> ORGANISM: Homo sapiens

<400> SEQUENCE: 111

Thr Val Met Asp Ile Asp Thr Ser Gly Thr Phe Asn Val
1               5                   10

<210> SEQ ID NO 112
<211> LENGTH: 9
<212> TYPE: PRT
<213> ORGANISM: Homo sapiens

<400> SEQUENCE: 112

Val Leu Gly Glu Val Lys Val Gly Val
1               5

<210> SEQ ID NO 113
<211> LENGTH: 9
<212> TYPE: PRT
<213> ORGANISM: Homo sapiens

<400> SEQUENCE: 113

Val Leu Met Asp Lys Leu Val Glu Leu
1               5

<210> SEQ ID NO 114
<211> LENGTH: 9
<212> TYPE: PRT
<213> ORGANISM: Homo sapiens

<400> SEQUENCE: 114

Val Leu Ser Gln Val Tyr Ser Lys Val
1               5

<210> SEQ ID NO 115
<211> LENGTH: 10
<212> TYPE: PRT
<213> ORGANISM: Homo sapiens

<400> SEQUENCE: 115
```

```
Val Val Leu Asp Asp Lys Asp Tyr Phe Leu
1               5                   10

<210> SEQ ID NO 116
<211> LENGTH: 9
<212> TYPE: PRT
<213> ORGANISM: Homo sapiens

<400> SEQUENCE: 116

Trp Val Ile Pro Ala Ile Ser Ala Val
1               5

<210> SEQ ID NO 117
<211> LENGTH: 9
<212> TYPE: PRT
<213> ORGANISM: Homo sapiens

<400> SEQUENCE: 117

Tyr Ala Phe Pro Lys Ser Ile Thr Val
1               5

<210> SEQ ID NO 118
<211> LENGTH: 10
<212> TYPE: PRT
<213> ORGANISM: Homo sapiens

<400> SEQUENCE: 118

Tyr Leu Asp Asp Glu Lys Asn Trp Gly Leu
1               5                   10

<210> SEQ ID NO 119
<211> LENGTH: 10
<212> TYPE: PRT
<213> ORGANISM: Homo sapiens

<400> SEQUENCE: 119

Tyr Leu Asp Lys Asn Leu Thr Val Ser Val
1               5                   10

<210> SEQ ID NO 120
<211> LENGTH: 9
<212> TYPE: PRT
<213> ORGANISM: Homo sapiens

<400> SEQUENCE: 120

Tyr Leu Gly Glu Glu Tyr Val Lys Ala
1               5

<210> SEQ ID NO 121
<211> LENGTH: 10
<212> TYPE: PRT
<213> ORGANISM: Homo sapiens

<400> SEQUENCE: 121

Tyr Leu Ile Thr Gly Asn Leu Glu Lys Leu
1               5                   10

<210> SEQ ID NO 122
<211> LENGTH: 12
<212> TYPE: PRT
<213> ORGANISM: Homo sapiens

<400> SEQUENCE: 122

Tyr Leu Ser Gln Ala Ala Asp Gly Ala Lys Val Leu
1               5                   10
```

```
<210> SEQ ID NO 123
<211> LENGTH: 12
<212> TYPE: PRT
<213> ORGANISM: Homo sapiens

<400> SEQUENCE: 123

Tyr Leu Trp Asp Leu Asp His Gly Phe Ala Gly Val
1               5                   10

<210> SEQ ID NO 124
<211> LENGTH: 9
<212> TYPE: PRT
<213> ORGANISM: Homo sapiens

<400> SEQUENCE: 124

Leu Leu Ile Asp Val Val Thr Tyr Leu
1               5

<210> SEQ ID NO 125
<211> LENGTH: 9
<212> TYPE: PRT
<213> ORGANISM: Homo sapiens

<400> SEQUENCE: 125

Ala Leu Tyr Gly Arg Leu Glu Val Val
1               5

<210> SEQ ID NO 126
<211> LENGTH: 9
<212> TYPE: PRT
<213> ORGANISM: Homo sapiens

<400> SEQUENCE: 126

Thr Leu Leu Asp Ser Pro Ile Lys Val
1               5

<210> SEQ ID NO 127
<211> LENGTH: 9
<212> TYPE: PRT
<213> ORGANISM: Homo sapiens

<400> SEQUENCE: 127

Val Leu Ile Gly Ser Asn His Ser Leu
1               5

<210> SEQ ID NO 128
<211> LENGTH: 9
<212> TYPE: PRT
<213> ORGANISM: Homo sapiens

<400> SEQUENCE: 128

Gly Leu Ala Phe Ser Leu Asn Gly Val
1               5

<210> SEQ ID NO 129
<211> LENGTH: 9
<212> TYPE: PRT
<213> ORGANISM: Homo sapiens

<400> SEQUENCE: 129

Ser Gln Ala Asp Val Ile Pro Ala Val
1               5
```

```
<210> SEQ ID NO 130
<211> LENGTH: 10
<212> TYPE: PRT
<213> ORGANISM: Homo sapiens

<400> SEQUENCE: 130

Ala Leu Asp Ala Gly Ala Val Tyr Thr Leu
1               5                   10

<210> SEQ ID NO 131
<211> LENGTH: 10
<212> TYPE: PRT
<213> ORGANISM: Homo sapiens

<400> SEQUENCE: 131

Ala Leu Asp Ser Gly Ala Phe Gln Ser Val
1               5                   10

<210> SEQ ID NO 132
<211> LENGTH: 9
<212> TYPE: PRT
<213> ORGANISM: Homo sapiens

<400> SEQUENCE: 132

Ala Leu His Glu Glu Val Val Gly Val
1               5

<210> SEQ ID NO 133
<211> LENGTH: 9
<212> TYPE: PRT
<213> ORGANISM: Homo sapiens

<400> SEQUENCE: 133

Ala Leu Leu Glu Met Asp Ala Arg Leu
1               5

<210> SEQ ID NO 134
<211> LENGTH: 10
<212> TYPE: PRT
<213> ORGANISM: Homo sapiens

<400> SEQUENCE: 134

Ala Leu Leu Glu Thr Asn Pro Tyr Leu Leu
1               5                   10

<210> SEQ ID NO 135
<211> LENGTH: 9
<212> TYPE: PRT
<213> ORGANISM: Homo sapiens

<400> SEQUENCE: 135

Ala Leu Leu Gly Lys Ile Glu Lys Val
1               5

<210> SEQ ID NO 136
<211> LENGTH: 9
<212> TYPE: PRT
<213> ORGANISM: Homo sapiens

<400> SEQUENCE: 136

Ala Leu Leu Asn Gln His Tyr Gln Val
1               5

<210> SEQ ID NO 137
<211> LENGTH: 9
```

-continued

```
<212> TYPE: PRT
<213> ORGANISM: Homo sapiens

<400> SEQUENCE: 137

Ala Leu Pro Thr Val Leu Val Gly Val
1               5

<210> SEQ ID NO 138
<211> LENGTH: 9
<212> TYPE: PRT
<213> ORGANISM: Homo sapiens

<400> SEQUENCE: 138

Ala Leu Ser Gln Val Thr Leu Leu Leu
1               5

<210> SEQ ID NO 139
<211> LENGTH: 9
<212> TYPE: PRT
<213> ORGANISM: Homo sapiens

<400> SEQUENCE: 139

Ala Leu Ser Ser Lys Pro Ala Glu Val
1               5

<210> SEQ ID NO 140
<211> LENGTH: 9
<212> TYPE: PRT
<213> ORGANISM: Homo sapiens

<400> SEQUENCE: 140

Ala Leu Thr Ser Ile Ser Ala Gly Val
1               5

<210> SEQ ID NO 141
<211> LENGTH: 9
<212> TYPE: PRT
<213> ORGANISM: Homo sapiens

<400> SEQUENCE: 141

Ala Met Gly Glu Lys Ser Phe Ser Val
1               5

<210> SEQ ID NO 142
<211> LENGTH: 9
<212> TYPE: PRT
<213> ORGANISM: Homo sapiens

<400> SEQUENCE: 142

Ala Val Ile Gly Gly Leu Ile Tyr Val
1               5

<210> SEQ ID NO 143
<211> LENGTH: 12
<212> TYPE: PRT
<213> ORGANISM: Homo sapiens

<400> SEQUENCE: 143

Phe Ile Leu Pro Asp Ser Leu Pro Leu Asp Thr Leu
1               5                   10

<210> SEQ ID NO 144
<211> LENGTH: 8
<212> TYPE: PRT
<213> ORGANISM: Homo sapiens
```

```
<400> SEQUENCE: 144

Phe Ile Gln Leu Ile Thr Gly Val
1               5

<210> SEQ ID NO 145
<211> LENGTH: 10
<212> TYPE: PRT
<213> ORGANISM: Homo sapiens

<400> SEQUENCE: 145

Phe Leu Ile Ala Glu Tyr Phe Glu His Val
1               5                   10

<210> SEQ ID NO 146
<211> LENGTH: 10
<212> TYPE: PRT
<213> ORGANISM: Homo sapiens

<400> SEQUENCE: 146

Phe Leu Trp Thr Glu Gln Ala His Thr Val
1               5                   10

<210> SEQ ID NO 147
<211> LENGTH: 10
<212> TYPE: PRT
<213> ORGANISM: Homo sapiens

<400> SEQUENCE: 147

Gly Leu Ala Pro Gly Gly Leu Ala Val Val
1               5                   10

<210> SEQ ID NO 148
<211> LENGTH: 9
<212> TYPE: PRT
<213> ORGANISM: Homo sapiens

<400> SEQUENCE: 148

Gly Leu Phe Ala Pro Leu Val Phe Leu
1               5

<210> SEQ ID NO 149
<211> LENGTH: 11
<212> TYPE: PRT
<213> ORGANISM: Homo sapiens

<400> SEQUENCE: 149

Gly Leu Leu Ser Gly Leu Asp Ile Met Glu Val
1               5                   10

<210> SEQ ID NO 150
<211> LENGTH: 10
<212> TYPE: PRT
<213> ORGANISM: Homo sapiens

<400> SEQUENCE: 150

Gly Leu Ser Asn Leu Gly Ile Lys Ser Ile
1               5                   10

<210> SEQ ID NO 151
<211> LENGTH: 9
<212> TYPE: PRT
<213> ORGANISM: Homo sapiens

<400> SEQUENCE: 151
```

His Leu Ala Lys Val Thr Ala Glu Val
1               5

<210> SEQ ID NO 152
<211> LENGTH: 9
<212> TYPE: PRT
<213> ORGANISM: Homo sapiens

<400> SEQUENCE: 152

Lys Leu Asp Asn Asn Leu Asp Ser Val
1               5

<210> SEQ ID NO 153
<211> LENGTH: 9
<212> TYPE: PRT
<213> ORGANISM: Homo sapiens

<400> SEQUENCE: 153

Lys Leu Ile Glu Val Asn Glu Glu Leu
1               5

<210> SEQ ID NO 154
<211> LENGTH: 9
<212> TYPE: PRT
<213> ORGANISM: Homo sapiens

<400> SEQUENCE: 154

Lys Leu Thr Asp His Leu Lys Tyr Val
1               5

<210> SEQ ID NO 155
<211> LENGTH: 11
<212> TYPE: PRT
<213> ORGANISM: Homo sapiens

<400> SEQUENCE: 155

Leu Leu Glu Pro Tyr Lys Pro Pro Ser Ala Gln
1               5                   10

<210> SEQ ID NO 156
<211> LENGTH: 10
<212> TYPE: PRT
<213> ORGANISM: Homo sapiens

<400> SEQUENCE: 156

Leu Leu Phe Pro His Pro Val Asn Gln Val
1               5                   10

<210> SEQ ID NO 157
<211> LENGTH: 9
<212> TYPE: PRT
<213> ORGANISM: Homo sapiens

<400> SEQUENCE: 157

Gln Leu Leu Pro Asn Leu Arg Ala Val
1               5

<210> SEQ ID NO 158
<211> LENGTH: 9
<212> TYPE: PRT
<213> ORGANISM: Homo sapiens

<400> SEQUENCE: 158

Arg Ile Ile Ser Gly Leu Val Lys Val

```
1               5

<210> SEQ ID NO 159
<211> LENGTH: 10
<212> TYPE: PRT
<213> ORGANISM: Homo sapiens

<400> SEQUENCE: 159

Arg Leu Phe Pro Asp Gly Ile Val Thr Val
1               5                   10

<210> SEQ ID NO 160
<211> LENGTH: 9
<212> TYPE: PRT
<213> ORGANISM: Homo sapiens

<400> SEQUENCE: 160

Arg Leu Leu Ala Lys Ile Ile Cys Leu
1               5

<210> SEQ ID NO 161
<211> LENGTH: 9
<212> TYPE: PRT
<213> ORGANISM: Homo sapiens

<400> SEQUENCE: 161

Arg Leu Leu Asp Glu Gln Phe Ala Val
1               5

<210> SEQ ID NO 162
<211> LENGTH: 9
<212> TYPE: PRT
<213> ORGANISM: Homo sapiens

<400> SEQUENCE: 162

Arg Leu Met Ser Ala Leu Thr Gln Val
1               5

<210> SEQ ID NO 163
<211> LENGTH: 9
<212> TYPE: PRT
<213> ORGANISM: Homo sapiens

<400> SEQUENCE: 163

Arg Leu Thr Glu Ser Val Leu Tyr Leu
1               5

<210> SEQ ID NO 164
<211> LENGTH: 9
<212> TYPE: PRT
<213> ORGANISM: Homo sapiens

<400> SEQUENCE: 164

Arg Met Leu Ile Lys Leu Leu Glu Val
1               5

<210> SEQ ID NO 165
<211> LENGTH: 9
<212> TYPE: PRT
<213> ORGANISM: Homo sapiens

<400> SEQUENCE: 165

Arg Val Ile Glu His Val Glu Gln Val
1               5
```

<210> SEQ ID NO 166
<211> LENGTH: 9
<212> TYPE: PRT
<213> ORGANISM: Homo sapiens

<400> SEQUENCE: 166

Ser Ile Leu Asp Ile Val Thr Lys Val
1               5

<210> SEQ ID NO 167
<211> LENGTH: 9
<212> TYPE: PRT
<213> ORGANISM: Homo sapiens

<400> SEQUENCE: 167

Ser Leu Ala Glu Ser Ser Phe Asp Val
1               5

<210> SEQ ID NO 168
<211> LENGTH: 9
<212> TYPE: PRT
<213> ORGANISM: Homo sapiens

<400> SEQUENCE: 168

Ser Leu Ala Val Leu Val Pro Ile Val
1               5

<210> SEQ ID NO 169
<211> LENGTH: 9
<212> TYPE: PRT
<213> ORGANISM: Homo sapiens

<400> SEQUENCE: 169

Ser Leu Phe Glu Trp Phe His Pro Leu
1               5

<210> SEQ ID NO 170
<211> LENGTH: 9
<212> TYPE: PRT
<213> ORGANISM: Homo sapiens

<400> SEQUENCE: 170

Ser Leu His Asn Gly Val Ile Gln Leu
1               5

<210> SEQ ID NO 171
<211> LENGTH: 9
<212> TYPE: PRT
<213> ORGANISM: Homo sapiens

<400> SEQUENCE: 171

Ser Leu Ile Pro Ala Val Leu Thr Val
1               5

<210> SEQ ID NO 172
<211> LENGTH: 9
<212> TYPE: PRT
<213> ORGANISM: Homo sapiens

<400> SEQUENCE: 172

Ser Leu Leu Asn Phe Leu Gln His Leu
1               5

<210> SEQ ID NO 173

```
<211> LENGTH: 9
<212> TYPE: PRT
<213> ORGANISM: Homo sapiens

<400> SEQUENCE: 173

Ser Leu Thr Ser Glu Ile His Phe Leu
1               5

<210> SEQ ID NO 174
<211> LENGTH: 10
<212> TYPE: PRT
<213> ORGANISM: Homo sapiens

<400> SEQUENCE: 174

Thr Leu Ala Glu Leu Gly Ala Val Gln Val
1               5                   10

<210> SEQ ID NO 175
<211> LENGTH: 9
<212> TYPE: PRT
<213> ORGANISM: Homo sapiens

<400> SEQUENCE: 175

Thr Leu Phe Glu His Leu Pro His Ile
1               5

<210> SEQ ID NO 176
<211> LENGTH: 8
<212> TYPE: PRT
<213> ORGANISM: Homo sapiens

<400> SEQUENCE: 176

Thr Leu Gly Gln Ile Trp Asp Val
1               5

<210> SEQ ID NO 177
<211> LENGTH: 9
<212> TYPE: PRT
<213> ORGANISM: Homo sapiens

<400> SEQUENCE: 177

Val Leu Asp Glu Pro Tyr Glu Lys Val
1               5

<210> SEQ ID NO 178
<211> LENGTH: 9
<212> TYPE: PRT
<213> ORGANISM: Homo sapiens

<400> SEQUENCE: 178

Tyr Ile Phe Thr Thr Pro Lys Ser Val
1               5

<210> SEQ ID NO 179
<211> LENGTH: 9
<212> TYPE: PRT
<213> ORGANISM: Homo sapiens

<400> SEQUENCE: 179

Tyr Ile His Asn Ile Leu Tyr Glu Val
1               5

<210> SEQ ID NO 180
<211> LENGTH: 11
<212> TYPE: PRT
```

```
<213> ORGANISM: Homo sapiens

<400> SEQUENCE: 180

Tyr Leu Gly Pro His Ile Ala Ser Val Thr Leu
1               5                   10

<210> SEQ ID NO 181
<211> LENGTH: 9
<212> TYPE: PRT
<213> ORGANISM: Homo sapiens

<400> SEQUENCE: 181

Tyr Leu Leu Glu Lys Phe Val Ala Val
1               5

<210> SEQ ID NO 182
<211> LENGTH: 9
<212> TYPE: PRT
<213> ORGANISM: Homo sapiens

<400> SEQUENCE: 182

Tyr Leu Leu His Phe Pro Met Ala Leu
1               5

<210> SEQ ID NO 183
<211> LENGTH: 11
<212> TYPE: PRT
<213> ORGANISM: Homo sapiens

<400> SEQUENCE: 183

Tyr Leu Tyr Asn Asn Glu Glu Gln Val Gly Leu
1               5                   10

<210> SEQ ID NO 184
<211> LENGTH: 11
<212> TYPE: PRT
<213> ORGANISM: Homo sapiens

<400> SEQUENCE: 184

Val Val Leu Asp Gly Gly Gln Ile Val Thr Val
1               5                   10

<210> SEQ ID NO 185
<211> LENGTH: 13
<212> TYPE: PRT
<213> ORGANISM: Homo sapiens

<400> SEQUENCE: 185

Ala Leu Phe Pro Ala Leu Arg Pro Gly Gly Phe Gln Ala
1               5                   10

<210> SEQ ID NO 186
<211> LENGTH: 9
<212> TYPE: PRT
<213> ORGANISM: Homo sapiens

<400> SEQUENCE: 186

Val Leu Leu Ala Gln Ile Ile Gln Val
1               5

<210> SEQ ID NO 187
<211> LENGTH: 9
<212> TYPE: PRT
<213> ORGANISM: Homo sapiens
```

```
<400> SEQUENCE: 187

Ser Tyr Pro Thr Phe Phe Pro Arg Phe
1               5

<210> SEQ ID NO 188
<211> LENGTH: 10
<212> TYPE: PRT
<213> ORGANISM: Homo sapiens

<400> SEQUENCE: 188

Arg Tyr Ser Ala Gly Trp Asp Ala Lys Phe
1               5                   10

<210> SEQ ID NO 189
<211> LENGTH: 11
<212> TYPE: PRT
<213> ORGANISM: Homo sapiens

<400> SEQUENCE: 189

Ala Phe Ser Pro Asp Ser His Tyr Leu Leu Phe
1               5                   10

<210> SEQ ID NO 190
<211> LENGTH: 9
<212> TYPE: PRT
<213> ORGANISM: Homo sapiens

<400> SEQUENCE: 190

Arg Tyr Asn Glu Lys Cys Phe Lys Leu
1               5

<210> SEQ ID NO 191
<211> LENGTH: 9
<212> TYPE: PRT
<213> ORGANISM: Homo sapiens

<400> SEQUENCE: 191

Lys Tyr Pro Asp Ile Ile Ser Arg Ile
1               5

<210> SEQ ID NO 192
<211> LENGTH: 9
<212> TYPE: PRT
<213> ORGANISM: Homo sapiens

<400> SEQUENCE: 192

Ser Tyr Ile Thr Lys Pro Glu Lys Trp
1               5

<210> SEQ ID NO 193
<211> LENGTH: 9
<212> TYPE: PRT
<213> ORGANISM: Homo sapiens

<400> SEQUENCE: 193

Ile Tyr Pro Gly Ala Phe Val Asp Leu
1               5

<210> SEQ ID NO 194
<211> LENGTH: 9
<212> TYPE: PRT
<213> ORGANISM: Homo sapiens

<400> SEQUENCE: 194
```

-continued

Gln Tyr Ala Ser Arg Phe Val Gln Leu
1               5

<210> SEQ ID NO 195
<211> LENGTH: 11
<212> TYPE: PRT
<213> ORGANISM: Homo sapiens

<400> SEQUENCE: 195

Arg Tyr Ala Pro Pro Ser Phe Ser Glu Phe
1               5                   10

<210> SEQ ID NO 196
<211> LENGTH: 9
<212> TYPE: PRT
<213> ORGANISM: Homo sapiens

<400> SEQUENCE: 196

Ala Tyr Leu Lys Trp Ile Ser Gln Ile
1               5

<210> SEQ ID NO 197
<211> LENGTH: 9
<212> TYPE: PRT
<213> ORGANISM: Homo sapiens

<400> SEQUENCE: 197

Arg Trp Pro Lys Lys Ser Ala Glu Phe
1               5

<210> SEQ ID NO 198
<211> LENGTH: 9
<212> TYPE: PRT
<213> ORGANISM: Homo sapiens

<400> SEQUENCE: 198

Leu Tyr Trp Ser His Pro Arg Lys Phe
1               5

<210> SEQ ID NO 199
<211> LENGTH: 9
<212> TYPE: PRT
<213> ORGANISM: Homo sapiens

<400> SEQUENCE: 199

Lys Phe Val Thr Val Gln Ala Thr Phe
1               5

<210> SEQ ID NO 200
<211> LENGTH: 9
<212> TYPE: PRT
<213> ORGANISM: Homo sapiens

<400> SEQUENCE: 200

Ala Tyr Leu Leu Gln Pro Ser Gln Phe
1               5

<210> SEQ ID NO 201
<211> LENGTH: 9
<212> TYPE: PRT
<213> ORGANISM: Homo sapiens

<400> SEQUENCE: 201

Ala Tyr Val Asn Thr Phe His Asn Ile
1               5

```
<210> SEQ ID NO 202
<211> LENGTH: 9
<212> TYPE: PRT
<213> ORGANISM: Homo sapiens

<400> SEQUENCE: 202

Ala Tyr Gly Thr Tyr Arg Ser Asn Phe
1               5

<210> SEQ ID NO 203
<211> LENGTH: 9
<212> TYPE: PRT
<213> ORGANISM: Homo sapiens

<400> SEQUENCE: 203

Tyr Tyr Gly Ile Leu Gln Glu Lys Ile
1               5

<210> SEQ ID NO 204
<211> LENGTH: 9
<212> TYPE: PRT
<213> ORGANISM: Homo sapiens

<400> SEQUENCE: 204

Lys Tyr Arg Leu Thr Tyr Ala Tyr Phe
1               5

<210> SEQ ID NO 205
<211> LENGTH: 9
<212> TYPE: PRT
<213> ORGANISM: Homo sapiens

<400> SEQUENCE: 205

Val Tyr Gly Leu Gln Arg Asn Leu Leu
1               5

<210> SEQ ID NO 206
<211> LENGTH: 9
<212> TYPE: PRT
<213> ORGANISM: Homo sapiens

<400> SEQUENCE: 206

Lys Trp Pro Glu Thr Pro Leu Leu Leu
1               5

<210> SEQ ID NO 207
<211> LENGTH: 9
<212> TYPE: PRT
<213> ORGANISM: Homo sapiens

<400> SEQUENCE: 207

Ile Tyr Leu Glu Arg Phe Pro Ile Phe
1               5

<210> SEQ ID NO 208
<211> LENGTH: 11
<212> TYPE: PRT
<213> ORGANISM: Homo sapiens

<400> SEQUENCE: 208

Ser Tyr Asn Pro Ala Glu Asn Ala Val Leu Leu
1               5                   10
```

```
<210> SEQ ID NO 209
<211> LENGTH: 9
<212> TYPE: PRT
<213> ORGANISM: Homo sapiens

<400> SEQUENCE: 209

Val Phe His Pro Arg Gln Glu Leu Ile
1               5

<210> SEQ ID NO 210
<211> LENGTH: 9
<212> TYPE: PRT
<213> ORGANISM: Homo sapiens

<400> SEQUENCE: 210

Ala Tyr Pro Ala Ile Arg Tyr Leu Leu
1               5

<210> SEQ ID NO 211
<211> LENGTH: 9
<212> TYPE: PRT
<213> ORGANISM: Homo sapiens

<400> SEQUENCE: 211

Ile Tyr Ile Pro Ser Tyr Phe Asp Phe
1               5

<210> SEQ ID NO 212
<211> LENGTH: 9
<212> TYPE: PRT
<213> ORGANISM: Homo sapiens

<400> SEQUENCE: 212

Val Tyr Gly Asp Val Ile Ser Asn Ile
1               5

<210> SEQ ID NO 213
<211> LENGTH: 9
<212> TYPE: PRT
<213> ORGANISM: Homo sapiens

<400> SEQUENCE: 213

Tyr Tyr Asn Lys Val Ser Thr Val Phe
1               5

<210> SEQ ID NO 214
<211> LENGTH: 9
<212> TYPE: PRT
<213> ORGANISM: Homo sapiens

<400> SEQUENCE: 214

Ile Tyr Val Thr Ser Ile Glu Gln Ile
1               5

<210> SEQ ID NO 215
<211> LENGTH: 9
<212> TYPE: PRT
<213> ORGANISM: Homo sapiens

<400> SEQUENCE: 215

Ile Tyr Thr Gly Asn Ile Ser Ser Phe
1               5

<210> SEQ ID NO 216
<211> LENGTH: 9
```

```
<212> TYPE: PRT
<213> ORGANISM: Homo sapiens

<400> SEQUENCE: 216

Ile Tyr Ala Asp Val Gly Glu Glu Phe
1               5

<210> SEQ ID NO 217
<211> LENGTH: 9
<212> TYPE: PRT
<213> ORGANISM: Homo sapiens

<400> SEQUENCE: 217

Asp Tyr Ile Pro Tyr Val Phe Lys Leu
1               5

<210> SEQ ID NO 218
<211> LENGTH: 9
<212> TYPE: PRT
<213> ORGANISM: Homo sapiens

<400> SEQUENCE: 218

Val Tyr Gln Gly Ala Ile Arg Gln Ile
1               5

<210> SEQ ID NO 219
<211> LENGTH: 10
<212> TYPE: PRT
<213> ORGANISM: Homo sapiens

<400> SEQUENCE: 219

Gly Val Met Ala Gly Asp Ile Tyr Ser Val
1               5                   10

<210> SEQ ID NO 220
<211> LENGTH: 10
<212> TYPE: PRT
<213> ORGANISM: Homo sapiens

<400> SEQUENCE: 220

Ser Leu Leu Glu Lys Glu Leu Glu Ser Val
1               5                   10

<210> SEQ ID NO 221
<211> LENGTH: 10
<212> TYPE: PRT
<213> ORGANISM: Homo sapiens

<400> SEQUENCE: 221

Ala Leu Cys Glu Glu Asn Met Arg Gly Val
1               5                   10

<210> SEQ ID NO 222
<211> LENGTH: 8
<212> TYPE: PRT
<213> ORGANISM: Homo sapiens

<400> SEQUENCE: 222

Leu Thr Asp Ile Thr Lys Gly Val
1               5

<210> SEQ ID NO 223
<211> LENGTH: 11
<212> TYPE: PRT
<213> ORGANISM: Homo sapiens
```

<400> SEQUENCE: 223

Phe Leu Phe Asn Thr Glu Asn Lys Leu Leu Leu
1               5                   10

<210> SEQ ID NO 224
<211> LENGTH: 9
<212> TYPE: PRT
<213> ORGANISM: Homo sapiens

<400> SEQUENCE: 224

Ala Leu Ala Ser Val Ile Lys Glu Leu
1               5

<210> SEQ ID NO 225
<211> LENGTH: 9
<212> TYPE: PRT
<213> ORGANISM: Homo sapiens

<400> SEQUENCE: 225

Lys Met Asp Pro Val Ala Tyr Arg Val
1               5

<210> SEQ ID NO 226
<211> LENGTH: 11
<212> TYPE: PRT
<213> ORGANISM: Homo sapiens

<400> SEQUENCE: 226

Ala Val Leu Gly Pro Leu Gly Leu Gln Glu Val
1               5                   10

<210> SEQ ID NO 227
<211> LENGTH: 9
<212> TYPE: PRT
<213> ORGANISM: Homo sapiens

<400> SEQUENCE: 227

Ala Leu Leu Lys Val Asn Gln Glu Leu
1               5

<210> SEQ ID NO 228
<211> LENGTH: 9
<212> TYPE: PRT
<213> ORGANISM: Homo sapiens

<400> SEQUENCE: 228

Tyr Leu Ile Thr Ser Val Glu Leu Leu
1               5

<210> SEQ ID NO 229
<211> LENGTH: 10
<212> TYPE: PRT
<213> ORGANISM: Homo sapiens

<400> SEQUENCE: 229

Lys Met Phe Glu Ser Phe Ile Glu Ser Val
1               5                   10

<210> SEQ ID NO 230
<211> LENGTH: 9
<212> TYPE: PRT
<213> ORGANISM: Homo sapiens

<400> SEQUENCE: 230

Val Leu Thr Glu Phe Thr Arg Glu Val
1               5

<210> SEQ ID NO 231
<211> LENGTH: 10
<212> TYPE: PRT
<213> ORGANISM: Homo sapiens

<400> SEQUENCE: 231

Arg Leu Phe Asn Asp Pro Val Ala Met Val
1               5                   10

<210> SEQ ID NO 232
<211> LENGTH: 9
<212> TYPE: PRT
<213> ORGANISM: Homo sapiens

<400> SEQUENCE: 232

Lys Leu Ala Glu Ile Val Lys Gln Val
1               5

<210> SEQ ID NO 233
<211> LENGTH: 9
<212> TYPE: PRT
<213> ORGANISM: Homo sapiens

<400> SEQUENCE: 233

Ala Leu Leu Gly Lys Leu Asp Ala Ile
1               5

<210> SEQ ID NO 234
<211> LENGTH: 9
<212> TYPE: PRT
<213> ORGANISM: Homo sapiens

<400> SEQUENCE: 234

Tyr Leu Glu Pro Tyr Leu Lys Glu Val
1               5

<210> SEQ ID NO 235
<211> LENGTH: 9
<212> TYPE: PRT
<213> ORGANISM: Homo sapiens

<400> SEQUENCE: 235

Lys Leu Phe Glu Glu Ile Arg Glu Ile
1               5

<210> SEQ ID NO 236
<211> LENGTH: 11
<212> TYPE: PRT
<213> ORGANISM: Homo sapiens

<400> SEQUENCE: 236

Ala Leu Ala Asp Lys Glu Leu Leu Pro Ser Val
1               5                   10

<210> SEQ ID NO 237
<211> LENGTH: 9
<212> TYPE: PRT
<213> ORGANISM: Homo sapiens

<400> SEQUENCE: 237

Ala Leu Arg Gly Glu Ile Glu Thr Val

<210> SEQ ID NO 238
<211> LENGTH: 10
<212> TYPE: PRT
<213> ORGANISM: Homo sapiens

<400> SEQUENCE: 238

Ala Met Pro Pro Pro Pro Gln Gly Val
1               5                   10

<210> SEQ ID NO 239
<211> LENGTH: 10
<212> TYPE: PRT
<213> ORGANISM: Homo sapiens

<400> SEQUENCE: 239

Phe Leu Leu Gly Phe Ile Pro Ala Lys Ala
1               5                   10

<210> SEQ ID NO 240
<211> LENGTH: 10
<212> TYPE: PRT
<213> ORGANISM: Homo sapiens

<400> SEQUENCE: 240

Phe Leu Trp Glu Arg Pro Thr Leu Leu Val
1               5                   10

<210> SEQ ID NO 241
<211> LENGTH: 11
<212> TYPE: PRT
<213> ORGANISM: Homo sapiens

<400> SEQUENCE: 241

Phe Val Leu Pro Leu Leu Gly Leu His Glu Ala
1               5                   10

<210> SEQ ID NO 242
<211> LENGTH: 9
<212> TYPE: PRT
<213> ORGANISM: Homo sapiens

<400> SEQUENCE: 242

Gly Leu Phe Ala Pro Val His Lys Val
1               5

<210> SEQ ID NO 243
<211> LENGTH: 10
<212> TYPE: PRT
<213> ORGANISM: Homo sapiens

<400> SEQUENCE: 243

Gly Leu Leu Asp Asn Pro Glu Leu Arg Val
1               5                   10

<210> SEQ ID NO 244
<211> LENGTH: 9
<212> TYPE: PRT
<213> ORGANISM: Homo sapiens

<400> SEQUENCE: 244

Lys Ile Ala Glu Leu Leu Glu Asn Val
1               5

```
<210> SEQ ID NO 245
<211> LENGTH: 9
<212> TYPE: PRT
<213> ORGANISM: Homo sapiens

<400> SEQUENCE: 245

Lys Leu Gly Ala Val Phe Asn Gln Val
1               5

<210> SEQ ID NO 246
<211> LENGTH: 9
<212> TYPE: PRT
<213> ORGANISM: Homo sapiens

<400> SEQUENCE: 246

Lys Leu Ile Ser Ser Tyr Tyr Asn Val
1               5

<210> SEQ ID NO 247
<211> LENGTH: 11
<212> TYPE: PRT
<213> ORGANISM: Homo sapiens

<400> SEQUENCE: 247

Lys Leu Leu Asp Thr Met Val Asp Thr Phe Leu
1               5                   10

<210> SEQ ID NO 248
<211> LENGTH: 9
<212> TYPE: PRT
<213> ORGANISM: Homo sapiens

<400> SEQUENCE: 248

Lys Leu Asn Asp Leu Ile Gln Arg Leu
1               5

<210> SEQ ID NO 249
<211> LENGTH: 9
<212> TYPE: PRT
<213> ORGANISM: Homo sapiens

<400> SEQUENCE: 249

Leu Leu Leu Gly Glu Arg Val Ala Leu
1               5

<210> SEQ ID NO 250
<211> LENGTH: 9
<212> TYPE: PRT
<213> ORGANISM: Homo sapiens

<400> SEQUENCE: 250

Asn Leu Ala Glu Val Val Glu Arg Val
1               5

<210> SEQ ID NO 251
<211> LENGTH: 10
<212> TYPE: PRT
<213> ORGANISM: Homo sapiens

<400> SEQUENCE: 251

Arg Leu Phe Ala Asp Ile Leu Asn Asp Val
1               5                   10

<210> SEQ ID NO 252
```

```
<211> LENGTH: 9
<212> TYPE: PRT
<213> ORGANISM: Homo sapiens

<400> SEQUENCE: 252

Arg Thr Ile Glu Tyr Leu Glu Glu Val
1               5

<210> SEQ ID NO 253
<211> LENGTH: 9
<212> TYPE: PRT
<213> ORGANISM: Homo sapiens

<400> SEQUENCE: 253

Arg Val Pro Pro Pro Pro Gln Ser Val
1               5

<210> SEQ ID NO 254
<211> LENGTH: 9
<212> TYPE: PRT
<213> ORGANISM: Homo sapiens

<400> SEQUENCE: 254

Arg Val Gln Glu Ala Ile Ala Glu Val
1               5

<210> SEQ ID NO 255
<211> LENGTH: 10
<212> TYPE: PRT
<213> ORGANISM: Homo sapiens

<400> SEQUENCE: 255

Ser Leu Phe Gly Gln Asp Val Lys Ala Val
1               5                   10

<210> SEQ ID NO 256
<211> LENGTH: 11
<212> TYPE: PRT
<213> ORGANISM: Homo sapiens

<400> SEQUENCE: 256

Ser Leu Phe Gln Gly Val Glu Phe His Tyr Val
1               5                   10

<210> SEQ ID NO 257
<211> LENGTH: 10
<212> TYPE: PRT
<213> ORGANISM: Homo sapiens

<400> SEQUENCE: 257

Ser Leu Leu Glu Lys Ala Gly Pro Glu Leu
1               5                   10

<210> SEQ ID NO 258
<211> LENGTH: 10
<212> TYPE: PRT
<213> ORGANISM: Homo sapiens

<400> SEQUENCE: 258

Ser Leu Met Gly Pro Val Val His Glu Val
1               5                   10

<210> SEQ ID NO 259
<211> LENGTH: 10
<212> TYPE: PRT
```

<213> ORGANISM: Homo sapiens

<400> SEQUENCE: 259

Thr Leu Ile Thr Asp Gly Met Arg Ser Val
1               5                   10

<210> SEQ ID NO 260
<211> LENGTH: 10
<212> TYPE: PRT
<213> ORGANISM: Homo sapiens

<400> SEQUENCE: 260

Thr Leu Met Asp Met Arg Leu Ser Gln Val
1               5                   10

<210> SEQ ID NO 261
<211> LENGTH: 10
<212> TYPE: PRT
<213> ORGANISM: Homo sapiens

<400> SEQUENCE: 261

Val Leu Phe Gln Glu Ala Leu Trp His Val
1               5                   10

<210> SEQ ID NO 262
<211> LENGTH: 10
<212> TYPE: PRT
<213> ORGANISM: Homo sapiens

<400> SEQUENCE: 262

Val Leu Pro Asn Phe Leu Pro Tyr Asn Val
1               5                   10

<210> SEQ ID NO 263
<211> LENGTH: 9
<212> TYPE: PRT
<213> ORGANISM: Homo sapiens

<400> SEQUENCE: 263

Val Leu Tyr Pro Ser Leu Lys Glu Ile
1               5

<210> SEQ ID NO 264
<211> LENGTH: 11
<212> TYPE: PRT
<213> ORGANISM: Homo sapiens

<400> SEQUENCE: 264

Val Met Gln Asp Pro Glu Phe Leu Gln Ser Val
1               5                   10

<210> SEQ ID NO 265
<211> LENGTH: 11
<212> TYPE: PRT
<213> ORGANISM: Homo sapiens

<400> SEQUENCE: 265

Trp Leu Ile Glu Asp Gly Lys Val Val Thr Val
1               5                   10

<210> SEQ ID NO 266
<211> LENGTH: 11
<212> TYPE: PRT
<213> ORGANISM: Homo sapiens

```
<400> SEQUENCE: 266

Ser Leu Leu Glu Ser Asn Lys Asp Leu Leu
1               5                   10

<210> SEQ ID NO 267
<211> LENGTH: 9
<212> TYPE: PRT
<213> ORGANISM: Homo sapiens

<400> SEQUENCE: 267

Ala Leu Asn Glu Asn Ile Asn Gln Val
1               5

<210> SEQ ID NO 268
<211> LENGTH: 11
<212> TYPE: PRT
<213> ORGANISM: Homo sapiens

<400> SEQUENCE: 268

Lys Leu Tyr Gln Glu Val Glu Ile Ala Ser Val
1               5                   10

<210> SEQ ID NO 269
<211> LENGTH: 10
<212> TYPE: PRT
<213> ORGANISM: Homo sapiens

<400> SEQUENCE: 269

Tyr Leu Met Glu Gly Ser Tyr Asn Lys Val
1               5                   10

<210> SEQ ID NO 270
<211> LENGTH: 9
<212> TYPE: PRT
<213> ORGANISM: Homo sapiens

<400> SEQUENCE: 270

Ser Val Leu Asp Gln Lys Ile Leu Leu
1               5

<210> SEQ ID NO 271
<211> LENGTH: 9
<212> TYPE: PRT
<213> ORGANISM: Homo sapiens

<400> SEQUENCE: 271

Leu Leu Leu Asp Lys Leu Ile Leu Leu
1               5

<210> SEQ ID NO 272
<211> LENGTH: 11
<212> TYPE: PRT
<213> ORGANISM: Homo sapiens

<400> SEQUENCE: 272

Gln Gln Leu Asp Ser Lys Phe Leu Glu Gln Val
1               5                   10

<210> SEQ ID NO 273
<211> LENGTH: 10
<212> TYPE: PRT
<213> ORGANISM: Homo sapiens

<400> SEQUENCE: 273
```

Ala Ile Leu Glu Thr Ala Pro Lys Glu Val
1               5                   10

<210> SEQ ID NO 274
<211> LENGTH: 9
<212> TYPE: PRT
<213> ORGANISM: Homo sapiens

<400> SEQUENCE: 274

Ala Leu Ala Glu Ala Leu Lys Glu Val
1               5

<210> SEQ ID NO 275
<211> LENGTH: 10
<212> TYPE: PRT
<213> ORGANISM: Homo sapiens

<400> SEQUENCE: 275

Ala Leu Ile Glu Gly Ala Gly Ile Leu Leu
1               5                   10

<210> SEQ ID NO 276
<211> LENGTH: 11
<212> TYPE: PRT
<213> ORGANISM: Homo sapiens

<400> SEQUENCE: 276

Ala Leu Leu Glu Ala Asp Val Asn Ile Lys Leu
1               5                   10

<210> SEQ ID NO 277
<211> LENGTH: 11
<212> TYPE: PRT
<213> ORGANISM: Homo sapiens

<400> SEQUENCE: 277

Ala Leu Leu Glu Glu Asn Ser Thr Pro Gln Leu
1               5                   10

<210> SEQ ID NO 278
<211> LENGTH: 9
<212> TYPE: PRT
<213> ORGANISM: Homo sapiens

<400> SEQUENCE: 278

Ala Leu Thr Ser Val Val Val Thr Leu
1               5

<210> SEQ ID NO 279
<211> LENGTH: 9
<212> TYPE: PRT
<213> ORGANISM: Homo sapiens

<400> SEQUENCE: 279

Ala Leu Trp Thr Gly Met His Thr Ile
1               5

<210> SEQ ID NO 280
<211> LENGTH: 9
<212> TYPE: PRT
<213> ORGANISM: Homo sapiens

<400> SEQUENCE: 280

Ala Thr Leu Asn Ile Ile His Ser Val
1               5

<210> SEQ ID NO 281
<211> LENGTH: 11
<212> TYPE: PRT
<213> ORGANISM: Homo sapiens

<400> SEQUENCE: 281

Gly Leu Leu Ala Gly Asp Arg Leu Val Glu Val
1               5                   10

<210> SEQ ID NO 282
<211> LENGTH: 10
<212> TYPE: PRT
<213> ORGANISM: Homo sapiens

<400> SEQUENCE: 282

Gly Gln Phe Pro Ser Tyr Leu Glu Thr Val
1               5                   10

<210> SEQ ID NO 283
<211> LENGTH: 10
<212> TYPE: PRT
<213> ORGANISM: Homo sapiens

<400> SEQUENCE: 283

Ile Leu Ser Gly Ile Gly Val Ser Gln Val
1               5                   10

<210> SEQ ID NO 284
<211> LENGTH: 9
<212> TYPE: PRT
<213> ORGANISM: Homo sapiens

<400> SEQUENCE: 284

Lys Leu Asp Ala Phe Val Glu Gly Val
1               5

<210> SEQ ID NO 285
<211> LENGTH: 11
<212> TYPE: PRT
<213> ORGANISM: Homo sapiens

<400> SEQUENCE: 285

Lys Leu Leu Asp Leu Ser Asp Ser Thr Ser Val
1               5                   10

<210> SEQ ID NO 286
<211> LENGTH: 9
<212> TYPE: PRT
<213> ORGANISM: Homo sapiens

<400> SEQUENCE: 286

Lys Val Leu Asp Lys Val Phe Arg Ala
1               5

<210> SEQ ID NO 287
<211> LENGTH: 9
<212> TYPE: PRT
<213> ORGANISM: Homo sapiens

<400> SEQUENCE: 287

Leu Ile Gly Glu Phe Leu Glu Lys Val
1               5

-continued

<210> SEQ ID NO 288
<211> LENGTH: 9
<212> TYPE: PRT
<213> ORGANISM: Homo sapiens

<400> SEQUENCE: 288

Leu Leu Asp Asp Ser Leu Val Ser Ile
1               5

<210> SEQ ID NO 289
<211> LENGTH: 11
<212> TYPE: PRT
<213> ORGANISM: Homo sapiens

<400> SEQUENCE: 289

Leu Leu Leu Glu Glu Gly Gly Leu Val Gln Val
1               5                   10

<210> SEQ ID NO 290
<211> LENGTH: 10
<212> TYPE: PRT
<213> ORGANISM: Homo sapiens

<400> SEQUENCE: 290

Asn Leu Ile Asp Leu Asp Asp Leu Tyr Val
1               5                   10

<210> SEQ ID NO 291
<211> LENGTH: 9
<212> TYPE: PRT
<213> ORGANISM: Homo sapiens

<400> SEQUENCE: 291

Gln Leu Ile Asp Tyr Glu Arg Gln Leu
1               5

<210> SEQ ID NO 292
<211> LENGTH: 9
<212> TYPE: PRT
<213> ORGANISM: Homo sapiens

<400> SEQUENCE: 292

Arg Ile Pro Ala Tyr Phe Val Thr Val
1               5

<210> SEQ ID NO 293
<211> LENGTH: 11
<212> TYPE: PRT
<213> ORGANISM: Homo sapiens

<400> SEQUENCE: 293

Phe Leu Ala Ser Glu Ser Leu Ile Lys Gln Ile
1               5                   10

<210> SEQ ID NO 294
<211> LENGTH: 9
<212> TYPE: PRT
<213> ORGANISM: Homo sapiens

<400> SEQUENCE: 294

Arg Leu Ile Asp Leu His Thr Asn Val
1               5

<210> SEQ ID NO 295
<211> LENGTH: 9

<212> TYPE: PRT
<213> ORGANISM: Homo sapiens

<400> SEQUENCE: 295

Ser Leu Phe Ser Ser Pro Pro Glu Ile
1               5

<210> SEQ ID NO 296
<211> LENGTH: 10
<212> TYPE: PRT
<213> ORGANISM: Homo sapiens

<400> SEQUENCE: 296

Ser Leu Leu Ser Gly Arg Ile Ser Thr Leu
1               5                   10

<210> SEQ ID NO 297
<211> LENGTH: 9
<212> TYPE: PRT
<213> ORGANISM: Homo sapiens

<400> SEQUENCE: 297

Thr Leu Phe Tyr Ser Leu Arg Glu Val
1               5

<210> SEQ ID NO 298
<211> LENGTH: 11
<212> TYPE: PRT
<213> ORGANISM: Homo sapiens

<400> SEQUENCE: 298

Thr Met Ala Lys Glu Ser Ser Ile Ile Gly Val
1               5                   10

<210> SEQ ID NO 299
<211> LENGTH: 9
<212> TYPE: PRT
<213> ORGANISM: Homo sapiens

<400> SEQUENCE: 299

Ala Leu Leu Arg Val Thr Pro Phe Ile
1               5

<210> SEQ ID NO 300
<211> LENGTH: 9
<212> TYPE: PRT
<213> ORGANISM: Homo sapiens

<400> SEQUENCE: 300

Thr Leu Ala Gln Gln Pro Thr Ala Val
1               5

<210> SEQ ID NO 301
<211> LENGTH: 9
<212> TYPE: PRT
<213> ORGANISM: Homo sapiens

<400> SEQUENCE: 301

Val Leu Ala Asp Phe Gly Ala Arg Val
1               5

<210> SEQ ID NO 302
<211> LENGTH: 9
<212> TYPE: PRT
<213> ORGANISM: Homo sapiens

```
<400> SEQUENCE: 302

Lys Ile Gln Glu Ile Leu Thr Gln Val
1               5

<210> SEQ ID NO 303
<211> LENGTH: 10
<212> TYPE: PRT
<213> ORGANISM: Homo sapiens

<400> SEQUENCE: 303

Gly Val Tyr Asp Gly Glu Glu His Ser Val
1               5                   10

<210> SEQ ID NO 304
<211> LENGTH: 9
<212> TYPE: PRT
<213> ORGANISM: Homo sapiens

<400> SEQUENCE: 304

Ser Leu Ile Asp Gln Phe Phe Gly Val
1               5

<210> SEQ ID NO 305
<211> LENGTH: 9
<212> TYPE: PRT
<213> ORGANISM: Homo sapiens

<400> SEQUENCE: 305

Gly Val Leu Glu Asn Ile Phe Gly Val
1               5

<210> SEQ ID NO 306
<211> LENGTH: 10
<212> TYPE: PRT
<213> ORGANISM: Homo sapiens

<400> SEQUENCE: 306

Lys Leu Val Glu Phe Asp Phe Leu Gly Ala
1               5                   10

<210> SEQ ID NO 307
<211> LENGTH: 9
<212> TYPE: PRT
<213> ORGANISM: Homo sapiens

<400> SEQUENCE: 307

Ala Val Val Glu Phe Leu Thr Ser Val
1               5

<210> SEQ ID NO 308
<211> LENGTH: 9
<212> TYPE: PRT
<213> ORGANISM: Homo sapiens

<400> SEQUENCE: 308

Ala Leu Leu Arg Thr Val Val Ser Val
1               5

<210> SEQ ID NO 309
<211> LENGTH: 9
<212> TYPE: PRT
<213> ORGANISM: Homo sapiens

<400> SEQUENCE: 309
```

Gly Leu Ile Glu Ile Ile Ser Asn Ala
1               5

<210> SEQ ID NO 310
<211> LENGTH: 9
<212> TYPE: PRT
<213> ORGANISM: Homo sapiens

<400> SEQUENCE: 310

Ser Leu Trp Gly Gly Asp Val Val Leu
1               5

<210> SEQ ID NO 311
<211> LENGTH: 9
<212> TYPE: PRT
<213> ORGANISM: Homo sapiens

<400> SEQUENCE: 311

Phe Leu Ile Pro Ile Tyr His Gln Val
1               5

<210> SEQ ID NO 312
<211> LENGTH: 9
<212> TYPE: PRT
<213> ORGANISM: Homo sapiens

<400> SEQUENCE: 312

Arg Leu Gly Ile Lys Pro Glu Ser Val
1               5

<210> SEQ ID NO 313
<211> LENGTH: 11
<212> TYPE: PRT
<213> ORGANISM: Homo sapiens

<400> SEQUENCE: 313

Leu Thr Ala Pro Pro Glu Ala Leu Leu Met Val
1               5                   10

<210> SEQ ID NO 314
<211> LENGTH: 9
<212> TYPE: PRT
<213> ORGANISM: Homo sapiens

<400> SEQUENCE: 314

Tyr Leu Ala Pro Phe Leu Arg Asn Val
1               5

<210> SEQ ID NO 315
<211> LENGTH: 10
<212> TYPE: PRT
<213> ORGANISM: Homo sapiens

<400> SEQUENCE: 315

Lys Val Leu Asp Gly Ser Pro Ile Glu Val
1               5                   10

<210> SEQ ID NO 316
<211> LENGTH: 9
<212> TYPE: PRT
<213> ORGANISM: Homo sapiens

<400> SEQUENCE: 316

Leu Leu Arg Glu Lys Val Glu Phe Leu

```
<210> SEQ ID NO 317
<211> LENGTH: 9
<212> TYPE: PRT
<213> ORGANISM: Homo sapiens

<400> SEQUENCE: 317

Lys Leu Pro Glu Lys Trp Glu Ser Val
1               5

<210> SEQ ID NO 318
<211> LENGTH: 9
<212> TYPE: PRT
<213> ORGANISM: Homo sapiens

<400> SEQUENCE: 318

Lys Leu Asn Glu Ile Asn Glu Lys Ile
1               5

<210> SEQ ID NO 319
<211> LENGTH: 9
<212> TYPE: PRT
<213> ORGANISM: Homo sapiens

<400> SEQUENCE: 319

Lys Leu Phe Asn Glu Phe Ile Gln Leu
1               5

<210> SEQ ID NO 320
<211> LENGTH: 11
<212> TYPE: PRT
<213> ORGANISM: Homo sapiens

<400> SEQUENCE: 320

Gly Leu Ala Asp Asn Thr Val Ile Ala Lys Val
1               5                   10

<210> SEQ ID NO 321
<211> LENGTH: 10
<212> TYPE: PRT
<213> ORGANISM: Homo sapiens

<400> SEQUENCE: 321

Gly Val Ile Ala Glu Ile Leu Arg Gly Val
1               5                   10

<210> SEQ ID NO 322
<211> LENGTH: 10
<212> TYPE: PRT
<213> ORGANISM: Homo sapiens

<400> SEQUENCE: 322

Ile Leu Tyr Asp Ile Pro Asp Ile Arg Leu
1               5                   10

<210> SEQ ID NO 323
<211> LENGTH: 11
<212> TYPE: PRT
<213> ORGANISM: Homo sapiens

<400> SEQUENCE: 323

Lys Ile Ile Asp Glu Asp Gly Leu Leu Asn Leu
1               5                   10
```

<210> SEQ ID NO 324
<211> LENGTH: 10
<212> TYPE: PRT
<213> ORGANISM: Homo sapiens

<400> SEQUENCE: 324

Arg Leu Phe Glu Thr Lys Ile Thr Gln Val
1               5                   10

<210> SEQ ID NO 325
<211> LENGTH: 9
<212> TYPE: PRT
<213> ORGANISM: Homo sapiens

<400> SEQUENCE: 325

Arg Leu Ser Glu Ala Ile Val Thr Val
1               5

<210> SEQ ID NO 326
<211> LENGTH: 9
<212> TYPE: PRT
<213> ORGANISM: Homo sapiens

<400> SEQUENCE: 326

Ala Leu Ser Asp Gly Val His Lys Ile
1               5

<210> SEQ ID NO 327
<211> LENGTH: 9
<212> TYPE: PRT
<213> ORGANISM: Homo sapiens

<400> SEQUENCE: 327

Gly Leu Asn Glu Glu Ile Ala Arg Val
1               5

<210> SEQ ID NO 328
<211> LENGTH: 11
<212> TYPE: PRT
<213> ORGANISM: Homo sapiens

<400> SEQUENCE: 328

Arg Leu Glu Glu Asp Asp Gly Asp Val Ala Met
1               5                   10

<210> SEQ ID NO 329
<211> LENGTH: 9
<212> TYPE: PRT
<213> ORGANISM: Homo sapiens

<400> SEQUENCE: 329

Ser Leu Ile Glu Asp Leu Ile Leu Leu
1               5

<210> SEQ ID NO 330
<211> LENGTH: 9
<212> TYPE: PRT
<213> ORGANISM: Homo sapiens

<400> SEQUENCE: 330

Ser Met Ser Ala Asp Val Pro Leu Val
1               5

<210> SEQ ID NO 331

```
<211> LENGTH: 11
<212> TYPE: PRT
<213> ORGANISM: Homo sapiens

<400> SEQUENCE: 331

Ser Leu Leu Ala Gln Asn Thr Ser Trp Leu Leu
1               5                   10

<210> SEQ ID NO 332
<211> LENGTH: 9
<212> TYPE: PRT
<213> ORGANISM: Homo sapiens

<400> SEQUENCE: 332

Ala Met Leu Ala Val Leu His Thr Val
1               5

<210> SEQ ID NO 333
<211> LENGTH: 11
<212> TYPE: PRT
<213> ORGANISM: Homo sapiens

<400> SEQUENCE: 333

Gly Leu Ala Glu Asp Ile Asp Lys Gly Glu Val
1               5                   10

<210> SEQ ID NO 334
<211> LENGTH: 12
<212> TYPE: PRT
<213> ORGANISM: Homo sapiens

<400> SEQUENCE: 334

Ser Ile Leu Thr Ile Glu Asp Gly Ile Phe Glu Val
1               5                   10

<210> SEQ ID NO 335
<211> LENGTH: 11
<212> TYPE: PRT
<213> ORGANISM: Homo sapiens

<400> SEQUENCE: 335

Ser Leu Leu Pro Val Asp Ile Arg Gln Tyr Leu
1               5                   10

<210> SEQ ID NO 336
<211> LENGTH: 9
<212> TYPE: PRT
<213> ORGANISM: Homo sapiens

<400> SEQUENCE: 336

Tyr Leu Pro Thr Phe Phe Leu Thr Val
1               5

<210> SEQ ID NO 337
<211> LENGTH: 11
<212> TYPE: PRT
<213> ORGANISM: Homo sapiens

<400> SEQUENCE: 337

Thr Leu Leu Ala Ala Glu Phe Leu Lys Gln Val
1               5                   10

<210> SEQ ID NO 338
<211> LENGTH: 12
<212> TYPE: PRT
```

```
<213> ORGANISM: Homo sapiens

<400> SEQUENCE: 338

Lys Leu Phe Asp Ser Asp Pro Ile Thr Val Thr Val
1               5                   10

<210> SEQ ID NO 339
<211> LENGTH: 9
<212> TYPE: PRT
<213> ORGANISM: Homo sapiens

<400> SEQUENCE: 339

Arg Leu Ile Ser Lys Phe Asp Thr Val
1               5

<210> SEQ ID NO 340
<211> LENGTH: 9
<212> TYPE: PRT
<213> ORGANISM: Homo sapiens

<400> SEQUENCE: 340

Lys Val Phe Asp Glu Val Ile Glu Val
1               5

<210> SEQ ID NO 341
<211> LENGTH: 9
<212> TYPE: PRT
<213> ORGANISM: Homo sapiens

<400> SEQUENCE: 341

Tyr Leu Ala Ile Gly Ile His Glu Leu
1               5

<210> SEQ ID NO 342
<211> LENGTH: 9
<212> TYPE: PRT
<213> ORGANISM: Homo sapiens

<400> SEQUENCE: 342

Ala Met Ser Ser Lys Phe Phe Leu Val
1               5

<210> SEQ ID NO 343
<211> LENGTH: 9
<212> TYPE: PRT
<213> ORGANISM: Homo sapiens

<400> SEQUENCE: 343

Leu Leu Leu Pro Asp Tyr Tyr Leu Val
1               5

<210> SEQ ID NO 344
<211> LENGTH: 9
<212> TYPE: PRT
<213> ORGANISM: Homo sapiens

<400> SEQUENCE: 344

Val Tyr Ile Ser Ser Leu Ala Leu Leu
1               5

<210> SEQ ID NO 345
<211> LENGTH: 9
<212> TYPE: PRT
<213> ORGANISM: Homo sapiens
```

```
<400> SEQUENCE: 345

Ser Tyr Asn Pro Leu Trp Leu Arg Ile
1               5

<210> SEQ ID NO 346
<211> LENGTH: 10
<212> TYPE: PRT
<213> ORGANISM: Homo sapiens

<400> SEQUENCE: 346

Leu Tyr Gln Ile Leu Gln Gly Ile Val Phe
1               5                   10

<210> SEQ ID NO 347
<211> LENGTH: 9
<212> TYPE: PRT
<213> ORGANISM: Homo sapiens

<400> SEQUENCE: 347

Ala Leu Asn Pro Ala Asp Ile Thr Val
1               5

<210> SEQ ID NO 348
<211> LENGTH: 9
<212> TYPE: PRT
<213> ORGANISM: Homo sapiens

<400> SEQUENCE: 348

Ala Tyr Lys Pro Gly Ala Leu Thr Phe
1               5
```